US007271315B2

(12) United States Patent
Metz et al.

(10) Patent No.: US 7,271,315 B2
(45) **Date of Patent: *Sep. 18, 2007**

(54) PUFA POLYKETIDE SYNTHASE SYSTEMS AND USES THEREOF

(75) Inventors: James G. Metz, Longmont, CO (US); James H. Flatt, Colorado Springs, CO (US); Jerry M. Kuner, Longmont, CO (US); William R. Barclay, Boulder, CO (US)

(73) Assignee: Martek Biosciences Corporation, Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/452,138

(22) Filed: Jun. 12, 2006

(65) Prior Publication Data

US 2007/0089199 A1 Apr. 19, 2007

Related U.S. Application Data

(63) Continuation-in-part of application No. 10/124,800, filed on Apr. 16, 2002, now Pat. No. 7,247,461, and a continuation-in-part of application No. 09/231,899, filed on Jan. 14, 1999, now Pat. No. 6,566,583.

(60) Provisional application No. 60/784,616, filed on Mar. 21, 2006, provisional application No. 60/689,167, filed on Jun. 10, 2005, provisional application No. 60/323,269, filed on Sep. 18, 2001, provisional application No. 60/298,796, filed on Jun. 15, 2001, provisional application No. 60/284,066, filed on Apr. 16, 2001.

(51) Int. Cl.

| | |
|---|---|
| ***A01H 1/00*** | (2006.01) |
| ***A01H 9/00*** | (2006.01) |
| ***A01H 5/00*** | (2006.01) |
| ***C12P 7/64*** | (2006.01) |
| ***C12N 5/00*** | (2006.01) |

(52) U.S. Cl. ...................... 800/278; 800/281; 800/295; 800/298; 435/134; 435/410

(58) Field of Classification Search ..................... None
See application file for complete search history.

(56) References Cited

U.S. PATENT DOCUMENTS 5,130,242 A 7/1992 Barclay (Continued)

FOREIGN PATENT DOCUMENTS

EP 0823475 2/1998

(Continued)

OTHER PUBLICATIONS

DATABASE Geneseq 'Online! Dec. 11, 2000, “S. aggregatum PKS cluster ORF6 homolog DNA.” XP002368912, retrieved from EBI accession No. GSN:AAA71567Database accession No. AAA71567—& DATABASE Geneseq 'Online! Dec. 11, 2000, “S. aggregatum PKS cluster ORF6 homolog protein.” XP002368914 retrieved from EBI accession No. GSP:AAB10482 Database accession No. AAB10482 & WO 00/42195 A (Calgene, LLC) Jul. 20, 2000.

(Continued)

*Primary Examiner*—Nashaat T. Nashed
(74) *Attorney, Agent, or Firm*—Sheridan Ross P.C.

(57) ABSTRACT

Disclosed are the complete polyunsaturated fatty acid (PUFA) polyketide synthase (PKS) systems from *Schizochytrium*, and biologically active fragments and homologues thereof. More particularly, this invention relates to nucleic acids encoding such PUFA PKS systems, to proteins and domains thereof that comprise such PUFA PKS systems, to genetically modified organisms (plants and microorganisms) comprising such PUFA PKS systems, and to methods of making and using the PUFA PKS systems disclosed herein. This invention also relates to genetically modified plants and microorganisms and methods to efficiently produce lipids enriched in various polyunsaturated fatty acids (PUFAs) as well as other bioactive molecules by manipulation of a PUFA polyketide synthase (PKS) system.

20 Claims, 8 Drawing Sheets

Orf A 307 kDa
KS MAT 9X ACP KR

Orf B 225 kDa
KS CLF AT ER

Orf C 166 kDa
DH DH ER

U.S. PATENT DOCUMENTS

| | | | |
|---|---|---|---|
| 5,246,841 | A | 9/1993 | Yazawa et al. |
| 5,639,790 | A | 6/1997 | Voelker et al. |
| 5,672,491 | A | 9/1997 | Khosla et al. |
| 5,683,898 | A | 11/1997 | Yazawa et al. |
| 6,033,883 | A | 3/2000 | Barr et al. |
| 6,140,486 | A | 10/2000 | Facciotti et al. |
| 6,566,583 | B1 | 5/2003 | Facciotti et al. |
| 7,211,418 | B2 | 5/2007 | Metz |
| 7,217,856 | B2 | 5/2007 | Weaver et al. |
| 2002/0194641 | A1 | 12/2002 | Metz |
| 2003/0101486 | A1 | 5/2003 | Facciotti |
| 2004/0005672 | A1 | 1/2004 | Santi et al. |
| 2005/0266440 | A1 | 12/2005 | Metz |
| 2005/0273883 | A1 | 12/2005 | Metz |
| 2005/0273884 | A1 | 12/2005 | Metz |

FOREIGN PATENT DOCUMENTS

| | | |
|---|---|---|
| WO | 9323545 | 11/1993 |
| WO | 9621735 | 7/1996 |
| WO | 9846764 | 10/1998 |
| WO | 9855625 | 12/1998 |
| WO | 0042195 | 7/2000 |

OTHER PUBLICATIONS

Nicholson et al., "Design and utility of oligonucleotide gene probes for fungal polyketide synthases", Chem & Bio (London) vol. 8, No. 2, Feb. 2001, pp. 157-178, XP002338562.

Kealey et al., "Production of a polyketide natural product in non-polyketide-producing prokaryotic and eukaryotic hosts", Proceedings of the National Academy of Sciences of the United States of America, vol. 95, No. 2, Jan. 20, 1998, pp. 505-509, XP002338563.

Jez et al., "Structural control of polyketide formation in plant-specific polyketide synthases", Chem and Bio (London), vol. 7, No. 12, Dec. 2000, pp. 919-930, XP002338564.

Chuck et al., "Molecular recognition of diketide substrates by a beta-ketoacyl-acyl carrier protein synthase domain within a bimodular polyketide synthase", Chem and Bio, Current Bio, (London), GB,, vol. 4, No. 10, 1997, pp. 757-766, XP000884721.

Wallis et al., "Polyunsaturated fatty acid synthesis: what will they think of next?", Tibs Trends in Bio Sciences, Elsevier Publ., Cambridge, EN, vol. 27, No. 9, Sep. 2002, pp. 467-473, XP004378766.

Abbadi et al., Eur. J. Lipid Sci. Technol., 103:106-113 (2001).

Allen et al., Appl. Envir. Microbiol., 65(4):1710-1720 (1999).

Bateman et al., Nucl. Acids Res., 30(1):276-280 (2002).

Bentley et al., Annu. Rev. Microbiol., 53:411-46 (1999).

Bisang et al., Nature, 401:502-505 (1999).

Bork, TIG, 12(10):425-427 (1996).

Brenner, TIG, 15(4):132-133 (1999).

Broun et al., Science, 282:1315-1317 (1998).

Creelman et al., Annu. Rev. Plan Physiol. Plant Mol. Biol., 48:355-81 (1997).

DeLong & Yayanos, Appl. Environ. Microbiol., 51(4):730-737 (1986).

Doerks, TIG, 14(6):248-250 (1998).

Facciotti et al., "Cloning and Characterization of Polyunsaturated Fatty Acids (PUFA) Genes from Marine Bacteria" in Proceedings of the international symposium on progress and prospect of marine biotechnology (China Ocean Pres 1999), pp. 404-405 Abstract.

Heath et al., J. Biol. Chem., 271(44):27795-27801 (1996).

Hopwood & Sherman, Annu. Rev. Genet., 24:37-66 (1990).

Hutchinson, Annu. Rev. Microbiol., 49:201-238 (1995).

Jostensen & Landfald, FEMS Microbiology Letters, 151:95-101 (1997).

Katz & Donadio, Annu. Rev. Microbiol., 47:875-912 (1993).

Keating et al., Curr. Opin. Chem. Biol., 3:598-606 (1999).

Kyle et al., HortScience, 25:1523-26 (1990).

Magnuson, Microbil. Rev., 57(3):522-542 (1993) Abstract.

Metz et al., Science, 293:290-293 (2001).

Nakahara, Yukagaku, 44(10):821-7 (1995).

Nasu et al., J. Ferment. Bioeng., 122:467-473 (1997).

Nichols et al., Curr. Opin. Biotechnol., 10:240-246 (1999).

Nogi et al., Extremophiles, 2:1-7 (1998).

Parker-Barnes et al., PNAS, 97(15):8284-8289 (2000).

Sánchez et al., Chemistry & Biolosy, 8:725-738 (2001).

Shanklin et al., Annu. Rev. Plant Physiol. Plant Mol. Biol., 49:611-41 (1998).

Smith et al., Nature Biotechnol., 15:1222-1223 (1997).

Somerville Am. J. Clin. Nutr., 58(2 supp):270S-275S (1993).

Van de Loo, Proc. Natl. Acad. Sci. USA, 92:6743-6747 (1995).

Watanabe et al., J. Biochem., 122:467-473 (1997).

Yalpani et al., The Plant Cell, 13:1401-1409 (2001).

Yazawa, Lipids, 31(supp):S297-S300 (1996).

Leadlay, P. Combinatorial Approaches to Polyketides Biosynthesis.

Wiesmann et al. Chemistry & Biology (Sep. 1995) 2: 583-589.

Wiesmann et al. Biochemistry (1997) 36: 13849-13855.

Wiesmann et al. Biochemistry (1998) 37: 11012-11017.

Harlow et al. Antibodies: A Laboratory Manual (1988) Cold Spring Harbor Laboratory Press, p. 76.

GenBank Accession No. U09865. Alcaligenes euthrophus pyruvate dehydrogenase (pdhA), dihydrolipoamide acetyltransferase (pdhB), dihydrolipoamide dehydrogenase (pdhL), and ORF3 genes, complete cds (1994).

Oliynuk et al., Chemistry & Biology (1996) 3: 833-839.

PUFA POLYKETIDE SYNTHASE SYSTEMS AND USES THEREOF

CROSS-REFERENCE TO RELATED APPLICATIONS

This application claims the benefit of priority under 35 U.S.C. § 119(e) from U.S. Provisional Application No. 60/784,616, filed Mar. 21, 2006, and from U.S. Provisional Application No. 60/689,167, filed Jun. 10, 2005. This application is also a continuation-in-part of U.S. patent application Ser. No. 10/124,800, filed Apr. 16, 2002 now U.S. Pat. No. 7,247,461, which claims priority under 35 U.S.C. § 119(e) from: U.S. Provisional Application Ser. No. 60/284,066, filed Apr. 16, 2001; U.S. Provisional Application Ser. No. 60/298,796, filed Jun. 15, 2001; and U.S. Provisional Application Ser. No. 60/323,269, filed Sep. 18, 2001. U.S. patent application Ser. No. 10/124,800 is also a continuation-in-part of U.S. application Ser. No. 09/231,899, filed Jan. 14, 1999, now U.S. Pat. No. 6,566,583. Each of the above-identified patent applications is incorporated herein by reference in its entirety.

This application does not claim the benefit of priority from U.S. application Ser. No. 09/090,793, filed Jun. 4, 1998, now U.S. Pat. No. 6,140,486, although U.S. application Ser. No. 09/090,793 is incorporated herein by reference in its entirety.

REFERENCE TO SEQUENCE LISTING

This application contains a Sequence Listing submitted on a compact disc, in duplicate. Each of the two compact discs, which are identical to each other pursuant to 37 CFR § 1.52(e)(4), contains the following file: "Sequence Listing", having a size in bytes of 301 KB, recorded on 12 Jun. 2006. The information contained on the compact disc is hereby incorporated by reference in its entirety pursuant to 37 CFR § 1.77(b)(4).

FIELD OF THE INVENTION

This invention relates to polyunsaturated fatty acid (PUFA) polyketide synthase (PKS) systems from *Schizochytrium*. More particularly, this invention relates to nucleic acids encoding such PUFA PKS systems, to such PUFA PKS systems, to genetically modified organisms comprising such PUFA PKS systems, and to methods of making and using such PUFA PKS systems disclosed herein. This invention also relates to PUFA PKS systems from non-bacterial and bacterial organisms identified using the *Schizochytrium* PUFA PKS systems described herein.

BACKGROUND OF THE INVENTION

Polyketide synthase (PKS) systems are generally known in the art as enzyme complexes related to fatty acid synthase (FAS) systems, but which are often highly modified to produce specialized products that typically show little resemblance to fatty acids. It has now been shown, however, that polyketide synthase systems exist in marine bacteria and certain eukaryotic organisms that are capable of synthesizing polyunsaturated fatty acids (PUFAs) from acetyl-CoA and malonyl-CoA. The PKS pathways for PUFA synthesis in *Shewanella* and another marine bacteria, *Vibrio marinus*, are described in detail in U.S. Pat. No. 6,140,486. The PKS pathways for PUFA synthesis in the eukaryotic Thraustochytrid, *Schizochytrium* is described in detail in U.S. Pat. No. 6,566,583. The PKS pathways for PUFA synthesis in eukaryotes such as members of Thraustochytriales, including the structural description of a PUFA PKS system in *Schizochytrium* and the identification of a PUFA PKS system in *Thraustochytrium*, including details regarding uses of these systems, are described in detail in U.S. Patent Application Publication No. 20020194641, published Dec. 19, 2002 (corresponding to U.S. patent application Ser. No. 10/124,800, filed Apr. 16, 2002). U.S. Patent Application Publication No. 20040235127, published Nov. 25, 2004 (corresponding to U.S. patent application Ser. No. 10/810,352, filed Mar. 24, 2004), discloses the structural description of a PUFA PKS system in *Thraustochytrium*, and further detail regarding the production of eicosapentaenoic acid (C20:5, ω-3) (EPA) and other PUFAs using such systems. U.S. Patent Application Publication No. 20050100995, published May 12, 2005 (corresponding to U.S. patent application Ser. No. 10/965,017, filed Oct. 13, 2004), discloses the structural and functional description of PUFA PKS systems in *Shewanella olleyana* and *Shewanella japonica*, and uses of such systems. These applications also disclose the genetic modification of organisms, including microorganisms and plants, with the genes comprising the PUFA PKS pathway and the production of PUFAs by such organisms. Furthermore, PCT Patent Publication No. WO 05/097982 describes a PUFA PKS system in Ulkenia, U.S. Patent Application Publication No. 20050014231 describes PUFA PKS genes and proteins from *Thraustochytrium aureum*.

Researchers have attempted to exploit polyketide synthase (PKS) systems that have been traditionally described in the literature as falling into one of three basic types, typically referred to as: Type I (modular or iterative), Type II, and Type III. For purposes of clarity, it is noted that the Type I modular PKS system has previously also been referred to as simply a "modular" PKS system, and the Type I iterative PKS system has previously also been referred to simply as a "Type I" PKS system. The Type II system is characterized by separable proteins, each of which carries out a distinct enzymatic reaction. The enzymes work in concert to produce the end product and each individual enzyme of the system typically participates several times in the production of the end product. This type of system operates in a manner analogous to the fatty acid synthase (FAS) systems found in plants and bacteria. Type I iterative PKS systems are similar to the Type II system in that the enzymes are used in an iterative fashion to produce the end product. The Type I iterative differs from Type II in that enzymatic activities, instead of being associated with separable proteins, occur as domains of larger proteins. This system is analogous to the Type I FAS systems found in animals and fungi.

In contrast to the Type II systems, in Type I modular PKS systems, each enzyme domain is used only once in the production of the end product. The domains are found in very large proteins and the product of each reaction is passed on to another domain in the PKS protein. Additionally, in the PKS systems described above, if a carbon-carbon double bond is incorporated into the end product, it is usually in the trans configuration.

Type III systems have been more recently discovered and belong to the plant chalcone synthase family of condensing enzymes. Type III PKSs are distinct from type I and type II PKS systems and utilize free CoA substrates in iterative condensation reactions to usually produce a heterocyclic end product.

Polyunsaturated fatty acids (PUFAs) are considered to be useful for nutritional, pharmaceutical, industrial, and other purposes. The current supply of PUFAs from natural sources and from chemical synthesis is not sufficient for commercial needs. A major current source for PUFAs is from marine fish; however, fish stocks are declining, and this may not be a sustainable resource. Additionally, contamination, from both heavy metals and toxic organic molecules, is a serious issue with oil derived from marine fish. Vegetable oils derived from oil seed crops are relatively inexpensive and do not have the contamination issues associated with fish oils. However, the PUFAs found in commercially developed plant oils are typically limited to linoleic acid (eighteen carbons with 2 double bonds, in the delta 9 and 12 positions—18:2 delta 9,12) and linolenic acid (18:3 delta 9,12, 15). In the conventional pathway (i.e., the "standard" pathway or "classical" pathway) for PUFA synthesis, medium chain-length saturated fatty acids (products of a fatty acid synthase (FAS) system) are modified by a series of elongation and desaturation reactions. The substrates for the elongation reaction are fatty acyl-CoA (the fatty acid chain to be elongated) and malonyl-CoA (the source of the 2 carbons added during each elongation reaction). The product of the elongase reaction is a fatty acyl-CoA that has two additional carbons in the linear chain. The desaturases create cis double bonds in the preexisting fatty acid chain by extraction of 2 hydrogens in an oxygen-dependant reaction. The substrates for the desaturases are either acyl-CoA (in some animals) or the fatty acid that is esterified to the glycerol backbone of a phospholipid (e.g. phosphatidylcholine).

Therefore, because a number of separate desaturase and elongase enzymes are required for fatty acid synthesis from linoleic and linolenic acids to produce the more unsaturated and longer chain PUFAs, engineering plant host cells for the expression of PUFAs such as EPA and docosahexaenoic acid (DHA) may require expression of several separate enzymes to achieve synthesis. Additionally, for production of useable quantities of such PUFAs, additional engineering efforts may be required. Therefore, it is of interest to obtain genetic material involved in PUFA biosynthesis from species that naturally produce these fatty acids (e.g., from a PUFA PKS system) and to express the isolated material alone or in combination in a heterologous system which can be manipulated to allow production of commercial quantities of PUFAs.

There have been many efforts to produce PUFAs in oil-seed crop plants by modification of the endogenously-produced fatty acids. Genetic modification of these plants with various individual genes for fatty acid elongases and desaturases has produced leaves or seeds containing measurable levels of PUFAs such as EPA, but also containing significant levels of mixed shorter-chain and less unsaturated PUFAs (Qi et al., *Nature Biotech.* 22:739 (2004); PCT Publication No. WO 04/071467; Abbadi et al., *Plant Cell* 16:1 (2004)); Napier and Sayanova, Proceedings of the Nutrition Society (2005), 64:387-393; Robert et al., Functional Plant Biology (2005) 32:473-479; or U.S. Patent Application Publication 2004/0172682.

Improvement in both microbial and plant production of PUFAs is a highly desirable commercial goal. Therefore, there remains a need in the art for a method to efficiently and effectively produce quantities of lipids (e.g., triacylglycerol (TAG) and phospholipid (PL)) enriched in desired PUFAs, particularly in commercially useful organisms such as microorganisms and oil-seed plants.

SUMMARY OF THE INVENTION

One embodiment of the present invention relates to an isolated nucleic acid molecule comprising a nucleic acid sequence selected from: (a) a nucleic acid sequence selected from: SEQ ID NO:1, SEQ ID NO:3, and SEQ ID NO:5; (b) a nucleic acid sequence encoding an amino acid sequence selected from: SEQ ID NO:2, SEQ ID NO:4 and SEQ ID NO:6; (c) a nucleic acid sequence encoding an amino acid sequence that is at least 90% identical to SEQ ID NO:2 or that is a fragment of SEQ ID NO:2, wherein said amino acid sequence has β-keto acyl-ACP synthase (KS) activity, malonyl-CoA:ACP acyltransferase (MAT) activity, acyl carrier protein (ACP) activity and ketoreductase (KR) activity, and wherein said amino acid sequence comprises an aspartate at a position corresponding to amino acid 667 of SEQ ID NO:2 and a histidine at a position corresponding to amino acid 668 of SEQ ID NO:2; (d) a nucleic acid sequence encoding an amino acid sequence that is at least 90% identical to SEQ ID NO:4 or that is a fragment of SEQ ID NO:4, wherein said amino acid sequence has KS activity, chain length factor (CLF) activity, acyl transferase (AT) activity, and enoyl ACP-reductase (ER) activity, and wherein said amino acid sequence comprises a valine at a position corresponding to amino acid 371 of SEQ ID NO:4 and a glutamate at a position corresponding to amino acid 1415 of SEQ ID NO:4; and (e) a nucleic acid sequence encoding an amino acid sequence that is at least 90% identical to SEQ ID NO:6 or that is a fragment of SEQ ID NO:6, wherein said amino acid sequence has FabA-like β-hydroxy acyl-ACP dehydrase (DH) activity and ER activity, and wherein said amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

In one aspect, the nucleic acid molecule comprising a nucleic acid sequence selected from: (a) a nucleic acid sequence encoding an amino acid sequence that is at least 95% identical to SEQ ID NO:2 or that is a fragment of SEQ ID NO:2, wherein said amino acid sequence has β-keto acyl-ACP synthase (KS) activity, malonyl-CoA:ACP acyltransferase (MAT) activity, acyl carrier protein (ACP) activity and ketoreductase (KR) activity, and wherein said amino acid sequence comprises an aspartate at a position corresponding to amino acid 667 of SEQ ID NO:2 and a histidine at a position corresponding to amino acid 668 of SEQ ID NO:2; (b) a nucleic acid sequence encoding an amino acid sequence that is at least 95% identical to SEQ ID NO:4 or that is a fragment of SEQ ID NO:4, wherein said amino acid sequence has KS activity, chain length factor (CLF) activity, acyl transferase (AT) activity, and enoyl ACP-reductase (ER) activity, and wherein said amino acid sequence comprises a valine at a position corresponding to amino acid 371 of SEQ ID NO:4 and a glutamate at a position corresponding to amino acid 1415 of SEQ ID NO:4; and (c) a nucleic acid sequence encoding an amino acid sequence that is at least 95% identical to SEQ ID NO:6 or that is a fragment of SEQ ID NO:6, wherein said amino acid sequence has FabA-like β-hydroxy acyl-ACP dehydrase (DH) activity and ER activity, and wherein said amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

In one aspect, the nucleic acid molecule comprises a nucleic acid sequence encoding an amino acid sequence selected from SEQ ID NO:2, SEQ ID NO:4 and SEQ ID NO:6. In another aspect, the nucleic acid molecule comprises a nucleic acid sequence selected from: SEQ ID NO:1, SEQ ID NO:3, and SEQ ID NO:5.

In one aspect of this embodiment, the nucleic acid molecule of (a) comprises a nucleic acid sequence encoding the amino acid sequence encoded by a plasmid selected from: pKJ1126 (ATCC Accession No. PTA-7648), pJK306 (ATCC Accession No. PTA-7641), and pJK320 (ATCC Accession No. PTA-7644). In one aspect of this embodiment, the nucleic acid molecule of (b) comprises a nucleic acid sequence encoding the amino acid sequence encoded by a plasmid selected from: pJK1129 (ATCC Accession No. PTA-7649), and pJK324 (ATCC Accession No. PTA-7643). In another aspect of this embodiment, the nucleic acid molecule of (c) comprises a nucleic acid sequence encoding the amino acid sequence encoded by a plasmid selected from: pJK1131 (ATCC Accession No. PTA-7650) and pBR002 (ATCC Accession No. PTA-7642).

Another embodiment of the present invention relates to an isolated nucleic acid molecule comprising a nucleic acid sequence selected from: (a) a first nucleic acid sequence encoding a first amino acid sequence that has β-keto acyl-ACP synthase (KS) activity, malonyl-CoA:ACP acyltransferase (MAT) activity, acyl carrier protein (ACP) activity and ketoreductase (KR) activity, wherein the first nucleic acid sequence hybridizes under very high stringency conditions to the complement of a second nucleic acid sequence encoding a second amino acid sequence of SEQ ID NO:2, and wherein said first amino acid sequence comprises an aspartate at a position corresponding to amino acid 667 of SEQ ID NO:2 and a histidine at a position corresponding to amino acid 668 of SEQ ID NO:2; (b) a first nucleic acid sequence encoding a first amino acid sequence that has KS activity, chain length factor (CLF) activity, acyl transferase (AT) activity, and enoyl ACP-reductase (ER) activity, wherein the first nucleic acid sequence hybridizes under very high stringency conditions to the complement of a second nucleic acid sequence encoding a second amino acid sequence of SEQ ID NO:4, and wherein said first amino acid sequence comprises a valine at a position corresponding to amino acid 371 of SEQ ID NO:4 and a glutamate at a position corresponding to amino acid 1415 of SEQ ID NO:4; and (c) a first nucleic acid sequence encoding a first amino acid sequence that has FabA-like β-hydroxy acyl-ACP dehydrase (DH) activity and ER activity, wherein the first nucleic acid sequence hybridizes under very high stringency conditions to the complement of a second nucleic acid sequence encoding a second amino acid sequence of SEQ ID NO:6, and wherein said first amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6. In one aspect of this embodiment, the first nucleic acid sequence is isolated from a *Schizochytrium*, such as, but not limited to, *Schizochytrium* ATCC 20888.

Yet another embodiment of the present invention relates to an isolated nucleic acid molecule comprising a nucleic acid sequence selected from: (a) a nucleic acid sequence of SEQ ID NO:9; (b) a nucleic acid sequence encoding an amino acid sequence of SEQ ID NO:10; and (c) a nucleic acid sequence encoding an amino acid sequence that is at least 90% identical to SEQ ID NO:10 or that is a fragment of SEQ ID NO:10, wherein the amino acid sequence has malonyl-CoA:ACP acyltransferase (MAT) activity, and wherein said amino acid sequence comprises an aspartate at a position corresponding to amino acid 93 of SEQ ID NO:10 and a histidine at a position corresponding to amino acid 94 of SEQ ID NO:10. In one aspect of this embodiment, the nucleic acid molecule comprises a nucleic acid sequence encoding an amino acid sequence that is at least 95% identical to SEQ ID NO:10 or that is a fragment of SEQ ID NO:10, wherein the amino acid sequence has malonyl-CoA:ACP acyltransferase (MAT) activity, and wherein said amino acid sequence comprises an aspartate at a position corresponding to amino acid 93 of SEQ ID NO:10 and a histidine at a position corresponding to amino acid 94 of SEQ ID NO:10. In one aspect, the nucleic acid molecule comprises a nucleic acid sequence encoding an amino acid sequence of SEQ ID NO:10.

Another embodiment of the present invention relates to an isolated nucleic acid molecule comprising a nucleic acid sequence selected from: (a) a nucleic acid sequence of SEQ ID NO:19; (b) a nucleic acid sequence encoding an amino acid sequence of SEQ ID NO:20; and (c) a nucleic acid sequence encoding an amino acid sequence that is at least 90% identical to SEQ ID NO:20 or that is a fragment of SEQ ID NO:20, wherein the amino acid sequence has β-keto acyl-ACP synthase (KS) activity, and wherein said amino acid sequence comprises a valine at a position corresponding to amino acid 371 of SEQ ID NO:20. In one aspect of this embodiment, the nucleic acid molecule comprises a nucleic acid sequence encoding an amino acid sequence that is at least 95% identical to SEQ ID NO:20 or that is a fragment of SEQ ID NO:20, wherein the amino acid sequence has β-keto acyl-ACP synthase (KS) activity, and wherein said amino acid sequence comprises a valine at a position corresponding to amino acid 371 of SEQ ID NO:20. In one aspect, the nucleic acid molecule comprises a nucleic acid sequence encoding an amino acid sequence of SEQ ID NO:20.

Yet another embodiment of the present invention relates to an isolated nucleic acid molecule comprising a nucleic acid sequence selected from: (a) a nucleic acid sequence of SEQ ID NO:29; (b) a nucleic acid sequence encoding an amino acid sequence of SEQ ID NO:30; and (c) a nucleic acid sequence encoding an amino acid sequence that is at least 90% identical to SEQ ID NO:30 or that is a fragment of SEQ ID NO:30, wherein the amino acid sequence has FabA-like β-hydroxy acyl-ACP dehydrase (DH) activity, and wherein said amino acid sequence comprises the sequence of H-G-I-A-N-P-T-F-V-H-A-P-G-K-I (positions 876-890 of SEQ ID NO:6) at positions corresponding to amino acids 426-440 of SEQ ID NO:30. In one aspect, the nucleic acid molecule comprises a nucleic acid sequence encoding an amino acid sequence that is at least 95% identical to SEQ ID NO:30 or that is a fragment of SEQ ID NO:30, wherein the amino acid sequence has FabA-like β-hydroxy acyl-ACP dehydrase (DH) activity, and wherein said amino acid sequence comprises the sequence of H-G-I-A-N-P-T-F-V-H-A-P-G-K-I (positions 876-890 of SEQ ID NO:6) at positions corresponding to amino acids 426-440 of SEQ ID NO:30. In one aspect, the nucleic acid molecule comprises a nucleic acid sequence encoding an amino acid sequence of SEQ ID NO:30.

Another embodiment of the invention relates to a recombinant nucleic acid molecule comprising any of the nucleic acid molecules described above, operatively linked to at least one transcription control sequence.

Yet another embodiment of the invention relates to a recombinant cell transfected with any of the nucleic acid molecules described above. In one aspect, the recombinant cell is a microorganism. In another aspect, the recombinant cell is a plant cell.

Another embodiment of the present invention relates to an isolated nucleic acid molecule consisting essentially of a nucleic acid sequence that is fully complementary to any of the nucleic acid molecules described above.

Another embodiment of the present invention relates to a genetically modified microorganism that has been transformed with any of the nucleic acid molecules described above.

Yet another embodiment of the present invention relates to a genetically modified plant that has been transformed with any of the nucleic acid molecules described above.

Another embodiment of the present invention relates to a genetically modified microorganism that has been transformed with: (a) a nucleic acid molecule comprising a nucleic acid sequence encoding an amino acid sequence that is at least 90% identical to SEQ ID NO:2 or that is a fragment of SEQ ID NO:2, wherein said amino acid sequence has β-keto acyl-ACP synthase (KS) activity, malonyl-CoA:ACP acyltransferase (MAT) activity, acyl carrier protein (ACP) activity and ketoreductase (KR) activity, and wherein said amino acid sequence comprises an aspartate at a position corresponding to amino acid 667 of SEQ ID NO:2 and a histidine at a position corresponding to amino acid 668 of SEQ ID NO:2; (b) a nucleic acid molecule comprising a nucleic acid sequence encoding an amino acid sequence that is at least 90% identical to SEQ ID NO:4 or that is a fragment of SEQ ID NO:4, wherein said amino acid sequence has KS activity, chain length factor (CLF) activity, acyl transferase (AT) activity, and enoyl ACP-reductase (ER) activity, and wherein said amino acid sequence comprises a valine at a position corresponding to amino acid 371 of SEQ ID NO:4 and a glutamate at a position corresponding to amino acid 1415 of SEQ ID NO:4; and (c) a nucleic acid molecule comprising a nucleic acid sequence encoding an amino acid sequence that is at least 90% identical to SEQ ID NO:6 or that is a fragment of SEQ ID NO:6, wherein said amino acid sequence has FabA-like β-hydroxy acyl-ACP dehydrase (DH) activity and ER activity, and wherein said amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6. In one aspect, the microorganism has been transformed with a nucleic acid molecule comprising a nucleic acid sequence encoding SEQ ID NO:2, a nucleic acid molecule comprising a nucleic acid sequence encoding SEQ ID NO:4, and a nucleic acid molecule comprising a nucleic acid sequence encoding SEQ ID NO:6. In one aspect, the microorganism endogenously expresses a PUFA PKS system. In another aspect, the microorganism has been further transformed with a recombinant nucleic acid molecule encoding a phosphopantetheine transferase. The microorganism can include, but is not limited to, a Thraustochytriales microorganism, a bacterium or a yeast.

Yet another embodiment of the present invention relates to a method to produce a bioactive molecule, comprising culturing under conditions effective to produce said bioactive molecule a genetically modified organism described above. In one aspect, the bioactive molecule is a polyunsaturated fatty acid (PUFA).

Another embodiment of the present invention relates to a genetically modified plant or part of the plant, wherein said plant has been transformed with: (a) a nucleic acid molecule comprising a nucleic acid sequence encoding an amino acid sequence that is at least 90% identical to SEQ ID NO:2 or that is a fragment of SEQ ID NO:2, wherein said amino acid sequence has β-keto acyl-ACP synthase (KS) activity, malonyl-CoA:ACP acyltransferase (MAT) activity, acyl carrier protein (ACP) activity and ketoreductase (KR) activity, and wherein said amino acid sequence comprises an aspartate at a position corresponding to amino acid 667 of SEQ ID NO:2 and a histidine at a position corresponding to amino acid 668 of SEQ ID NO:2; (b) a nucleic acid molecule comprising a nucleic acid sequence encoding an amino acid sequence that is at least 90% identical to SEQ ID NO:4 or that is a fragment of SEQ ID NO:4, wherein said amino acid sequence has KS activity, chain length factor (CLF) activity, acyl transferase (AT) activity, and enoyl ACP-reductase (ER) activity, and wherein said amino acid sequence comprises a valine at a position corresponding to amino acid 371 of SEQ ID NO:4 and a glutamate at a position corresponding to amino acid 1415 of SEQ ID NO:4; and (c) a nucleic acid molecule comprising a nucleic acid sequence encoding an amino acid sequence that is at least 90% identical to SEQ ID NO:6 or that is a fragment of SEQ ID NO:6, wherein said amino acid sequence has FabA-like β-hydroxy acyl-ACP dehydrase (DH) activity and ER activity, and wherein said amino acid sequence comprises the sequence of H-G-I-A-N-P-T-F-V-H-A-P-G-K—I (positions 876-890 of SEQ ID NO:6) at positions corresponding to amino acids 876-890 of SEQ ID NO:6. In one aspect, the plant has been further genetically modified to express a recombinant nucleic acid molecule encoding a phosphopantetheine transferase. In one aspect, the plant is a dicotyledonous plant, and in another aspect, the plant is a monocotyledonous plant. In another aspect, the plant is selected from: canola, soybean, rapeseed, linseed, corn, safflower, sunflower and tobacco.

In one aspect, the plant is an oilseed plant and the part of the plant is a mature oilseed. In one aspect, the total fatty acid profile in the plant or part of the plant comprises at least about 0.5% by weight of at least one PUFA selected from DHA (docosahexaenoic acid (C22:6, n-3)) and DPA (docosapentaenoic acid (C22:5, n-6), and wherein the total fatty acids produced as a result of transformation with said nucleic acid molecules, other than said at least one PUFA, comprise less than about 10% of the total fatty acids produced by said plant. In one aspect, the total fatty acids produced as a result of transformation with said nucleic acid molecules, other than said at least one PUFA, comprise less than 5% by weight of the total fatty acids produced by said plant. In another aspect, the fatty acids consisting of gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds, comprise less than 5% by weight of the total fatty acids produced by said plant. In another aspect, gamma-linolenic acid (GLA; 18:3, n-6) comprises less than 1% by weight of the total fatty acids produced by said plant.

Yet another embodiment of the present invention relates to a plant or a part of the plant, wherein the total fatty acid profile in the plant or part of the plant comprises detectable amounts of DHA (docosahexaenoic acid (C22:6, n-3)) and DPA (docosapentaenoic acid (C22:5, n-6), wherein the ratio of DPAn-6 to DHA is 1:1 or greater than 1:1.

Another embodiment of the present invention relates to a plant or a part of the plant, wherein the total fatty acid profile in the plant or part of the plant comprises detectable amounts of DHA (docosahexaenoic acid (C22:6, n-3)) and DPA (docosapentaenoic acid (C22:5, n-6), wherein the ratio of DPAn-6 to DHA is less than 1:1. In either of the two embodiments above, in one aspect, the total fatty acid profile in the plant or part of the plant contains less than 5% by weight in total of all of the following PUFAs: gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds.

Yet another embodiment of the present invention relates to plant or a part of the plant, wherein the total fatty acid profile in the plant or part of the plant comprises at least about 0.5% by weight of at least one polyunsaturated fatty acid (PUFA) selected from DHA (C22:6n-3) and DPAn-6 (C22:5n-6), and wherein the total fatty acid profile in the plant or part of the plant contains less than 5% in total of all of the following PUFAs: gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds.

Another embodiment of the present invention relates to a plant or a part of the plant, wherein the total fatty acid profile in the plant or part of the plant comprises at least about 0.5% by weight of at least one polyunsaturated fatty acid (PUFA) selected from DHA (C22:6n-3) and DPAn-6 (C22:5n-6), and wherein the total fatty acid profile in the plant or part of the plant contains less than 1% of each of the following PUFAs: gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds.

Another embodiment of the present invention relates to a plant or a part of the plant, wherein the total fatty acid profile in the plant or part of the plant comprises at least about 0.5% by weight of at least one polyunsaturated fatty acid (PUFA) selected from DHA (C22:6n-3) and DPAn-6 (C22:5n-6), and wherein the total fatty acid profile in the plant or part of the plant contains less than 2% of gamma-linolenic acid (GLA; 18:3, n-6) and dihomo-gamma-linolenic acid (DGLA or HGLA; 20:3, n-6).

Another embodiment of the present invention relates to seeds obtained from any of the plants or part of plants described above, a food product comprising such seeds, an oil obtained from such seeds, and a food product comprising such oil. Also included in the invention is an oil blend comprising such oil and another oil, such as, but not limited to, a microbial oil, a fish oil, and a vegetable oil.

Yet another embodiment of the present invention relates to an oil comprising the following fatty acids: DHA (C22:6n-3), DPAn-6 (C22:5n-6), oleic acid (C18:1), linolenic acid (C18:3), linoleic acid (C18:2), C16:0, C18.0, C20:0, C20:1n-9, C20:2n-6, C22:1n-9; wherein the oil comprises less than 0.5% of any of the following fatty acids: gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds.

Another embodiment of the present invention relates to an oilseed plant that produces mature seeds in which the total seed fatty acid profile comprises at least 1.0% by weight of at least one polyunsaturated fatty acid selected from DHA (C22:6n-3) and DPAn-6 (C22:5n-6), and wherein the total fatty acid profile in the plant or part of the plant contains less than 5% in total of all of the following PUFAs: gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds.

Yet another embodiment of the present invention relates to an oilseed plant that produces mature seeds in which the total seed fatty acid profile comprises at least 1.0% by weight of at least one polyunsaturated fatty acid (PUFA) selected from DHA (C22:6n-3) and DPAn-6 (C22:5n-6), and wherein the total fatty acid profile in the plant or part of the plant contains less than 1% of gamma-linolenic acid (GLA; 18:3, n-6).

Another embodiment of the present invention relates to a method to produce a bioactive molecule, comprising growing under conditions effective to produce said bioactive molecule a genetically modified plant as described above. In one aspect, the bioactive molecule is a polyunsaturated fatty acid (PUFA).

Yet another embodiment of the present invention relates to a method to produce a plant that has a polyunsaturated fatty acid (PUFA) profile that differs from the naturally occurring plant, comprising genetically modifying said plant to express a PUFA PKS system comprising at least one of any of the nucleic acid molecules as described above.

Another embodiment of the present invention relates to a method to produce a recombinant microbe, comprising genetically modifying microbial cells to express at least one of any of the nucleic acid molecules as described above.

DETAILED DESCRIPTION OF THE INVENTION

Figure 1:
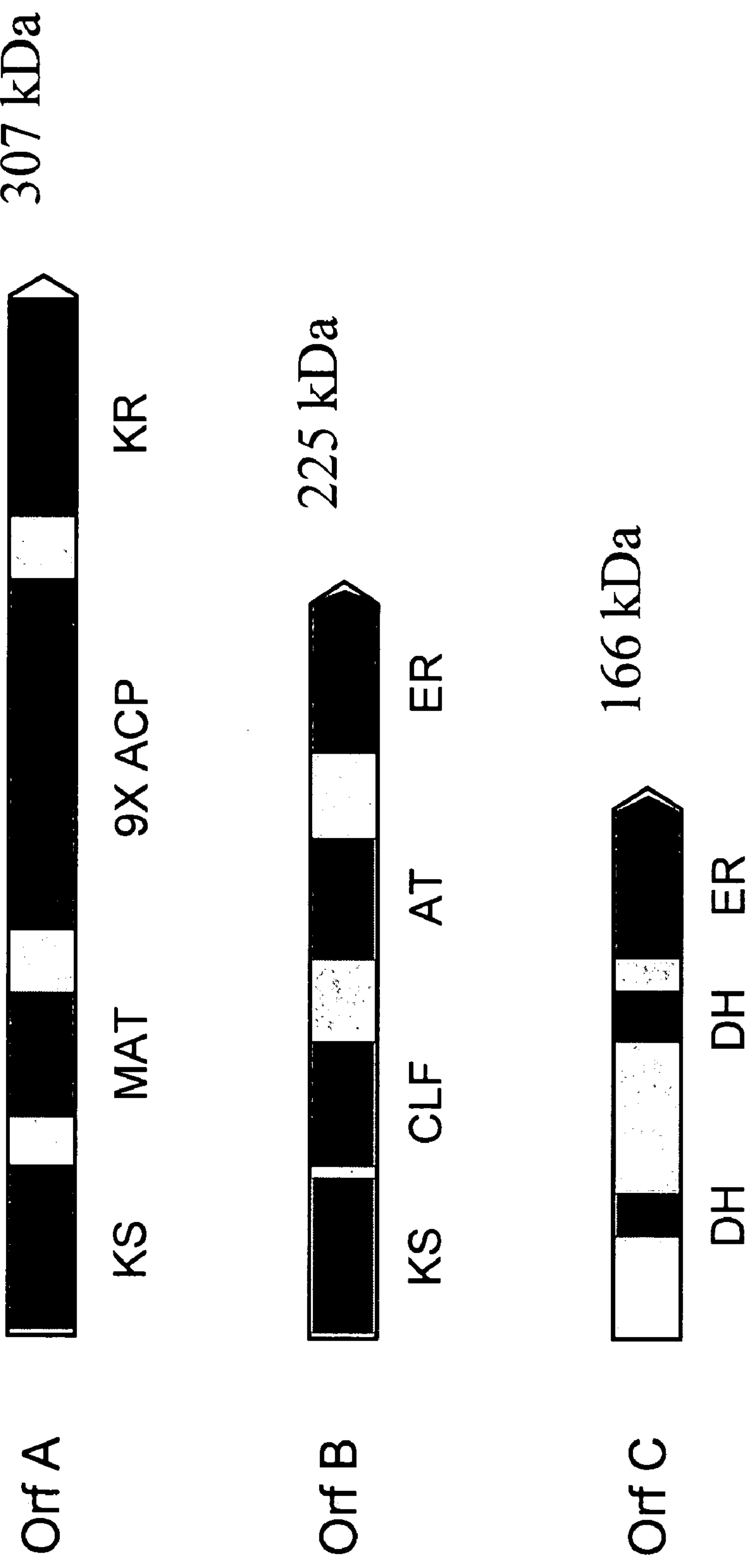
FIG. 1 is a graphical representation of the domain structure of the *Schizochytrium* PUFA PKS system.

The present invention generally relates to polyunsaturated fatty acid (PUFA) polyketide synthase (PKS) systems from *Schizochytrium*, to genetically modified organisms comprising *Schizochytrium* PUFA PKS systems, to methods of making and using such systems for the production of products of interest, including bioactive molecules, and to PUFA PKS systems identified using the structural information for the *Schizochytrium* PUFA PKS systems disclosed herein. In one preferred embodiment, the present invention relates to a method to produce PUFAs in an oil-seed plant that has been genetically modified to express a PUFA PKS system of the present invention. The oils produced by the plant contain at least one PUFA produced by the PUFA PKS system and are substantially free of the mixed shorter-chain and less unsaturated PUFAs that are fatty acid products produced by the modification of products of the FAS system.

As used herein, a PUFA PKS system (which may also be referred to as a PUFA synthase system or PUFA synthase) generally has the following identifying features: (1) it produces PUFAs, and particularly, long chain PUFAs, as a natural product of the system; and (2) it comprises several multifunctional proteins assembled into a complex that conducts both iterative processing of the fatty acid chain as well non-iterative processing, including trans-cis isomerization and enoyl reduction reactions in selected cycles. In addition, the ACP domains present in the PUFA synthase enzymes require activation by attachment of a cofactor (4-phosphopantetheine). Attachment of this cofactor is carried out by phosphopantetheinyl transferases (PPTase). If the endogenous PPTases of the host organism are incapable of activating the PUFA synthase ACP domains, then it is necessary to provide a PPTase that is capable of carrying out that function. The inventors have identified the Het I enzyme of *Nostoc* sp. as an exemplary and suitable PPTase for activating PUFA synthase ACP domains. Reference to a PUFA PKS system or a PUFA synthase refers collectively to all of the genes and their encoded products that work in a complex to produce PUFAs in an organism. Therefore, the PUFA PKS system refers specifically to a PKS system for which the natural products are PUFAs.

More specifically, first, a PUFA PKS system that forms the basis of this invention produces polyunsaturated fatty acids (PUFAs) and particularly, long chain PUFAs, as products (e.g., an organism that endogenously (naturally) contains such a PKS system makes PUFAs using this system). According to the present invention, PUFAs are fatty acids with a carbon chain length of at least 16 carbons, and more preferably at least 18 carbons, and more preferably at least 20 carbons, and more preferably 22 or more carbons, with at least 3 or more double bonds, and preferably 4 or more, and more preferably 5 or more, and even more preferably 6 or more double bonds, wherein all double bonds are in the cis configuration. Reference to long chain polyunsaturated fatty acids (LCPUFAs) herein more particularly refers to fatty acids of 18 and more carbon chain length, and preferably 20 and more carbon chain length, containing 3 or more double bonds. LCPUFAs of the omega-6 series include: gamma-linolenic acid (C18:3), di-homo-gammalinolenic acid (C20:3n-6), arachidonic acid (C20:4n-6), adrenic acid (also called docosatetraenoic acid or DTA) (C22:4n-6), and docosapentaenoic acid (C22:5n-6). The LCPUFAs of the omega-3 series include: alpha-linolenic acid (C18:3), eicosatrienoic acid (C20:3n-3), eicosatetraenoic acid (C20:4n-3), eicosapentaenoic acid (C20:5n-3), docosapentaenoic acid (C22:5n-3), and docosahexaenoic acid (C22:6n-3). The LCPUFAs also include fatty acids with greater than 22 carbons and 4 or more double bonds including but not limited to C28:8(n-3).

Second, a PUFA PKS system according to the present invention comprises several multifunctional proteins (and can include single function proteins, particularly for PUFA PKS systems from marine bacteria) that are assembled into a complex that conducts both iterative processing of the fatty acid chain as well non-iterative processing, including trans-cis isomerization and enoyl reduction reactions in selected cycles. These proteins can also be referred to herein as the core PUFA PKS enzyme complex or the core PUFA PKS system. The general functions of the domains and motifs contained within these proteins are individually known in the art and have been described in detail with regard to various PUFA PKS systems from marine bacteria and eukaryotic organisms (see, e.g., U.S. Pat. No. 6,140,486; U.S. Pat. No. 6,566,583; Metz et al., *Science* 293:290-293 (2001); U.S. Patent Application Publication No. 20020194641; U.S. Patent Application Publication No. 20040235127; and U.S. Patent Application Publication No. 20050100995). The domains may be found as a single protein (i.e., the domain and protein are synonymous) or as one of two or more (multiple) domains in a single protein, as mentioned above.

Before the discovery of a PUFA PKS system in marine bacteria (see U.S. Pat. No. 6,140,486), PKS systems were not known to possess this combination of iterative and selective enzymatic reactions, and they were not thought of as being able to produce carbon-carbon double bonds in the cis configuration. However, the PUFA PKS system described by the present invention has the capacity to introduce cis double bonds and the capacity to vary the reaction sequence in the cycle.

The present inventors propose to use these features of the PUFA PKS system to produce a range of bioactive molecules that could not be produced by the previously described (Type I iterative or modular, Type II, or Type III) PKS systems. These bioactive molecules include, but are not limited to, polyunsaturated fatty acids (PUFAs), antibiotics or other bioactive compounds, many of which will be discussed below. For example, using the knowledge of the PUFA PKS gene structures described herein, any of a number of methods can be used to alter the PUFA PKS genes, or combine portions of these genes with other synthesis systems, including other PKS systems, such that new products are produced. The inherent ability of this particular type of system to do both iterative and selective reactions will enable this system to yield products that would not be found if similar methods were applied to other types of PKS systems.

Preferably, a PUFA PKS system of the present invention comprises at least the following biologically active domains that are typically contained on three or more proteins: (a) at least one enoyl-ACP reductase (ER) domain; (b) multiple acyl carrier protein (ACP) domain(s) (e.g., at least from one to four, and preferably at least five ACP domains, and in some embodiments up to six, seven, eight, nine, or more than nine ACP domains); (c) at least two β-ketoacyl-ACP synthase (KS) domains; (d) at least one acyltransferase (AT) domain; (e) at least one β-ketoacyl-ACP reductase (KR) domain; (f) at least two FabA-like β-hydroxyacyl-ACP dehydrase (DH) domains; (g) at least one chain length factor (CLF) domain; (h) at least one malonyl-CoA:ACP acyltransferase (MAT) domain. In one embodiment, a PUFA PKS system according to the present invention also comprises at least one region containing a dehydratase (DH) conserved active site motif.

In a preferred embodiment, a *Schizochytrium* PUFA PKS system comprises at least the following biologically active domains: (a) two enoyl-ACP reductase (ER) domain; (b) nine acyl carrier protein (ACP) domains; (c) two β-ketoacyl-ACP synthase (KS) domains; (d) one acyltransferase (AT) domain; (e) one β-ketoacyl-ACP reductase (KR) domain; (f) two FabA-like β-hydroxyacyl-ACP dehydrase (DH) domains; (g) one chain length factor (CLF) domain; and (h) one malonyl-CoA:ACP acyltransferase (MAT) domain. In one embodiment, a *Schizochytrium* PUFA PKS system according to the present invention also comprises at least one region or domain containing a dehydratase (DH) conserved active site motif that is not a part of a FabA-like DH domain. The structural and functional characteristics of these domains are generally individually known in the art and will be described in detail below with regard to the PUFA PKS systems of the present invention.

A PUFA PKS system can additionally include one or more accessory proteins, which are defined herein as proteins that are not considered to be part of the core PUFA PKS system as described above (i.e., not part of the PUFA synthase enzyme complex itself), but which may be, or are, necessary for PUFA production or at least for efficient PUFA production using the core PUFA synthase enzyme complex of the present invention, particularly in certain host organisms (e.g., plants). For example, in order to produce PUFAs, a PUFA PKS system must work with an accessory protein that transfers a 4'-phosphopantetheinyl moiety from Coenzyme A to the acyl carrier protein (ACP) domain(s). Therefore, a PUFA PKS system can be considered to include at least one 4'-phosphopantetheinyl transferase (PPTase) domain, or such a domain can be considered to be an accessory domain or protein to the PUFA PKS system. When genetically modifying organisms (e.g., microorganisms or plants) to express a PUFA PKS system according to the present invention, some host organisms may endogenously express accessory proteins that are needed to work with the PUFA PKS to produce PUFAs (e.g., PPTases). However, some organisms may be transformed with nucleic acid molecules encoding one or more accessory proteins described herein to enable and/or to enhance production of PUFAs by the organism, even if the organism endogenously produces a homologous accessory protein (i.e., some heterologous accessory proteins may operate more effectively or efficiently with the transformed PUFA synthase proteins than the host cells' endogenous accessory protein). The present invention provides an example of bacteria, yeast and plants that have been genetically modified with the PUFA PKS system of the present invention that includes an accessory PPTase. Structural and functional characteristics of PPTases will be described in more detail below.

According to the present invention, reference to a "standard" or "classical" pathway for the production of PUFAs refers to the fatty acid synthesis pathway where medium chain-length saturated fatty acids (products of a fatty acid synthase (FAS) system) are modified by a series of elongation and desaturation reactions. The substrates for the elongation reaction are fatty acyl-CoA (the fatty acid chain to be elongated) and malonyl-CoA (the source of the 2 carbons added during each elongation reaction). The product of the elongase reaction is a fatty acyl-CoA that has two additional carbons in the linear chain. The desaturases create cis double bonds in the preexisting fatty acid chain by extraction of 2 hydrogens in an oxygen-dependant reaction. Such pathways and the genes involved in such pathways are well-known in the literature.

As used herein, the term "lipid" includes phospholipids (PL); free fatty acids; esters of fatty acids; triacylglycerols (TAG); diacylglycerides; monoacylglycerides; phosphatides; waxes (esters of alcohols and fatty acids); sterols and sterol esters; carotenoids; xanthophylls (e.g., oxycarotenoids); hydrocarbons; and other lipids known to one of ordinary skill in the art. The terms "polyunsaturated fatty acid" and "PUFA" include not only the free fatty acid form, but other forms as well, such as the TAG form and the PL form.

A PUFA PKS system described according to the present invention is a non-bacterial PUFA PKS system. In other words, the PUFA PKS system of the present invention is isolated from an organism that is not a bacteria, or is a homologue of or derived from a PUFA PKS system from an organism that is not a bacteria, such as a eukaryote or an archaebacterium. Eukaryotes are separated from prokaryotes based on the degree of differentiation of the cells, with eukaryotes being more differentiated than prokaryotes. In general, prokaryotes do not possess a nuclear membrane, do not exhibit mitosis during cell division, have only one chromosome, their cytoplasm contains 70S ribosomes, they do not possess any mitochondria, endoplasmic reticulum, chloroplasts, lysosomes or golgi apparatus, their flagella (if present) consists of a single fibril. In contrast, eukaryotes have a nuclear membrane, they do exhibit mitosis during cell division, they have many chromosomes, their cytoplasm contains 80S ribosomes, they do possess mitochondria, endoplasmic reticulum, chloroplasts (in algae), lysosomes and golgi apparatus, and their flagella (if present) consists of many fibrils. In general, bacteria are prokaryotes, while algae, fungi, protist, protozoa and higher plants are eukaryotes. The PUFA PKS systems of the marine bacteria (e.g., Shewanella and Vibrio marinus) are not the basis of the present invention, although the present invention does contemplate the use of domains from these bacterial PUFA PKS systems in conjunction with domains from the non-bacterial (e.g., *Schizochytrium*) PUFA PKS systems of the present invention. For example, according to the present invention, genetically modified organisms can be produced which incorporate non-bacterial PUFA PKS functional domains with bacterial PUFA PKS functional domains, as well as PKS functional domains or proteins from other PKS systems (Type I iterative or modular, Type II, or Type III) or FAS systems.

*Schizochytrium* is a Thraustochytrid marine microorganism that accumulates large quantities of triacylglycerols rich in DHA and docosapentaenoic acid (DPA; 22:5 ω-6); e.g., 30% DHA+DPA by dry weight (Barclay et al., *J. Appl. Phycol.* 6, 123 (1994)). In eukaryotes that synthesize 20- and 22-carbon PUFAs by an elongation/desaturation pathway, the pools of 18-, 20- and 22-carbon intermediates are relatively large so that in vivo labeling experiments using [$^{14}$C]-acetate reveal clear precursor-product kinetics for the predicted intermediates (Gellerman et al., *Biochim. Biophys. Acta* 573:23 (1979)). Furthermore, radiolabeled intermediates provided exogenously to such organisms are converted to the final PUFA products. The present inventors have shown that [1-$^{14}$C]-acetate was rapidly taken up by *Schizochytrium* cells and incorporated into fatty acids, but at the shortest labeling time (1 min), DHA contained 31% of the label recovered in fatty acids, and this percentage remained essentially unchanged during the 10-15 min of [$^{14}$C]-acetate incorporation and the subsequent 24 hours of culture growth (See U.S. Patent Application Publication No. 20020194641, supra). Similarly, DPA represented 10% of the label throughout the experiment. There is no evidence for a precursor-product relationship between 16- or 18-carbon fatty acids and the 22-carbon polyunsaturated fatty acids. These results are consistent with rapid synthesis of DHA from [$^{14}$C]-acetate involving very small (possibly enzyme-bound) pools of intermediates. A cell-free homogenate derived from *Schizochytrium* cultures incorporated [1-$^{14}$C]-malonyl-CoA into DHA, DPA, and saturated fatty acids. The same biosynthetic activities were retained by a 100,000×g supernatant fraction but were not present in the membrane pellet. Thus, DHA and DPA synthesis in *Schizochytrium* does not involve membrane-bound desaturases or fatty acid elongation enzymes like those described for other eukaryotes (Parker-Barnes et al., 2000, supra; Shanklin et al., 1998, supra). These fractionation data contrast with those obtained from the *Shewanella* enzymes (See Metz et al., 2001, supra) and may indicate use of a different (soluble) acyl acceptor molecule, such as CoA, by the *Schizochytrium* enzyme.

Figure 2:
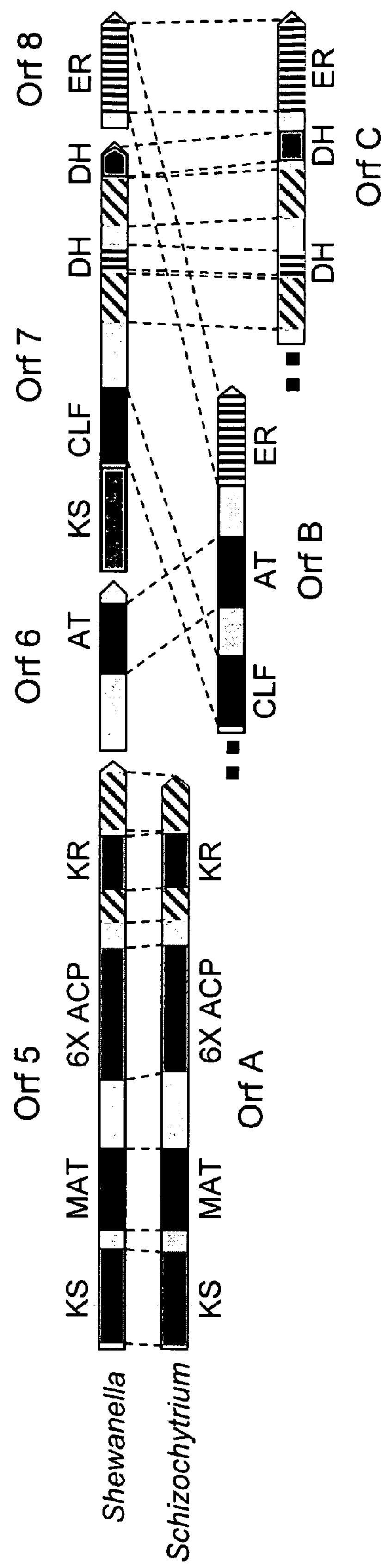
FIG. 2 shows a comparison of PKS domains from *Schizochytrium* and *Shewanella.*

As described in U.S. Pat. No. 6,566,583, a cDNA library from *Schizochytrium* was constructed and approximately 8,000 random clones (ESTs) were sequenced. Within this dataset, only one moderately expressed gene (0.3% of all sequences) was identified as a fatty acid desaturase, although a second putative desaturase was represented by a single clone (0.01%). By contrast, sequences that exhibited homology to 8 of the 11 domains of the *Shewanella* PKS genes shown in FIG. 2 were all identified at frequencies of 0.2-0.5%. In U.S. Pat. No. 6,566,583, several cDNA clones showing homology to the *Shewanella* PKS genes were sequenced, and various clones were assembled into nucleic acid sequences representing two partial open reading frames and one complete open reading frame.

Nucleotides 390-4443 of the cDNA sequence containing the first partial open reading frame described in U.S. application Ser. No. 09/231,899 (denoted therein as SEQ ID NO:69) match nucleotides 4677-8730 (plus the stop codon) of the sequence denoted herein as OrfA (SEQ ID NO:1). A cDNA clone described in U.S. application Ser. No. 09/231,899 as cDNA clone LIB3033-047-B5 comprises at least a portion of nucleotides 4677-8730 of SEQ ID NO:1 described herein, to the best of the present inventors' knowledge. Specifically, the sequence of the insert in cDNA clone LIB3033-047-B5 begins at nucleotide 6719 of SEQ ID NO:1 and extends to the end of the Orf (position 8730 of SEQ ID NO:1), plus about 71 nucleotides beyond the end of the Orf represented by SEQ ID NO:1. cDNA clone LIB3033-047-B5 (denoted cDNA clone LIB3033-047-B5 in the form of an *E. coli* plasmid vector containing "Orf6 homolog" partial gene sequence from *Schizochytrium* sp.) was deposited with the American Type Culture Collection (ATCC), 10801 University Boulevard, Manassas, Va. 20110-2209 USA on Jun. 8, 2006, and assigned ATCC Accession No. PTA-7646. The nucleotide sequence of cDNA clone LIB3033-047-B5, and the amino acid sequence encoded by this cDNA clone are encompassed by the present invention. A second cDNA clone described in U.S. application Ser. No. 09/231,899 as cDNA clone LIB3033-046-E6 shared homology to the ACP domain of ORF6, contained 6 ACP repeats, and comprises at least a portion of nucleotides of SEQ ID NO:1 of the present invention. This cDNA clone did not have a poly-A-tail, and therefore, was a partial cDNA with additional regions of the cDNA found downstream of the sequence. The nucleotide sequence of cDNA clone LIB3033-046-E6, and the amino acid sequence encoded by this cDNA clone are encompassed by the present invention.

Nucleotides 1-4867 of the cDNA sequence containing the second partial open reading frame described in U.S. application Ser. No. 09/231,899 (denoted therein as SEQ ID NO:71) matches nucleotides 1311-6177 (plus the stop codon) of the sequence denoted herein as OrfB (SEQ ID NO:3), with the exception of the nucleotide at position 2933 of SEQ ID NO:71 of the '899 application, which corresponds to the nucleotide at position 4243 of SEQ ID NO:3 set forth herein. This single nucleotide change (C to G) results in a single amino acid change in SEQ ID NO:4 disclosed herein, as compared to SEQ ID NO:72 of the '899 application. Specifically, the glutamine residue at position 978 of SEQ ID NO:72 in the '899 application is changed to a glutamate at position 1415 of SEQ ID NO:4. This amino acid occurs in the linker region between the AT domain and the ER domain of SEQ ID NO:4. A cDNA clone described in U.S. application Ser. No. 09/231,899 as cDNA clone LIB3033-046-D2 comprises nucleotides 1311-6177 of SEQ ID NO:3 described herein, plus about 382 additional nucleotides beyond the end of the Orf represented here as SEQ ID NO:3, to the best of the present inventors' knowledge. cDNA clone LIB3033-046-D2 (denoted cDNA clone LIB3033-046-D2 in the form of an *E. coli* plasmid vector containing "hglC/Orf7/Orf8/Orf9 homolog" gene from *Schizochytrium*) was deposited with the American Type Culture Collection (ATCC), 10801 University Boulevard, Manassas, Va. 20110-2209 USA on Jun. 8, 2006, and assigned ATCC Accession No. PTA-7645. The nucleotide sequence of cDNA clone LIB3033-046-D2, and the amino acid sequence encoded by this cDNA clone are encompassed by the present invention.

Nucleotides 145-4653 of the cDNA sequence containing the complete open reading frame described in U.S. application Ser. No. 09/231,899 (denoted therein as SEQ ID NO:76 and incorrectly designated as a partial open reading frame) matches nucleotides 1-2624 and 2675-4506 of the sequence denoted herein as OrfC (SEQ ID NO:5). Sequencing of the genomic DNA encoding OrfC revealed that there is an additional nucleotide at each of positions 2769, 2806 and 2818 of SEQ ID NO:76 of the '899 application which resulted in a frame shift and a short change in the amino acid sequence of the corresponding protein. Therefore, amino acid positions 924-939 of SEQ ID NO:73 of the '899 application represent an incorrect sequence. Positions 876-890 of SEQ ID NO:5 herein represent the correct amino acid sequence in this region. This sequence is located in the DH2 domain of OrfC (discussed below). A cDNA clone described in U.S. application Ser. No. 09/231,899 as cDNA clone LEB81-042-B9 comprises a portion of the 5' sequence of SEQ ID NO:5. To the best of the present inventors' knowledge, the sequence of the insert in LIB81-042-B9 contains 145 nucleotides upstream of the start codon of SEQ ID NO:5 and extends 2361 nucleotides into the Orf. cDNA clone LIB81-042-B9 (denoted cDNA clone LIB81-042-B9 in the form of an *E. coli* plasmid vector containing "Orf8 homolog" partial gene sequence from *Schizochytrium* sp.) was deposited with the American Type Culture Collection (ATCC), 10801 University Boulevard, Manassas, Va. 20110-2209 USA on Jun. 8, 2006, and assigned ATCC Accession No. PTA-7647. The nucleotide sequence of cDNA clone LIB81-042-B9, and the amino acid sequence encoded by this cDNA clone are encompassed by the present invention. A second cDNA clone described in U.S. application Ser. No. 09/231,899 as cDNA clone LIB81-015-D5 aligns with *Shewanella* ORF8 and also with *Shewanella* ORF9. The open reading frame of LIB81-015-D5 aligns with SEQ ID NO:5 beginning at nucleotide 2526 of SEQ ID NO:5 and extends to the end of the Orf (i.e., position 4506), plus about 115 bp including a poly A tail beyond SEQ ID NO:5. The nucleotide sequence of cDNA clone LIB81-015-D5, and the amino acid sequence encoded by this cDNA clone are encompassed by the present invention.

Further sequencing of cDNA and genomic clones by the present inventors allowed the identification of the full-length genomic sequence of each of OrfA, OrfB and OrfC in *Schizochytrium*, including in *Schizochytrium* sp. ATCC 20888 and the mutated daughter strain of ATCC 20888, denoted *Schizochytrium* sp., strain N230D. N230D was one of more than 1,000 randomly-chosen survivors of chemically mutagenised (NTG; 1-methyl-3-nitro-1-nitrosoguanidine) *Schizochytrium* ATCC 20888 screened for variations in fatty acid content. This particular strain was valued for its improved DHA productivity. Further, the complete identification of the domains with homology to those in *Shewanella* (see FIG. 2) were identified. It is noted that in *Schizochytrium*, the Orfs of the genomic DNA and cDNA are identical, due to the lack of introns in the organism genome, to the best of the present inventors' knowledge. Therefore, reference to a nucleotide sequence of Orfs from *Schizochytrium* can refer to genomic DNA or cDNA.

FIG. 1 is a graphical representation of the three open reading frames from the *Schizochytrium* PUFA PKS system, and includes the domain structure of this PUFA PKS system. The domain structure of each open reading frame is as follows:

Open Reading Frame A (OrfA):

The complete nucleotide sequence for OrfA is represented herein as SEQ ID NO:1. Nucleotides 4677-8730 of SEQ ID NO:1 correspond to nucleotides 390-4443 of the sequence denoted as SEQ ID NO:69 in U.S. application Ser. No. 09/231,899. Therefore, nucleotides 1-4676 of SEQ ID NO:1 represent additional sequence that was not disclosed in U.S. application Ser. No. 09/231,899. This novel region of SEQ ID NO:1 encodes the following domains in OrfA: (1) the ORFA-KS domain; (2) the ORFA-MAT domain; and (3) at least a portion of the ACP domain region (e.g., at least ACP domains 14). It is noted that nucleotides 1-389 of SEQ ID NO:69 in U.S. application Ser. No. 09/231,899 do not exactly match with the 389 nucleotides that are upstream of position 4677 in SEQ ID NO:1 disclosed herein. Therefore, positions 1-389 of SEQ ID NO:69 in U.S. Application Ser. No. 09/231,899 appear to be incorrectly placed next to nucleotides 390-4443 of that sequence. Most of these first 389 nucleotides (about positions 60-389) are a match with an upstream portion of OrfA (SEQ ID NO: 1) of the present invention and therefore, it is believed that an error occurred in the effort to prepare the contig of the cDNA constructs in U.S. application Ser. No. 09/231,899. The region in which the alignment error occurred in U.S. application Ser. No. 09/231,899 is within the region of highly repetitive sequence (i.e., the ACP region, discussed below), which probably created some confusion in the assembly of that sequence from various cDNA clones.

OrfA is a 8730 nucleotide sequence (not including the stop codon) which encodes a 2910 amino acid sequence, represented herein as SEQ ID NO:2. Within OrfA are twelve domains: (a) one β-keto acyl-ACP synthase (KS) domain; (b) one malonyl-CoA:ACP acyltransferase (MAT) domain; (c) nine acyl carrier protein (ACP) domains; and (d) one ketoreductase (KR) domain.

A nucleotide sequence for OrfA has been deposited with GenBank as Accession No. AF378327 (amino acid sequence Accession No. AAK728879). The nucleotide sequence represented by GenBank Accession No. AF378327 differs from the sequence represented herein as SEQ ID NO:1 by the point nucleotide changes: (1) at position 1999 (A to G, resulting in an amino acid change from an asparagine to an aspartic acid at position 667 of SEQ ID NO:2); (2) at position 2003 (C to A, resulting in an amino acid change from a proline to a histidine at position 668 of SEQ ID NO:2); and (3) at position 2238 (A to C, resulting in no amino acid change at position 746 of SEQ ID NO:2). Each of the two amino acid changes from the amino acid sequence encoded by GenBank Accession No. AAK728879 are located in the MAT domain (SEQ ID NO:10) of SEQ ID NO:2.

Genomic DNA clones (plasmids) encoding OrfA from both *Schizochytrium* sp. ATCC 20888 and a daughter strain of ATCC 20888, denoted *Schizochytrium* sp., strain N230D, have been isolated and sequenced. A genomic clone described herein as JK1126, isolated from *Schizochytrium* sp. ATCC 20888, comprises, to the best of the present inventors' knowledge, the nucleotide sequence spanning from position 1 to 4119 and from position 5498 to 8730 of SEQ ID NO:1, and encodes the corresponding amino acid sequence of SEQ ID NO:2. Indeed, it is expected that JK1126 comprises SEQ ID NO:1 in its entirety and encodes SEQ ID NO:2. Genomic clone pJK1126 (denoted pJK1126 OrfA genomic clone, in the form of an *E. coli* plasmid vector containing "OrfA" gene from *Schizochytrium* ATCC 20888) was deposited with the American Type Culture Collection (ATCC), 10801 University Boulevard, Manassas, Va. 20110-2209 USA on Jun. 8, 2006, and assigned ATCC Accession No. PTA-7648. The nucleotide sequence of pJK1126 OrfA genomic clone, and the amino acid sequence encoded by this plasmid are encompassed by the present invention.

Two genomic clones described herein as pJK306 OrfA genomic clone and pJK320 OrfA genomic clone, isolated from *Schizochytrium* sp. N230D, together (overlapping clones) comprise, to the best of the present inventors' knowledge, the nucleotide sequence of SEQ ID NO:1, and encode the amino acid sequence of SEQ ID NO:2. Genomic clone pJK306 (denoted pJK306 OrfA genomic clone, in the form of an *E. coli* plasmid containing 5' portion of OrfA gene from *Schizochytrium* sp. N230D (2.2 kB overlap with pJK320)) was deposited with the American Type Culture Collection (ATCC), 10801 University Boulevard, Manassas, Va. 20110-2209 USA on Jun. 8, 2006, and assigned ATCC Accession No. PTA-7641. The nucleotide sequence of pJK306 OrfA genomic clone, and the amino acid sequence encoded by this plasmid are encompassed by the present invention. Genomic clone pJK320 (denoted pJK320 OrfA genomic clone, in the form of an *E. coli* plasmid containing 3' portion of OrfA gene from *Schizochytrium* sp. N230D (2.2 kB overlap with pJK306)) was deposited with the American Type Culture Collection (ATCC), 10801 University Boulevard, Manassas, Va. 20110-2209 USA on Jun. 8, 2006, and assigned ATCC Accession No. PTA-7644. The nucleotide sequence of pJK320 OrfA genomic clone, and the amino acid sequence encoded by this plasmid are encompassed by the present invention.

OrfA was compared with known sequences in a standard BLAST search (BLAST 2.0 Basic BLAST homology search using blastp for amino acid searches, blastn for nucleic acid searches, and blastX for nucleic acid searches and searches of the translated amino acid sequence in all 6 open reading frames with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety)). At the nucleic acid level, OrfA has no significant homology to any known nucleotide sequence. At the amino acid level, the sequences with the greatest degree of homology to ORFA were: *Nostoc* sp. 7120 heterocyst glycolipid synthase (Accession No. NC_003272), which was 42% identical to ORFA over 1001 amino acid residues; and *Moritella marinus* (*Vibrio marinus*) ORF8 (Accession No. AB025342), which was 40% identical to ORFA over 993 amino acid residues.

The first domain in OrfA is a KS domain, also referred to herein as ORFA-KS. This domain is contained within the nucleotide sequence spanning from a starting point of between about positions 1 and 40 of SEQ ID NO:1 (OrfA) to an ending point of between about positions 1428 and 1500 of SEQ ID NO:1 (based on homology to other PUFA PKS domains, the position of the domain spans from about position 1 to about position 1500; based on Pfam analysis, a KS core region spans from about position 40 to about position 1428). The nucleotide sequence containing the sequence encoding the ORFA-KS domain is represented herein as SEQ ID NO:7 (positions 1-1500 of SEQ ID NO:1).

The amino acid sequence containing the KS domain spans from a starting point of between about positions 1 and 14 of SEQ ID NO:2 (ORFA) to an ending point of between about positions 476 and 500 of SEQ ID NO:2 (again, referring to the overall homology to PUFA PKS KS domains and to Pfam core regions, respectively). The amino acid sequence containing the ORFA-KS domain is represented herein as SEQ ID NO:8 (positions 1-500 of SEQ ID NO:2). It is noted that the ORFA-KS domain contains an active site motif: DXAC* (*acyl binding site $C_{215}$).

According to the present invention, a domain or protein having 3-keto acyl-ACP synthase (KS) biological activity (function) is characterized as the enzyme that carries out the initial step of the FAS (and PKS) elongation reaction cycle. The acyl group destined for elongation is linked to a cysteine residue at the active site of the enzyme by a thioester bond. In the multi-step reaction, the acyl-enzyme undergoes condensation with malonyl-ACP to form -keto acyl-ACP, $CO_2$ and free enzyme. The KS plays a key role in the elongation cycle and in many systems has been shown to possess greater substrate specificity than other enzymes of the reaction cycle. For example, *E. coli* has three distinct KS enzymes—each with its own particular role in the physiology of the organism (Magnuson et al., *Microbiol. Rev.* 57, 522 (1993)). The two KS domains of the PUFA-PKS systems could have distinct roles in the PUFA biosynthetic reaction sequence.

As a class of enzymes, KS's have been well characterized. The sequences of many verified KS genes are know, the active site motifs have been identified and the crystal structures of several have been determined. Proteins (or domains of proteins) can be readily identified as belonging to the KS family of enzymes by homology to known KS sequences.

The second domain in OrfA is a MAT domain, also referred to herein as ORFA-MAT. This domain is contained within the nucleotide sequence spanning from a starting point of between about positions 1723 and 1798 of SEQ ID NO:1 (OrfA) to an ending point of between about positions 2805 and 3000 of SEQ ID NO:1 (based on homology to other PUFA PKS domains, the position of the MAT domain spans from about position 1723 to about position 3000; based on Pfam analysis, a MAT core region spans from about position 1798 to about position 2805). The nucleotide sequence containing the sequence encoding the ORFA-MAT domain is represented herein as SEQ ID NO:9 (positions 1723-3000 of SEQ ID NO:1). The amino acid sequence containing the MAT domain spans from a starting point of between about positions 575 and 600 of SEQ ID NO:2 (ORFA) to an ending point of between about positions 935 and 1000 of SEQ ID NO:2 (again, referring to the overall homology to PUFA PKS MAT domains and to Pfam core regions, respectively). The amino acid sequence containing the ORFA-MAT domain is represented herein as SEQ ID NO:10 (positions 575-1000 of SEQ ID NO:2). The MAT domain comprises an aspartate at position 93 and a histidine at position 94 (corresponding to positions 667 and 668, respectively, of SEQ ID NO:2). It is noted that the ORFA-MAT domain contains an active site motif: GHS*XG (*acyl binding site $S_{706}$), represented herein as SEQ ID NO:11.

According to the present invention, a domain or protein having malonyl-CoA:ACP acyltransferase (MAT) biological activity (function) is characterized as one that transfers the malonyl moiety from malonyl-CoA to ACP. In addition to the active site motif (GxSxG), these enzymes possess an extended motif R and Q amino acids in key positions) that identifies them as MAT enzymes (in contrast to the AT domain of *Schizochytrium* Orf B). In some PKS systems (but not the PUFA PKS domain) MAT domains will preferentially load methyl- or ethyl-malonate on to the ACP group (from the corresponding CoA ester), thereby introducing branches into the linear carbon chain. MAT domains can be recognized by their homology to known MAT sequences and by their extended motif structure.

Domains 3-11 of OrfA are nine tandem ACP domains, also referred to herein as ORFA-ACP (the first domain in the sequence is ORFA-ACP1, the second domain is ORFA-ACP2, the third domain is ORFA-ACP3, etc.). The first ACP domain, ORFA-ACP1, is contained within the nucleotide sequence spanning from about position 3343 to about position 3600 of SEQ ID NO:1 (OrfA). The nucleotide sequence containing the sequence encoding the ORFA-ACP1 domain is represented herein as SEQ ID NO:12 (positions 3343-3600 of SEQ ID NO:1). The amino acid sequence containing the first ACP domain spans from about position 1115 to about position 1200 of SEQ ID NO:2. The amino acid sequence containing the ORFA-ACP1 domain is represented herein as SEQ ID NO:13 (positions 1115-1200 of SEQ ID NO:2). It is noted that the ORFA-ACP1 domain contains an active site motif: LGIDS* (*pantetheine binding motif $S_{1157}$), represented herein by SEQ ID NO:14.

The nucleotide and amino acid sequences of all nine ACP domains are highly conserved and therefore, the sequence for each domain is not represented herein by an individual sequence identifier. However, based on the information disclosed herein, one of skill in the art can readily determine the sequence containing each of the other eight ACP domains (see discussion below).

All nine ACP domains together span a region of OrfA of from about position 3283 to about position 6288 of SEQ ID NO:1, which corresponds to amino acid positions of from about 1095 to about 2096 of SEQ ID NO:2. The nucleotide sequence for the entire ACP region containing all nine domains is represented herein as SEQ ID NO:16. The region represented by SEQ ID NO:16 includes the linker segments between individual ACP domains. The repeat interval for the nine domains is approximately every 330 nucleotides of SEQ ID NO:16 (the actual number of amino acids measured between adjacent active site serines ranges from 104 to 116 amino acids). Each of the nine ACP domains contains a pantetheine binding motif LGIDS* (represented herein by SEQ ID NO:14), wherein S* is the pantetheine binding site serine (S). The pantetheine binding site serine (S) is located near the center of each ACP domain sequence. At each end of the ACP domain region and between each ACP domain is a region that is highly enriched for proline (P) and alanine (A), which is believed to be a linker region. For example, between ACP domains 1 and 2 is the sequence: APAPVKAAAPAAPVASAPAPA, represented herein as SEQ ID NO:15. The locations of the active site serine residues (i.e., the pantetheine binding site) for each of the nine ACP domains, with respect to the amino acid sequence of SEQ ID NO:2, are as follows: ACP1=$S_{1157}$; ACP2=$S_{1266}$; ACP3=$S_{1377}$; ACP4=$S_{1488}$; ACP5=$S_{1604}$; ACP6=$S_{1715}$; ACP7=$S_{1819}$; ACP8=$S_{1930}$; and ACP9=$S_{2034}$. Given that the average size of an ACP domain is about 85 amino acids, excluding the linker, and about 110 amino acids including the linker, with the active site serine being approximately in the center of the domain, one of skill in the art can readily determine the positions of each of the nine ACP domains in OrfA.

According to the present invention, a domain or protein having acyl carrier protein (ACP) biological activity (function) is characterized as being small polypeptides (typically, 80 to 100 amino acids long), that function as carriers for growing fatty acyl chains via a thioester linkage to a covalently bound co-factor of the protein. They occur as separate units or as domains within larger proteins. ACPs are converted from inactive apo-forms to functional holo-forms by transfer of the phosphopantetheinyl moiety of CoA to a highly conserved serine residue of the ACP. Acyl groups are attached to ACP by a thioester linkage at the free terminus of the phosphopantetheinyl moiety. ACPs can be identified by labeling with radioactive pantetheine and by sequence homology to known ACPs. The presence of variations of the above mentioned motif (LGIDS*) is also a signature of an ACP.

Domain 12 in OrfA is a KR domain, also referred to herein as ORFA-KR. This domain is contained within the nucleotide sequence spanning from a starting point of about position 6598 of SEQ ID NO:1 to an ending point of about position 8730 of SEQ ID NO:1. The nucleotide sequence containing the sequence encoding the ORFA-KR domain is represented herein as SEQ ID NO:17 (positions 6598-8730 of SEQ ID NO:1). The amino acid sequence containing the KR domain spans from a starting point of about position 2200 of SEQ ID NO:2 (ORFA) to an ending point of about position 2910 of SEQ ID NO:2. The amino acid sequence containing the ORFA-KR domain is represented herein as SEQ ID NO:18 (positions 2200-2910 of SEQ ID NO:2). Within the KR domain is a core region with homology to short chain aldehyde-dehydrogenases (KR is a member of this family). This core region spans from about position 7198 to about position 7500 of SEQ ID NO:1, which corresponds to amino acid positions 2400-2500 of SEQ ID NO:2.

According to the present invention, a domain or protein having ketoreductase activity, also referred to as 3-ketoacyl-ACP reductase (KR) biological activity (function), is characterized as one that catalyzes the pyridine-nucleotide-dependent reduction of 3-keto acyl forms of ACP. It is the first reductive step in the de novo fatty acid biosynthesis elongation cycle and a reaction often performed in polyketide biosynthesis. Significant sequence similarity is observed with one family of enoyl ACP reductases (ER), the other reductase of FAS (but not the ER family present in the PUFA PKS system), and the short-chain alcohol dehydrogenase family. Pfam analysis of the PUFA PKS region indicated above reveals the homology to the short-chain alcohol dehydrogenase family in the core region. Blast analysis of the same region reveals matches in the core area to known KR enzymes as well as an extended region of homology to domains from the other characterized PUFA PKS systems.

Open Reading Frame B (Or/fB):

The complete nucleotide sequence for OrfB is represented herein as SEQ ID NO:3. Nucleotides 1311-6177 of SEQ ID NO:3 correspond to nucleotides 1-4867 of the sequence denoted as SEQ ID NO:71 in U.S. application Ser. No. 09/231,899, with the exception of the nucleotide at position 2933 of SEQ ID NO:71 of the '899 application or nucleotide 4243 of SEQ ID NO:3 herein, as discussed above. The cDNA sequence in U.S. application Ser. No. 09/231,899 contains about 345 additional nucleotides beyond the stop codon, including a polyA tail). Therefore, nucleotides 1-1310 of SEQ ID NO:1 represent additional sequence that was not disclosed in U.S. application Ser. No. 09/231,899. This novel region of SEQ ID NO:3 contains most of the KS domain encoded by OrfB.

OrfB is a 6177 nucleotide sequence (not including the stop codon) which encodes a 2059 amino acid sequence, represented herein as SEQ ID NO:4. Within OrfB are four domains: (a) one β-keto acyl-ACP synthase (KS) domain; (b) one chain length factor (CLF) domain; (c) one acyl transferase (AT) domain; and, (d) one enoyl ACP-reductase (ER) domain.

A nucleotide sequence for OrfB has been deposited with GenBank as Accession No. AF378328 (amino acid sequence Accession No. AAK728880). The nucleotide sequence represented by GenBank Accession No. AF378328 differs from the nucleotide sequence represented herein as SEQ ID NO:3 by the point nucleotide changes: (1) at position 852 (T to C, resulting in no amino acid change at position 284 of SEQ ID NO:4); (2) at position 1110 (S to C, resulting in no amino acid change at position 370 of SEQ ID NO:4); (3) at position 1112 (Y to T, resulting in the resolution of an ambiguous amino acid call to a definite valine call at position 371 of SEQ ID NO:4); and (4) at position 4243 (C to G, resulting in a change from a glutamine to a glutamate at position 1415 of SEQ ID NO:4). The single amino acid change from the amino acid sequence encoded by GenBank Accession No. AAK728880 is located in the linker region located between the AT domain and the ER domain of SEQ ID NO:4.

Genomic DNA clones (plasmids) encoding OrfB from both *Schizochytrium* sp. ATCC 20888 and a daughter strain of ATCC 20888, denoted *Schizochytrium* sp., strain N230D, have been isolated and sequenced. A genomic clone described herein as pJK1129, isolated from *Schizochytrium* sp. ATCC 20888, comprises, to the best of the present inventors' knowledge, the nucleotide sequence of SEQ ID NO:3, and encodes the amino acid sequence of SEQ ID NO:4. Genomic clone pJK1129 (denoted pJK1129 OrfB genomic clone, in the form of an *E. coli* plasmid vector containing "OrfB" gene from *Schizochytrium* ATCC 20888) was deposited with the American Type Culture Collection (ATCC), 10801 University Boulevard, Manassas, Va. 20110-2209 USA on Jun. 8, 2006, and assigned ATCC Accession No. PTA-7649. The nucleotide sequence of pJK1129 OrfB genomic clone, and the amino acid sequence encoded by this plasmid are encompassed by the present invention.

A genomic clone described herein as pJK324 OrfB genomic clone, isolated from *Schizochytrium* sp. N230D, comprises, to the best of the present inventors' knowledge, the nucleotide sequence of SEQ ID NO:3, and encodes the amino acid sequence of SEQ ID NO:4. Genomic clone pJK324 (denoted pJK324 OrfB genomic clone, in the form of an *E. coli* plasmid containing the OrfB gene sequence from *Schizochytrium* sp. N230D) was deposited with the American Type Culture Collection (ATCC), 10801 University Boulevard, Manassas, Va. 20110-2209 USA on Jun. 8, 2006, and assigned ATCC Accession No. PTA-7643. The nucleotide sequence of pJK324 OrfB genomic clone, and the amino acid sequence encoded by this plasmid are encompassed by the present invention.

OrfB was compared with known sequences in a standard BLAST search as described above. At the nucleic acid level, OrfB has no significant homology to any known nucleotide sequence. At the amino acid level, the sequences with the greatest degree of homology to ORFB were: *Shewanella* sp. hypothetical protein (Accession No. U73935), which was 53% identical to ORFB over 458 amino acid residues; *Moritella marinus* (*Vibrio marinus*) ORF11 (Accession No. AB025342), which was 53% identical to ORFB over 460 amino acid residues; *Photobacterium profundum* omega-3 polyunsaturated fatty acid synthase PfaD (Accession No.

AF409100), which was 52% identical to ORFB over 457 amino acid residues; and *Nostoc* sp. 7120 hypothetical protein (Accession No. NC_003272), which was 53% identical to ORFB over 430 amino acid residues.

The first domain in OrfB is a KS domain, also referred to herein as ORFB-KS. This domain is contained within the nucleotide sequence spanning from a starting point of between about positions 1 and 43 of SEQ ID NO:3 (OrfB) to an ending point of between about positions 1332 and 1350 of SEQ ID NO:3 (based on homology to other PUFA PKS domains, the position of the KS domain spans from about position 1 to about position 1350; based on Pfam analysis, a KS core region spans from about position 43 to about position 1332). The nucleotide sequence containing the sequence encoding the ORFB-KS domain is represented herein as SEQ ID NO:19 (positions 1-1350 of SEQ ID NO:3). The amino acid sequence containing the KS domain spans from a starting point of between about positions 1 and 15 of SEQ ID NO:4 (ORFB) to an ending point of between about positions 444 and 450 of SEQ ID NO:4 (again, referring to the overall homology to PUFA PKS KS domains and to Pfam core regions, respectively). The amino acid sequence containing the ORFB-KS domain is represented herein as SEQ ID NO:20 (positions 1-450 of SEQ ID NO:4). This KS domain comprises a valine at position 371 of SEQ ID NO:20 (also position 371 of SEQ ID NO:20). It is noted that the ORFB-KS domain contains an active site motif: DXAC* (*acyl binding site $C_{196}$). KS biological activity and methods of identifying proteins or domains having such activity is described above.

The second domain in OrfB is a CLF domain, also referred to herein as ORFB-CLF. This domain is contained within the nucleotide sequence spanning from a starting point of between about positions 1378 and 1402 of SEQ ID NO:3 (OrfB) to an ending point of between about positions 2682 and 2700 of SEQ ID NO:3 (based on homology to other PUFA PKS domains, the position of the CLF domain spans from about position 1378 to about position 2700; based on Pfam analysis, a CLF core region spans from about position 1402 to about position 2682). The nucleotide sequence containing the sequence encoding the ORFB-CLF domain is represented herein as SEQ ID NO:21 (positions 1378-2700 of SEQ ID NO:3). The amino acid sequence containing the CLF domain spans from a starting point of between about positions 460 and 468 of SEQ ID NO:4 (ORFB) to an ending point of between about positions 894 and 900 of SEQ ID NO:4 (again, referring to the overall homology to PUFA PKS CLF domains and to Pfam core regions, respectively). The amino acid sequence containing the ORFB-CLF domain is represented herein as SEQ ID NO:22 (positions 460-900 of SEQ ID NO:4). It is noted that the ORFB-CLF domain contains a KS active site motif without the acyl-binding cysteine.

According to the present invention, a domain or protein is referred to as a chain length factor (CLF) based on the following rationale. The CLF was originally described as characteristic of Type II (dissociated enzymes) PKS systems and was hypothesized to play a role in determining the number of elongation cycles, and hence the chain length, of the end product. CLF amino acid sequences show homology to KS domains (and are thought to form heterodimers with a KS protein), but they lack the active site cysteine. CLF's role in PKS systems is currently controversial. New evidence (C. Bisang et al., *Nature* 401, 502 (1999)) suggests a role in priming (providing the initial acyl group to be elongated) the PKS systems. In this role the CLF domain is thought to decarboxylate malonate (as malonyl-ACP), thus forming an acetate group that can be transferred to the KS active site. This acetate therefore acts as the 'priming' molecule that can undergo the initial elongation (condensation) reaction. Homologues of the Type II CLF have been identified as 'loading' domains in some modular PKS systems. A domain with the sequence features of the CLF is found in all currently identified PUFA PKS systems and in each case is found as part of a multidomain protein.

The third domain in OrfB is an AT domain, also referred to herein as ORFB-AT. This domain is contained within the nucleotide sequence spanning from a starting point of between about positions 2701 and 3598 of SEQ ID NO:3 (OrfB) to an ending point of between about positions 3975 and 4200 of SEQ ID NO:3 (based on homology to other PUFA PKS domains, the position of the AT domain spans from about position 2701 to about position 4200; based on Pfam analysis, an AT core region spans from about position 3598 to about position 3975). The nucleotide sequence containing the sequence encoding the ORFB-AT domain is represented herein as SEQ ID NO:23 (positions 2701-4200 of SEQ ID NO:3). The amino acid sequence containing the AT domain spans from a starting point of between about positions 901 and 1200 of SEQ ID NO:4 (ORFB) to an ending point of between about positions 1325 and 1400 of SEQ ID NO:4 (again, referring to the overall homology to PUFA PKS AT domains and to Pfam core regions, respectively). The amino acid sequence containing the ORFB-AT domain is represented herein as SEQ ID NO:24 (positions 901-1400 of SEQ ID NO:4). It is noted that the ORFB-AT domain contains an active site motif of GxS*xG (*acyl binding site $S_{1140}$) that is characteristic of acyltransferse (AT) proteins.

An "acyltransferase" or "AT" refers to a general class of enzymes that can carry out a number of distinct acyl transfer reactions. The *Schizochytrium* domain shows good homology to a domain present in all of the other PUFA PKS systems currently examined and very weak homology to some acyltransferases whose specific functions have been identified (e.g. to malonyl-CoA:ACP acyltransferase, MAT). In spite of the weak homology to MAT, this AT domain is not believed to function as a MAT because it does not possess an extended motif structure characteristic of such enzymes (see MAT domain description, above). For the purposes of this disclosure, the functions of the AT domain in a PUFA PKS system include, but are not limited to: transfer of the fatty acyl group from the ORFA ACP domain(s) to water (i.e. a thioesterase—releasing the fatty acyl group as a free fatty acid), transfer of a fatty acyl group to an acceptor such as CoA, transfer of the acyl group among the various ACP domains, or transfer of the fatty acyl group to a lipophilic acceptor molecule (e.g. to lysophosphadic acid).

The fourth domain in OrfB is an ER domain, also referred to herein as ORFB-ER. This domain is contained within the nucleotide sequence spanning from a starting point of about position 4648 of SEQ ID NO:3 (OrfB) to an ending point of about position 6177 of SEQ ID NO:3. The nucleotide sequence containing the sequence encoding the ORFB-ER domain is represented herein as SEQ ID NO:25 (positions 4648-6177 of SEQ ID NO:3). The amino acid sequence containing the ER domain spans from a starting point of about position 1550 of SEQ ID NO:4 (ORFB) to an ending point of about position 2059 of SEQ ID NO:4. The amino acid sequence containing the ORFB-ER domain is represented herein as SEQ ID NO:26 (positions 1550-2059 of SEQ ID NO:4).

According to the present invention, this domain has enoyl reductase (ER) biological activity. The ER enzyme reduces the trans-double bond (introduced by the DH activity) in the fatty acyl-ACP, resulting in fully saturating those carbons. The ER domain in the PUFA-PKS shows homology to a newly characterized family of ER enzymes (Heath et al., *Nature* 406, 145 (2000)). Heath and Rock identified this new class of ER enzymes by cloning a gene of interest from *Streptococcus pneumoniae*, purifying a protein expressed from that gene, and showing that it had ER activity in an in vitro assay. The sequence of the *Schizochytrium* ER domain of OrfB shows homology to the *S. pneumoniae* ER protein. All of the PUFA PKS systems currently examined contain at least one domain with very high sequence homology to the *Schizochytrium* ER domain. The *Schizochytrium* PUFA PKS system contains two ER domains (one on OrfB and one on OrfC).

Open Reading Frame C (OrfC):

The complete nucleotide sequence for OrfC is represented herein as SEQ ID NO:5. Nucleotides 1-4506 of SEQ ID NO:5 (i.e., the entire open reading frame sequence, not including the stop codon) nearly correspond to nucleotides 145-4653 of the sequence denoted as SEQ ID NO:76 in U.S. application Ser. No. 09/231,899. The cDNA sequence in U.S. application Ser. No. 09/231,899 contains about 144 nucleotides upstream of the start codon for OrfC and about 110 nucleotides beyond the stop codon, including a polyA tail. In addition, as discussed above, nucleotides 145-4653 of the cDNA sequence containing the complete open reading frame described in U.S. application Ser. No. 09/231,899 (denoted therein as SEQ ID NO:76) match nucleotides 1-2624 and 2675-4506 of the sequence denoted herein as OrfC (SEQ ID NO:5). OrfC is a 4506 nucleotide sequence (not including the stop codon) which encodes a 1502 amino acid sequence, represented herein as SEQ ID NO:6. Within OrfC are three domains: (a) two FabA-like β-hydroxy acyl-ACP dehydrase (DH) domains; and (b) one enoyl ACP-reductase (ER) domain.

A nucleotide sequence for OrfC has been deposited with GenBank as Accession No. AF378329 (amino acid sequence Accession No. AAK728881). The nucleotide sequence represented by AF378329 differs from the nucleotide sequence represented herein as SEQ ID NO:5 by the point nucleotide insertions: (1) at position 2625 (an insertion of an A); (2) at position 2662 (an insertion of a C); and (3) at position 2674 (an insertion of an A). This resulted in a frame shift out of frame at position 2625 and then back into frame at position 2675. The amino acid sequence encoded by GenBank Accession No. AAK728881 differs from the amino acid sequence encoded by SEQ ID NO:5 (i.e., SEQ ID NO:6) in the region spanning from positions 876-891 of GenBank Accession No. AAK728881 or positions 876-890 of SEQ ID NO:6. This change in sequence occurs in the DH2 domain of OrfC (discussed below).

Genomic DNA clones (plasmids) encoding OrfC from both *Schizochytrium* sp. ATCC 20888 and a daughter strain of ATCC 20888, denoted *Schizochytrium* sp., strain N230D, have been isolated and sequenced. A genomic clone described herein as pJK1131, isolated from *Schizochytrium* sp. ATCC 20888, comprises, to the best of the present inventors' knowledge, the nucleotide sequence of SEQ ID NO:5, and encodes the amino acid sequence of SEQ ID NO:6. Genomic clone pJK1131 (denoted pJK1131 OrfC genomic clone, in the form of an *E. coli* plasmid vector containing "OrfC" gene from *Schizochytrium* ATCC 20888) was deposited with the American Type Culture Collection (ATCC), 10801 University Boulevard, Manassas, Va. 20110-2209 USA on Jun. 8, 2006, and assigned ATCC Accession No. PTA-7650. The nucleotide sequence of pJK1131 OrfC genomic clone, and the amino acid sequence encoded by this plasmid are encompassed by the present invention.

A genomic clone described herein as pBR002 OrfC genomic clone, isolated from *Schizochytrium* sp. N230D, comprises, to the best of the present inventors' knowledge, the nucleotide sequence of SEQ ID NO:5, and encodes the amino acid sequence of SEQ ID NO:6. Genomic clone pBR002 (denoted pBR002 OrfC genomic clone, in the form of an *E. coli* plasmid vector containing the OrfC gene sequence from *Schizochytrium* sp. N230D) was deposited with the American Type Culture Collection (ATCC), 10801 University Boulevard, Manassas, Va. 20110-2209 USA on Jun. 8, 2006, and assigned ATCC Accession No. PTA-7642. The nucleotide sequence of pBR002 OrfC genomic clone, and the amino acid sequence encoded by this plasmid are encompassed by the present invention.

OrfC was compared with known sequences in a standard BLAST search as described above. At the nucleic acid level, OrfC has no significant homology to any known nucleotide sequence. At the amino acid level (Blastp), the sequences with the greatest degree of homology to ORFC were: *Moritella marinus* (*Vibrio marinus*) ORF11 (Accession No. ABO25342), which is 45% identical to ORFC over 514 amino acid residues, *Shewanella* sp. hypothetical protein 8 (Accession No. U73935), which is 49% identical to ORFC over 447 amino acid residues, *Nostoc* sp. hypothetical protein (Accession No. NC_003272), which is 49% identical to ORFC over 430 amino acid residues, and *Shewanella* sp. hypothetical protein 7 (Accession No. U73935), which is 37% identical to ORFC over 930 amino acid residues.

The first domain in OrfC is a DH domain, also referred to herein as ORFC-DH1. This is one of two DH domains in OrfC, and therefore is designated DH1. This domain is contained within the nucleotide sequence spanning from a starting point of between about positions 1 and 778 of SEQ ID NO:5 (OrfC) to an ending point of between about positions 1233 and 1350 of SEQ ID NO:5 (based on homology to other PUFA PKS domains, the position of the DH1 domain spans from about position 1 to about position 1350; based on Pfam analysis, a DH core region spans from about position 778 to about position 1233). The nucleotide sequence containing the sequence encoding the ORFC-DH1 domain is represented herein as SEQ ID NO:27 (positions 1-1350 of SEQ ID NO:5). The amino acid sequence containing the DH1 domain spans from a starting point of between about positions 1 and 260 of SEQ ID NO:6 (ORFC) to an ending point of between about positions 411 and 450 of SEQ ID NO:6 (again, referring to the overall homology to PUFA PKS DH domains and to Pfam core regions, respectively). The amino acid sequence containing the ORFC-DH1 domain is represented herein as SEQ ID NO:28 (positions 1-450 of SEQ ID NO:6).

The characteristics of both the DH domains (see below for DH 2) in the PUFA PKS systems have been described in the preceding sections. This class of enzyme removes HOH from a β-keto acyl-ACP and leaves a trans double bond in the carbon chain. The DH domains of the PUFA PKS systems show homology to bacterial DH enzymes associated with their FAS systems (rather than to the DH domains of other PKS systems). A subset of bacterial DH's, the FabA-like DH's, possesses cis-trans isomerase activity (Heath et al., *J. Biol. Chem.*, 271, 27795 (1996)). It is the homologies to the FabA-like DH's that indicate that one or both of the DH domains is responsible for insertion of the cis double bonds in the PUFA PKS products.

The second domain in OrfC is a DH domain, also referred to herein as ORFC-DH2. This is the second of two DH domains in OrfC, and therefore is designated DH2. This domain is contained within the nucleotide sequence spanning from a starting point of between about positions 1351 and 2437 of SEQ ID NO:5 (OrfC) to an ending point of between about positions 2607 and 2847 of SEQ ID NO:5 (based on homology to other PUFA PKS domains, the position of the DH2 domain spans from about position 1351 to about position 2845; based on Pfam analysis, a DH core region spans from about position 2437 to about position 2847). The nucleotide sequence containing the sequence encoding the ORFC-DH2 domain is represented herein as SEQ ID NO:29 (positions 1351-2847 of SEQ ID NO:5). The amino acid sequence containing the DH2 domain spans from a starting point of between about positions 451 and 813 of SEQ ID NO:6 (ORFC) to an ending point of between about positions 869 and 949 of SEQ ID NO:6 (again, referring to the overall homology to PUFA PKS DH domains and to Pfam core regions, respectively). The amino acid sequence containing the ORFC-DH2 domain is represented herein as SEQ ID NO:30 (positions 451-949 of SEQ ID NO:6). This DH domain comprises the amino acids H-G-I-A-N-P-T-F-V-H-A-P-G-K-I (positions 876-890 of SEQ ID NO:6) at positions 426-440 of SEQ ID NO:30. DH biological activity has been described above.

The third domain in OrfC is an ER domain, also referred to herein as ORFC-ER. This domain is contained within the nucleotide sequence spanning from a starting point of about position 2995 of SEQ ID NO:5 (OrfC) to an ending point of about position 4506 of SEQ ID NO:5. The nucleotide sequence containing the sequence encoding the ORFC-ER domain is represented herein as SEQ ID NO:31 (positions 2995-4506 of SEQ ID NO:5). The amino acid sequence containing the ER domain spans from a starting point of about position 999 of SEQ ID NO:6 (ORFC) to an ending point of about position 1502 of SEQ ID NO:6. The amino acid sequence containing the ORFC-ER domain is represented herein as SEQ ID NO:32 (positions 999-1502 of SEQ ID NO:6). ER biological activity has been described above.

Accessory Proteins

According to the present invention, a domain or protein having 4'-phosphopantetheinyl transferase (PPTase) biological activity (function) is characterized as the enzyme that transfers a 4'-phosphopantetheinyl moiety from Coenzyme A to the acyl carrier protein (ACP). This transfer to an invariant serine reside of the ACP activates the inactive apo-form to the holo-form. In both polyketide and fatty acid synthesis, the phosphopantetheine group forms thioesters with the growing acyl chains. The PPTases are a family of enzymes that have been well characterized in fatty acid synthesis, polyketide synthesis, and non-ribosomal peptide synthesis. The sequences of many PPTases are known, and crystal structures have been determined (e.g., Reuter K, Mofid M R, Marahiel M A, Ficner R. "Crystal structure of the surfactin synthetase-activating enzyme sfp: a prototype of the 4'-phosphopantetheinyl transferase superfamily" EMBO J. 1999 Dec. 1; 18(23):6823-31) as well as mutational analysis of amino acid residues important for activity (Mofid M R, Finking R, Essen L O, Marahiel M A. "Structure-based mutational analysis of the 4'-phosphopantetheinyl transferases Sfp from *Bacillus subtilis*: carrier protein recognition and reaction mechanism" Biochemistry. 2004 Apr. 13; 43(14):4128-36).

The present inventors have identified two sequences (genes) in the *Arabidopsis* whole genome database that are likely to encode PPTases. These sequences (GenBank Accession numbers; AAG51443 and AAC05345) are currently listed as encoding "Unknown Proteins". They can be identified as putative PPTases based on the presence in the translated protein sequences of several signature motifs including; G(I/V)D and WxxKE(A/S)xxK (SEQ ID NO:33), (listed in Lambalot et al., 1996 as characteristic of all PPTases). In addition, these two putative proteins contain two additional motifs typically found in PPTases typically associated with PKS and non-ribosomal peptide synthesis systems; i.e., FN(I/L/V)SHS (SEQ ID NO:34) and (I/V/L) G(I/L/V)D(I/L/V) (SEQ ID NO:35). Furthermore, these motifs occur in the expected relative positions in the protein sequences. It is likely that homologues of the *Arabidopsis* genes are present in other plants, such as tobacco. Again, these genes can be cloned and expressed to see if the enzymes they encode can activate the *Schizochytrium* ORFA ACP domains, or alternatively, OrfA could be expressed directly in the transgenic plant (either targeted to the plastid or the cytoplasm).

Another heterologous PPTase which has been demonstrated by the inventors to recognize the OrfA ACP domains described herein as substrates is the Het I protein of *Nostoc* sp. PCC 7120 (formerly called *Anabaena* sp. PCC 7120).

One embodiment of the present invention relates to an isolated nucleic acid molecule comprising a nucleic acid sequence from a non-bacterial PUFA PKS system, a homologue thereof, a fragment thereof, and/or a nucleic acid sequence that is complementary to any of such nucleic acid sequences. In one aspect, the present invention relates to an isolated nucleic acid molecule comprising a nucleic acid sequence selected from the group consisting of: (a) a nucleic acid sequence encoding an amino acid sequence selected from the group consisting of: SEQ ID NO:2, SEQ ID NO:4, SEQ ID NO:6, and biologically active fragments thereof; (b) a nucleic acid sequence encoding an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and biologically active fragments thereof; (c) a nucleic acid sequence encoding an amino acid sequence that is at least about 60% identical to at least 500 consecutive amino acids of said amino acid sequence of (a), wherein said amino acid sequence has a biological activity of at least one domain of a polyunsaturated fatty acid (PUFA) polyketide synthase (PKS) system; (d) a nucleic acid sequence encoding an amino acid sequence that is at least about 60% identical to said amino acid sequence of (b), wherein said amino acid sequence has a biological activity of at least one domain of a polyunsaturated fatty acid (PUFA) polyketide synthase (PKS) system; or (e) a nucleic acid sequence that is fully complementary to the nucleic acid sequence of (a), (b), (c), or (d). In a further embodiment, nucleic acid sequences including a sequence encoding the active site domains or other functional motifs described above for several of the PUFA PKS domains are encompassed by the invention.

According to the present invention, an amino acid sequence that has a biological activity of at least one domain of a PUFA PKS system is an amino acid sequence that has the biological activity of at least one domain of the PUFA PKS system described in detail herein, as exemplified by the *Schizochytrium* PUFA PKS system. The biological activities of the various domains within the *Schizochytrium* PUFA PKS system have been described in detail above. Therefore, an isolated nucleic acid molecule of the present invention can encode the translation product of any PUFA PKS open reading frame, PUFA PKS domain, biologically active fragment thereof, or any homologue of a naturally occurring PUFA PKS open reading frame or domain which has biological activity. A homologue of given protein or domain is a protein or polypeptide that has an amino acid sequence which differs from the naturally occurring reference amino acid sequence (i.e., of the reference protein or domain) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). Preferred homologues of a PUFA PKS protein or domain are described in detail below. It is noted that homologues can include synthetically produced homologues, naturally occurring allelic variants of a given protein or domain, or homologous sequences from organisms other than the organism from which the reference sequence was derived.

In general, the biological activity or biological action of a protein or domain refers to any function(s) exhibited or performed by the protein or domain that is ascribed to the naturally occurring form of the protein or domain as measured or observed in vivo (i.e., in the natural physiological environment of the protein) or in vitro (i.e., under laboratory conditions). Biological activities of PUFA PKS systems and the individual proteins/domains that make up a PUFA PKS system have been described in detail elsewhere herein. Modifications of a protein or domain, such as in a homologue or mimetic (discussed below), may result in proteins or domains having the same biological activity as the naturally occurring protein or domain, or in proteins or domains having decreased or increased biological activity as compared to the naturally occurring protein or domain. Modifications which result in a decrease in expression or a decrease in the activity of the protein or domain, can be referred to as inactivation (complete or partial), down-regulation, or decreased action of a protein or domain. Similarly, modifications which result in an increase in expression or an increase in the activity of the protein or domain, can be referred to as amplification, overproduction, activation, enhancement, up-regulation or increased action of a protein or domain. A functional domain of a PUFA PKS system is a domain (i.e., a domain can be a portion of a protein) that is capable of performing a biological function (i.e., has biological activity).

In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on PUFA PKS system biological activity as described herein. Protein homologues (e.g., proteins encoded by nucleic acid homologues) have been discussed in detail above.

A nucleic acid molecule homologue can be produced using a number of methods known to those skilled in the art (see, for example, Sambrook et al., *Molecular Cloning: A Laboratory Manual*, Cold Spring Harbor Labs Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule of the present invention is a size sufficient to form a probe or oligonucleotide primer that is capable of forming a stable hybrid (e.g., under moderate, high or very high stringency conditions) with the complementary sequence of a nucleic acid molecule useful in the present invention, or of a size sufficient to encode an amino acid sequence having a biological activity of at least one domain of a PUFA PKS system according to the present invention. As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a sequence sufficient to encode a biologically active fragment of a domain of a PUFA PKS system, an entire domain of a PUFA PKS system, several domains within an open reading frame (Orf) of a PUFA PKS system, an entire Orf of a PUFA PKS system, or more than one Orf of a PUFA PKS system.

In one embodiment of the present invention, an isolated nucleic acid molecule comprises or consists essentially of a nucleic acid sequence encoding an amino acid sequence selected from the group of: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, or biologically active fragments thereof. In one aspect, the nucleic acid sequence is selected from the group of: SEQ ID NO:1, SEQ ID NO:3, SEQ ID NO:5, SEQ ID NO:7, SEQ ID NO:9, SEQ ID NO:12, SEQ ID NO:17, SEQ ID NO:19, SEQ ID NO:21, SEQ ID NO:23, SEQ ID NO:25, SEQ ID NO:27, SEQ ID NO:29, and SEQ ID NO:31.

In one embodiment of the present invention, any of the above-described PUFA PKS amino acid sequences, as well as homologues of such sequences, can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

The present invention also includes an isolated nucleic acid molecule comprising a nucleic acid sequence encoding an amino acid sequence having a biological activity of at least one domain of a PUFA PKS system. In one aspect, such a nucleic acid sequence encodes a homologue of any of the *Schizochytrium* PUFA PKS ORFs or domains, including: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, wherein the homologue has a biological activity of at least one (or two, three, four or more) domain of a PUFA PKS system as described previously herein.

In one aspect of the invention, a homologue of a *Schizochytrium* PUFA PKS protein or domain encompassed by the present invention comprises an amino acid sequence that is at least about 60% identical to at least 500 consecutive amino acids of an amino acid sequence chosen from: SEQ ID NO:2, SEQ ID NO:4, and SEQ ID NO:6; wherein said amino acid sequence has a biological activity of at least one domain of a PUFA PKS system. In a further aspect, the amino acid sequence of the homologue is at least about 60% identical to at least about 600 consecutive amino acids, and more preferably to at least about 700 consecutive amino acids, and more preferably to at least about 800 consecutive amino acids, and more preferably to at least about 900 consecutive amino acids, and more preferably to at least about 1000 consecutive amino acids, and more preferably to at least about 1100 consecutive amino acids, and more preferably to at least about 1200 consecutive amino acids, and more preferably to at least about 1300 consecutive amino acids, and more preferably to at least about 1400 consecutive amino acids, and more preferably to at least about 1500 consecutive amino acids of any of SEQ ID NO:2, SEQ ID NO:4 and SEQ ID NO:6, or to the full length of SEQ ID NO:6. In a further aspect, the amino acid sequence of the homologue is at least about 60% identical to at least about 1600 consecutive amino acids, and more preferably to at least about 1700 consecutive amino acids, and more preferably to at least about 1800 consecutive amino acids, and more preferably to at least about 1900 consecutive amino acids, and more preferably to at least about 2000 consecutive amino acids of any of SEQ ID NO:2 or SEQ ID NO:4, or to the full length of SEQ ID NO:4. In a further aspect, the amino acid sequence of the homologue is at least about 60% identical to at least about 2100 consecutive amino acids, and more preferably to at least about 2200 consecutive amino acids, and more preferably to at least about 2300 consecutive amino acids, and more preferably to at least about 2400 consecutive amino acids, and more preferably to at least about 2500 consecutive amino acids, and more preferably to at least about 2600 consecutive amino acids, and more preferably to at least about 2700 consecutive amino acids, and more preferably to at least about 2800 consecutive amino acids, and even more preferably, to the full length of SEQ ID NO:2.

In another aspect, a homologue of a *Schizochytrium* PUFA PKS protein or domain encompassed by the present invention comprises an amino acid sequence that is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical to an amino acid sequence chosen from: SEQ ID NO:2, SEQ ID NO:4, or SEQ ID NO:6, over any of the consecutive amino acid lengths described in the paragraph above, wherein the amino acid sequence has a biological activity of at least one domain of a PUFA PKS system.

In one aspect of the invention, a homologue of a *Schizochytrium* PUFA PKS protein or domain encompassed by the present invention comprises an amino acid sequence that is at least about 60% identical to an amino acid sequence chosen from: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, wherein said amino acid sequence has a biological activity of at least one domain of a PUFA PKS system. In a further aspect, the amino acid sequence of the homologue is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical to an amino acid sequence chosen from: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, wherein the amino acid sequence has a biological activity of at least one domain of a PUFA PKS system.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

As used herein, unless otherwise specified, reference to a percent (%) identity refers to an evaluation of homology which is performed using: (1) a BLAST 2.0 Basic BLAST homology search using blastp for amino acid searches, blastn for nucleic acid searches, and blastX for nucleic acid searches and searches of translated amino acids in all 6 open reading frames, all with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST). It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:

Reward for match=1

Penalty for mismatch=−2

Open gap (5) and extension gap (2) penalties gap x_dropoff (50) expect (10) word size (11) filter (on)

For blastp, using 0 BLOSUM62 matrix:

Open gap (11) and extension gap (1) penalties gap x_dropoff (50) expect (10) word size (3) filter (on).

In another embodiment of the invention, an amino acid sequence having the biological activity of at least one domain of a PUFA PKS system of the present invention includes an amino acid sequence that is sufficiently similar to a naturally occurring PUFA PKS protein or polypeptide that a nucleic acid sequence encoding the amino acid sequence is capable of hybridizing under moderate, high, or very high stringency conditions (described below) to (i.e., with) a nucleic acid molecule encoding the naturally occurring PUFA PKS protein or polypeptide (i.e., to the complement of the nucleic acid strand encoding the naturally occurring PUFA PKS protein or polypeptide). Preferably, an amino acid sequence having the biological activity of at least one domain of a PUFA PKS system of the present invention is encoded by a nucleic acid sequence that hybridizes under moderate, high or very high stringency conditions to the complement of a nucleic acid sequence that encodes a protein comprising an amino acid sequence represented by any of SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, or SEQ ID NO:32.

In another embodiment of the invention, a nucleotide sequence of the present invention is a nucleotide sequence isolated from (obtainable from), identical to, or a homologue of, the nucleotide sequence from a *Schizochytrium*, wherein the nucleotide sequence from a *Schizochytrium* (including either strand of a DNA molecule from *Schizochytrium*) hybridizes under moderate, high, or very high stringency conditions to a nucleotide sequence encoding an amino acid sequence represented by any of SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. In one embodiment, the *Schizochytrium* is *Schizochytrium* ATCC 20888. In another embodiment, the *Schizochytrium* is a daughter strain of *Schizochytrium* 20888, including mutated strains thereof (e.g., N230D).

Methods to deduce a complementary sequence are known to those skilled in the art. It should be noted that since amino acid sequencing and nucleic acid sequencing technologies are not entirely error-free, the sequences presented herein, at best, represent apparent sequences of PUFA PKS domains and proteins of the present invention, or of the nucleotide sequences encoding such amino acid sequences.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M $Na^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M $Na^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

Yet another embodiment of the present invention includes a nucleic acid molecule comprising, consisting essentially of, or consisting of, a nucleic acid sequence that is identical to, or that is a homologue of (as defined above) the nucleic acid sequence of a cDNA plasmid clone selected from LIB3033-046-D2 (ATCC Accession No. PTA-7645), LIB3033-047-B5 (ATCC Accession No. PTA-7646), or LIB81-042-B9 (ATCC Accession No. PTA-7647). In another embodiment, the present invention includes a nucleic acid molecule comprising, consisting essentially of, or consisting of, a nucleic acid sequence that is identical to, or that is a homologue of (as defined above) the nucleic acid sequence of a genomic plasmid selected from: pJK1126 (ATCC Accession No. PTA-7648), pJK1129 (ATCC Accession No. PTA-7649), pJK1131 (ATCC Accession No. PTA-7650), pJK306 (ATCC Accession No. PTA-7641), pJK320 (ATCC Accession No. PTA-7644), pJK324 (ATCC Accession No. PTA-7643), or pBR002 (ATCC Accession No. PTA-7642).

Yet another embodiment of the present invention includes a nucleic acid molecule comprising, consisting essentially of, or consisting of, a nucleic acid sequence that encodes an amino acid sequence that is identical to, or that is a homologue of (as defined above) the amino acid sequence encoded by a cDNA plasmid clone selected from LIB3033-046-D2 (ATCC Accession No. PTA-7645), LIB3033-047-B5 (ATCC Accession No. PTA-7646), or LIB81-042-B9 (ATCC Accession No. PTA-7647). In another embodiment, the present invention includes a nucleic acid molecule comprising, consisting essentially of, or consisting of, a nucleic acid sequence that encodes an amino acid sequence that is identical to, or that is a homologue of (as defined above) the amino acid sequence encoded by a genomic plasmid selected from: pJK1126 (ATCC Accession No. PTA-7648), pJK1129 (ATCC Accession No. PTA-7649), pJK1131 (ATCC Accession No. PTA-7650), pJK306 (ATCC Accession No. PTA-7641), pJK320 (ATCC Accession No. PTA-7644), pJK324 (ATCC Accession No. PTA-7643), or pBR002 (ATCC Accession No. PTA-7642).

Another embodiment of the present invention includes a recombinant nucleic acid molecule comprising a recombinant vector and a nucleic acid molecule comprising a nucleic acid sequence encoding an amino acid sequence having a biological activity of at least one domain or protein of a PUFA PKS system as described herein. Such nucleic acid sequences and domains or proteins are described in detail above. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid molecules of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., a PUFA PKS domain) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete or inactivate an endogenous gene within the host cell or microorganism (i.e., used for targeted gene disruption or knock-out technology). Such a vector may also be known in the art as a "knock-out" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to bind to the target gene such that the target gene and the insert undergo homologous recombination, whereby the endogenous target gene is deleted, inactivated or attenuated (i.e., by at least a portion of the endogenous target gene being mutated or deleted).

Typically, a recombinant nucleic acid molecule includes at least one nucleic acid molecule of the present invention operatively linked to one or more transcription control sequences. As used herein, the phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to a transcription control sequence in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

The present inventors have found that the *Schizochytrium* PUFA PKS Orfs A and B are closely linked in the genome and region between the Orfs has been sequenced. The Orfs are oriented in opposite directions and 4244 base pairs separate the start (ATG) codons (i.e. they are arranged as follows: 3'OrfA5'-4244 bp-5'OrfB3'). Examination of the 4244 bp intergenic region did not reveal any obvious Orfs (no significant matches were found on a BlastX search). Both Orfs A and B are highly expressed in *Schizochytrium*, at least during the time of oil production, implying that active promoter elements are embedded in this intergenic region. These genetic elements are believed to have utility as a bi-directional promoter sequence for transgenic applications. For example, in a preferred embodiment, one could clone this region, place any genes of interest at each end and introduce the construct into *Schizochytrium* (or some other host in which the promoters can be shown to function). It is predicted that the regulatory elements, under the appropriate conditions, would provide for coordinated, high level expression of the two introduced genes. The complete nucleotide sequence for the regulatory region containing *Schizochytrium* PUFA PKS regulatory elements (e.g., a promoter) is represented herein as SEQ ID NO:36.

In a similar manner, OrfC is highly expressed in *Schizochytrium* during the time of oil production and regulatory elements are expected to reside in the region upstream of its start codon. A region of genomic DNA upstream of OrfC has been cloned and sequenced and is represented herein as (SEQ ID NO:37). This sequence contains the 3886 nt immediately upstream of the OrfC start codon. Examination of this region did not reveal any obvious Orfs (i.e., no significant matches were found on a BlastX search). It is believed that regulatory elements contained in this region, under the appropriate conditions, will provide for high-level expression of a gene placed behind them. Additionally, under the appropriate conditions, the level of expression may be coordinated with genes under control of the A-B intergenic region (SEQ ID NO:36).

Therefore, in one embodiment, a recombinant nucleic acid molecule useful in the present invention, as disclosed herein, can include a PUFA PKS regulatory region contained within SEQ ID NO:36 and/or SEQ ID NO:37. Such a regulatory region can include any portion (fragment) of SEQ ID NO:36 and/or SEQ ID NO:37 that has at least basal PUFA PKS transcriptional activity (at least basal promoter activity).

One or more recombinant molecules of the present invention can be used to produce an encoded product (e.g., a PUFA PKS domain, protein, or system) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one other recombinant nucleic acid molecule.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass transfection of animal cells, plant cells and transformation of microbial cells, to the extent that the terms pertain to the introduction of exogenous nucleic acids into a cell. Therefore, transfection techniques include, but are not limited to, transformation, particle bombardment, electroporation, microinjection, lipofection, adsorption, infection and protoplast fusion.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

General discussion above with regard to recombinant nucleic acid molecules and transfection of host cells is intended to be applied to any recombinant nucleic acid molecule discussed herein, including those encoding any amino acid sequence having a biological activity of at least one domain from a PUFA PKS, those encoding amino acid sequences from other PKS systems, and those encoding other proteins or domains.

This invention also relates to PUFA PKS systems (and proteins or domains thereof) from microorganisms other than those described specifically herein that are homologous in structure, domain organization and/or function to a *Schizochytrium* PUFA PKS system (and proteins or domains thereof) as described herein. In one embodiment, the microorganism is a non-bacterial microorganism, and preferably, the microorganism is a eukaryotic microorganism. In addition, this invention relates to use of these microorganisms and the PUFA PKS systems or components thereof from these microorganisms in the various applications for a PUFA PKS system (e.g., genetically modified organisms and methods of producing bioactive molecules) according to the present invention. Such microorganisms have the following characteristics: (a) produces at least one PUFA; and (b) has an ability to produce increased PUFAs under dissolved oxygen conditions of less than about 5% of saturation in the fermentation medium, as compared to production of PUFAs by said microorganism under dissolved oxygen conditions of greater than 5% of saturation, more preferably 10% of saturation, more preferably greater than 15% of saturation and more preferably greater than 20% of saturation in the fermentation medium. A screening process for identification of microorganisms comprising a PUFA PKS system is described in detail in U.S. Patent Application Publication No. 20020194641, supra. The knowledge of the structure and function of the PUFA PKS proteins and domains described herein, and the nucleotide sequence encoding the same, are useful tools for the identification, confirmation, and/or isolation of homologues of such proteins or polynucleotides.

According to the present invention, the term "Thraustochytrid" refers to any members of the order Thraustochytriales, which includes the family Thraustochytriaceae, and the term "Labyrinthulid" refers to any member of the order Labyrinthulales, which includes the family Labyrinthulaceae. The members of the family Labyrinthulaceae have been considered to be members of the order Thraustochytriales, but in revisions of the taxonomy of such organisms, the family is now considered to be a member of the order Labyrinthulales, and both Labyrinthulales and Thraustochytriales are considered to be members of the phylum Labyrinthulomycota.

Developments have resulted in frequent revision of the taxonomy of the Thraustochytrids (thraustochytrids). Taxonomic theorists generally place Thraustochytrids with the algae or algae-like protists. However, because of taxonomic uncertainty, it would be best for the purposes of the present invention to consider the strains described in the present invention as Thraustochytrids to include the following organisms: Order: Thraustochytriales; Family: Thraustochytriaceae; Genera: *Thraustochytrium* (Species: sp., *arudimentale, aureum, benthicola, globosum, kinnei, motivum, multirudimentale, pachydermum, proliferum, roseum, striatum*), *Ulkenia* (previously considered by some to be a member of *Thraustochytrium*) (Species: sp., *amoeboidea, kerguelensis, minuta, profunda, radiata, sailens, sarkariana, schizochytrops, visurgensis, yorkensis*), *Schizochytrium* (Species: sp., *aggregatum, limnaceum, mangrovei, minutum, octosporum*), *Japonochytrium* (Species: sp., *marinum*), *Aplanochytrium* (Species: sp., *haliotidis, kerguelensis, profunda, stocchinoi*), *Althornia* (Species: sp., *crouchii*), or *Elina* (Species: sp., *marisalba, sinorifica*).

Strains described in the present invention as Labyrinthulids include the following organisms: Order: Labyrinthulales, Family: Labyrinthulaceae, Genera: *Labyrinthula* (Species: sp., *algeriensis, coenocystis, chattonii, macrocystis, macrocystis atlantica, macrocystis macrocystis, marina, minuta, roscoffensis, valkanovii, vitellina, vitellina pacifica, vitellina vitellina, zopfii*), *Labyrinthuloides* (Species: sp., *haliotidis, yorkensis*), *Labyrinthomyxa* (Species: sp., *marina*), *Diplophrys* (Species: sp., *archeri*), *Pyrrhosorus* (Species: sp., *marinus*), *Sorodiplophrys* (Species: sp., *stercorea*) or *Chlamydomyxa* (Species: sp., *labyrinthuloides,*

*montana*) (although there is currently not a consensus on the exact taxonomic placement of *Pyrrhosorus, Sorodiplophrys* or *Chlamydomyxa*).

It is recognized that at the time of this invention, revision in the taxonomy of Thraustochytrids places the genus *Labyrinthuloides* in the family of Labyrinthulaceae and confirms the placement of the two families Thraustochytriaceae and Labyrinthulaceae within the Stramenopile lineage. It is noted that the Labyrinthulaceae are sometimes commonly called labyrinthulids or labyrinthula, or labyrinthuloides and the Thraustochytriaceae are commonly called thraustochytrids.

To produce significantly high yields of various bioactive molecules using the PUFA PKS system of the present invention, an organism, preferably a microorganism or a plant, can be genetically modified to affect the activity of a PUFA PKS system. In one aspect, such an organism can endogenously contain and express a PUFA PKS system, and the genetic modification can be a genetic modification of one or more of the functional domains of the endogenous PUFA PKS system, whereby the modification has some effect on the activity of the PUFA PKS system. In another aspect, such an organism can endogenously contain and express a PUFA PKS system, and the genetic modification can be an introduction of at least one exogenous nucleic acid sequence (e.g., a recombinant nucleic acid molecule), wherein the exogenous nucleic acid sequence encodes at least one biologically active domain or protein from the same or a second PKS system and/or a protein that affects the activity of said PUFA PKS system (e.g., a phosphopantetheinyl transferases (PPTase), discussed below). In yet another aspect, the organism does not necessarily endogenously (naturally) contain a PUFA PKS system, but is genetically modified to introduce at least one recombinant nucleic acid molecule encoding an amino acid sequence having the biological activity of at least one domain of a PUFA PKS system. In this aspect, PUFA PKS activity is affected by introducing or increasing PUFA PKS activity in the organism. Various embodiments associated with each of these aspects will be discussed in greater detail below.

Therefore, according to the present invention, one embodiment relates to a genetically modified microorganism, wherein the microorganism expresses a PKS system comprising at least one biologically active domain of a polyunsaturated fatty acid (PUFA) polyketide synthase (PKS) system. The at least one domain of the PUFA PKS system is encoded by a nucleic acid sequence described herein. The genetic modification affects the activity of the PKS system in the organism. The genetically modified microorganism can include any one or more of the above-identified nucleic acid sequences, and/or any of the other homologues of any of the *Schizochytrium* PUFA PKS ORFs or domains as described in detail above.

As used herein, a genetically modified microorganism can include a genetically modified bacterium, protist, microalgae, fungus, or other microbe, and particularly, any of the genera of the order Thraustochytriales (e.g., a Thraustochytrid) described herein. Such a genetically modified microorganism has a genome which is modified (i.e., mutated or changed) from its normal (i.e., wild-type or naturally occurring) form such that the desired result is achieved (i.e., increased or modified PUFA PKS activity and/or production of a desired product using the PUFA PKS system or component thereof). Genetic modification of a microorganism can be accomplished using classical strain development and/or molecular genetic techniques. Such techniques known in the art and are generally disclosed for microorganisms, for example, in Sambrook et al., 1989, *Molecular Cloning: A Laboratory Manual*, Cold Spring Harbor Labs Press. The reference Sambrook et al., ibid., is incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

Preferred microorganism host cells to modify according to the present invention include, but are not limited to, any bacteria, protist, microalga, fungus, or protozoa. In one aspect, preferred microorganisms to genetically modify include, but are not limited to, any microorganism of the order Thraustochytriales or any microorganism of the order Labyrinthulales. Particularly preferred host cells for use in the present invention could include microorganisms from a genus including, but not limited to: *Thraustochytrium, Ulkenia, Schizochytrium, Japonochytrium, Aplanochytrium, Althornia, Elina, Labyrinthula, Labyrinthuloides, Labyrinthomyxa, Diplophrys, Pyrrhosorus, Sorodiplophrys* or *Chlamydomyxa*. Other examples of suitable host microorganisms for genetic modification include, but are not limited to, yeast including *Saccharomyces cerevisiae, Saccharomyces carlsbergensis*, or other yeast such as *Candida, Kluyveromyces*, or other fungi, for example, filamentous fungi such as *Aspergillus, Neurospora, Penicillium*, etc. Bacterial cells also may be used as hosts. This includes *Escherichia coli*, which can be useful in fermentation processes. Alternatively, a host such as a *Lactobacillus* species or *Bacillus* species can be used as a host.

Another embodiment of the present invention relates to a genetically modified plant or part of a plant (e.g., wherein the plant has been genetically modified to express a PUFA PKS system described herein), which includes at least the core PUFA PKS enzyme complex and, in one embodiment, at least one PUFA PKS accessory protein, (e.g., a PPTase), so that the plant produces PUFAs. Preferably, the plant is an oil seed plant, wherein the oil seeds or oil in the oil seeds contain PUFAs produced by the PUFA PKS system. Such oils contain a detectable amount of at least one target or primary PUFA that is the product of the PUFA PKS system. Plants are not known to endogenously contain a PUFA PKS system, and therefore, the PUFA PKS systems of the present invention represent an opportunity to produce plants with unique fatty acid production capabilities. It is a particularly preferred embodiment of the present invention to genetically engineer plants to produce one or more PUFAs in the same plant, including, EPA, DHA, DPA, ARA, GLA, SDA and others. The present invention offers the ability to create any one of a number of "designer oils" in various ratios and forms. Moreover, the disclosure of the PUFA PKS genes from the particular marine organisms described herein offer the opportunity to more readily extend the range of PUFA production and successfully produce such PUFAs within temperature ranges used to grow most crop plants.

Methods for the genetic engineering of plants are well known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763.

Another generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.,* 4:2731 (1985), Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., *In Abstracts of VIIth International Congress on Plant Cell and Tissue Culture IAPTC, A*2-38, p. 53 (1990); D'Halluin et al., *Plant Cell* 4:1495-1505 (1992) and Spencer et al., *Plant Mol. Biol.* 24:51-61 (1994).

As used herein, a genetically modified plant can include any genetically modified plant including higher plants and particularly, any consumable plants or plants useful for producing a desired bioactive molecule of the present invention. "Plant parts", as used herein, include any parts of a plant, including, but not limited to, seeds (immature or mature), oils, pollen, embryos, flowers, fruits, shoots, leaves, roots, stems, explants, etc. A genetically modified plant has a genome that is modified (i.e., mutated or changed) from its normal (i.e., wild-type or naturally occurring) form such that the desired result is achieved (e.g., PUFA PKS activity and production of PUFAs). Genetic modification of a plant can be accomplished using classical strain development and/or molecular genetic techniques. Methods for producing a transgenic plant, wherein a recombinant nucleic acid molecule encoding a desired amino acid sequence is incorporated into the genome of the plant, are known in the art. A preferred plant to genetically modify according to the present invention is preferably a plant suitable for consumption by animals, including humans.

Preferred plants to genetically modify according to the present invention (i.e., plant host cells) include, but are not limited to any higher plants, including both dicotyledonous and monocotyledonous plants, and particularly consumable plants, including crop plants and especially plants used for their oils. Such plants can include, for example: canola, soybeans, rapeseed, linseed, corn, safflowers, sunflowers and tobacco. Other preferred plants include those plants that are known to produce compounds used as pharmaceutical agents, flavoring agents, nutraceutical agents, functional food ingredients or cosmetically active agents or plants that are genetically engineered to produce these compounds/agents.

According to the present invention, a genetically modified microorganism or plant includes a microorganism or plant that has been modified using recombinant technology. As used herein, genetic modifications that result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications that result in an increase in gene expression or function can be referred to as amplification, overproduction, overexpression, activation, enhancement, addition, or up-regulation of a gene.

The genetic modification of a microorganism or plant according to the present invention preferably affects the activity of the PKS system expressed by the plant, whether the PKS system is endogenous and genetically modified, endogenous with the introduction of recombinant nucleic acid molecules into the organism, or provided completely by recombinant technology. According to the present invention, to "affect the activity of a PKS system" includes any genetic modification that causes any detectable or measurable change or modification in the PKS system expressed by the organism as compared to in the absence of the genetic modification. A detectable change or modification in the PKS system can include, but is not limited to: the introduction of PKS system activity into an organism such that the organism now has measurable/detectable PKS system activity (i.e., the organism did not contain a PKS system prior to the genetic modification), the introduction into the organism of a functional domain from a different PKS system than a PKS system endogenously expressed by the organism such that the PKS system activity is modified (e.g., a bacterial PUFA PKS domain or a type I PKS domain is introduced into an organism that endogenously expresses a non-bacterial PUFA PKS system), a change in the amount of a bioactive molecule produced by the PKS system (e.g., the system produces more (increased amount) or less (decreased amount) of a given product as compared to in the absence of the genetic modification), a change in the type of a bioactive molecule produced by the PKS system (e.g., the system produces a new or different product, or a variant of a product that is naturally produced by the system), and/or a change in the ratio of multiple bioactive molecules produced by the PKS system (e.g., the system produces a different ratio of one PUFA to another PUFA, produces a completely different lipid profile as compared to in the absence of the genetic modification, or places various PUFAs in different positions in a triacylglycerol as compared to the natural configuration). Such a genetic modification includes any type of genetic modification and specifically includes modifications made by recombinant technology and by classical mutagenesis.

It should be noted that reference to increasing the activity of a functional domain or protein in a PUFA PKS system refers to any genetic modification in the organism containing the domain or protein (or into which the domain or protein is to be introduced) which results in increased functionality of the domain or protein system and can include higher activity of the domain or protein (e.g., specific activity or in vivo enzymatic activity), reduced inhibition or degradation of the domain or protein system, and overexpression of the domain or protein. For example, gene copy number can be increased, expression levels can be increased by use of a promoter that gives higher levels of expression than that of the native promoter, or a gene can be altered by genetic engineering or classical mutagenesis to increase the activity of the domain or protein encoded by the gene.

Similarly, reference to decreasing the activity of a functional domain or protein in a PUFA PKS system refers to any genetic modification in the organism containing such domain or protein (or into which the domain or protein is to be introduced) which results in decreased functionality of the domain or protein and includes decreased activity of the domain or protein, increased inhibition or degradation of the domain or protein and a reduction or elimination of expression of the domain or protein. For example, the action of domain or protein of the present invention can be decreased by blocking or reducing the production of the domain or protein, "knocking out" the gene or portion thereof encoding the domain or protein, reducing domain or protein activity, or inhibiting the activity of the domain or protein. Blocking or reducing the production of a domain or protein can include placing the gene encoding the domain or protein under the control of a promoter that requires the presence of an inducing compound in the growth medium. By establishing conditions such that the inducer becomes depleted from the medium, the expression of the gene encoding the domain or protein (and therefore, of protein synthesis) could be turned off. Blocking or reducing the activity of domain or protein could also include using an excision technology approach similar to that described in U.S. Pat. No. 4,743,546, incorporated herein by reference. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In one embodiment of the present invention, a genetic modification includes a modification of a nucleic acid sequence encoding an amino acid sequence that has a biological activity of at least one domain of a non-bacterial PUFA PKS system as described herein. Such a modification can be to an amino acid sequence within an endogenously (naturally) expressed non-bacterial PUFA PKS system, whereby a microorganism that naturally contains such a system is genetically modified by, for example, classical mutagenesis and selection techniques and/or molecular genetic techniques, include genetic engineering techniques. Genetic engineering techniques can include, for example, using a targeting recombinant vector to delete a portion of an endogenous gene, or to replace a portion of an endogenous gene with a heterologous sequence. Examples of heterologous sequences that could be introduced into a host genome include sequences encoding at least one functional domain from another PKS system, such as a different non-bacterial PUFA PKS system, a bacterial PUFA PKS system, a type I PKS system, a type II PKS system, or a modular PKS system. Other heterologous sequences to introduce into the genome of a host includes a sequence encoding a protein or functional domain that is not a domain of a PKS system, but which will affect the activity of the endogenous PKS system. For example, one could introduce into the host genome a nucleic acid molecule encoding a phosphopantetheinyl transferase (discussed below). Specific modifications that could be made to an endogenous PUFA PKS system are discussed in detail below.

In another aspect of this embodiment of the invention, the genetic modification can include: (1) the introduction of a recombinant nucleic acid molecule encoding an amino acid sequence having a biological activity of at least one domain of a non-bacterial PUFA PKS system; and/or (2) the introduction of a recombinant nucleic acid molecule encoding a protein or functional domain that affects the activity of a PUFA PKS system, into a host. The host can include: (1) a host cell that does not express any PKS system, wherein all functional domains of a PKS system are introduced into the host cell, and wherein at least one functional domain is from a non-bacterial PUFA PKS system; (2) a host cell that expresses a PKS system (endogenous or recombinant) having at least one functional domain of a non-bacterial PUFA PKS system, wherein the introduced recombinant nucleic acid molecule can encode at least one additional non-bacterial PUFA PKS domain function or another protein or domain that affects the activity of the host PKS system; and (3) a host cell that expresses a PKS system (endogenous or recombinant) which does not necessarily include a domain function from a non-bacterial PUFA PKS, and wherein the introduced recombinant nucleic acid molecule includes a nucleic acid sequence encoding at least one functional domain of a non-bacterial PUFA PKS system. In other words, the present invention intends to encompass any genetically modified organism (e.g., microorganism or plant), wherein the organism comprises at least one non-bacterial PUFA PKS domain function (either endogenously or by recombinant modification), and wherein the genetic modification has a measurable effect on the non-bacterial PUFA PKS domain function or on the PKS system when the organism comprises a functional PKS system.

Therefore, using the PUFA PKS systems of the present invention, gene mixing can be used to extend the range of PUFA products (and ratios thereof) to include EPA, DPA, DHA, ARA, GLA, SDA and others, as well as to produce a wide variety of bioactive molecules, including antibiotics, other pharmaceutical compounds, and other desirable products. The method to obtain these bioactive molecules includes not only the mixing of genes from various organisms but also various methods of genetically modifying the non-bacterial PUFA PKS genes disclosed herein. Knowledge of the genetic basis and domain structure of the non-bacterial PUFA PKS system of the present invention provides a basis for designing novel genetically modified organisms which produce a variety of bioactive molecules. Although mixing and modification of any PKS domains and related genes are contemplated by the present inventors, by way of example, various possible manipulations of the PUFA-PKS system are discussed in U.S. Patent Application Publication No. 20020194641, U.S. Patent Application Publication No. 20040235127, and U.S. Patent Application Publication No. 20050100995, supra with regard to genetic modification and bioactive molecule production.

The comparison of the *Schizochytrium* PUFA PKS architecture (domain organization) with other PUFA PKS system architecture illustrates nature's ability to alter domain order as well as incorporate new domains to create novel end products. In addition, the genes can now be manipulated in the laboratory to create new products. Proposed herein is the manipulation of PUFA PKS systems in either a directed or random way to influence the end products. For example, in a preferred embodiment, one could envision substituting one of the DH (FabA-like) domains of the PUFA-PKS system for a DH domain that did not posses isomerization activity, potentially creating a molecule with a mix of cis- and trans-double bonds. The current products of the *Schizochytrium* PUFA PKS system are DHA and DPA (C22:5 ω6). If one manipulated the system to produce C20 fatty acids, one would expect the products to be EPA and ARA (C20:4 ω6). This could provide a new source for ARA. One could also substitute domains from related PUFA-PKS systems that produced a different DHA to DPA ratio, for example, by using genes from *Thraustochytrium* 23B.

Additionally, one could envision specifically altering one of the ER domains (e.g. removing, or inactivating) in the *Schizochytrium* PUFA PKS system (other PUFA PKS systems described so far do not have two ER domains) to affect the end product profile. Similar strategies could be attempted in a directed manner for each of the distinct domains of the PUFA-PKS proteins using more or less sophisticated approaches. Of course one would not be limited to the manipulation of single domains. Finally, one could extend the approach by mixing domains from the PUFA-PKS system and other PKS or FAS systems (e.g., type I, type II, type III) to create an entire range of new end products. For example, one could introduce the PUFA-PKS DH domains into systems that do not normally incorporate cis double bonds into their end products.

Accordingly, encompassed by the present invention are methods to genetically modify microbial or plant cells by: genetically modifying at least one nucleic acid sequence in the organism that encodes an amino acid sequence having the biological activity of at least one functional domain of a PUFA PKS system according to the present invention, and/or expressing at least one recombinant nucleic acid molecule comprising a nucleic acid sequence encoding such amino acid sequence. Various embodiments of such sequences, methods to genetically modify an organism, and specific modifications have been described in detail above. Typically, the method is used to produce a particular genetically modified organism that produces a particular bioactive molecule or molecules.

In one embodiment of the present invention, it is contemplated that a mutagenesis program could be combined with a selective screening process to obtain bioactive molecules of interest. This would include methods to search for a range of bioactive compounds. This search would not be restricted to production of those molecules with cis double bonds. The mutagenesis methods could include, but are not limited to: chemical mutagenesis, gene shuffling, switching regions of the genes encoding specific enzymatic domains, or mutagenesis restricted to specific regions of those genes, as well as other methods.

For example, high throughput mutagenesis methods could be used to influence or optimize production of the desired bioactive molecule. Once an effective model system has been developed, one could modify these genes in a high throughput manner. Utilization of these technologies can be envisioned on two levels. First, if a sufficiently selective screen for production of a product of interest (e.g., ARA) can be devised, it could be used to attempt to alter the system to produce this product (e.g., in lieu of, or in concert with, other strategies such as those discussed above). Additionally, if the strategies outlined above resulted in a set of genes that did produce the product of interest, the high throughput technologies could then be used to optimize the system. For example, if the introduced domain only functioned at relatively low temperatures, selection methods could be devised to permit removing that limitation. In one embodiment of the invention, screening methods are used to identify additional non-bacterial organisms having novel PKS systems similar to the PUFA PKS system of *Schizochytrium*, as described herein (see above). Homologous PKS systems identified in such organisms can be used in methods similar to those described herein for the *Schizochytrium*, as well as for an additional source of genetic material from which to create, further modify and/or mutate a PUFA PKS system for expression in that microorganism, in another microorganism, or in a higher plant, to produce a variety of compounds.

It is recognized that many genetic alterations, either random or directed, which one may introduce into a native (endogenous, natural) PUFA PKS system, will result in an inactivation of enzymatic functions. A preferred embodiment of the invention includes a system to select for only those modifications that do not block the ability of the PUFA PKS system to produce a product. For example, the FabB-strain of *E. coli* is incapable of synthesizing unsaturated fatty acids and requires supplementation of the medium with fatty acids that can substitute for its normal unsaturated fatty acids in order to grow (see Metz et al., 2001, supra). However, this requirement (for supplementation of the medium) can be removed when the strain is transformed with a functional PUFA-PKS system (i.e. one that produces a PUFA product in the *E. coli* host—see (Metz et al., 2001, supra, FIG. 2A). The transformed FabB-strain now requires a functional PUFA-PKS system (to produce the unsaturated fatty acids) for growth without supplementation. The key element in this example is that production of a wide range of unsaturated fatty acid will suffice (even unsaturated fatty acid substitutes such as branched chain fatty acids). Therefore, in another preferred embodiment of the invention, one could create a large number of mutations in one or more of the PUFA PKS genes disclosed herein, and then transform the appropriately modified FabB-strain (e.g. create mutations in an expression construct containing an ER domain and transform a FabB-strain having the other essential domains on a separate plasmid—or integrated into the chromosome) and select only for those transformants that grow without supplementation of the medium (i.e., that still possessed an ability to produce a molecule that could complement the FabB-defect). Additional screens could be developed to look for particular compounds (e.g. use of GC for fatty acids) being produced in this selective subset of an active PKS system. One could envision a number of similar selective screens for bioactive molecules of interest.

In one embodiment of invention, a genetically modified organism has a modification that changes at least one product produced by the endogenous PKS system, as compared to a wild-type organism.

In one embodiment, a genetically modified organism has been modified by transfecting the organism with a recombinant nucleic acid molecule encoding a protein that regulates the chain length of fatty acids produced by the PUFA PKS system. For example, the protein that regulates the chain length of fatty acids produced by the PUFA PKS system can be a chain length factor that directs the synthesis of C20 units or C22 units.

In another embodiment, a genetically modified organism expresses a PUFA PKS system comprising a genetic modification in a domain selected from the group consisting of a domain encoding β-hydroxy acyl-ACP dehydrase (DH) and a domain encoding β-ketoacyl-ACP synthase (KS), wherein the modification alters the ratio of long chain fatty acids produced by the PUFA PKS system as compared to in the absence of the modification. In one aspect of this embodiment, the modification is selected from the group consisting of a deletion of all or a part of the domain, a substitution of a homologous domain from a different organism for the domain, and a mutation of the domain.

In another embodiment, a genetically modified organism expresses a PUFA PKS system comprising a modification in an enoyl-ACP reductase (ER) domain, wherein the modification results in the production of a different compound as compared to in the absence of the modification. In one aspect of this embodiment, the modification is selected from the group consisting of a deletion of all or a part of the ER domain, a substitution of an ER domain from a different organism for the ER domain, and a mutation of the ER domain.

In one embodiment of the invention, the genetically modified organism produces a polyunsaturated fatty acid (PUFA) profile that differs from the naturally occurring organism without a genetic modification.

Many other genetic modifications useful for producing bioactive molecules will be apparent to those of skill in the art, given the present disclosure, and various other modifications have been discussed previously herein. The present invention contemplates any genetic modification related to a PUFA PKS system as described herein which results in the production of a desired bioactive molecule.

As described above, in one embodiment of the present invention, a genetically modified microorganism or plant includes a microorganism or plant which has an enhanced ability to synthesize desired bioactive molecules (products) or which has a newly introduced ability to synthesize specific products (e.g., to synthesize a specific antibiotic). According to the present invention, "an enhanced ability to synthesize" a product refers to any enhancement, or up-regulation, in a pathway related to the synthesis of the product such that the microorganism or plant produces an increased amount of the product (including any production of a product where there was none before) as compared to the wild-type microorganism or plant, cultured or grown, under the same conditions. Methods to produce such genetically modified organisms have been described in detail above. In one preferred embodiment, the present invention relates to a genetically modified plant or part of a plant (e.g., wherein the plant has been genetically modified to express a PUFA PKS system described herein), which includes at least the core PUFA PKS enzyme complex and, in one embodiment, at least one PUFA PKS accessory protein, (e.g., a PPTase), so that the plant produces PUFAs. Preferably, the plant is an oil seed plant, wherein the oil seeds or oil in the oil seeds contain PUFAs produced by the PUFA PKS system. Such oils contain a detectable amount of at least one target or primary PUFA that is the product of the PUFA PKS system.

The present inventors demonstrate herein the production of PUFAs in a plant that has been genetically modified to express the genes encoding a PUFA PKS system from *Schizochytrium* of the present invention and a PUFA PKS accessory enzyme, 4'-phosphopantetheinyl transferase (PPTase). The oils produced by these plants contain significant quantities of both DHA (docosahexaenoic acid (C22:6, n-3)) and DPA (docosapentaenoic acid (C22:5, n-6), which are the predominant PUFAs (the primary PUFAs) produced by the *Schizochytrium* from which the PUFA PKS genes were derived. Significantly, oils from plants that produce PUFAs using the PUFA PKS pathway have a different fatty acid profile than plants that are genetically engineered to produce the same PUFAs by the "standard" pathway described above. In particular, oils from plants that have been genetically engineered to produce specific PUFAs by the PUFA PKS pathway are substantially free of the various intermediate products and side products that accumulate in oils that are produced as a result of the use of the standard PUFA synthesis pathway. This characteristic is discussed in detail below.

More particularly, efforts to produce long chain PUFAs in plants by the "standard" pathway have all taken the same basic approach, which is dictated by this synthesis pathway. These efforts relied on modification of the plants' endogenous fatty acids by introduction of genes encoding various elongases and desaturases. Plants typically produce 18 carbon fatty acids (e.g., oleic acid, linoleic acid, linolenic acid) via the Type II fatty acid synthase (FAS) in its plastids. Often, a single double bond is formed while that fatty acid is attached to ACP, and then the oleic acid (18:1) is cleaved from the ACP by the action of an acyl-ACP thioesterase. The free fatty acid is exported from the plastid and converted to an acyl-CoA. The 18:1 can be esterified to phosphatidylcholine (PC) and up to two more cis double bonds can be added. The newly introduced elongases can utilize substrates in the acyl-CoA pool to add carbons in two-carbon increments. Newly introduced desaturases can utilize either fatty acids esterified to PC, or those in the acyl-CoA pool, depending on the source of the enzyme. One consequence of this scheme for long chain PUFA production, however, is that intermediates or side products in the pathway accumulate, which often represent the majority of the novel fatty acids in the plant oil, rather than the target long chain PUFA.

For example, using the standard or classical pathway as described above, when the target PUFA product (i.e., the PUFA product that one is targeting for production, trying to produce, attempting to produce, by using the standard pathway) is DHA or EPA, for example (e.g., produced using elongases and desaturases that will produce the DHA or EPA from the products of the FAS system), a variety of intermediate products and side products will be produced in addition to the DHA or EPA, and these intermediate or side products frequently represent the majority of the products produced by the pathway, or are at least present in significant amounts in the lipids of the production organism. Such intermediate and side products include, but are not limited to, fatty acids having fewer carbons and/or fewer double bonds than the target, or primary PUFA, and can include unusual fatty acid side products that may have the same number of carbons as the target or primary PUFA, but which may have double bonds in unusual positions. By way of example, in the production of EPA using the standard pathway (e.g., see U.S. Patent Application Publication 2004/0172682), while the target PUFA of the pathway is EPA (i.e., due to the use of elongases and desaturases that specifically act on the products of the FAS system to produce EPA), the oils produced by the system include a variety of intermediate and side products including: gamma-linolenic acid (GLA; 18:3, n-6); stearidonic acid (STA or SDA; 18:4, n-3); dihomo-gamma-linolenic acid (DGLA or HGLA; 20:3, n-6), arachidonic acid (ARA, C20:4, n-6); eicosatrienoic acid (ETA; 20:3, n-9) and various other intermediate or side products, such as 20:0; 20:1 (Δ5); 20:1 (Δ11); 20:2 (Δ8,11); 20:2 (Δ11,14); 20:3 (Δ5,11,14); 20:3 (Δ11,14,17); mead acid (20:3; Δ5,8,11); or 20:4 (Δ5,1,14,17). Intermediates of the system can also include long chain PUFAs that are not the target of the genetic modification (e.g., a standard pathway enzyme system for producing DHA can actually produce more EPA as an intermediate product than DHA).

In contrast, the PUFA PKS synthase of the present invention does not utilize the fatty acid products of FAS systems. Instead, it produces the final PUFA product (the primary PUFA product) from the same small precursor molecule that is utilized by FASs and elongases (malonyl-CoA). Therefore, intermediates in the synthesis cycle are not released in any significant amount, and the PUFA product (also referred to herein as the primary PUFA product) is efficiently transferred to phospholipids (PL) and triacylglycerol (TAG) fractions of the lipids. Indeed, a PUFA PKS system may produce two target or primary PUFA products (e.g., the PUFA PKS system from *Schizochytrium* produces both DHA and DPA n-6 as primary products), but DPA is not an intermediate in the pathway to produce DHA. Rather, each is a separate product of the same PUFA PKS system. Therefore, the PUFA PKS genes of the present invention are an excellent means of producing oils containing PUFAs, and particularly, LCPUFAs in a heterologous host, such as a plant, wherein the oils are substantially free (defined below) of the intermediates and side products that contaminate oils produced by the "standard" PUFA pathway.

Therefore, it is an object of the present invention to produce, via the genetic manipulation of plants as described herein, polyunsaturated fatty acids and, by extension, oils obtained from such plants (e.g., obtained from the oil seeds of such plants) comprising these PUFAs. Examples of PUFAs that can be produced by the present invention include, but are not limited to, DHA (docosahexaenoic acid (C22:6, n-3)), ARA (eicosatetraenoic acid or arachidonic acid (C20:4, n-6)), DPA (docosapentaenoic acid (C22:5, n-6 or n-3)), and EPA (eicosapentaenoic acid (C20:5, n-3)). The present invention allows for the production of commercially valuable lipids enriched in one or more desired (target or primary) PUFAs by the present inventors' development of genetically modified plants through the use of the polyketide synthase system of the present invention, as well as components thereof, that produces PUFAs.

According to the present invention, reference to a "primary PUFA", "target PUFA", "intended PUFA", or "desired PUFA" refers to the particular PUFA or PUFAs that are the intended product of the enzyme pathway that is used to produce the PUFA(s). For example, when using elongases and desaturases to modify products of the FAS system in the classical pathway for PUFA production, one can select particular combinations of elongases and desaturases that, when used together, will produce a target or desired PUFA (e.g., DHA or EPA). As discussed above, such target or desired PUFA produced by the standard pathway may not actually be a "primary" PUFA in terms of the amount of PUFA as a percentage of total fatty acids produced by the system, due to the formation of intermediates and side products that can actually represent the majority of products produced by the system. However, one may use the term "primary PUFA" even in that instance to refer to the target or intended PUFA product produced by the elongases or desaturases used in the system.

In contrast to the classical pathway for PUFA production, when using a PUFA PKS system, a given PUFA PKS system derived from a particular organism (or created from combining proteins and domains from PUFA PKS systems) will produce particular PUFA(s), such that selection of a PUFA PKS system from a particular organism will result in the production of specified target or primary PUFAs. For example, use of a PUFA PKS system from *Schizochytrium* according to the present invention will result in the production of DHA and DPAn-6 as the target or primary PUFAs. However, as discussed above, the use of various proteins and domains with proteins and domains from other PUFA PKS systems or other PKS systems (that produce bioactive molecules other than PUFAs) can be combined ("mixed and matched") to result in the production of different PUFA profiles.

When using a PUFA PKS system of the present invention, oils produced by the organism, such as a plant, are substantially free of intermediate or side products that are not the target or primary PUFA products and that are not naturally produced by the endogenous FAS system in the wild-type organism (e.g., wild-type plants produce some shorter or medium chain PUFAs, such as 18 carbon PUFAs, via the FAS system, but there will be new, or additional, fatty acids produced in the plant as a result of genetic modification with a PUFA PKS system). In other words, as compared to the profile of total fatty acids from the wild-type plant (not genetically modified) or the parent plant used as a recipient for the indicated genetic modification, the majority of additional fatty acids in the profile of total fatty acids produced by plants that have been genetically modified with the PUFA PKS system of the present invention (or a component thereof), comprise the target or intended PUFA products of the PUFA PKS system (i.e., the majority of additional fatty acids in the total fatty acids that are produced by the genetically modified plant are the target PUFA(s)).

According to the present invention, reference to "intermediate products" or "side products" of an enzyme system that produces PUFAs refers to any products, and particularly, fatty acid products, that are produced by the enzyme system as a result of the production of the target or primary PUFA of the system. Intermediate and side products are particularly significant in the standard pathway for PUFA synthesis and are substantially less significant in the PUFA PKS pathway, as discussed above. It is noted that a primary or target PUFA of one enzyme system may be an intermediate of a different enzyme system where the primary or target product is a different PUFA, and this is particularly true of products of the standard pathway of PUFA production, since the PUFA PKS system of the present invention substantially avoids the production of intermediates. For example, when using the standard pathway to produce EPA, fatty acids such as GLA, DGLA and SDA are produced as intermediate products in significant quantities (e.g., U.S. Patent Application Publication 2004/0172682 illustrates this point). Similarly, and also illustrated by U.S. Patent Application Publication 2004/0172682, when using the standard pathway to produce DHA, in addition to the fatty acids mentioned above, ETA and EPA (notably the target PUFA in the first example above) are produced in significant quantities and in fact, may be present in significantly greater quantities relative to the total fatty acid product than the target PUFA itself. This latter point is shown in U.S. Patent Application Publication 2004/0172682, where a plant that was engineered to produce DHA by the standard pathway produces more EPA as a percentage of total fatty acids than DHA.

Furthermore, to be "substantially free" of intermediate or side products of the system for synthesizing PUFAs, or to not have intermediate or side products present in substantial amounts, means that any intermediate or side product fatty acids that are produced in the genetically modified plant (and/or parts of plants and/or seed oil fraction) as a result of the enzyme system for producing PUFAS (i.e., that are not produced by the wild-type plant or the parent plant used as a recipient for the indicated genetic modification), are present in a quantity that is less than about 10% by weight of the total fatty acids produced by the plant, and more preferably less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% by weight of the total fatty acids produced by the plant.

In a preferred embodiment, to be "substantially free" of intermediate or side products of the system for synthesizing PUFAs, or to not have intermediate or side products present in substantial amounts, means that any intermediate or side product fatty acids that are produced in the genetically modified plant (and/or parts of plants and/or seed oil fraction) as a result of the enzyme system for producing PUFAS (i.e., that are not produced by the wild-type plant or the parent plant used as a recipient for the indicated genetic modification), are present in a quantity that is less than about 10% by weight of the total additional fatty acids produced by the plant (additional fatty acids being those that are not produced by the wild-type plant or the parent plant used as a recipient for the indicated genetic modification), and more preferably less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% of the total additional fatty acids produced by the plant. Therefore, in contrast to the fatty acid profile of plants that have been genetically modified to produce PUFAs via the standard pathway, the majority of fatty acid products resulting from the genetic modification with a PUFA PKS system will be the target or intended fatty acid products.

When the target product of a PUFA PKS system is a long chain PUFA, such as DHA or DPA (n-6 or n-3) produced by the PUFA PKS system of the invention described herein, intermediate products and side products that are not present in substantial amounts in the total lipids of plants genetically modified with such PUFA PKS can include, but are not limited to: gamma-linolenic acid (GLA; 18:3, n-6); stearidonic acid (STA or SDA; 18:4, n-3); dihomo-gamma-linolenic acid (DGLA or HGLA; 20:3, n-6), arachidonic acid (ARA, C20:4, n-6); eicosatrienoic acid (ETA; 20:3, n-9) and various other intermediate or side products, such as 20:0; 20:1 (Δ5); 20:1 (Δ11); 20:2 (Δ8,11); 20:2 (Δ11,14); 20:3 (Δ5,11,14); 20:3 (Δ11,14,17); mead acid (20:3; Δ5,8,11); or 20:4 (Δ5,1,14,17). In addition, when the target product is a particular PUFA, such as DHA, the intermediate products and side products that are not present in substantial amounts in the total lipids of the genetically modified plants also include other PUFAs, including other PUFAs that are a natural product of a different PUFA PKS system, such as EPA in this example. It is to be noted that the PUFA PKS system of the present invention can also be used, if desired, to produce as a target PUFA a PUFA that can include GLA, SDA or DGLA (referring to embodiments where oils are produced using components of a PUFA PKS system described herein).

Using the knowledge of the genetic basis and domain structure of the PUFA PKS system described herein, the present inventors have designed and produced constructs encoding such a PUFA PKS system and have successfully produced transgenic plants expressing the PUFA PKS system. The transgenic plants produce oils containing PUFAs, and the oils are substantially free of intermediate products that accumulate in a standard PUFA pathway (see Example 3). The present inventors have also demonstrated the use of the constructs to produce PUFAs in another eukaryote, yeast, as a proof-of-concept experiment prior to the production of the transgenic plants (see Example 2). The examples demonstrate that transformation of both yeast and plants with a PUFA PKS system that produces DHA and DPAn-6 as the target PUFAs produces both of these PUFAs as the primary additional fatty acids in the total fatty acids of the plant (i.e., subtracting fatty acids that are produced in the wild-type plant), and in the yeast and further, that any other fatty acids that are not present in the fatty acids of the wild-type plant are virtually undetectable. Specific characteristics of genetically modified plants and parts and oils thereof of the present invention are described in detail elsewhere herein.

Accordingly, one embodiment of the present invention is a method to produce desired bioactive molecules (also referred to as products or compounds) by growing or culturing a genetically modified microorganism or a genetically modified plant of the present invention (described in detail above). Such a method includes the step of culturing in a fermentation medium or growing in a suitable environment, such as soil, a microorganism or plant, respectively, that has a genetic modification as described previously herein and in accordance with the present invention. In a preferred embodiment, method to produce bioactive molecules of the present invention includes the step of culturing under conditions effective to produce the bioactive molecule a genetically modified organism that expresses a PKS system comprising at least one biologically active domain of a polyunsaturated fatty acid (PUFA) polyketide synthase (PKS) system as described herein.

In the method of production of desired bioactive compounds of the present invention, a genetically modified microorganism is cultured or grown in a suitable medium, under conditions effective to produce the bioactive compound. An appropriate, or effective, medium refers to any medium in which a genetically modified microorganism of the present invention, when cultured, is capable of producing the desired product. Such a medium is typically an aqueous medium comprising assimilable carbon, nitrogen and phosphate sources. Such a medium can also include appropriate salts, minerals, metals and other nutrients. Microorganisms of the present invention can be cultured in conventional fermentation bioreactors. The microorganisms can be cultured by any fermentation process which includes, but is not limited to, batch, fed-batch, cell recycle, and continuous fermentation. Preferred growth conditions for potential host microorganisms according to the present invention are well known in the art. The desired bioactive molecules produced by the genetically modified microorganism can be recovered from the fermentation medium using conventional separation and purification techniques. For example, the fermentation medium can be filtered or centrifuged to remove microorganisms, cell debris and other particulate matter, and the product can be recovered from the cell-free supernatant by conventional methods, such as, for example, ion exchange, chromatography, extraction, solvent extraction, membrane separation, electrodialysis, reverse osmosis, distillation, chemical derivatization and crystallization. Alternatively, microorganisms producing the desired compound, or extracts and various fractions thereof, can be used without removal of the microorganism components from the product.

In the method for production of desired bioactive compounds of the present invention, a genetically modified plant is cultured in a fermentation medium or grown in a suitable medium such as soil. An appropriate, or effective, fermentation medium has been discussed in detail above. A suitable growth medium for higher plants includes any growth medium for plants, including, but not limited to, soil, sand, any other particulate media that support root growth (e.g. vermiculite, perlite, etc.) or Hydroponic culture, as well as suitable light, water and nutritional supplements which optimize the growth of the higher plant. The genetically modified plants of the present invention are engineered to produce significant quantities of the desired product through the activity of the PKS system that is genetically modified according to the present invention. The compounds can be recovered through purification processes which extract the compounds from the plant. In a preferred embodiment, the compound is recovered by harvesting the plant. In this embodiment, the plant can be consumed in its natural state or further processed into consumable products.

Bioactive molecules, according to the present invention, include any molecules (compounds, products, etc.) that have a biological activity, and that can be produced by a PKS system that comprises at least one amino acid sequence having a biological activity of at least one functional domain of a non-bacterial PUFA PKS system as described herein. Such bioactive molecules can include, but are not limited to: a polyunsaturated fatty acid (PUFA), an anti-inflammatory formulation, a chemotherapeutic agent, an active excipient, an osteoporosis drug, an anti-depressant, an anti-convulsant, an anti-Heliobactor pylori drug, a drug for treatment of neurodegenerative disease, a drug for treatment of degenerative liver disease, an antibiotic, and a cholesterol lowering formulation. One advantage of the non-bacterial PUFA PKS system of the present invention is the ability of such a system to introduce carbon-carbon double bonds in the cis configuration, and molecules including a double bond at every third carbon. This ability can be utilized to produce a variety of compounds.

With respect to microorganisms, preferably, bioactive compounds of interest are produced by the genetically modified microorganism in an amount that is greater than about 0.05%, and preferably greater than about 0.1%, and more preferably greater than about 0.25%, and more preferably greater than about 0.5%, and more preferably greater than about 0.75%, and more preferably greater than about 1%, and more preferably greater than about 2.5%, and more preferably greater than about 5%, and more preferably greater than about 10%, and more preferably greater than about 15%, and even more preferably greater than about 20% of the dry weight of the microorganism. For lipid compounds, preferably, such compounds are produced in an amount that is greater than about 5% of the dry weight of the microorganism. For other bioactive compounds, such as antibiotics or compounds that are synthesized in smaller amounts, those strains possessing such compounds at of the dry weight of the microorganism are identified as predictably containing a novel PKS system of the type described above. In some embodiments, particular bioactive molecules (compounds) are secreted by the microorganism, rather than accumulating. Therefore, such bioactive molecules are generally recovered from the culture medium and the concentration of molecule produced will vary depending on the microorganism and the size of the culture.

Preferably, a genetically modified organism (e.g., microorganism or plant) of the invention produces one or more polyunsaturated fatty acids including, but not limited to, EPA (C20:5, n-3), DHA (C22:6, n-3), DPA (C22:5, n-6 or n-3), ARA (C20:4, n-6), GLA (C18:3, n-6), ALA (C18:3, n-3), and/or SDA (C18:4, n-3)), and more preferably, one or more long chain fatty acids, including, but not limited to, EPA (C20:5, n-3), DHA (C22:6, n-3), DPA (C22:5, n-6 or n-3), or DTA (C22:4, n-6). In a particularly preferred embodiment, a genetically modified organism of the invention produces one or more polyunsaturated fatty acids including, but not limited to, EPA (C20:5, n-3), DHA (C22:6, n-3), and/or DPA (C22:5, n-6 or n-3).

Preferably, a genetically modified organism of the invention produces at least one PUFA (the target PUFA), wherein the total fatty acid profile in the organism (or a part of the organism that accumulates PUFAs, such as mature seeds or oil from such seeds, if the organism is an oil seed plant), comprises a detectable amount of this PUFA or PUFAs. Preferably, the PUFA is at least a 20 carbon PUFA and comprises at least 3 double bonds, and more preferably at least 4 double bonds, and even more preferably, at least 5 double bonds. In one embodiment, the PUFA is a PUFA that is not naturally produced by the organism (i.e., the wild-type organism in the absence of genetic modification or the parent organism used as a recipient for the indicated genetic modification).

Preferably, the total fatty acid profile in the organism (or part of the organism that accumulates PUFAs) comprises at least 0.1% of the target PUFA(s) by weight of the total fatty acids, and more preferably at least about 0.2%, and more preferably at least about 0.3%, and more preferably at least about 0.4%, and more preferably at least about 0.5%, and more preferably at least about 1%, and more preferably at least about 2%, and more preferably at least about 3%, and more preferably at least about 4%, and more preferably at least about 5%, and more preferably at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably more that 75% of at least one polyunsaturated fatty acid (the target PUFA) by weight of the total fatty acids, or any percentage from 0.1% to 75%, or greater than 75% (up to 100% or about 100%), in 0.1% increments, of the target PUFA(s). As generally used herein, reference to a percentage amount of PUFA production is by weight of the total fatty acids produced by the organism, unless otherwise stated (e.g., in some cases, percentage by weight is relative to the total fatty acids produced by an enzyme complex, such as a PUFA PKS system). In one embodiment, total fatty acids produced by a plant are presented as a weight percent as determined by gas chromatography (GC) analysis of a fatty acid methyl ester (FAME) preparation.

As described above, it is an additional characteristic of the total fatty acids produced by a plant (and/or parts of plants or seed oil fraction) that has been genetically modified to express a PUFA PKS of the present invention that these total fatty acids produced by the plant comprise less than about 10% by weight of any fatty acids other than the target PUFA(s) that are produced by the enzyme complex that produces the target PUFA(s) (e.g., DHA and DPAn-6 are the target PUFAs if the entire PUFA PKS system of the invention is used). Preferably, any fatty acids that are produced by the enzyme complex that produces the target PUFA(s) other than the target PUFA(s) are present at less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% by weight of the total fatty acids produced by the plant.

In another embodiment, any fatty acids that are produced by the enzyme complex that produces the target PUFA(s) other than the target PUFA(s) are present at less than about 10% by weight of the total fatty acids that are produced by the enzyme complex that produces the target PUFA(s) in the plant (i.e., this measurement is limited to those total fatty acids that are produced by the enzyme complex that produces the target PUFAs), and more preferably less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% by weight of the total fatty acids that are produced by the enzyme complex that produces the target PUFA(s) in the plant.

In another aspect of this embodiment of the invention, the total fatty acids produced by the plant (and/or parts of plants or seed oil fraction) contain less than (or do not contain any more than) 10% PUFAs having 18 or more carbons by weight of the total fatty acids produced by the plant, other than the target PUFA(s) or the PUFAs that are present in the wild-type plant (not genetically modified) or the parent plant used as a recipient for the indicated genetic modification. In further aspects, the total fatty acids produced by the plant (and/or parts of plants or seed oil fraction) contain less than 9% PUFAs having 18 or more carbons, or less than 8% PUFAs having 18 or more carbons, or less than 7% PUFAs having 18 or more carbons, or less than 6% PUFAs having 18 or more carbons, or less than 5% PUFAs having 18 or more carbons, or less than 4% PUFAs having 18 or more carbons, or less than 3% PUFAs having 18 or more carbons, or less than 2% PUFAs having 18 or more carbons, or less than 1% PUFAs having 18 or more carbons by weight of the total fatty acids produced by the plant, other than the target PUFA(s) or the PUFAs that are present in the wild-type plant (not genetically modified) or the parent plant used as a recipient for the indicated genetic modification.

In another aspect of this embodiment of the invention, the total fatty acids produced by the plant (and/or parts of plants or seed oil fraction) contain less than (or do not contain any more than) 10% PUFAs having 20 or more carbons by weight of the total fatty acids produced by the plant, other than the target PUFA(s) or the PUFAs that are present in the wild-type plant (not genetically modified) or the parent plant used as a recipient for the indicated genetic modification. In further aspects, the total fatty acids produced by the plant (and/or parts of plants or seed oil fraction) contain less than 9% PUFAs having 20 or more carbons, or less than 8% PUFAs having 20 or more carbons, or less than 7% PUFAs having 20 or more carbons, or less than 6% PUFAs having 20 or more carbons, or less than 5% PUFAs having 20 or more carbons, or less than 4% PUFAs having 20 or more carbons, or less than 3% PUFAs having 20 or more carbons, or less than 2% PUFAs having 20 or more carbons, or less than 1% PUFAs having 20 or more carbons by weight of the total fatty acids produced by the plant, other than the target PUFA(s) or the PUFAs that are present in the wild-type plant (not genetically modified) or the parent plant used as a recipient for the indicated genetic modification.

In one embodiment, the total fatty acids in the plant (and/or parts of plants or seed oil fraction) contain less than about 10% by weight of the total fatty acids produced by the plant, and more preferably less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% of a fatty acid selected from any one or more of: gamma-linolenic acid (GLA; 18:3, n-6); stearidonic acid (STA or SDA; 18:4, n-3); dihomo-gamma-linolenic acid (DGLA or HGLA; 20:3, n-6), arachidonic acid (ARA, C20:4, n-6); eicosatrienoic acid (ETA; 20:3, n-9) and various other fatty acids, such as 20:0; 20:1 (Δ5); 20:1 (Δ11); 20:2 (Δ8,11); 20:2 (Δ11,14); 20:3 (Δ5,11,14); 20:3 (Δ11,14, 17); mead acid (20:3; Δ5,8,11); or 20:4 (Δ5,1,14,17).

In another embodiment, the fatty acids that are produced by the enzyme system that produces the long chain PUFAs in the plant contain less than about 10% by weight of the total fatty acids produced by the plant, and more preferably less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% of a fatty acid selected from: gamma-linolenic acid (GLA; 18:3, n-6); stearidonic acid (STA or SDA; 18:4, n-3); dihomo-gamma-linolenic acid (DGLA or HGLA; 20:3, n-6), arachidonic acid (ARA, C20:4, n-6); eicosatrienoic acid (ETA; 20:3, n-9) and various other fatty acids, such as 20:0; 20:1 (Δ5); 20:1 (Δ11); 20:2 (Δ8,11); 20:2 (Δ11,14); 20:3 (Δ5,11,14); 20:3 (Δ11,14, 17); mead acid (20:3; A5,8,11); or 20:4 (Δ5,1,14,17).

In another embodiment, the fatty acids that are produced by the enzyme system that produces the long chain PUFAs in the plant contain less than about 10% by weight of the total fatty acids produced by the plant, and more preferably less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% of all of the following PUFAs: gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds.

In another embodiment, the fatty acids that are produced by the enzyme system that produces the long chain PUFAs in the plant contain less than about 10% by weight of the total fatty acids produced by the plant, and more preferably less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% of each of the following PUFAs: gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds.

In another embodiment, the fatty acids that are produced by the enzyme system that produces the long chain PUFAs in the plant contain less than about 10% by weight of the total fatty acids produced by the plant, and more preferably less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% of any one or more of the following PUFAs: gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds.

In one aspect of this embodiment of the invention, a genetically modified plant produces at least two target PUFAs (e.g., DHA and DPAn-6), and the total fatty acid profile in the plant, or the part of the plant that accumulates PUFAs (including oils from the oil seeds), comprises a detectable amount of these PUFAs. In this embodiment, the PUFAs are preferably each at least a 20 carbon PUFA and comprise at least 3 double bonds, and more preferably at least 4 double bonds, and even more preferably, at least 5 double bonds. Such PUFAs are most preferably chosen from DHA, DPAn-6 and EPA. In one aspect, the plant produces DHA and DPAn-6 (the products of a PUFA PKS system described herein), and the ratio of DHA to DPAn-6 is from about 1:10 to about 10:1, including any ratio in between. In a one embodiment, the ratio of DHA to DPA is from about 1:1 to about 3:1, and in another embodiment, about 2.5:1.

Figure 5:
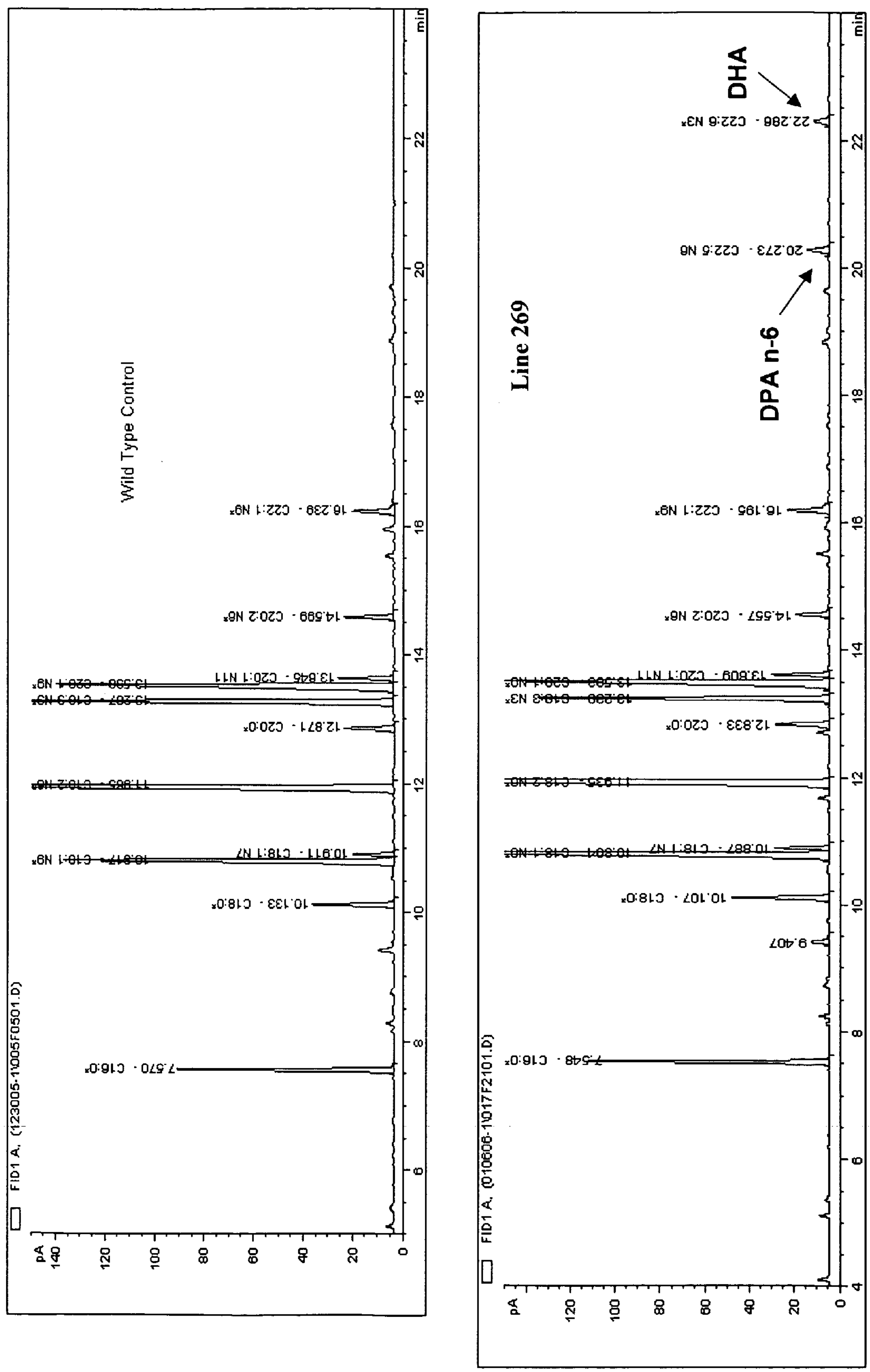
FIG. 5 shows GC FAME profiles of wild-type *Arabidopsis* and *Arabidopsis* Line 269 (plastid targeted).

In another aspect of this embodiment of the invention, the plant produces the total fatty acid profile represented by FIG. 5.

The invention further includes any seeds produced by the plants described above, as well as any oils produced by the plants or seeds described above. The invention also includes any products produced using the plants, seed or oils described herein.

One embodiment of the present invention relates to a method to modify an endproduct containing at least one fatty acid, comprising adding to said endproduct an oil produced by a recombinant host cell that expresses at least one recombinant nucleic acid molecule comprising a nucleic acid sequence encoding at least one biologically active domain of a PUFA PKS system as described herein.

Preferably, the endproduct is selected from the group consisting of a food, a dietary supplement, a pharmaceutical formulation, a humanized animal milk, and an infant formula. Suitable pharmaceutical formulations include, but are not limited to, an anti-inflammatory formulation, a chemotherapeutic agent, an active excipient, an osteoporosis drug, an anti-depressant, an anti-convulsant, an *anti-Heliobactor pylon* drug, a drug for treatment of neurodegenerative disease, a drug for treatment of degenerative liver disease, an antibiotic, and a cholesterol lowering formulation. In one embodiment, the endproduct is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

Suitable food products include, but are not limited to, fine bakery wares, bread and rolls, breakfast cereals, processed and unprocessed cheese, condiments (ketchup, mayonnaise, etc.), dairy products (milk, yogurt), puddings and gelatine desserts, carbonated drinks, teas, powdered beverage mixes, processed fish products, fruit-based drinks, chewing gum, hard confectionery, frozen dairy products, processed meat products, nut and nut-based spreads, pasta, processed poultry products, gravies and sauces, potato chips and other chips or crisps, chocolate and other confectionery, soups and soup mixes, soya based products (milks, drinks, creams, whiteners), vegetable oil-based spreads, and vegetable-based drinks.

Yet another embodiment of the present invention relates to a method to produce a humanized animal milk. This method includes the steps of genetically modifying milk-producing cells of a milk-producing animal with at least one recombinant nucleic acid molecule comprising a nucleic acid sequence encoding at least one biologically active domain of a PUFA PKS system as described herein.

Methods to genetically modify a host cell and to produce a genetically modified non-human, milk-producing animal, are known in the art. Examples of host animals to modify include cattle, sheep, pigs, goats, yaks, etc., which are amenable to genetic manipulation and cloning for rapid expansion of a transgene expressing population. For animals, PKS-like transgenes can be adapted for expression in target organelles, tissues and body fluids through modification of the gene regulatory regions. Of particular interest is the production of PUFAs in the breast milk of the host animal.

Each publication or reference cited herein is incorporated herein by reference in its entirety.

The following examples are provided for the purpose of illustration and are not intended to limit the scope of the present invention.

EXAMPLES

Example 1

The following example demonstrates that *Schizochytrium* Orfs A, B and C encode a functional DHA/DPA synthesis enzyme via functional expression in *E. coli.*

General Preparation of *E. coli* Transformants

The three genes encoding the *Schizochytrium* PUFA PKS system that produce DHA and DPA (Orfs A, B & C; SEQ ID NO:1, SEQ ID NO:3 and SEQ ID NO:5, respectively) were cloned into a single *E. coli* expression vector (derived from pET21c (Novagen)). The genes are transcribed as a single message (by the T7 RNA-polymerase), and a ribosome-binding site cloned in front of each of the genes initiates translation. Modification of the Orf B coding sequence was needed to obtain production of a full-length Orf B protein in *E. coli* (see below). An accessory gene, encoding a PPTase (see below) was cloned into a second plasmid (derived from pACYC184, New England Biolabs).

The Orf B gene is predicted to encode a protein with a mass of ~224 kDa. Initial attempts at expression of the gene in *E. coli* resulted in accumulation of a protein with an apparent molecular mass of ~165 kDa (as judged by comparison to proteins of known mass during SDS-PAGE). Examination of the Orf B nucleotide sequence revealed a region containing 15 sequential serine codons—all of them being the TCT codon. The genetic code contains 6 different serine codons, and three of these are used frequently in *E. coli*. The inventors used four overlapping oligonucleotides in combination with a polymerase chain reaction protocol to resynthesize a small portion of the Orf B gene (a ~195 base pair, BspHI to SacII restriction enzyme fragment) that contained the serine codon repeat region. In the synthetic Orf B fragment, a random mixture of the 3 serine codons commonly used by *E. coli* was used, and some other potentially problematic codons were changed as well (i.e., other codons rarely used by *E. coli*). The BspHI to SacII fragment present in the original Orf B was replaced by the resynthesized fragment (to yield Orf B*) and the modified gene was cloned into the relevant expression vectors. The modified OrfB* still encodes the amino acid sequence of SEQ ID NO:4. Expression of the modified Orf B* clone in *E. coli* resulted in the appearance of a ~224 kDa protein, indicating that the full-length product of OrfB was produced. The sequence of the resynthesized Orf B* BspHI to SacII fragment is represented herein as SEQ ID NO:38. Referring to SEQ ID NO:38, the nucleotide sequence of the resynthesized BspHI to SacII region of Orf B is shown. The BspHI restriction site and the SacII restriction site are identified. The BspHI site starts at nucleotide 4415 of the Orf B CDS (SEQ ID NO:3) (note: there are a total of three BspHI sites in the Orf B CDS, while the SacII site is unique).

The ACP domains of the Orf A protein (SEQ ID NO:2 in *Schizochytrium*) must be activated by addition of phosphopantetheine group in order to function. The enzymes that catalyze this general type of reaction are called phosphopantetheine transferases (PPTases). *E. coli* contains two endogenous PPTases, but it was anticipated that they would not recognize the Orf A ACP domains from *Schizochytrium*. This was confirmed by expressing Orfs A, B* (see above) and C in *E. coli* without an additional PPTase. In this transformant, no DHA production was detected. The inventors tested two heterologous PPTases in the *E. coli* PUFA PKS expression system: (1) sfp (derived from *Bacillus subtilis*) and (2) Het I (from the cyanobacterium Nostoc strain 7120).

The sfp PPTase has been well characterized and is widely used due to its ability to recognize a broad range of substrates. Based on published sequence information (Nakana, et al., 1992, *Molecular and General Genetics* 232: 313-321), an expression vector for sfp was built by cloning the coding region, along with defined up- and downstream flanking DNA sequences, into a pACYC-184 cloning vector. Oligonucleotides were used to amplify the region of interest from genomic *B. subtilus* DNA. The oligonucleotides:

```
CGGGGTACCCGGGAGCCGCCTTGGCTTTGT;
(forward; SEQ ID NO: 39)
and

AAACTGCAGCCCGGGTCCAGCTGGCAGGCACCCTG,
(reverse; SEQ ID NO: 40)
```

were used to amplify the region of interest from genomic *B. subtilus* DNA. Convenient restriction enzyme sites were included in the oligonucleotides to facilitate cloning in an intermediate, high copy number vector and finally into the EcoRV site of pACYC184 to create the plasmid: pBR301. Examination of extracts of *E. coli* transformed with this plasmid revealed the presence of a novel protein with the mobility expected for sfp. Co-expression of the sfp construct in cells expressing the Orf A, B*, C proteins, under certain conditions, resulted in DHA production. This experiment demonstrated that sfp was able to activate the *Schizochytrium* Orf A ACP domains. In addition, the regulatory elements associated with the sfp gene were used to create an expression cassette into which other genes could be inserted. Specifically, the sfp coding region (along with three nucleotides immediately upstream of the ATG) in pBR301 was replaced with a 53 base pair section of DNA designed so that it contains several unique (for this construct) restriction enzyme sites. The initial restriction enzyme site in this region is NdeI. The ATG sequence embedded in this site is utilized as the initiation methionine codon for introduced genes. The additional restriction sites (BglLL, NotI, SmaI, PmeII, HindIII, SpeI and XhoI) were included to facilitate the cloning process. The functionality of this expression vector cassette was tested by using PCR to generate a version of sfp with a NdeI site at the 5' end and an XhoI site ate the 3' end. This fragment was cloned into the expression cassette and transferred into *E. coli* along with the Orf A, B* and C expression vector. Under appropriate conditions, these cells accumulated DHA, demonstrating that a functional sfp had been produced.

Het I is present in a cluster of genes in Nostoc known to be responsible for the synthesis of long chain hydroxy-fatty acids that are a component of a glyco-lipid layer present in heterocysts of that organism (Black and Wolk, 1994, *J. Bacteriol.* 176, 2282-2292; Campbell et al., 1997, *Arch. Microbiol.* 167, 251-258). Het I activates the ACP domains of a protein, Hgl E, present in that cluster. The two ACP domains of Hgl E have a high degree of sequence homology to the ACP domains found in *Schizochytrium* Orf A. A Het I expression construct was made using PCR. Specifically, SEQ ID NO:41 represents the amino acid sequence of the Nostoc Het I protein. The endogenous start codon of Het I has not been identified (there is no methionine present in the putative protein). There are several potential alternative start codons (e.g., TTG and ATT) near the 5' end of the open reading frame. No methionine codons (ATG) are present in the sequence. A Het I expression construct was made by using PCR to replace the furthest 5' potential alternative start codon (TTG) with a methionine codon (ATG, as part of the above described NdeI restriction enzyme recognition site), and introducing an XhoI site at the 3' end of the coding sequence. The modified HetI coding sequence was then inserted into the NdeI and XhoI sites of the pACYC184 vector construct containing the sfp regulatory elements. Expression of this Het I construct in *E. coli* resulted in the appearance of a new protein of the size expected from the sequence data. Co-expression of Het I with *Schizochytrium* Orfs A, B*, C in *E. coli* under several conditions resulted in the accumulation of DHA and DPA in those cells. In all of the experiments in which sfp and Het I were compared, more DHA and DPA accumulated in the cells containing the Het I construct than in cells containing the sfp construct.

Production of DHA and DPA in *E. coli* Transformants

The two plasmids encoding: (1) the *Schizochytrium* PUFA PKS genes (Orfs A, B* and C) and (2) the PPTase (from sfp or from Het I) were transformed into *E. coli* strain BL21 which contains an inducible T7 RNA polymerase gene. Synthesis of the *Schizochytrium* proteins was induced by addition of IPTG to the medium, while PPTase expression was controlled by a separate regulatory element (see above). Cells were grown under various defined conditions and using either of the two heterologous PPTase genes. The cells were harvested and the fatty acids were converted to methyl-esters (FAME) and analyzed using gas-liquid chromatography.

Under several conditions, DHA and DPA were detected in *E. coli* cells expressing the *Schizochytrium* PUFA PKS genes, plus either of the two heterologous PPTases (data not shown). No DHA or DPA was detected in FAMEs prepared from control cells (i.e., cells transformed with a plasmid lacking one of the Orfs). The ratio of DHA to DPA observed in *E. coli* approximates that of the endogenous DHA and DPA production observed in *Schizochytrium*. The highest level of PUFA (DHA plus DPA), representing ~17% of the total FAME, was found in cells grown at 32° C. in 765 medium (recipe available from the American Type Culture Collection) supplemented with 10% (by weight) glycerol. PUFA accumulation was also observed when cells were grown in Luria Broth supplemented with 5 or 10% glycerol, and when grown at 20° C. Selection for the presence of the respective plasmids was maintained by inclusion of the appropriate antibiotics during the growth, and IPTG (to a final concentration of 0.5 mM) was used to induce expression of Orfs A, B* and C. Co-expression of Het I or sfp with *Schizochytrium* Orfs A, B*, C in *E. coli* under several conditions resulted in the accumulation of DHA and DPA in those cells. In all of the experiments in which sfp and Het I were compared, more DHA and DPA accumulated in the cells containing the Het I construct than in cells containing the sfp construct.

Example 2

The following example shows the expression of genes encoding the *Schizochytrium* PUFA synthase (sOrfA, sOrfB and native Orf C) along with Het I in baker's yeast (*Saccharomyces cerevisiae*).

The *Schizochytrium* PUFA synthase genes and Het I were expressed in yeast using materials obtained from Invitrogen (Invitrogen Corporation, Carlsbad, Calif.). The INVscl strain of *Saccharomyces cerevisiae* was used along with the following transformation vectors: pYESLeu (sOrfA), pYES3/CT (sOrfB), pYES2/CT (OrfC) and pYESHis (HetI). To accommodate yeast codon useage, the nucleotide sequences for OrfA (SEQ ID NO:1) and for OrfB (SEQ ID NO:3) were resynthesized. The nucleotide sequence for the resynthesized OrfA (contained in pYESLeu), designated sOrfA, is represented herein by SEQ ID NO:43. SEQ ID NO:43 still encodes the OrfA amino acid sequence of SEQ ID NO:2. The nucleotide sequence for the resynthesized OrfB (contained in pYES3/CT), designated sOrfB, is represented herein by SEQ ID NO:44. SEQ ID NO:44 still encodes the OrfB amino acid sequence of SEQ ID NO:4. The OrfC nucleotide sequence used in these experiments (contained in pYES2/CT) is the wild-type OrfC, represented by SEQ ID NO:5, and encoding SEQ ID NO:6.

Some of the vectors were modified to accommodate specific cloning requirements (e.g., restriction sites for cloning). Appropriate selection media were used (as specified by Invitrogen), depending on the particular experiment. The genes were cloned, in each case, behind a GAL1 promoter and expression was induced by re-suspension of washed cells in media containing galactose according to guidelines provide by Invitrogen. Cells were grown at 30° C. and harvested (by centrifugation) after being transferred to the induction medium. The cell pellets were freeze dried and FAMEs were prepared using acidic methanol, extracted into hexane and analyzed by GC.

Figure 3:
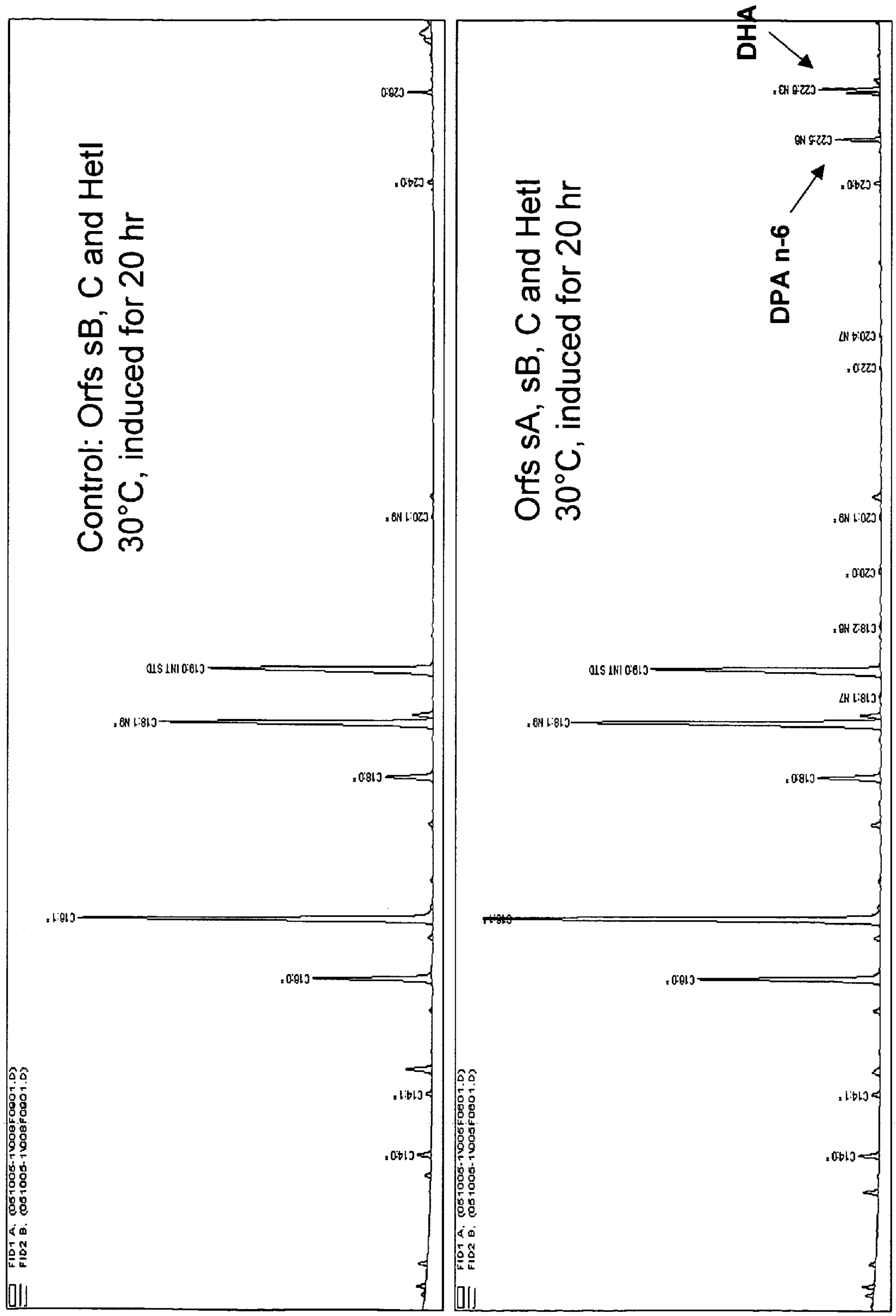
FIG. 3 shows a GC FAME profile of control yeast and yeast expressing Orfs sA, sB, C and Het I.
Figure 4:
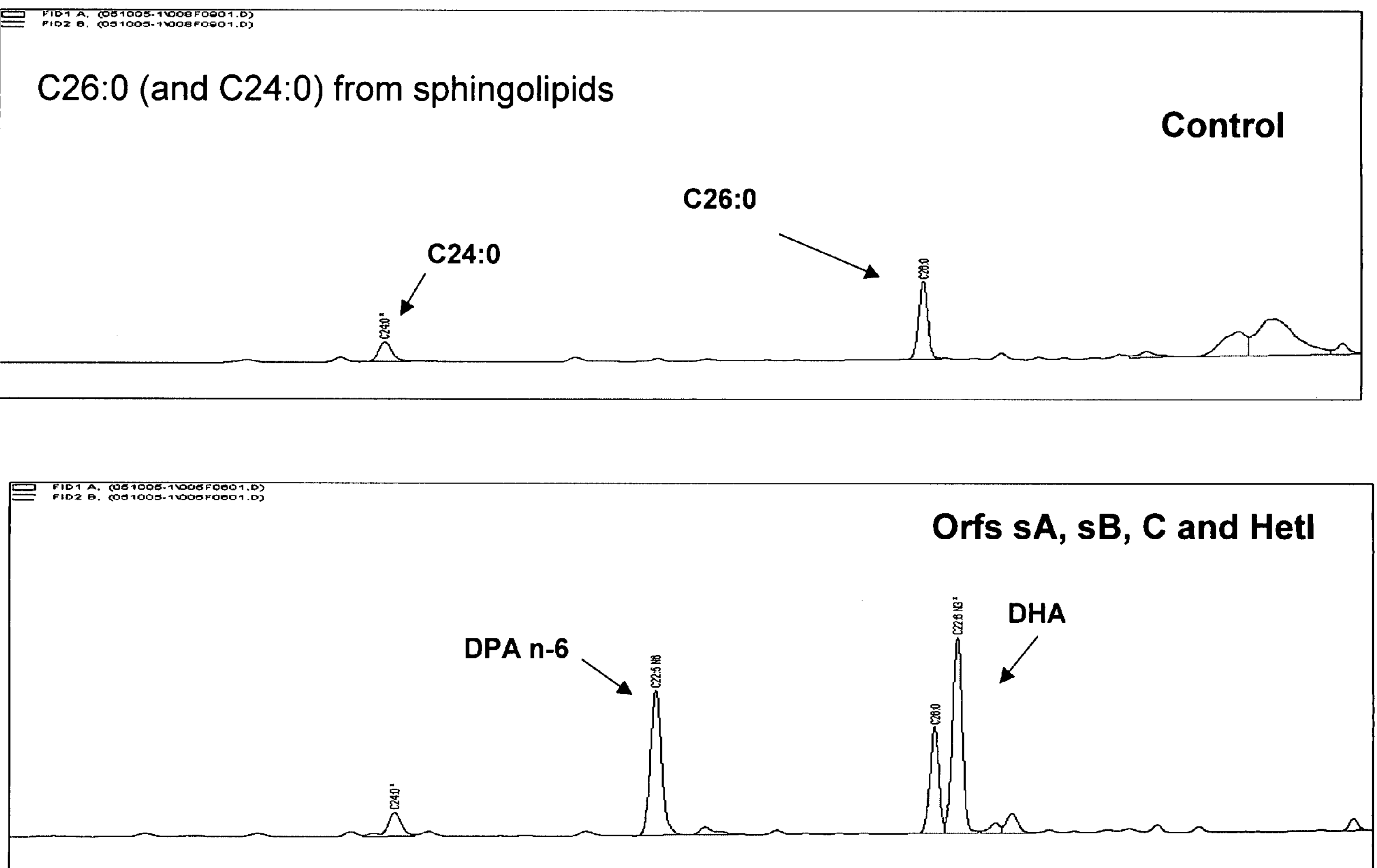
FIG. 4 shows a GC FAME profile of the PUFA region from FIG. 3.

A comparison of the fatty acid profile from yeast cells expressing the *Schizochytrium* PUFA synthase system (sOrfA, sOrf B, OrfC and Het 1) and one obtained from control cells (lacking the sOrfA gene) collected ~20 hrs after induction, showed that two novel FAME peaks have appeared in the profile of the strain expressing the complete PUFA synthase system (FIG. 3). These two peaks were identified as DPAn-6 and DHA by comparison of the elution time with authentic standards and subsequently by MS analyses. As predicted from the characterization of the *Schizochytrium* PUFA synthase, aside from DHA and DPAn-6, no other novel peaks are evident in the profile. FIG. 4 shows the region of the GC chromatogram of FIG. 3 which contains the PUFA FAMEs. Both the control cells and the cell expressing the PUFA synthase contain a peak that elutes near the DHA FAME. This has been identified as C26:0 FAME and (based on literature references) is derived from sphingolipids. Although it elutes close to the DHA peak, the resolution is sufficient so that it does not interfere with the quantitation of DHA. The DPA n-6 peak is well separated from other endogenous yeast lipids in the FAME profile. In this particular example, the cells expressing the *Schizochytrium* PUFA synthase system accumulated 2.4% DHA and 2.0% DPA n-6 (as a percentage of the total FAMEs). The sum of DHA and DPA n-6=4.4% of the measured fatty acids in the cells. The ratio of DHA to DPA n-6 observed in the cells was ~1.2:1.

Example 3

The following examples describes the expression of genes encoding the *Schizochytrium* PUFA synthase (Orf A, Orf B* and Orf C) along with Het I in *Arabidopsis.*

The *Schizochytrium* Orfs A, B* (see Example 1) and C along with Het I were cloned (separately or in various combinations including all 4 genes on one Super-construct) into the appropriate binary vectors for introduction of the genes into plants. Each gene was cloned behind a linin promoter and was followed by a linin terminator sequence (Chaudhary et al., 2001; PCT Publication Number No. WO 01/16340 A1). For localization of the PUFA synthase in the cytoplasm of plant cells, no additional protein encoding sequences were appended to the 5'end of the Orfs. For directing the proteins to the plastid, additional 5' sequences encoding a plastid targeting sequence derived from a *Brassica napus* acyl-ACP thioesterase were added to the Orfs. The amino acid sequence of the encoded targeting peptide is: MLKLSCNVTNHLHTFSFFSDSSLFIPVNRRTLAVS (SEQ ID NO:42). The nucleotide sequences encoding this peptide were placed in frame with the start methionine codons of each PUFA synthase Orf as well as the start codon of Het I.

More specifically, for one experiment described herein, the constructs and plants were prepared as follows:

Construction of pSBS4107: Acyl-ACP Transit Peptide-HetI. Acyl-ACP Transit Peptide-ORFC This plant binary vector contained a double expression cassette which targeted the co-expression of HetI (SEQ ID NO:41) and ORFC (SEQ ID NO:6) to the plastid. The first expression cassette began with a signal peptide (SEQ ID NO:42) derived from an acyl-ACP thioesterase gene from *Brassica juncea* (GenBank Accession No. AJ294419) to target expression of the polypeptides to the plastid. The signal peptide was synthesized from two overlapping oligos with an engineered AflIII site at the 5' end and an NcoI/SwaI/XmaI multiple cloning site at the 3' end. Immediately downstream was a sequence encoding for PPTase from Nostoc, encoded by HetI, to enable DHA to bind phosphopantetheine attachment sites. The second expression cassette also began with the acyl-ACP signal peptide followed immediately in-frame with a cDNA encoding ORFC (SEQ ID NO:5).

The backbone of this plasmid, pSBS4055, was based on the plant binary vector, pPZP200, described by Hajdukiewicz et al. (*Plant Molecular Biology,* 1994, 25:989-994).

Figure 6:
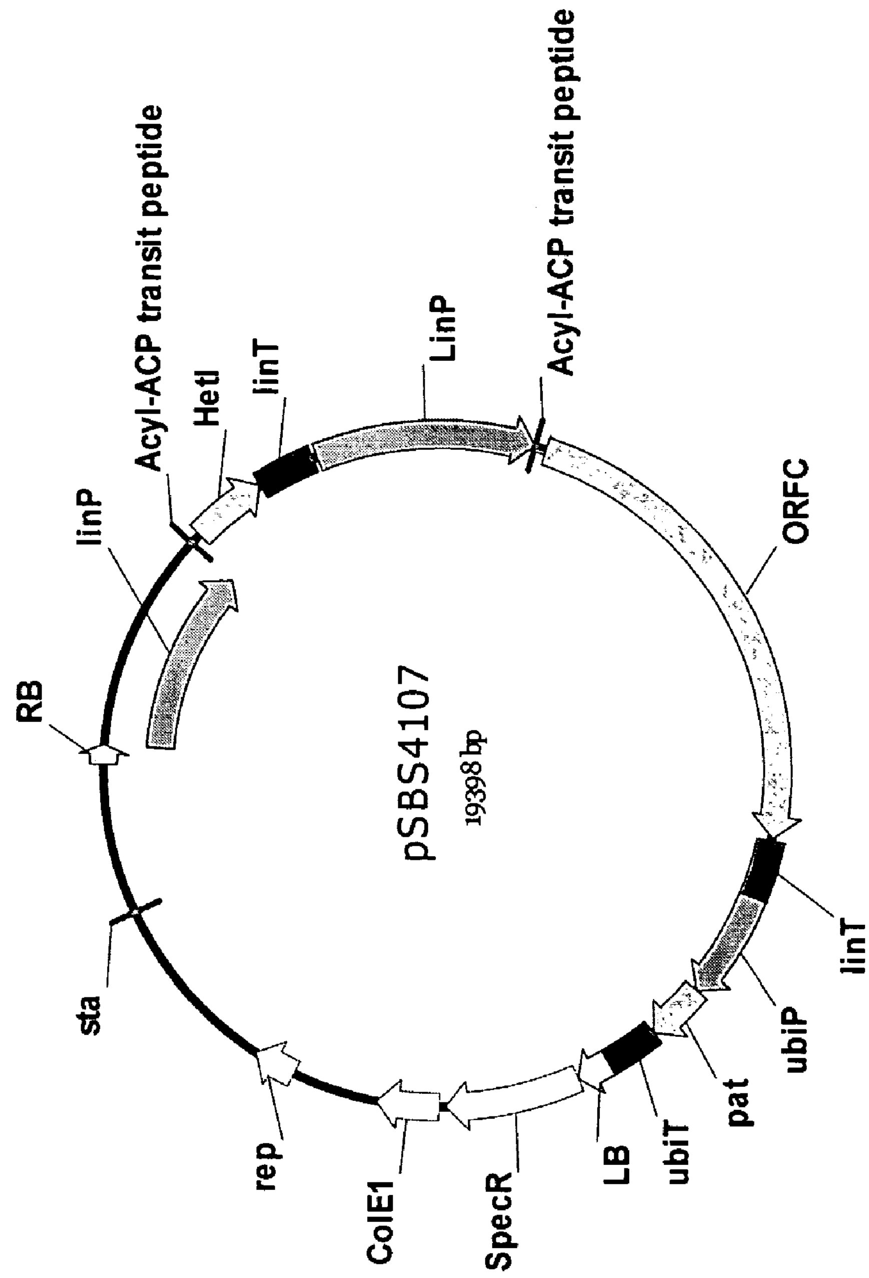
FIG. 6 is a schematic diagram showing the construction of pSBS4107: Acyl-ACP transit peptide-HetI: Acyl-ACP transit peptide-ORFC.

In place of the described multiple cloning site, a pat gene conferring host plant phosphinothricine resistance (Wohlleben et al., 1988, *Gene* 70:25-37) driven by the ubiquitin promoter/terminator from *Petroselinum crispum* (Kawalleck et al., 1993, *Plant. Mol. Bio.,* 21:673-684), was inserted between the left and right border sequences. In addition to this cassette, two separate Linin promoter/terminators in tandem from *Linum usitatissumum* (Flax or Linseed) (Chaudhary et al., 2001; PCT Publication Number No. WO 01/16340 A1) were used to drive expression of ACP-HetI and ACP-ORFC. Standard restriction cloning was used to fuse the synthetic Acyl-ACP signal peptide in-frame with cDNAs encoding for either HetI or ORFC using NcoI/XmaI and NcoI/SwaI restriction endonuclease sites, respectively, to the 3' end of the Linin promoter. The result was plasmid pSBS4107: a DNA sequence encoding the Acyl-ACP signal peptide-HetI and Acyl-ACP signal peptide-ORFC polypeptides being placed in a binary vector under expression control of the linin promoter/terminator. The linin promoter controls the specific-temporal and tissue-specific expression of the transgene during seed development. The Acyl-ACP signal peptide targets the expression of the protein to the plastid (Loader et al., 1993, *Plant Mol Biol* 23:769-778). The complete plasmid map with annotated elements is shown in FIG. 6.

Construction of pSBS5720: Acyl-ACP Transit Peptide-ORFB

This plant binary vector contained an expression cassette which targeted the expression of ORFB (SEQ ID NO:4) to the plastid. Again, the expression cassette began with a signal peptide derived from an acyl-ACP thioesterase gene from *Brassica juncea* (SEQ ID NO:42) to target expression of the polypeptide to the plastid. The signal peptide was synthesized as above. Immediately downstream was a cDNA sequence encoding for ORFB (SEQ ID NO:3, except for the resynthesized BspHI to SacII region of Orf B, represented by SEQ ID NO:38; see Example 1 above).

Figure 7:
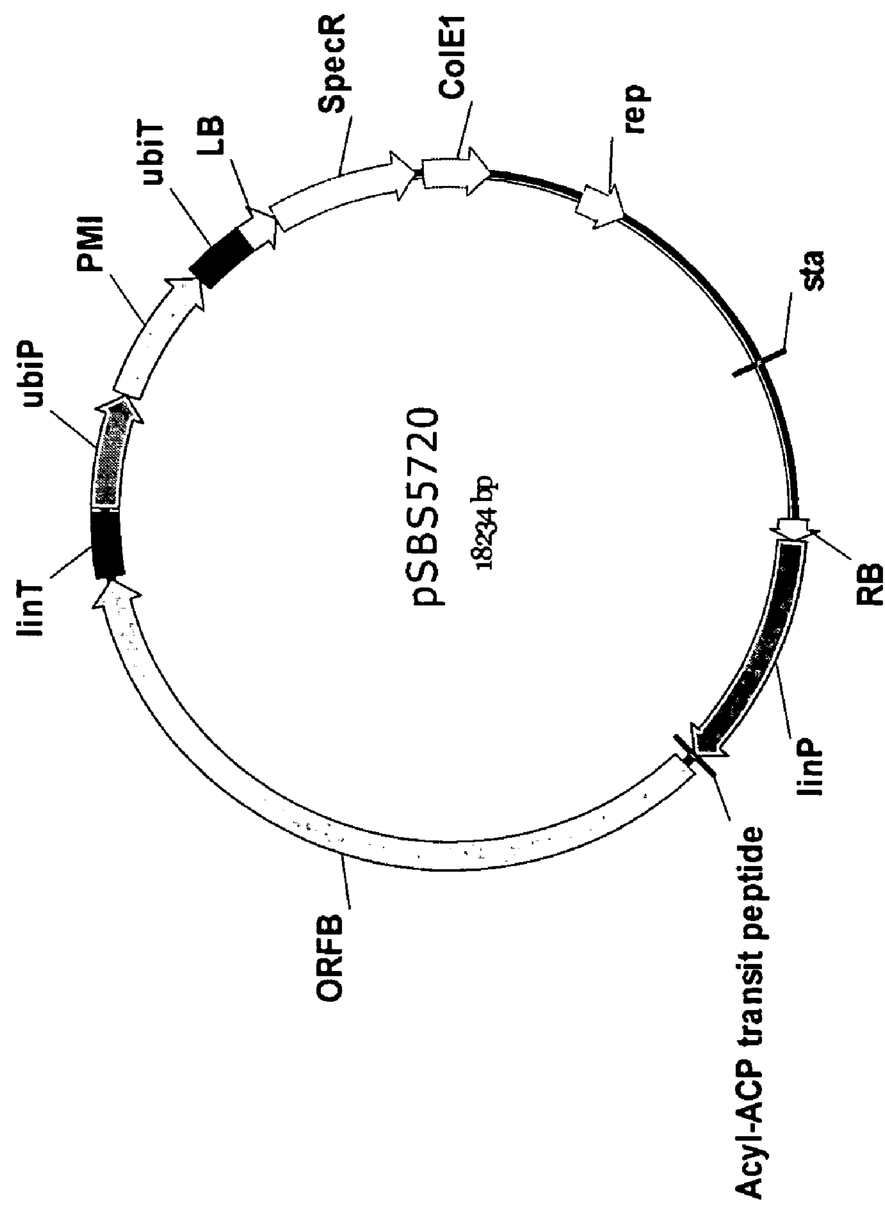
FIG. 7 is a schematic diagram showing the construction of pSBS5720: Acyl-ACP transit peptide-ORFB.

The backbone of this plasmid, pSBS4055, was based on the plant binary vector, pPZP200, described by Hajdukiewicz et al. (*Plant Molecular Biology,* 1994, 25:989-994). In place of the described multiple cloning site, a phosphomannose isomerase (PMI) gene conferring host plant positive selection for mannose-6-phosphate driven by the ubiquitin promoter/terminator from *Petroselinum crispum* (Kawalleck et al., 1993, *Plant. Mol. Bio.,* 21:673-684), was inserted between the left and right border sequences. In addition to this cassette, a Linin promoter/terminator from *Linum usitatissumum* (Flax or Linseed) (Chaudhary et al., 2001; PCT Publication Number WO 01/16340 A1) was used to drive expression of ACP-ORFB. Standard restriction cloning was used to fuse the synthetic Acyl-ACP signal peptide in-frame with cDNAs encoding for ORFB, to the 3' end of the Linin promoter. The result was plasmid pSBS5720: a DNA sequence encoding the Acyl-ACP signal peptide-ORFB polypeptide being placed in a binary vector under expression control of the linin promoter/terminator. The linin promoter controls the specific-temporal and tissue-specific expression of the transgene during seed development. The Acyl-ACP signal peptide targets the expression of the protein to the plastid (Loader et al., 1993, *Plant Mol Biol* 23:769-778). The complete plasmid map with annotated elements is shown in FIG. 7.

Construction of pSBS4757: Acyl-ACP Transit Peptide-ORFA

This plant binary vector contained an expression cassette which targeted the expression of ORFA (SEQ ID NO:2) to the plastid. Again the expression cassette began with a signal peptide derived from an acyl-ACP thioesterase gene from *Brassica juncea* (SEQ ID NO:42) to target expression of the polypeptide to the plastid. The signal peptide was synthesized as above. Immediately downstream was a cDNA sequence encoding for ORFA (SEQ ID NO:1).

Figure 8:
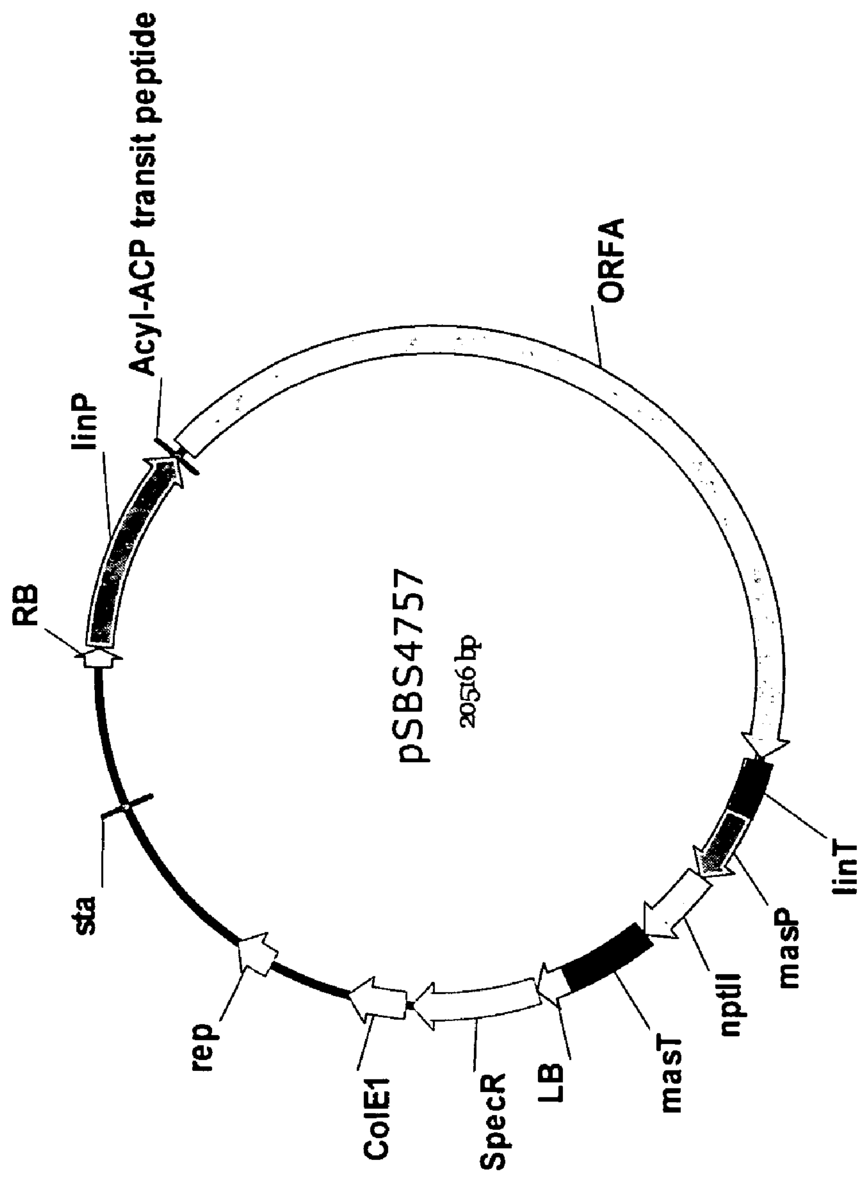
FIG. 8 is a schematic diagram showing the construction of pSBS4757: Acyl-ACP transit peptide-ORFA.

The backbone of this plasmid, pSBS4055, was based on the plant binary vector, pPZP200, described by Hajdukiewicz et al. (*Plant Molecular Biology,* 1994, 25:989-994). In place of the described multiple cloning site, a neomycin phosphotransferase (nptII) gene conferring host plant Kanamycin resistance driven by the mannopine synthase promoter/terminator, was inserted between the left and right border sequences. In addition, a Linin promoter/terminator from *Linum usitatissumum* (Flax or Linseed) (Chaudhary et al., 2001; PCT Publication Number WO 01/16340 A1) were used to drive expression of ACP-ORFA. Standard restriction cloning was used to fuse the synthetic Acyl-ACP signal peptide in-frame with a cDNA encoding for ORFA to the 3' end of the Linin promoter. The result was plasmid pSBS4757: a DNA sequence encoding the Acyl-ACP signal peptide-ORFA polypeptide being placed in a binary vector under expression control of the linin promoter/terminator. The linin promoter controls the specific-temporal and tissue-specific expression of the transgene during seed development. The Acyl-ACP signal peptide targets the expression of the protein to the plastid (Loader et al., 1993, *Plant Mol Biol* 23:769-778). The complete plasmid map with annotated elements is shown in FIG. 8.

Standard methods were used for introduction of the genes into *Arabidopsis* (floral dipping into suspension of *Agrobacterium* strains containing the appropriate vectors; see Clough and Bent, *Plant J.;* 16(6):735-43, 1998 Dec). Seeds obtained from those plants were plated on selective medium and allowed to germinate. Some of the plants that grew were taken to maturity and the seeds analyzed for PUFA content. Based on PUFA content some of those seeds were taken forward to the next generation. Pooled seeds obtained from those plants were analyzed for their fatty acid content. Analysis of a plant line transformed with the constructs specifically described above and denoted 269 is described in more detail below.

The top panel of FIG. 5 shows the typical fatty acid profile of wild type *Arabidopsis* seeds as represented by GC separation and FID detection of FAMEs prepared from a pooled seed sample. The predominant fatty acids of wild type *Arabidopsis* seeds as represented by GC separation and FID detection of FAMEs prepared from a pooled seed sample are: 16:0, 18:0, 16:1, 18:1, 20:1, 20:2 and 22:1. No DHA or DPA n-6 are present in the samples from wild type seed. The lower panel of FIG. 5 shows the fatty acid profile of a pooled seed sample from one of the transgenic *Arabidopsis* lines (line 269) expressing the *Schizochytrium* PUFA synthase genes and Het I gene. The proteins expressed from these transgenes contain plastid targeting sequences. Two FAME peaks are present in the profile from the transgenic plant seeds that are not present in the profile from wild type seeds. The elution pattern of these two peaks exactly corresponds to the elution of authentic DHA and DPA n-6 (using FAMEs prepared from *Schizochytrium* oil as standards, as well as a commercially purchased DHA standard from NuCheck Prep). In this particular example, the DHA peak represents 0.8% of total calculated FAMEs while the DPA n-6 peak represents 1.7%. The sum of novel PUFAs is 2.5% of total FAMEs. The appearance of DHA and DPA n-6 in the seed fatty acid profile demonstrates that introduced *Schizochytrium* PUFA synthase system functions when expressed in the plant cell and the proteins are targeted to the plastid.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A genetically modified plant or plant part, wherein cells of the plant are transfected with at least one recombinant nucleic acid molecule encoding a polyketide synthase (PKS) system for the production of polyunsaturated fatty acids (PUFAs) and a phosphopantetheine transferase, wherein the PKS system comprises the following proteins:

a) a protein comprising an amino acid sequence that is at least 95% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 95% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 95% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

2. The genetically modified plant or plant part of claim 1, wherein the PKS system comprises the following proteins:

a) a protein comprising an amino acid sequence that is at least 96% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 96% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 96% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

3. The genetically modified plant or plant part of claim 1, wherein the PKS system comprises the following proteins:

a) a protein comprising an amino acid sequence that is at least 97% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 97% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 97% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

4. The genetically modified plant or plant part of claim 1, wherein the PKS system comprises the following proteins:

a) a protein comprising an amino acid sequence that is at least 98% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 98% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 98% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

5. The genetically modified plant or plant part of claim 1, wherein the PKS system comprises the following proteins:

a) a protein comprising an amino acid sequence that is at least 99% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 99% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 99% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

6. The genetically modified plant or plant part of claim 1, wherein said plant is a dicotyledonous plant.

7. The genetically modified plant or plant part of claim 1, wherein said plant is a monocotyledonous plant.

8. The genetically modified plant or plant part of claim 1, wherein said plant is selected from the group consisting of: canola, soybean, rapeseed, linseed, corn, safflower, sunflower and tobacco.

9. The genetically modified plant or plant part of claim 1, wherein the plant is an oilseed plant and wherein the plant part is a mature oilseed.

10. The genetically modified plant or plant part of claim 1, wherein the total fatty acid profile in the plant or plant part comprises at least about 0.5% by weight of at least one PUFA selected from the group consisting of DHA (docosahexaenoic acid (C22:6, n-3)) and DPA (docosapentaenoic acid (C22:5, n-6), and wherein the total fatty acids produced as a result of transformation with said nucleic acid molecules, other than said at least one PUFA, comprise less than about 10% of the total fatty acids produced by said plant or plant part.

11. The genetically modified plant or plant part of claim 10, wherein the total fatty acids produced as a result of transformation with said nucleic acid molecules, other than said at least one PUFA, comprise less than 5% by weight of the total fatty acids produced by said plant or plant part.

12. The genetically modified plant or plant part of claim 10, wherein the fatty acids consisting of: gamma-linolenic acid (GLA; 18:3, n-6), PUFAs having 18 carbons and four carbon-carbon double bonds, PUFAs having 20 carbons and three carbon-carbon double bonds, and PUFAs having 22 carbons and two or three carbon-carbon double bonds, comprise less than 5% by weight of the total fatty acids produced by said plant or plant part.

13. The genetically modified plant or plant part of claim 10, wherein gamma-linolenic acid (GLA; 18:3, n-6) comprises less than 1% by weight of the total fatty acids produced by said plant or plant part.

14. A method to produce at least one polyunsaturated fatty acid (PUFA), comprising growing the genetically modified plant or plant part of any one of claims 1 to 13, to produce at least one PUFA.

15. A method to produce a genetically modified plant that has a polyunsaturated fatty acid (PUFA) profile that differs from the naturally occurring plant and that produces at least one long chain polyunsaturated fatty acid (PUFA), comprising transfecting plant cells with at least one recombinant nucleic acid molecule encoding a polyketide synthase (PKS) system for the production of polyunsaturated fatty acids (PUFAs) and a phosphopantetheine transferase, and producing the plant from the plant cells, wherein the PKS system comprises the following proteins:

a) a protein comprising an amino acid sequence that is at least 95% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 95% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 95% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

16. A recombinant plant cell, wherein the plant cell expresses at least one recombinant nucleic acid molecule encoding a polyketide synthase (PKS) system for the production of polyunsaturated fatty acids (PUFAs), wherein the PKS system comprises the following proteins:

a) a protein comprising an amino acid sequence that is at least 95% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 95% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 95% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

17. The recombinant plant cell of claim 16, wherein the PKS system comprises the following proteins:

a) a protein comprising an amino acid sequence that is at least 96% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 96% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 96% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

18. The recombinant plant cell of claim 16, wherein the PKS system comprises the following proteins:

a) a protein comprising an amino acid sequence that is at least 97% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 97% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 97% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

19. The recombinant plant cell of claim 16, wherein the PKS system comprises the following proteins:

a) a protein comprising an amino acid sequence that is at least 98% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 98% identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 98% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

20. The recombinant plant cell of claim 16, wherein the PKS system comprises the following proteins:

a) a protein comprising an amino acid sequence that is at least 99% identical to SEQ ID NO:2 and has β-keto acyl-ACP synthase (KS) activity, malonyl-CoA:ACP acyltransferase (MAT) activity, acyl carrier protein (ACP) activity and ketoreductase (KR) activity, wherein the amino acid sequence comprises an aspartate at a position corresponding to amino acid 667 of SEQ ID NO:2 and a histidine at a position corresponding to amino acid 668 of SEQ ID NO:2;

b) a protein comprising an amino acid sequence that is at least 990o identical to SEQ ID NO:4 and has KS activity, chain length factor (CLF) activity, acyl transferase (AT) activity, and enoyl ACP-reductase (ER) activity, wherein the amino acid sequence comprises a valine at a position corresponding to amino acid 371 of SEQ ID NO:4 and a glutamate at a position corresponding to amino acid 1415 of SEQ ID NO:4; and c) a protein comprising an amino acid sequence that is at least 99% identical to SEQ ID NO:6 and has FabA-like β-hydroxy acyl-ACP dehydrase (DH) activity and ER activity, wherein the amino acid sequence comprises the sequence of H-G-I-A-N-P-T-F-V-H-A-P-G-K-I (positions 876-890 of SEQ ID NO:6) at positions corresponding to amino acids 876-890 of SEQ ID NO:6.

* * * * *

UNITED STATES PATENT AND TRADEMARK OFFICE

CERTIFICATE OF CORRECTION

PATENT NO. : 7,271,315 B2
APPLICATION NO. : 11/452138
DATED : September 18, 2007
INVENTOR(S) : James Metz et al.

It is certified that error appears in the above-identified patent and that said Letters Patent is hereby corrected as shown below:

On the Cover page: item

(60) Please delete the term"and" after "7,247,461" and insert --which is-- therefor.

Signed and Sealed this

Eleventh Day of December, 2007

JON W. DUDAS
*Director of the United States Patent and Trademark Office*

SEQUENCE LISTING

```
<160> NUMBER OF SEQ ID NOS: 44

<210> SEQ ID NO 1
<211> LENGTH: 8733
<212> TYPE: DNA
<213> ORGANISM: Schizochytrium sp.
<220> FEATURE:
<221> NAME/KEY: CDS
<222> LOCATION: (1)..(8733)

<400> SEQUENCE: 1

atg gcg gcc cgt ctg cag gag caa aag gga ggc gag atg gat acc cgc       48
Met Ala Ala Arg Leu Gln Glu Gln Lys Gly Gly Glu Met Asp Thr Arg
1               5                   10                  15

att gcc atc atc ggc atg tcg gcc atc ctc ccc tgc ggc acg acc gtg       96
Ile Ala Ile Ile Gly Met Ser Ala Ile Leu Pro Cys Gly Thr Thr Val
            20                  25                  30

cgc gag tcg tgg gag acc atc cgc gcc ggc atc gac tgc ctg tcg gat      144
Arg Glu Ser Trp Glu Thr Ile Arg Ala Gly Ile Asp Cys Leu Ser Asp
        35                  40                  45

ctc ccc gag gac cgc gtc gac gtg acg gcg tac ttt gac ccc gtc aag      192
Leu Pro Glu Asp Arg Val Asp Val Thr Ala Tyr Phe Asp Pro Val Lys
    50                  55                  60

acc acc aag gac aag atc tac tgc aag cgc ggt ggc ttc att ccc gag      240
Thr Thr Lys Asp Lys Ile Tyr Cys Lys Arg Gly Gly Phe Ile Pro Glu
65                  70                  75                  80

tac gac ttt gac gcc cgc gag ttc gga ctc aac atg ttc cag atg gag      288
Tyr Asp Phe Asp Ala Arg Glu Phe Gly Leu Asn Met Phe Gln Met Glu
                85                  90                  95

gac tcg gac gca aac cag acc atc tcg ctt ctc aag gtc aag gag gcc      336
Asp Ser Asp Ala Asn Gln Thr Ile Ser Leu Leu Lys Val Lys Glu Ala
            100                 105                 110

ctc cag gac gcc ggc atc gac gcc ctc ggc aag gaa aag aag aac atc      384
Leu Gln Asp Ala Gly Ile Asp Ala Leu Gly Lys Glu Lys Lys Asn Ile
        115                 120                 125

ggc tgc gtg ctc ggc att ggc ggc ggc caa aag tcc agc cac gag ttc      432
Gly Cys Val Leu Gly Ile Gly Gly Gly Gln Lys Ser Ser His Glu Phe
    130                 135                 140

tac tcg cgc ctt aat tat gtt gtc gtg gag aag gtc ctc cgc aag atg      480
Tyr Ser Arg Leu Asn Tyr Val Val Val Glu Lys Val Leu Arg Lys Met
145                 150                 155                 160

ggc atg ccc gag gag gac gtc aag gtc gcc gtc gaa aag tac aag gcc      528
Gly Met Pro Glu Glu Asp Val Lys Val Ala Val Glu Lys Tyr Lys Ala
                165                 170                 175

aac ttc ccc gag tgg cgc ctc gac tcc ttc cct ggc ttc ctc ggc aac      576
Asn Phe Pro Glu Trp Arg Leu Asp Ser Phe Pro Gly Phe Leu Gly Asn
            180                 185                 190

gtc acc gcc ggt cgc tgc acc aac acc ttc aac ctc gac ggc atg aac      624
Val Thr Ala Gly Arg Cys Thr Asn Thr Phe Asn Leu Asp Gly Met Asn
        195                 200                 205

tgc gtt gtc gac gcc gca tgc gcc tcg tcc ctc atc gcc gtc aag gtc      672
Cys Val Val Asp Ala Ala Cys Ala Ser Ser Leu Ile Ala Val Lys Val
    210                 215                 220

gcc atc gac gag ctg ctc tac ggt gac tgc gac atg atg gtc acc ggt      720
Ala Ile Asp Glu Leu Leu Tyr Gly Asp Cys Asp Met Met Val Thr Gly
225                 230                 235                 240
```

-continued

```
gcc acc tgc acg gat aac tcc atc ggc atg tac atg gcc ttc tcc aag      768
Ala Thr Cys Thr Asp Asn Ser Ile Gly Met Tyr Met Ala Phe Ser Lys
                245                 250                 255

acc ccc gtg ttc tcc acg gac ccc agc gtg cgc gcc tac gac gaa aag      816
Thr Pro Val Phe Ser Thr Asp Pro Ser Val Arg Ala Tyr Asp Glu Lys
            260                 265                 270

aca aag ggc atg ctc atc ggc gag ggc tcc gcc atg ctc gtc ctc aag      864
Thr Lys Gly Met Leu Ile Gly Glu Gly Ser Ala Met Leu Val Leu Lys
        275                 280                 285

cgc tac gcc gac gcc gtc cgc gac ggc gat gag atc cac gct gtt att      912
Arg Tyr Ala Asp Ala Val Arg Asp Gly Asp Glu Ile His Ala Val Ile
    290                 295                 300

cgc ggc tgc gcc tcc tcc agt gat ggc aag gcc gcc ggc atc tac acg      960
Arg Gly Cys Ala Ser Ser Ser Asp Gly Lys Ala Ala Gly Ile Tyr Thr
305                 310                 315                 320

ccc acc att tcg ggc cag gag gag gcc ctc cgc cgc gcc tac aac cgc     1008
Pro Thr Ile Ser Gly Gln Glu Glu Ala Leu Arg Arg Ala Tyr Asn Arg
                325                 330                 335

gcc tgt gtc gac ccg gcc acc gtc act ctc gtc gag ggt cac ggc acc     1056
Ala Cys Val Asp Pro Ala Thr Val Thr Leu Val Glu Gly His Gly Thr
            340                 345                 350

ggt act ccc gtt ggc gac cgc atc gag ctc acc gcc ttg cgc aac ctc     1104
Gly Thr Pro Val Gly Asp Arg Ile Glu Leu Thr Ala Leu Arg Asn Leu
        355                 360                 365

ttt gac aag gcc tac ggc gag ggc aac acc gaa aag gtc gct gtg ggc     1152
Phe Asp Lys Ala Tyr Gly Glu Gly Asn Thr Glu Lys Val Ala Val Gly
    370                 375                 380

agc atc aag tcc agc atc ggc cat ctc aag gcc gtc gcc ggt ctc gcc     1200
Ser Ile Lys Ser Ser Ile Gly His Leu Lys Ala Val Ala Gly Leu Ala
385                 390                 395                 400

ggt atg atc aag gtc atc atg gcg ctc aag cac aag act ctc ccg ggc     1248
Gly Met Ile Lys Val Ile Met Ala Leu Lys His Lys Thr Leu Pro Gly
                405                 410                 415

acc atc aac gtc gac aac cca ccc aac ctc tac gac aac acg ccc atc     1296
Thr Ile Asn Val Asp Asn Pro Pro Asn Leu Tyr Asp Asn Thr Pro Ile
            420                 425                 430

aac gag tcc tcg ctc tac att aac acc atg aac cgc ccc tgg ttc ccg     1344
Asn Glu Ser Ser Leu Tyr Ile Asn Thr Met Asn Arg Pro Trp Phe Pro
        435                 440                 445

ccc cct ggt gtg ccc cgc cgc gcc ggc att tcg agc ttt ggc ttt ggt     1392
Pro Pro Gly Val Pro Arg Arg Ala Gly Ile Ser Ser Phe Gly Phe Gly
    450                 455                 460

ggc gcc aac tac cac gcc gtc ctc gag gag gcc gag ccc gag cac acg     1440
Gly Ala Asn Tyr His Ala Val Leu Glu Glu Ala Glu Pro Glu His Thr
465                 470                 475                 480

acc gcg tac cgc ctc aac aag cgc ccg cag ccc gtg ctc atg atg gcc     1488
Thr Ala Tyr Arg Leu Asn Lys Arg Pro Gln Pro Val Leu Met Met Ala
                485                 490                 495

gcc acg ccc gcg gcc ctc cag tcg ctc tgc gag gcc cag ctc aag gag     1536
Ala Thr Pro Ala Ala Leu Gln Ser Leu Cys Glu Ala Gln Leu Lys Glu
            500                 505                 510

ttc gag gcc gcc atc aag gag aac gag acc gtc aag aac acc gcc tac     1584
Phe Glu Ala Ala Ile Lys Glu Asn Glu Thr Val Lys Asn Thr Ala Tyr
        515                 520                 525

atc aag tgc gtc aag ttc ggc gag cag ttc aaa ttc cct ggc tcc atc     1632
Ile Lys Cys Val Lys Phe Gly Glu Gln Phe Lys Phe Pro Gly Ser Ile
    530                 535                 540

ccg gcc aca aac gcg cgc ctc ggc ttc ctc gtc aag gat gct gag gat     1680
Pro Ala Thr Asn Ala Arg Leu Gly Phe Leu Val Lys Asp Ala Glu Asp
```

-continued

```
545                 550                 555                 560

gcc tgc tcc acc ctc cgt gcc atc tgc gcc caa ttc gcc aag gat gtc      1728
Ala Cys Ser Thr Leu Arg Ala Ile Cys Ala Gln Phe Ala Lys Asp Val
                565                 570                 575

acc aag gag gcc tgg cgc ctc ccc cgc gag ggc gtc agc ttc cgc gcc      1776
Thr Lys Glu Ala Trp Arg Leu Pro Arg Glu Gly Val Ser Phe Arg Ala
            580                 585                 590

aag ggc atc gcc acc aac ggc gct gtc gcc gcg ctc ttc tcc ggc cag      1824
Lys Gly Ile Ala Thr Asn Gly Ala Val Ala Ala Leu Phe Ser Gly Gln
        595                 600                 605

ggc gcg cag tac acg cac atg ttt agc gag gtg gcc atg aac tgg ccc      1872
Gly Ala Gln Tyr Thr His Met Phe Ser Glu Val Ala Met Asn Trp Pro
    610                 615                 620

cag ttc cgc cag agc att gcc gcc atg gac gcc gcc cag tcc aag gtc      1920
Gln Phe Arg Gln Ser Ile Ala Ala Met Asp Ala Ala Gln Ser Lys Val
625                 630                 635                 640

gct gga agc gac aag gac ttt gag cgc gtc tcc cag gtc ctc tac ccg      1968
Ala Gly Ser Asp Lys Asp Phe Glu Arg Val Ser Gln Val Leu Tyr Pro
                645                 650                 655

cgc aag ccg tac gag cgt gag ccc gag cag gac cac aag aag atc tcc      2016
Arg Lys Pro Tyr Glu Arg Glu Pro Glu Gln Asp His Lys Lys Ile Ser
            660                 665                 670

ctc acc gcc tac tcg cag ccc tcg acc ctg gcc tgc gct ctc ggt gcc      2064
Leu Thr Ala Tyr Ser Gln Pro Ser Thr Leu Ala Cys Ala Leu Gly Ala
        675                 680                 685

ttt gag atc ttc aag gag gcc ggc ttc acc ccg gac ttt gcc gcc ggc      2112
Phe Glu Ile Phe Lys Glu Ala Gly Phe Thr Pro Asp Phe Ala Ala Gly
    690                 695                 700

cat tcg ctc ggt gag ttc gcc gcc ctc tac gcc gcg ggc tgc gtc gac      2160
His Ser Leu Gly Glu Phe Ala Ala Leu Tyr Ala Ala Gly Cys Val Asp
705                 710                 715                 720

cgc gac gag ctc ttt gag ctt gtc tgc cgc cgc gcc cgc atc atg ggc      2208
Arg Asp Glu Leu Phe Glu Leu Val Cys Arg Arg Ala Arg Ile Met Gly
                725                 730                 735

ggc aag gac gca ccg gcc acc ccc aag ggc tgc atg gcc gcc gtc att      2256
Gly Lys Asp Ala Pro Ala Thr Pro Lys Gly Cys Met Ala Ala Val Ile
            740                 745                 750

ggc ccc aac gcc gag aac atc aag gtc cag gcc gcc aac gtc tgg ctc      2304
Gly Pro Asn Ala Glu Asn Ile Lys Val Gln Ala Ala Asn Val Trp Leu
        755                 760                 765

ggc aac tcc aac tcg cct tcg cag acc gtc atc acc ggc tcc gtc gaa      2352
Gly Asn Ser Asn Ser Pro Ser Gln Thr Val Ile Thr Gly Ser Val Glu
    770                 775                 780

ggt atc cag gcc gag agc gcc cgc ctc cag aag gag ggc ttc cgc gtc      2400
Gly Ile Gln Ala Glu Ser Ala Arg Leu Gln Lys Glu Gly Phe Arg Val
785                 790                 795                 800

gtg cct ctt gcc tgc gag agc gcc ttc cac tcg ccc cag atg gag aac      2448
Val Pro Leu Ala Cys Glu Ser Ala Phe His Ser Pro Gln Met Glu Asn
                805                 810                 815

gcc tcg tcg gcc ttc aag gac gtc atc tcc aag gtc tcc ttc cgc acc      2496
Ala Ser Ser Ala Phe Lys Asp Val Ile Ser Lys Val Ser Phe Arg Thr
            820                 825                 830

ccc aag gcc gag acc aag ctc ttc agc aac gtc tct ggc gag acc tac      2544
Pro Lys Ala Glu Thr Lys Leu Phe Ser Asn Val Ser Gly Glu Thr Tyr
        835                 840                 845

ccc acg gac gcc cgc gag atg ctt acg cag cac atg acc agc agc gtc      2592
Pro Thr Asp Ala Arg Glu Met Leu Thr Gln His Met Thr Ser Ser Val
    850                 855                 860

aag ttc ctc acc cag gtc cgc aac atg cac cag gcc ggt gcg cgc atc      2640
```

-continued

```
Lys Phe Leu Thr Gln Val Arg Asn Met His Gln Ala Gly Ala Arg Ile
865                 870                 875                 880

ttt gtc gag ttc gga ccc aag cag gtg ctc tcc aag ctt gtc tcc gag      2688
Phe Val Glu Phe Gly Pro Lys Gln Val Leu Ser Lys Leu Val Ser Glu
                885                 890                 895

acc ctc aag gat gac ccc tcg gtt gtc acc gtc tct gtc aac ccg gcc      2736
Thr Leu Lys Asp Asp Pro Ser Val Val Thr Val Ser Val Asn Pro Ala
            900                 905                 910

tcg ggc acg gat tcg gac atc cag ctc cgc gac gcg gcc gtc cag ctc      2784
Ser Gly Thr Asp Ser Asp Ile Gln Leu Arg Asp Ala Ala Val Gln Leu
        915                 920                 925

gtt gtc gct ggc gtc aac ctt cag ggc ttt gac aag tgg gac gcc ccc      2832
Val Val Ala Gly Val Asn Leu Gln Gly Phe Asp Lys Trp Asp Ala Pro
    930                 935                 940

gat gcc acc cgc atg cag gcc atc aag aag aag cgc act acc ctc cgc      2880
Asp Ala Thr Arg Met Gln Ala Ile Lys Lys Lys Arg Thr Thr Leu Arg
945                 950                 955                 960

ctt tcg gcc gcc acc tac gtc tcg gac aag acc aag aag gtc cgc gac      2928
Leu Ser Ala Ala Thr Tyr Val Ser Asp Lys Thr Lys Lys Val Arg Asp
                965                 970                 975

gcc gcc atg aac gat ggc cgc tgc gtc acc tac ctc aag ggc gcc gca      2976
Ala Ala Met Asn Asp Gly Arg Cys Val Thr Tyr Leu Lys Gly Ala Ala
            980                 985                 990

ccg ctc atc aag gcc ccg gag ccc  gtt gtc gac gag gcc  gcc aag cgc    3024
Pro Leu Ile Lys Ala Pro Glu Pro  Val Val Asp Glu Ala  Ala Lys Arg
        995                 1000                 1005

gag gcc  gag cgt ctc cag aag  gag ctt cag gat gcc  cag cgc cag      3069
Glu Ala  Glu Arg Leu Gln Lys  Glu Leu Gln Asp Ala  Gln Arg Gln
    1010                 1015                 1020

ctc gac  gac gcc aag cgc gcc  gcc gcc gag gcc aac  tcc aag ctc      3114
Leu Asp  Asp Ala Lys Arg Ala  Ala Ala Glu Ala Asn  Ser Lys Leu
    1025                 1030                 1035

gcc gct  gcc aag gag gag gcc  aag acc gcc gct gct  tcg gcc aag      3159
Ala Ala  Ala Lys Glu Glu Ala  Lys Thr Ala Ala Ala  Ser Ala Lys
    1040                 1045                 1050

ccc gca  gtt gac act gct gtt  gtc gaa aag cat cgt  gcc atc ctc      3204
Pro Ala  Val Asp Thr Ala Val  Val Glu Lys His Arg  Ala Ile Leu
    1055                 1060                 1065

aag tcc  atg ctc gcg gag ctc  gat ggc tac gga tcg  gtc gac gct      3249
Lys Ser  Met Leu Ala Glu Leu  Asp Gly Tyr Gly Ser  Val Asp Ala
    1070                 1075                 1080

tct tcc  ctc cag cag cag cag  cag cag cag acg gcc  ccc gcc ccg      3294
Ser Ser  Leu Gln Gln Gln Gln  Gln Gln Gln Thr Ala  Pro Ala Pro
    1085                 1090                 1095

gtc aag  gct gct gcg cct gcc  gcc ccc gtt gcc tcg  gcc cct gcc      3339
Val Lys  Ala Ala Ala Pro Ala  Ala Pro Val Ala Ser  Ala Pro Ala
    1100                 1105                 1110

ccg gct  gtc tcg aac gag ctt  ctt gag aag gcc gag  act gtc gtc      3384
Pro Ala  Val Ser Asn Glu Leu  Leu Glu Lys Ala Glu  Thr Val Val
    1115                 1120                 1125

atg gag  gtc ctc gcc gcc aag  acc ggc tac gag acc  gac atg atc      3429
Met Glu  Val Leu Ala Ala Lys  Thr Gly Tyr Glu Thr  Asp Met Ile
    1130                 1135                 1140

gag gct  gac atg gag ctc gag  acc gag ctc ggc att  gac tcc atc      3474
Glu Ala  Asp Met Glu Leu Glu  Thr Glu Leu Gly Ile  Asp Ser Ile
    1145                 1150                 1155

aag cgt  gtc gag atc ctc tcc  gag gtc cag gcc atg  ctc aat gtc      3519
Lys Arg  Val Glu Ile Leu Ser  Glu Val Gln Ala Met  Leu Asn Val
    1160                 1165                 1170
```

-continued

```
gag gcc  aag gat gtc gat gcc  ctc agc cgc act cgc  act gtt ggt      3564
Glu Ala  Lys Asp Val Asp Ala  Leu Ser Arg Thr Arg  Thr Val Gly
    1175                 1180                 1185

gag gtt  gtc aac gcc atg aag  gcc gag atc gct ggc  agc tct gcc      3609
Glu Val  Val Asn Ala Met Lys  Ala Glu Ile Ala Gly  Ser Ser Ala
    1190                 1195                 1200

ccg gcg  cct gct gcc gct gct  ccg gct ccg gcc aag  gct gcc cct      3654
Pro Ala  Pro Ala Ala Ala Ala  Pro Ala Pro Ala Lys  Ala Ala Pro
    1205                 1210                 1215

gcc gcc  gct gcg cct gct gtc  tcg aac gag ctt ctc  gag aag gcc      3699
Ala Ala  Ala Ala Pro Ala Val  Ser Asn Glu Leu Leu  Glu Lys Ala
    1220                 1225                 1230

gag acc  gtc gtc atg gag gtc  ctc gcc gcc aag act  ggc tac gag      3744
Glu Thr  Val Val Met Glu Val  Leu Ala Ala Lys Thr  Gly Tyr Glu
    1235                 1240                 1245

act gac  atg atc gag tcc gac  atg gag ctc gag act  gag ctc ggc      3789
Thr Asp  Met Ile Glu Ser Asp  Met Glu Leu Glu Thr  Glu Leu Gly
    1250                 1255                 1260

att gac  tcc atc aag cgt gtc  gag atc ctc tcc gag  gtt cag gcc      3834
Ile Asp  Ser Ile Lys Arg Val  Glu Ile Leu Ser Glu  Val Gln Ala
    1265                 1270                 1275

atg ctc  aac gtc gag gcc aag  gac gtc gac gct ctc  agc cgc act      3879
Met Leu  Asn Val Glu Ala Lys  Asp Val Asp Ala Leu  Ser Arg Thr
    1280                 1285                 1290

cgc act  gtg ggt gag gtc gtc  aac gcc atg aag gct  gag atc gct      3924
Arg Thr  Val Gly Glu Val Val  Asn Ala Met Lys Ala  Glu Ile Ala
    1295                 1300                 1305

ggt ggc  tct gcc ccg gcg cct  gcc gcc gct gcc cca  ggt ccg gct      3969
Gly Gly  Ser Ala Pro Ala Pro  Ala Ala Ala Ala Pro  Gly Pro Ala
    1310                 1315                 1320

gct gcc  gcc cct gcg cct gcc  gcc gcc gcc cct gct  gtc tcg aac      4014
Ala Ala  Ala Pro Ala Pro Ala  Ala Ala Ala Pro Ala  Val Ser Asn
    1325                 1330                 1335

gag ctt  ctt gag aag gcc gag  acc gtc gtc atg gag  gtc ctc gcc      4059
Glu Leu  Leu Glu Lys Ala Glu  Thr Val Val Met Glu  Val Leu Ala
    1340                 1345                 1350

gcc aag  act ggc tac gag act  gac atg atc gag tcc  gac atg gag      4104
Ala Lys  Thr Gly Tyr Glu Thr  Asp Met Ile Glu Ser  Asp Met Glu
    1355                 1360                 1365

ctc gag  acc gag ctc ggc att  gac tcc atc aag cgt  gtc gag att      4149
Leu Glu  Thr Glu Leu Gly Ile  Asp Ser Ile Lys Arg  Val Glu Ile
    1370                 1375                 1380

ctc tcc  gag gtc cag gcc atg  ctc aac gtc gag gcc  aag gac gtc      4194
Leu Ser  Glu Val Gln Ala Met  Leu Asn Val Glu Ala  Lys Asp Val
    1385                 1390                 1395

gac gct  ctc agc cgc acc cgc  act gtt ggc gag gtc  gtc gat gcc      4239
Asp Ala  Leu Ser Arg Thr Arg  Thr Val Gly Glu Val  Val Asp Ala
    1400                 1405                 1410

atg aag  gcc gag atc gct ggt  ggc tct gcc ccg gcg  cct gcc gcc      4284
Met Lys  Ala Glu Ile Ala Gly  Gly Ser Ala Pro Ala  Pro Ala Ala
    1415                 1420                 1425

gct gct  cct gct ccg gct gct  gcc gcc cct gcg cct  gcc gcc cct      4329
Ala Ala  Pro Ala Pro Ala Ala  Ala Ala Pro Ala Pro  Ala Ala Pro
    1430                 1435                 1440

gcg cct  gct gtc tcg agc gag  ctt ctc gag aag gcc  gag act gtc      4374
Ala Pro  Ala Val Ser Ser Glu  Leu Leu Glu Lys Ala  Glu Thr Val
    1445                 1450                 1455

gtc atg  gag gtc ctc gcc gcc  aag act ggc tac gag  act gac atg      4419
Val Met  Glu Val Leu Ala Ala  Lys Thr Gly Tyr Glu  Thr Asp Met
    1460                 1465                 1470
```

-continued

```
atc gag  tcc gac atg gag ctc  gag acc gag ctc ggc  att gac tcc      4464
Ile Glu  Ser Asp Met Glu Leu  Glu Thr Glu Leu Gly  Ile Asp Ser
    1475                 1480                 1485

atc aag  cgt gtc gag att ctc  tcc gag gtc cag gcc  atg ctc aac      4509
Ile Lys  Arg Val Glu Ile Leu  Ser Glu Val Gln Ala  Met Leu Asn
    1490                 1495                 1500

gtc gag  gcc aag gac gtc gac  gct ctc agc cgc acc  cgc act gtt      4554
Val Glu  Ala Lys Asp Val Asp  Ala Leu Ser Arg Thr  Arg Thr Val
    1505                 1510                 1515

ggc gag  gtc gtc gat gcc atg  aag gcc gag atc gct  ggt ggc tct      4599
Gly Glu  Val Val Asp Ala Met  Lys Ala Glu Ile Ala  Gly Gly Ser
    1520                 1525                 1530

gcc ccg  gcg cct gcc gcc gct  gct cct gct ccg gct  gct gcc gcc      4644
Ala Pro  Ala Pro Ala Ala Ala  Ala Pro Ala Pro Ala  Ala Ala Ala
    1535                 1540                 1545

cct gcg  cct gcc gcc cct gcg  cct gcc gcc cct gcg  cct gct gtc      4689
Pro Ala  Pro Ala Ala Pro Ala  Pro Ala Ala Pro Ala  Pro Ala Val
    1550                 1555                 1560

tcg agc  gag ctt ctc gag aag  gcc gag act gtc gtc  atg gag gtc      4734
Ser Ser  Glu Leu Leu Glu Lys  Ala Glu Thr Val Val  Met Glu Val
    1565                 1570                 1575

ctc gcc  gcc aag act ggc tac  gag act gac atg att  gag tcc gac      4779
Leu Ala  Ala Lys Thr Gly Tyr  Glu Thr Asp Met Ile  Glu Ser Asp
    1580                 1585                 1590

atg gag  ctc gag acc gag ctc  ggc att gac tcc atc  aag cgt gtc      4824
Met Glu  Leu Glu Thr Glu Leu  Gly Ile Asp Ser Ile  Lys Arg Val
    1595                 1600                 1605

gag att  ctc tcc gag gtt cag  gcc atg ctc aac gtc  gag gcc aag      4869
Glu Ile  Leu Ser Glu Val Gln  Ala Met Leu Asn Val  Glu Ala Lys
    1610                 1615                 1620

gac gtc  gac gct ctc agc cgc  act cgc act gtt ggt  gag gtc gtc      4914
Asp Val  Asp Ala Leu Ser Arg  Thr Arg Thr Val Gly  Glu Val Val
    1625                 1630                 1635

gat gcc  atg aag gct gag atc  gct ggc agc tcc gcc  tcg gcg cct      4959
Asp Ala  Met Lys Ala Glu Ile  Ala Gly Ser Ser Ala  Ser Ala Pro
    1640                 1645                 1650

gcc gcc  gct gct cct gct ccg  gct gct gcc gct cct  gcg ccc gct      5004
Ala Ala  Ala Ala Pro Ala Pro  Ala Ala Ala Ala Pro  Ala Pro Ala
    1655                 1660                 1665

gcc gcc  gcc cct gct gtc tcg  aac gag ctt ctc gag  aaa gcc gag      5049
Ala Ala  Ala Pro Ala Val Ser  Asn Glu Leu Leu Glu  Lys Ala Glu
    1670                 1675                 1680

act gtc  gtc atg gag gtc ctc  gcc gcc aag act ggc  tac gag act      5094
Thr Val  Val Met Glu Val Leu  Ala Ala Lys Thr Gly  Tyr Glu Thr
    1685                 1690                 1695

gac atg  atc gag tcc gac atg  gag ctc gag act gag  ctc ggc att      5139
Asp Met  Ile Glu Ser Asp Met  Glu Leu Glu Thr Glu  Leu Gly Ile
    1700                 1705                 1710

gac tcc  atc aag cgt gtc gag  atc ctc tcc gag gtt  cag gcc atg      5184
Asp Ser  Ile Lys Arg Val Glu  Ile Leu Ser Glu Val  Gln Ala Met
    1715                 1720                 1725

ctc aac  gtc gag gcc aag gac  gtc gat gcc ctc agc  cgc acc cgc      5229
Leu Asn  Val Glu Ala Lys Asp  Val Asp Ala Leu Ser  Arg Thr Arg
    1730                 1735                 1740

act gtt  ggc gag gtt gtc gat  gcc atg aag gcc gag  atc gct ggt      5274
Thr Val  Gly Glu Val Val Asp  Ala Met Lys Ala Glu  Ile Ala Gly
    1745                 1750                 1755

ggc tct  gcc ccg gcg cct gcc  gcc gct gcc cct gct  ccg gct gcc      5319
Gly Ser  Ala Pro Ala Pro Ala  Ala Ala Ala Pro Ala  Pro Ala Ala
```

-continued

```
    1760                1765                1770

gcc gcc  cct gct gtc tcg aac  gag ctt ctc gag aag  gcc gag act      5364
Ala Ala  Pro Ala Val Ser Asn  Glu Leu Leu Glu Lys  Ala Glu Thr
    1775                1780                1785

gtc gtc  atg gag gtc ctc gcc  gcc aag act ggc tac  gag acc gac      5409
Val Val  Met Glu Val Leu Ala  Ala Lys Thr Gly Tyr  Glu Thr Asp
    1790                1795                1800

atg atc  gag tcc gac atg gag  ctc gag acc gag ctc  ggc att gac      5454
Met Ile  Glu Ser Asp Met Glu  Leu Glu Thr Glu Leu  Gly Ile Asp
    1805                1810                1815

tcc atc  aag cgt gtc gag att  ctc tcc gag gtt cag  gcc atg ctc      5499
Ser Ile  Lys Arg Val Glu Ile  Leu Ser Glu Val Gln  Ala Met Leu
    1820                1825                1830

aac gtc  gag gcc aag gac gtc  gat gct ctc agc cgc  act cgc act      5544
Asn Val  Glu Ala Lys Asp Val  Asp Ala Leu Ser Arg  Thr Arg Thr
    1835                1840                1845

gtt ggc  gag gtc gtc gat gcc  atg aag gct gag atc  gcc ggc agc      5589
Val Gly  Glu Val Val Asp Ala  Met Lys Ala Glu Ile  Ala Gly Ser
    1850                1855                1860

tcc gcc  ccg gcg cct gcc gcc  gct gct cct gct ccg  gct gct gcc      5634
Ser Ala  Pro Ala Pro Ala Ala  Ala Ala Pro Ala Pro  Ala Ala Ala
    1865                1870                1875

gct cct  gcg ccc gct gcc gct  gcc cct gct gtc tcg  agc gag ctt      5679
Ala Pro  Ala Pro Ala Ala Ala  Ala Pro Ala Val Ser  Ser Glu Leu
    1880                1885                1890

ctc gag  aag gcc gag acc gtc  gtc atg gag gtc ctc  gcc gcc aag      5724
Leu Glu  Lys Ala Glu Thr Val  Val Met Glu Val Leu  Ala Ala Lys
    1895                1900                1905

act ggc  tac gag act gac atg  att gag tcc gac atg  gag ctc gag      5769
Thr Gly  Tyr Glu Thr Asp Met  Ile Glu Ser Asp Met  Glu Leu Glu
    1910                1915                1920

act gag  ctc ggc att gac tcc  atc aag cgt gtc gag  atc ctc tcc      5814
Thr Glu  Leu Gly Ile Asp Ser  Ile Lys Arg Val Glu  Ile Leu Ser
    1925                1930                1935

gag gtt  cag gcc atg ctc aac  gtc gag gcc aag gac  gtc gat gcc      5859
Glu Val  Gln Ala Met Leu Asn  Val Glu Ala Lys Asp  Val Asp Ala
    1940                1945                1950

ctc agc  cgc acc cgc act gtt  ggc gag gtt gtc gat  gcc atg aag      5904
Leu Ser  Arg Thr Arg Thr Val  Gly Glu Val Val Asp  Ala Met Lys
    1955                1960                1965

gcc gag  atc gct ggt ggc tct  gcc ccg gcg cct gcc  gcc gct gcc      5949
Ala Glu  Ile Ala Gly Gly Ser  Ala Pro Ala Pro Ala  Ala Ala Ala
    1970                1975                1980

cct gct  ccg gct gcc gcc gcc  cct gct gtc tcg aac  gag ctt ctt      5994
Pro Ala  Pro Ala Ala Ala Ala  Pro Ala Val Ser Asn  Glu Leu Leu
    1985                1990                1995

gag aag  gcc gag acc gtc gtc  atg gag gtc ctc gcc  gcc aag act      6039
Glu Lys  Ala Glu Thr Val Val  Met Glu Val Leu Ala  Ala Lys Thr
    2000                2005                2010

ggc tac  gag acc gac atg atc  gag tcc gac atg gag  ctc gag acc      6084
Gly Tyr  Glu Thr Asp Met Ile  Glu Ser Asp Met Glu  Leu Glu Thr
    2015                2020                2025

gag ctc  ggc att gac tcc atc  aag cgt gtc gag att  ctc tcc gag      6129
Glu Leu  Gly Ile Asp Ser Ile  Lys Arg Val Glu Ile  Leu Ser Glu
    2030                2035                2040

gtt cag  gcc atg ctc aac gtc  gag gcc aag gac gtc  gac gct ctc      6174
Val Gln  Ala Met Leu Asn Val  Glu Ala Lys Asp Val  Asp Ala Leu
    2045                2050                2055

agc cgc  act cgc act gtt ggc  gag gtc gtc gat gcc  atg aag gct      6219
```

-continued

```
Ser Arg  Thr Arg Thr Val Gly  Glu Val Val Asp Ala  Met Lys Ala
    2060                 2065                 2070

gag atc  gct ggt ggc tct gcc  ccg gcg cct gcc gcc  gct gct cct      6264
Glu Ile  Ala Gly Gly Ser Ala  Pro Ala Pro Ala Ala  Ala Ala Pro
    2075                 2080                 2085

gcc tcg  gct ggc gcc gcg cct  gcg gtc aag att gac  tcg gtc cac      6309
Ala Ser  Ala Gly Ala Ala Pro  Ala Val Lys Ile Asp  Ser Val His
    2090                 2095                 2100

ggc gct  gac tgt gat gat ctt  tcc ctg atg cac gcc  aag gtg gtt      6354
Gly Ala  Asp Cys Asp Asp Leu  Ser Leu Met His Ala  Lys Val Val
    2105                 2110                 2115

gac atc  cgc cgc ccg gac gag  ctc atc ctg gag cgc  ccc gag aac      6399
Asp Ile  Arg Arg Pro Asp Glu  Leu Ile Leu Glu Arg  Pro Glu Asn
    2120                 2125                 2130

cgc ccc  gtt ctc gtt gtc gat  gac ggc agc gag ctc  acc ctc gcc      6444
Arg Pro  Val Leu Val Val Asp  Asp Gly Ser Glu Leu  Thr Leu Ala
    2135                 2140                 2145

ctg gtc  cgc gtc ctc ggc gcc  tgc gcc gtt gtc ctg  acc ttt gag      6489
Leu Val  Arg Val Leu Gly Ala  Cys Ala Val Val Leu  Thr Phe Glu
    2150                 2155                 2160

ggt ctc  cag ctc gct cag cgc  gct ggt gcc gct gcc  atc cgc cac      6534
Gly Leu  Gln Leu Ala Gln Arg  Ala Gly Ala Ala Ala  Ile Arg His
    2165                 2170                 2175

gtg ctc  gcc aag gat ctt tcc  gcg gag agc gcc gag  aag gcc atc      6579
Val Leu  Ala Lys Asp Leu Ser  Ala Glu Ser Ala Glu  Lys Ala Ile
    2180                 2185                 2190

aag gag  gcc gag cag cgc ttt  ggc gct ctc ggc ggc  ttc atc tcg      6624
Lys Glu  Ala Glu Gln Arg Phe  Gly Ala Leu Gly Gly  Phe Ile Ser
    2195                 2200                 2205

cag cag  gcg gag cgc ttc gag  ccc gcc gaa atc ctc  ggc ttc acg      6669
Gln Gln  Ala Glu Arg Phe Glu  Pro Ala Glu Ile Leu  Gly Phe Thr
    2210                 2215                 2220

ctc atg  tgc gcc aag ttc gcc  aag gct tcc ctc tgc  acg gct gtg      6714
Leu Met  Cys Ala Lys Phe Ala  Lys Ala Ser Leu Cys  Thr Ala Val
    2225                 2230                 2235

gct ggc  ggc cgc ccg gcc ttt  atc ggt gtg gcg cgc  ctt gac ggc      6759
Ala Gly  Gly Arg Pro Ala Phe  Ile Gly Val Ala Arg  Leu Asp Gly
    2240                 2245                 2250

cgc ctc  gga ttc act tcg cag  ggc act tct gac gcg  ctc aag cgt      6804
Arg Leu  Gly Phe Thr Ser Gln  Gly Thr Ser Asp Ala  Leu Lys Arg
    2255                 2260                 2265

gcc cag  cgt ggt gcc atc ttt  ggc ctc tgc aag acc  atc ggc ctc      6849
Ala Gln  Arg Gly Ala Ile Phe  Gly Leu Cys Lys Thr  Ile Gly Leu
    2270                 2275                 2280

gag tgg  tcc gag tct gac gtc  ttt tcc cgc ggc gtg  gac att gct      6894
Glu Trp  Ser Glu Ser Asp Val  Phe Ser Arg Gly Val  Asp Ile Ala
    2285                 2290                 2295

cag ggc  atg cac ccc gag gat  gcc gcc gtg gcg att  gtg cgc gag      6939
Gln Gly  Met His Pro Glu Asp  Ala Ala Val Ala Ile  Val Arg Glu
    2300                 2305                 2310

atg gcg  tgc gct gac att cgc  att cgc gag gtc ggc  att ggc gca      6984
Met Ala  Cys Ala Asp Ile Arg  Ile Arg Glu Val Gly  Ile Gly Ala
    2315                 2320                 2325

aac cag  cag cgc tgc acg atc  cgt gcc gcc aag ctc  gag acc ggc      7029
Asn Gln  Gln Arg Cys Thr Ile  Arg Ala Ala Lys Leu  Glu Thr Gly
    2330                 2335                 2340

aac ccg  cag cgc cag atc gcc  aag gac gac gtg ctg  ctc gtt tct      7074
Asn Pro  Gln Arg Gln Ile Ala  Lys Asp Asp Val Leu  Leu Val Ser
    2345                 2350                 2355
```

-continued

```
ggc ggc  gct cgc ggc atc acg  cct ctt tgc atc cgg  gag atc acg      7119
Gly Gly  Ala Arg Gly Ile Thr  Pro Leu Cys Ile Arg  Glu Ile Thr
    2360                 2365                 2370

cgc cag  atc gcg ggc ggc aag  tac att ctg ctt ggc  cgc agc aag      7164
Arg Gln  Ile Ala Gly Gly Lys  Tyr Ile Leu Leu Gly  Arg Ser Lys
    2375                 2380                 2385

gtc tct  gcg agc gaa ccg gca  tgg tgc gct ggc atc  act gac gag      7209
Val Ser  Ala Ser Glu Pro Ala  Trp Cys Ala Gly Ile  Thr Asp Glu
    2390                 2395                 2400

aag gct  gtg caa aag gct gct  acc cag gag ctc aag  cgc gcc ttt      7254
Lys Ala  Val Gln Lys Ala Ala  Thr Gln Glu Leu Lys  Arg Ala Phe
    2405                 2410                 2415

agc gct  ggc gag ggc ccc aag  ccc acg ccc cgc gct  gtc act aag      7299
Ser Ala  Gly Glu Gly Pro Lys  Pro Thr Pro Arg Ala  Val Thr Lys
    2420                 2425                 2430

ctt gtg  ggc tct gtt ctt ggc  gct cgc gag gtg cgc  agc tct att      7344
Leu Val  Gly Ser Val Leu Gly  Ala Arg Glu Val Arg  Ser Ser Ile
    2435                 2440                 2445

gct gcg  att gaa gcg ctc ggc  ggc aag gcc atc tac  tcg tcg tgc      7389
Ala Ala  Ile Glu Ala Leu Gly  Gly Lys Ala Ile Tyr  Ser Ser Cys
    2450                 2455                 2460

gac gtg  aac tct gcc gcc gac  gtg gcc aag gcc gtg  cgc gat gcc      7434
Asp Val  Asn Ser Ala Ala Asp  Val Ala Lys Ala Val  Arg Asp Ala
    2465                 2470                 2475

gag tcc  cag ctc ggt gcc cgc  gtc tcg ggc atc gtt  cat gcc tcg      7479
Glu Ser  Gln Leu Gly Ala Arg  Val Ser Gly Ile Val  His Ala Ser
    2480                 2485                 2490

ggc gtg  ctc cgc gac cgt ctc  atc gag aag aag ctc  ccc gac gag      7524
Gly Val  Leu Arg Asp Arg Leu  Ile Glu Lys Lys Leu  Pro Asp Glu
    2495                 2500                 2505

ttc gac  gcc gtc ttt ggc acc  aag gtc acc ggt ctc  gag aac ctc      7569
Phe Asp  Ala Val Phe Gly Thr  Lys Val Thr Gly Leu  Glu Asn Leu
    2510                 2515                 2520

ctc gcc  gcc gtc gac cgc gcc  aac ctc aag cac atg  gtc ctc ttc      7614
Leu Ala  Ala Val Asp Arg Ala  Asn Leu Lys His Met  Val Leu Phe
    2525                 2530                 2535

agc tcg  ctc gcc ggc ttc cac  ggc aac gtc ggc cag  tct gac tac      7659
Ser Ser  Leu Ala Gly Phe His  Gly Asn Val Gly Gln  Ser Asp Tyr
    2540                 2545                 2550

gcc atg  gcc aac gag gcc ctt  aac aag atg ggc ctc  gag ctc gcc      7704
Ala Met  Ala Asn Glu Ala Leu  Asn Lys Met Gly Leu  Glu Leu Ala
    2555                 2560                 2565

aag gac  gtc tcg gtc aag tcg  atc tgc ttc ggt ccc  tgg gac ggt      7749
Lys Asp  Val Ser Val Lys Ser  Ile Cys Phe Gly Pro  Trp Asp Gly
    2570                 2575                 2580

ggc atg  gtg acg ccg cag ctc  aag aag cag ttc cag  gag atg ggc      7794
Gly Met  Val Thr Pro Gln Leu  Lys Lys Gln Phe Gln  Glu Met Gly
    2585                 2590                 2595

gtg cag  atc atc ccc cgc gag  ggc ggc gct gat acc  gtg gcg cgc      7839
Val Gln  Ile Ile Pro Arg Glu  Gly Gly Ala Asp Thr  Val Ala Arg
    2600                 2605                 2610

atc gtg  ctc ggc tcc tcg ccg  gct gag atc ctt gtc  ggc aac tgg      7884
Ile Val  Leu Gly Ser Ser Pro  Ala Glu Ile Leu Val  Gly Asn Trp
    2615                 2620                 2625

cgc acc  ccg tcc aag aag gtc  ggc tcg gac acc atc  acc ctg cac      7929
Arg Thr  Pro Ser Lys Lys Val  Gly Ser Asp Thr Ile  Thr Leu His
    2630                 2635                 2640

cgc aag  att tcc gcc aag tcc  aac ccc ttc ctc gag  gac cac gtc      7974
Arg Lys  Ile Ser Ala Lys Ser  Asn Pro Phe Leu Glu  Asp His Val
    2645                 2650                 2655
```

```
atc cag  ggc cgc cgc gtg ctg  ccc atg acg ctg gcc  att ggc tcg      8019
Ile Gln  Gly Arg Arg Val Leu  Pro Met Thr Leu Ala  Ile Gly Ser
    2660                 2665                 2670

ctc gcg  gag acc tgc ctc ggc  ctc ttc ccc ggc tac  tcg ctc tgg      8064
Leu Ala  Glu Thr Cys Leu Gly  Leu Phe Pro Gly Tyr  Ser Leu Trp
    2675                 2680                 2685

gcc att  gac gac gcc cag ctc  ttc aag ggt gtc act  gtc gac ggc      8109
Ala Ile  Asp Asp Ala Gln Leu  Phe Lys Gly Val Thr  Val Asp Gly
    2690                 2695                 2700

gac gtc  aac tgc gag gtg acc  ctc acc ccg tcg acg  gcg ccc tcg      8154
Asp Val  Asn Cys Glu Val Thr  Leu Thr Pro Ser Thr  Ala Pro Ser
    2705                 2710                 2715

ggc cgc  gtc aac gtc cag gcc  acg ctc aag acc ttt  tcc agc ggc      8199
Gly Arg  Val Asn Val Gln Ala  Thr Leu Lys Thr Phe  Ser Ser Gly
    2720                 2725                 2730

aag ctg  gtc ccg gcc tac cgc  gcc gtc atc gtg ctc  tcc aac cag      8244
Lys Leu  Val Pro Ala Tyr Arg  Ala Val Ile Val Leu  Ser Asn Gln
    2735                 2740                 2745

ggc gcg  ccc ccg gcc aac gcc  acc atg cag ccg ccc  tcg ctc gat      8289
Gly Ala  Pro Pro Ala Asn Ala  Thr Met Gln Pro Pro  Ser Leu Asp
    2750                 2755                 2760

gcc gat  ccg gcg ctc cag ggc  tcc gtc tac gac ggc  aag acc ctc      8334
Ala Asp  Pro Ala Leu Gln Gly  Ser Val Tyr Asp Gly  Lys Thr Leu
    2765                 2770                 2775

ttc cac  ggc ccg gcc ttc cgc  ggc atc gat gac gtg  ctc tcg tgc      8379
Phe His  Gly Pro Ala Phe Arg  Gly Ile Asp Asp Val  Leu Ser Cys
    2780                 2785                 2790

acc aag  agc cag ctt gtg gcc  aag tgc agc gct gtc  ccc ggc tcc      8424
Thr Lys  Ser Gln Leu Val Ala  Lys Cys Ser Ala Val  Pro Gly Ser
    2795                 2800                 2805

gac gcc  gct cgc ggc gag ttt  gcc acg gac act gac  gcc cat gac      8469
Asp Ala  Ala Arg Gly Glu Phe  Ala Thr Asp Thr Asp  Ala His Asp
    2810                 2815                 2820

ccc ttc  gtg aac gac ctg gcc  ttt cag gcc atg ctc  gtc tgg gtg      8514
Pro Phe  Val Asn Asp Leu Ala  Phe Gln Ala Met Leu  Val Trp Val
    2825                 2830                 2835

cgc cgc  acg ctc ggc cag gct  gcg ctc ccc aac tcg  atc cag cgc      8559
Arg Arg  Thr Leu Gly Gln Ala  Ala Leu Pro Asn Ser  Ile Gln Arg
    2840                 2845                 2850

atc gtc  cag cac cgc ccg gtc  ccg cag gac aag ccc  ttc tac att      8604
Ile Val  Gln His Arg Pro Val  Pro Gln Asp Lys Pro  Phe Tyr Ile
    2855                 2860                 2865

acc ctc  cgc tcc aac cag tcg  ggc ggt cac tcc cag  cac aag cac      8649
Thr Leu  Arg Ser Asn Gln Ser  Gly Gly His Ser Gln  His Lys His
    2870                 2875                 2880

gcc ctt  cag ttc cac aac gag  cag ggc gat ctc ttc  att gat gtc      8694
Ala Leu  Gln Phe His Asn Glu  Gln Gly Asp Leu Phe  Ile Asp Val
    2885                 2890                 2895

cag gct  tcg gtc atc gcc acg  gac agc ctt gcc ttc  taa              8733
Gln Ala  Ser Val Ile Ala Thr  Asp Ser Leu Ala Phe
    2900                 2905                 2910
```

<210> SEQ ID NO 2
<211> LENGTH: 2910
<212> TYPE: PRT
<213> ORGANISM: Schizochytrium sp.

<400> SEQUENCE: 2

```
Met Ala Ala Arg Leu Gln Glu Gln Lys Gly Gly Glu Met Asp Thr Arg
1               5                   10                  15
```

-continued

```
Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45

Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Lys Asn Ile
        115                 120                 125

Gly Cys Val Leu Gly Ile Gly Gly Gly Gln Lys Ser Ser His Glu Phe
    130                 135                 140

Tyr Ser Arg Leu Asn Tyr Val Val Val Glu Lys Val Leu Arg Lys Met
145                 150                 155                 160

Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
            180                 185                 190

Val Thr Ala Gly Arg Cys Thr Asn Thr Phe Asn Leu Asp Gly Met Asn
        195                 200                 205

Cys Val Val Asp Ala Ala Cys Ala Ser Ser Leu Ile Ala Val Lys Val
    210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
            260                 265                 270

Thr Lys Gly Met Leu Ile Gly Glu Gly Ser Ala Met Leu Val Leu Lys
        275                 280                 285

Arg Tyr Ala Asp Ala Val Arg Asp Gly Asp Glu Ile His Ala Val Ile
    290                 295                 300

Arg Gly Cys Ala Ser Ser Ser Asp Gly Lys Ala Ala Gly Ile Tyr Thr
305                 310                 315                 320

Pro Thr Ile Ser Gly Gln Glu Glu Ala Leu Arg Arg Ala Tyr Asn Arg
                325                 330                 335

Ala Cys Val Asp Pro Ala Thr Val Thr Leu Val Glu Gly His Gly Thr
            340                 345                 350

Gly Thr Pro Val Gly Asp Arg Ile Glu Leu Thr Ala Leu Arg Asn Leu
        355                 360                 365

Phe Asp Lys Ala Tyr Gly Glu Gly Asn Thr Glu Lys Val Ala Val Gly
    370                 375                 380

Ser Ile Lys Ser Ser Ile Gly His Leu Lys Ala Val Ala Gly Leu Ala
385                 390                 395                 400

Gly Met Ile Lys Val Ile Met Ala Leu Lys His Lys Thr Leu Pro Gly
                405                 410                 415

Thr Ile Asn Val Asp Asn Pro Pro Asn Leu Tyr Asp Asn Thr Pro Ile
            420                 425                 430
```

-continued

```
Asn Glu Ser Ser Leu Tyr Ile Asn Thr Met Asn Arg Pro Trp Phe Pro
        435                 440                 445

Pro Pro Gly Val Pro Arg Arg Ala Gly Ile Ser Ser Phe Gly Phe Gly
    450                 455                 460

Gly Ala Asn Tyr His Ala Val Leu Glu Glu Ala Glu Pro Glu His Thr
465                 470                 475                 480

Thr Ala Tyr Arg Leu Asn Lys Arg Pro Gln Pro Val Leu Met Met Ala
                485                 490                 495

Ala Thr Pro Ala Ala Leu Gln Ser Leu Cys Glu Ala Gln Leu Lys Glu
            500                 505                 510

Phe Glu Ala Ala Ile Lys Glu Asn Glu Thr Val Lys Asn Thr Ala Tyr
        515                 520                 525

Ile Lys Cys Val Lys Phe Gly Glu Gln Phe Lys Phe Pro Gly Ser Ile
    530                 535                 540

Pro Ala Thr Asn Ala Arg Leu Gly Phe Leu Val Lys Asp Ala Glu Asp
545                 550                 555                 560

Ala Cys Ser Thr Leu Arg Ala Ile Cys Ala Gln Phe Ala Lys Asp Val
                565                 570                 575

Thr Lys Glu Ala Trp Arg Leu Pro Arg Glu Gly Val Ser Phe Arg Ala
            580                 585                 590

Lys Gly Ile Ala Thr Asn Gly Ala Val Ala Ala Leu Phe Ser Gly Gln
        595                 600                 605

Gly Ala Gln Tyr Thr His Met Phe Ser Glu Val Ala Met Asn Trp Pro
    610                 615                 620

Gln Phe Arg Gln Ser Ile Ala Ala Met Asp Ala Ala Gln Ser Lys Val
625                 630                 635                 640

Ala Gly Ser Asp Lys Asp Phe Glu Arg Val Ser Gln Val Leu Tyr Pro
                645                 650                 655

Arg Lys Pro Tyr Glu Arg Glu Pro Glu Gln Asp His Lys Lys Ile Ser
            660                 665                 670

Leu Thr Ala Tyr Ser Gln Pro Ser Thr Leu Ala Cys Ala Leu Gly Ala
        675                 680                 685

Phe Glu Ile Phe Lys Glu Ala Gly Phe Thr Pro Asp Phe Ala Ala Gly
    690                 695                 700

His Ser Leu Gly Glu Phe Ala Ala Leu Tyr Ala Ala Gly Cys Val Asp
705                 710                 715                 720

Arg Asp Glu Leu Phe Glu Leu Val Cys Arg Arg Ala Arg Ile Met Gly
                725                 730                 735

Gly Lys Asp Ala Pro Ala Thr Pro Lys Gly Cys Met Ala Ala Val Ile
            740                 745                 750

Gly Pro Asn Ala Glu Asn Ile Lys Val Gln Ala Ala Asn Val Trp Leu
        755                 760                 765

Gly Asn Ser Asn Ser Pro Ser Gln Thr Val Ile Thr Gly Ser Val Glu
    770                 775                 780

Gly Ile Gln Ala Glu Ser Ala Arg Leu Gln Lys Glu Gly Phe Arg Val
785                 790                 795                 800

Val Pro Leu Ala Cys Glu Ser Ala Phe His Ser Pro Gln Met Glu Asn
                805                 810                 815

Ala Ser Ser Ala Phe Lys Asp Val Ile Ser Lys Val Ser Phe Arg Thr
            820                 825                 830

Pro Lys Ala Glu Thr Lys Leu Phe Ser Asn Val Ser Gly Glu Thr Tyr
        835                 840                 845

Pro Thr Asp Ala Arg Glu Met Leu Thr Gln His Met Thr Ser Ser Val
```

-continued

```
    850                 855                 860

Lys Phe Leu Thr Gln Val Arg Asn Met His Gln Ala Gly Ala Arg Ile
865                 870                 875                 880

Phe Val Glu Phe Gly Pro Lys Gln Val Leu Ser Lys Leu Val Ser Glu
                885                 890                 895

Thr Leu Lys Asp Asp Pro Ser Val Val Thr Val Ser Val Asn Pro Ala
            900                 905                 910

Ser Gly Thr Asp Ser Asp Ile Gln Leu Arg Asp Ala Ala Val Gln Leu
        915                 920                 925

Val Val Ala Gly Val Asn Leu Gln Gly Phe Asp Lys Trp Asp Ala Pro
    930                 935                 940

Asp Ala Thr Arg Met Gln Ala Ile Lys Lys Lys Arg Thr Thr Leu Arg
945                 950                 955                 960

Leu Ser Ala Ala Thr Tyr Val Ser Asp Lys Thr Lys Lys Val Arg Asp
                965                 970                 975

Ala Ala Met Asn Asp Gly Arg Cys Val Thr Tyr Leu Lys Gly Ala Ala
            980                 985                 990

Pro Leu Ile Lys Ala Pro Glu Pro  Val Val Asp Glu Ala  Ala Lys Arg
        995                 1000                1005

Glu Ala  Glu Arg Leu Gln Lys  Glu Leu Gln Asp Ala  Gln Arg Gln
    1010                1015                1020

Leu Asp  Asp Ala Lys Arg Ala  Ala Ala Glu Ala Asn  Ser Lys Leu
    1025                1030                1035

Ala Ala  Ala Lys Glu Glu Ala  Lys Thr Ala Ala Ala  Ser Ala Lys
    1040                1045                1050

Pro Ala  Val Asp Thr Ala Val  Val Glu Lys His Arg  Ala Ile Leu
    1055                1060                1065

Lys Ser  Met Leu Ala Glu Leu  Asp Gly Tyr Gly Ser  Val Asp Ala
    1070                1075                1080

Ser Ser  Leu Gln Gln Gln Gln  Gln Gln Gln Thr Ala  Pro Ala Pro
    1085                1090                1095

Val Lys  Ala Ala Ala Pro Ala  Ala Pro Val Ala Ser  Ala Pro Ala
    1100                1105                1110

Pro Ala  Val Ser Asn Glu Leu  Leu Glu Lys Ala Glu  Thr Val Val
    1115                1120                1125

Met Glu  Val Leu Ala Ala Lys  Thr Gly Tyr Glu Thr  Asp Met Ile
    1130                1135                1140

Glu Ala  Asp Met Glu Leu Glu  Thr Glu Leu Gly Ile  Asp Ser Ile
    1145                1150                1155

Lys Arg  Val Glu Ile Leu Ser  Glu Val Gln Ala Met  Leu Asn Val
    1160                1165                1170

Glu Ala  Lys Asp Val Asp Ala  Leu Ser Arg Thr Arg  Thr Val Gly
    1175                1180                1185

Glu Val  Val Asn Ala Met Lys  Ala Glu Ile Ala Gly  Ser Ser Ala
    1190                1195                1200

Pro Ala  Pro Ala Ala Ala Ala  Pro Ala Pro Ala Lys  Ala Ala Pro
    1205                1210                1215

Ala Ala  Ala Ala Pro Ala Val  Ser Asn Glu Leu Leu  Glu Lys Ala
    1220                1225                1230

Glu Thr  Val Val Met Glu Val  Leu Ala Ala Lys Thr  Gly Tyr Glu
    1235                1240                1245

Thr Asp  Met Ile Glu Ser Asp  Met Glu Leu Glu Thr  Glu Leu Gly
    1250                1255                1260
```

-continued

Ile Asp Ser Ile Lys Arg Val Glu Ile Leu Ser Glu Val Gln Ala
1265 1270 1275

Met Leu Asn Val Glu Ala Lys Asp Val Asp Ala Leu Ser Arg Thr
1280 1285 1290

Arg Thr Val Gly Glu Val Val Asn Ala Met Lys Ala Glu Ile Ala
1295 1300 1305

Gly Gly Ser Ala Pro Ala Pro Ala Ala Ala Ala Pro Gly Pro Ala
1310 1315 1320

Ala Ala Ala Pro Ala Pro Ala Ala Ala Ala Pro Ala Val Ser Asn
1325 1330 1335

Glu Leu Leu Glu Lys Ala Glu Thr Val Val Met Glu Val Leu Ala
1340 1345 1350

Ala Lys Thr Gly Tyr Glu Thr Asp Met Ile Glu Ser Asp Met Glu
1355 1360 1365

Leu Glu Thr Glu Leu Gly Ile Asp Ser Ile Lys Arg Val Glu Ile
1370 1375 1380

Leu Ser Glu Val Gln Ala Met Leu Asn Val Glu Ala Lys Asp Val
1385 1390 1395

Asp Ala Leu Ser Arg Thr Arg Thr Val Gly Glu Val Val Asp Ala
1400 1405 1410

Met Lys Ala Glu Ile Ala Gly Gly Ser Ala Pro Ala Pro Ala Ala
1415 1420 1425

Ala Ala Pro Ala Pro Ala Ala Ala Ala Pro Ala Pro Ala Ala Pro
1430 1435 1440

Ala Pro Ala Val Ser Ser Glu Leu Leu Glu Lys Ala Glu Thr Val
1445 1450 1455

Val Met Glu Val Leu Ala Ala Lys Thr Gly Tyr Glu Thr Asp Met
1460 1465 1470

Ile Glu Ser Asp Met Glu Leu Glu Thr Glu Leu Gly Ile Asp Ser
1475 1480 1485

Ile Lys Arg Val Glu Ile Leu Ser Glu Val Gln Ala Met Leu Asn
1490 1495 1500

Val Glu Ala Lys Asp Val Asp Ala Leu Ser Arg Thr Arg Thr Val
1505 1510 1515

Gly Glu Val Val Asp Ala Met Lys Ala Glu Ile Ala Gly Gly Ser
1520 1525 1530

Ala Pro Ala Pro Ala Ala Ala Ala Pro Ala Pro Ala Ala Ala Ala
1535 1540 1545

Pro Ala Pro Ala Ala Pro Ala Pro Ala Ala Pro Ala Pro Ala Val
1550 1555 1560

Ser Ser Glu Leu Leu Glu Lys Ala Glu Thr Val Val Met Glu Val
1565 1570 1575

Leu Ala Ala Lys Thr Gly Tyr Glu Thr Asp Met Ile Glu Ser Asp
1580 1585 1590

Met Glu Leu Glu Thr Glu Leu Gly Ile Asp Ser Ile Lys Arg Val
1595 1600 1605

Glu Ile Leu Ser Glu Val Gln Ala Met Leu Asn Val Glu Ala Lys
1610 1615 1620

Asp Val Asp Ala Leu Ser Arg Thr Arg Thr Val Gly Glu Val Val
1625 1630 1635

Asp Ala Met Lys Ala Glu Ile Ala Gly Ser Ser Ala Ser Ala Pro
1640 1645 1650

-continued

```
Ala Ala Ala Ala Pro Ala Pro Ala Ala Ala Ala Pro Ala Pro Ala
    1655                1660                1665

Ala Ala Ala Pro Ala Val Ser Asn Glu Leu Leu Glu Lys Ala Glu
    1670                1675                1680

Thr Val Val Met Glu Val Leu Ala Ala Lys Thr Gly Tyr Glu Thr
    1685                1690                1695

Asp Met Ile Glu Ser Asp Met Glu Leu Glu Thr Glu Leu Gly Ile
    1700                1705                1710

Asp Ser Ile Lys Arg Val Glu Ile Leu Ser Glu Val Gln Ala Met
    1715                1720                1725

Leu Asn Val Glu Ala Lys Asp Val Asp Ala Leu Ser Arg Thr Arg
    1730                1735                1740

Thr Val Gly Glu Val Val Asp Ala Met Lys Ala Glu Ile Ala Gly
    1745                1750                1755

Gly Ser Ala Pro Ala Pro Ala Ala Ala Ala Pro Ala Pro Ala Ala
    1760                1765                1770

Ala Ala Pro Ala Val Ser Asn Glu Leu Leu Glu Lys Ala Glu Thr
    1775                1780                1785

Val Val Met Glu Val Leu Ala Ala Lys Thr Gly Tyr Glu Thr Asp
    1790                1795                1800

Met Ile Glu Ser Asp Met Glu Leu Glu Thr Glu Leu Gly Ile Asp
    1805                1810                1815

Ser Ile Lys Arg Val Glu Ile Leu Ser Glu Val Gln Ala Met Leu
    1820                1825                1830

Asn Val Glu Ala Lys Asp Val Asp Ala Leu Ser Arg Thr Arg Thr
    1835                1840                1845

Val Gly Glu Val Val Asp Ala Met Lys Ala Glu Ile Ala Gly Ser
    1850                1855                1860

Ser Ala Pro Ala Pro Ala Ala Ala Ala Pro Ala Pro Ala Ala Ala
    1865                1870                1875

Ala Pro Ala Pro Ala Ala Ala Ala Pro Ala Val Ser Ser Glu Leu
    1880                1885                1890

Leu Glu Lys Ala Glu Thr Val Val Met Glu Val Leu Ala Ala Lys
    1895                1900                1905

Thr Gly Tyr Glu Thr Asp Met Ile Glu Ser Asp Met Glu Leu Glu
    1910                1915                1920

Thr Glu Leu Gly Ile Asp Ser Ile Lys Arg Val Glu Ile Leu Ser
    1925                1930                1935

Glu Val Gln Ala Met Leu Asn Val Glu Ala Lys Asp Val Asp Ala
    1940                1945                1950

Leu Ser Arg Thr Arg Thr Val Gly Glu Val Val Asp Ala Met Lys
    1955                1960                1965

Ala Glu Ile Ala Gly Gly Ser Ala Pro Ala Pro Ala Ala Ala Ala
    1970                1975                1980

Pro Ala Pro Ala Ala Ala Ala Pro Ala Val Ser Asn Glu Leu Leu
    1985                1990                1995

Glu Lys Ala Glu Thr Val Val Met Glu Val Leu Ala Ala Lys Thr
    2000                2005                2010

Gly Tyr Glu Thr Asp Met Ile Glu Ser Asp Met Glu Leu Glu Thr
    2015                2020                2025

Glu Leu Gly Ile Asp Ser Ile Lys Arg Val Glu Ile Leu Ser Glu
    2030                2035                2040

Val Gln Ala Met Leu Asn Val Glu Ala Lys Asp Val Asp Ala Leu
```

```
    2045                2050                2055

Ser Arg  Thr Arg Thr Val Gly  Glu Val Val Asp Ala  Met Lys Ala
    2060                2065                2070

Glu Ile  Ala Gly Gly Ser Ala  Pro Ala Pro Ala Ala  Ala Ala Pro
    2075                2080                2085

Ala Ser  Ala Gly Ala Ala Pro  Ala Val Lys Ile Asp  Ser Val His
    2090                2095                2100

Gly Ala  Asp Cys Asp Asp Leu  Ser Leu Met His Ala  Lys Val Val
    2105                2110                2115

Asp Ile  Arg Arg Pro Asp Glu  Leu Ile Leu Glu Arg  Pro Glu Asn
    2120                2125                2130

Arg Pro  Val Leu Val Val Asp  Asp Gly Ser Glu Leu  Thr Leu Ala
    2135                2140                2145

Leu Val  Arg Val Leu Gly Ala  Cys Ala Val Val Leu  Thr Phe Glu
    2150                2155                2160

Gly Leu  Gln Leu Ala Gln Arg  Ala Gly Ala Ala Ala  Ile Arg His
    2165                2170                2175

Val Leu  Ala Lys Asp Leu Ser  Ala Glu Ser Ala Glu  Lys Ala Ile
    2180                2185                2190

Lys Glu  Ala Glu Gln Arg Phe  Gly Ala Leu Gly Gly  Phe Ile Ser
    2195                2200                2205

Gln Gln  Ala Glu Arg Phe Glu  Pro Ala Glu Ile Leu  Gly Phe Thr
    2210                2215                2220

Leu Met  Cys Ala Lys Phe Ala  Lys Ala Ser Leu Cys  Thr Ala Val
    2225                2230                2235

Ala Gly  Gly Arg Pro Ala Phe  Ile Gly Val Ala Arg  Leu Asp Gly
    2240                2245                2250

Arg Leu  Gly Phe Thr Ser Gln  Gly Thr Ser Asp Ala  Leu Lys Arg
    2255                2260                2265

Ala Gln  Arg Gly Ala Ile Phe  Gly Leu Cys Lys Thr  Ile Gly Leu
    2270                2275                2280

Glu Trp  Ser Glu Ser Asp Val  Phe Ser Arg Gly Val  Asp Ile Ala
    2285                2290                2295

Gln Gly  Met His Pro Glu Asp  Ala Ala Val Ala Ile  Val Arg Glu
    2300                2305                2310

Met Ala  Cys Ala Asp Ile Arg  Ile Arg Glu Val Gly  Ile Gly Ala
    2315                2320                2325

Asn Gln  Gln Arg Cys Thr Ile  Arg Ala Ala Lys Leu  Glu Thr Gly
    2330                2335                2340

Asn Pro  Gln Arg Gln Ile Ala  Lys Asp Asp Val Leu  Leu Val Ser
    2345                2350                2355

Gly Gly  Ala Arg Gly Ile Thr  Pro Leu Cys Ile Arg  Glu Ile Thr
    2360                2365                2370

Arg Gln  Ile Ala Gly Gly Lys  Tyr Ile Leu Leu Gly  Arg Ser Lys
    2375                2380                2385

Val Ser  Ala Ser Glu Pro Ala  Trp Cys Ala Gly Ile  Thr Asp Glu
    2390                2395                2400

Lys Ala  Val Gln Lys Ala Ala  Thr Gln Glu Leu Lys  Arg Ala Phe
    2405                2410                2415

Ser Ala  Gly Glu Gly Pro Lys  Pro Thr Pro Arg Ala  Val Thr Lys
    2420                2425                2430

Leu Val  Gly Ser Val Leu Gly  Ala Arg Glu Val Arg  Ser Ser Ile
    2435                2440                2445
```

-continued

```
Ala Ala  Ile Glu Ala Leu Gly  Gly Lys Ala Ile Tyr  Ser Ser Cys
    2450                 2455                 2460

Asp Val  Asn Ser Ala Ala Asp  Val Ala Lys Ala Val  Arg Asp Ala
    2465                 2470                 2475

Glu Ser  Gln Leu Gly Ala Arg  Val Ser Gly Ile Val  His Ala Ser
    2480                 2485                 2490

Gly Val  Leu Arg Asp Arg Leu  Ile Glu Lys Lys Leu  Pro Asp Glu
    2495                 2500                 2505

Phe Asp  Ala Val Phe Gly Thr  Lys Val Thr Gly Leu  Glu Asn Leu
    2510                 2515                 2520

Leu Ala  Ala Val Asp Arg Ala  Asn Leu Lys His Met  Val Leu Phe
    2525                 2530                 2535

Ser Ser  Leu Ala Gly Phe His  Gly Asn Val Gly Gln  Ser Asp Tyr
    2540                 2545                 2550

Ala Met  Ala Asn Glu Ala Leu  Asn Lys Met Gly Leu  Glu Leu Ala
    2555                 2560                 2565

Lys Asp  Val Ser Val Lys Ser  Ile Cys Phe Gly Pro  Trp Asp Gly
    2570                 2575                 2580

Gly Met  Val Thr Pro Gln Leu  Lys Lys Gln Phe Gln  Glu Met Gly
    2585                 2590                 2595

Val Gln  Ile Ile Pro Arg Glu  Gly Gly Ala Asp Thr  Val Ala Arg
    2600                 2605                 2610

Ile Val  Leu Gly Ser Ser Pro  Ala Glu Ile Leu Val  Gly Asn Trp
    2615                 2620                 2625

Arg Thr  Pro Ser Lys Lys Val  Gly Ser Asp Thr Ile  Thr Leu His
    2630                 2635                 2640

Arg Lys  Ile Ser Ala Lys Ser  Asn Pro Phe Leu Glu  Asp His Val
    2645                 2650                 2655

Ile Gln  Gly Arg Arg Val Leu  Pro Met Thr Leu Ala  Ile Gly Ser
    2660                 2665                 2670

Leu Ala  Glu Thr Cys Leu Gly  Leu Phe Pro Gly Tyr  Ser Leu Trp
    2675                 2680                 2685

Ala Ile  Asp Asp Ala Gln Leu  Phe Lys Gly Val Thr  Val Asp Gly
    2690                 2695                 2700

Asp Val  Asn Cys Glu Val Thr  Leu Thr Pro Ser Thr  Ala Pro Ser
    2705                 2710                 2715

Gly Arg  Val Asn Val Gln Ala  Thr Leu Lys Thr Phe  Ser Ser Gly
    2720                 2725                 2730

Lys Leu  Val Pro Ala Tyr Arg  Ala Val Ile Val Leu  Ser Asn Gln
    2735                 2740                 2745

Gly Ala  Pro Pro Ala Asn Ala  Thr Met Gln Pro Pro  Ser Leu Asp
    2750                 2755                 2760

Ala Asp  Pro Ala Leu Gln Gly  Ser Val Tyr Asp Gly  Lys Thr Leu
    2765                 2770                 2775

Phe His  Gly Pro Ala Phe Arg  Gly Ile Asp Asp Val  Leu Ser Cys
    2780                 2785                 2790

Thr Lys  Ser Gln Leu Val Ala  Lys Cys Ser Ala Val  Pro Gly Ser
    2795                 2800                 2805

Asp Ala  Ala Arg Gly Glu Phe  Ala Thr Asp Thr Asp  Ala His Asp
    2810                 2815                 2820

Pro Phe  Val Asn Asp Leu Ala  Phe Gln Ala Met Leu  Val Trp Val
    2825                 2830                 2835
```

-continued

```
Arg Arg  Thr Leu Gly Gln Ala  Ala Leu Pro Asn Ser  Ile Gln Arg
    2840                 2845                 2850

Ile Val  Gln His Arg Pro Val  Pro Gln Asp Lys Pro  Phe Tyr Ile
    2855                 2860                 2865

Thr Leu  Arg Ser Asn Gln Ser  Gly Gly His Ser Gln  His Lys His
    2870                 2875                 2880

Ala Leu  Gln Phe His Asn Glu  Gln Gly Asp Leu Phe  Ile Asp Val
    2885                 2890                 2895

Gln Ala  Ser Val Ile Ala Thr  Asp Ser Leu Ala Phe
    2900                 2905                 2910


<210> SEQ ID NO 3
<211> LENGTH: 6180
<212> TYPE: DNA
<213> ORGANISM: Schizochytrium sp.
<220> FEATURE:
<221> NAME/KEY: CDS
<222> LOCATION: (1)..(6180)

<400> SEQUENCE: 3

atg gcc gct cgg aat gtg agc gcc gcg cat gag atg cac gat gaa aag       48
Met Ala Ala Arg Asn Val Ser Ala Ala His Glu Met His Asp Glu Lys
1               5                   10                  15

cgc atc gcc gtc gtc ggc atg gcc gtc cag tac gcc gga tgc aaa acc       96
Arg Ile Ala Val Val Gly Met Ala Val Gln Tyr Ala Gly Cys Lys Thr
            20                  25                  30

aag gac gag ttc tgg gag gtg ctc atg aac ggc aag gtc gag tcc aag      144
Lys Asp Glu Phe Trp Glu Val Leu Met Asn Gly Lys Val Glu Ser Lys
        35                  40                  45

gtg atc agc gac aaa cga ctc ggc tcc aac tac cgc gcc gag cac tac      192
Val Ile Ser Asp Lys Arg Leu Gly Ser Asn Tyr Arg Ala Glu His Tyr
    50                  55                  60

aaa gca gag cgc agc aag tat gcc gac acc ttt tgc aac gaa acg tac      240
Lys Ala Glu Arg Ser Lys Tyr Ala Asp Thr Phe Cys Asn Glu Thr Tyr
65                  70                  75                  80

ggc acc ctt gac gag aac gag atc gac aac gag cac gaa ctc ctc ctc      288
Gly Thr Leu Asp Glu Asn Glu Ile Asp Asn Glu His Glu Leu Leu Leu
                85                  90                  95

aac ctc gcc aag cag gca ctc gca gag aca tcc gtc aaa gac tcg aca      336
Asn Leu Ala Lys Gln Ala Leu Ala Glu Thr Ser Val Lys Asp Ser Thr
            100                 105                 110

cgc tgc ggc atc gtc agc ggc tgc ctc tcg ttc ccc atg gac aac ctc      384
Arg Cys Gly Ile Val Ser Gly Cys Leu Ser Phe Pro Met Asp Asn Leu
        115                 120                 125

cag ggt gaa ctc ctc aac gtg tac caa aac cat gtc gag aaa aag ctc      432
Gln Gly Glu Leu Leu Asn Val Tyr Gln Asn His Val Glu Lys Lys Leu
    130                 135                 140

ggg gcc cgc gtc ttc aag gac gcc tcc cat tgg tcc gaa cgc gag cag      480
Gly Ala Arg Val Phe Lys Asp Ala Ser His Trp Ser Glu Arg Glu Gln
145                 150                 155                 160

tcc aac aaa ccc gag gcc ggt gac cgc cgc atc ttc atg gac ccg gcc      528
Ser Asn Lys Pro Glu Ala Gly Asp Arg Arg Ile Phe Met Asp Pro Ala
                165                 170                 175

tcc ttc gtc gcc gaa gaa ctc aac ctc ggc gcc ctt cac tac tcc gtc      576
Ser Phe Val Ala Glu Glu Leu Asn Leu Gly Ala Leu His Tyr Ser Val
            180                 185                 190

gac gca gca tgc gcc acg gcg ctc tac gtg ctc cgc ctc gcg cag gat      624
Asp Ala Ala Cys Ala Thr Ala Leu Tyr Val Leu Arg Leu Ala Gln Asp
        195                 200                 205

cat ctc gtc tcc ggc gcc gcc gac gtc atg ctc tgc ggt gcc acc tgc      672
```

-continued

```
His Leu Val Ser Gly Ala Ala Asp Val Met Leu Cys Gly Ala Thr Cys
    210                 215                 220

ctg ccg gag ccc ttt ttc atc ctt tcg ggc ttt tcc acc ttc cag gcc      720
Leu Pro Glu Pro Phe Phe Ile Leu Ser Gly Phe Ser Thr Phe Gln Ala
225                 230                 235                 240

atg ccc gtc ggc acg ggc cag aac gtg tcc atg ccg ctg cac aag gac      768
Met Pro Val Gly Thr Gly Gln Asn Val Ser Met Pro Leu His Lys Asp
                245                 250                 255

agc cag ggc ctc acc ccg ggt gag ggc ggc tcc atc atg gtc ctc aag      816
Ser Gln Gly Leu Thr Pro Gly Glu Gly Gly Ser Ile Met Val Leu Lys
            260                 265                 270

cgt ctc gat gat gcc atc cgc gac ggc gac cac atc tac ggc acc ctt      864
Arg Leu Asp Asp Ala Ile Arg Asp Gly Asp His Ile Tyr Gly Thr Leu
        275                 280                 285

ctc ggc gcc aat gtc agc aac tcc ggc aca ggt ctg ccc ctc aag ccc      912
Leu Gly Ala Asn Val Ser Asn Ser Gly Thr Gly Leu Pro Leu Lys Pro
    290                 295                 300

ctt ctc ccc agc gag aaa aag tgc ctc atg gac acc tac acg cgc att      960
Leu Leu Pro Ser Glu Lys Lys Cys Leu Met Asp Thr Tyr Thr Arg Ile
305                 310                 315                 320

aac gtg cac ccg cac aag att cag tac gtc gag tgc cac gcc acc ggc     1008
Asn Val His Pro His Lys Ile Gln Tyr Val Glu Cys His Ala Thr Gly
                325                 330                 335

acg ccc cag ggt gat cgt gtg gaa atc gac gcc gtc aag gcc tgc ttt     1056
Thr Pro Gln Gly Asp Arg Val Glu Ile Asp Ala Val Lys Ala Cys Phe
            340                 345                 350

gaa ggc aag gtc ccc cgt ttc ggt acc aca aag ggc aac ttt gga cac     1104
Glu Gly Lys Val Pro Arg Phe Gly Thr Thr Lys Gly Asn Phe Gly His
        355                 360                 365

acc ctc gtc gca gcc ggc ttt gcc ggt atg tgc aag gtc ctc ctc tcc     1152
Thr Leu Val Ala Ala Gly Phe Ala Gly Met Cys Lys Val Leu Leu Ser
    370                 375                 380

atg aag cat ggc atc atc ccg ccc acc ccg ggt atc gat gac gag acc     1200
Met Lys His Gly Ile Ile Pro Pro Thr Pro Gly Ile Asp Asp Glu Thr
385                 390                 395                 400

aag atg gac cct ctc gtc gtc tcc ggt gag gcc atc cca tgg cca gag     1248
Lys Met Asp Pro Leu Val Val Ser Gly Glu Ala Ile Pro Trp Pro Glu
                405                 410                 415

acc aac ggc gag ccc aag cgc gcc ggt ctc tcg gcc ttt ggc ttt ggt     1296
Thr Asn Gly Glu Pro Lys Arg Ala Gly Leu Ser Ala Phe Gly Phe Gly
            420                 425                 430

ggc acc aac gcc cat gcc gtc ttt gag gag cat gac ccc tcc aac gcc     1344
Gly Thr Asn Ala His Ala Val Phe Glu Glu His Asp Pro Ser Asn Ala
        435                 440                 445

gcc tgc acg ggc cac gac tcc att tct gcg ctc tcg gcc cgc tgc ggc     1392
Ala Cys Thr Gly His Asp Ser Ile Ser Ala Leu Ser Ala Arg Cys Gly
    450                 455                 460

ggt gaa agc aac atg cgc atc gcc atc act ggt atg gac gcc acc ttt     1440
Gly Glu Ser Asn Met Arg Ile Ala Ile Thr Gly Met Asp Ala Thr Phe
465                 470                 475                 480

ggc gct ctc aag gga ctc gac gcc ttc gag cgc gcc att tac acc ggc     1488
Gly Ala Leu Lys Gly Leu Asp Ala Phe Glu Arg Ala Ile Tyr Thr Gly
                485                 490                 495

gct cac ggt gcc atc cca ctc cca gaa aag cgc tgg cgc ttt ctc ggc     1536
Ala His Gly Ala Ile Pro Leu Pro Glu Lys Arg Trp Arg Phe Leu Gly
            500                 505                 510

aag gac aag gac ttt ctt gac ctc tgc ggc gtc aag gcc acc ccg cac     1584
Lys Asp Lys Asp Phe Leu Asp Leu Cys Gly Val Lys Ala Thr Pro His
        515                 520                 525
```

```
ggc tgc tac att gaa gat gtt gag gtc gac ttc cag cgc ctc cgc acg      1632
Gly Cys Tyr Ile Glu Asp Val Glu Val Asp Phe Gln Arg Leu Arg Thr
    530                 535                 540

ccc atg acc cct gaa gac atg ctc ctc cct cag cag ctt ctg gcc gtc      1680
Pro Met Thr Pro Glu Asp Met Leu Leu Pro Gln Gln Leu Leu Ala Val
545                 550                 555                 560

acc acc att gac cgc gcc atc ctc gac tcg gga atg aaa aag ggt ggc      1728
Thr Thr Ile Asp Arg Ala Ile Leu Asp Ser Gly Met Lys Lys Gly Gly
                565                 570                 575

aat gtc gcc gtc ttt gtc ggc ctc ggc acc gac ctc gag ctc tac cgt      1776
Asn Val Ala Val Phe Val Gly Leu Gly Thr Asp Leu Glu Leu Tyr Arg
            580                 585                 590

cac cgt gct cgc gtc gct ctc aag gag cgc gtc cgc cct gaa gcc tcc      1824
His Arg Ala Arg Val Ala Leu Lys Glu Arg Val Arg Pro Glu Ala Ser
        595                 600                 605

aag aag ctc aat gac atg atg cag tac att aac gac tgc ggc aca tcc      1872
Lys Lys Leu Asn Asp Met Met Gln Tyr Ile Asn Asp Cys Gly Thr Ser
    610                 615                 620

aca tcg tac acc tcg tac att ggc aac ctc gtc gcc acg cgc gtc tcg      1920
Thr Ser Tyr Thr Ser Tyr Ile Gly Asn Leu Val Ala Thr Arg Val Ser
625                 630                 635                 640

tcg cag tgg ggc ttc acg ggc ccc tcc ttt acg atc acc gag ggc aac      1968
Ser Gln Trp Gly Phe Thr Gly Pro Ser Phe Thr Ile Thr Glu Gly Asn
                645                 650                 655

aac tcc gtc tac cgc tgc gcc gag ctc ggc aag tac ctc ctc gag acc      2016
Asn Ser Val Tyr Arg Cys Ala Glu Leu Gly Lys Tyr Leu Leu Glu Thr
            660                 665                 670

ggc gag gtc gat ggc gtc gtc gtt gcg ggt gtc gat ctc tgc ggc agt      2064
Gly Glu Val Asp Gly Val Val Val Ala Gly Val Asp Leu Cys Gly Ser
        675                 680                 685

gcc gaa aac ctt tac gtc aag tct cgc cgc ttc aag gtg tcc acc tcc      2112
Ala Glu Asn Leu Tyr Val Lys Ser Arg Arg Phe Lys Val Ser Thr Ser
    690                 695                 700

gat acc ccg cgc gcc agc ttt gac gcc gcc gcc gat ggc tac ttt gtc      2160
Asp Thr Pro Arg Ala Ser Phe Asp Ala Ala Ala Asp Gly Tyr Phe Val
705                 710                 715                 720

ggc gag ggc tgc ggt gcc ttt gtg ctc aag cgt gag act agc tgc acc      2208
Gly Glu Gly Cys Gly Ala Phe Val Leu Lys Arg Glu Thr Ser Cys Thr
                725                 730                 735

aag gac gac cgt atc tac gct tgc atg gat gcc atc gtc cct ggc aac      2256
Lys Asp Asp Arg Ile Tyr Ala Cys Met Asp Ala Ile Val Pro Gly Asn
            740                 745                 750

gtc cct agc gcc tgc ttg cgc gag gcc ctc gac cag gcg cgc gtc aag      2304
Val Pro Ser Ala Cys Leu Arg Glu Ala Leu Asp Gln Ala Arg Val Lys
        755                 760                 765

ccg ggc gat atc gag atg ctc gag ctc agc gcc gac tcc gcc cgc cac      2352
Pro Gly Asp Ile Glu Met Leu Glu Leu Ser Ala Asp Ser Ala Arg His
    770                 775                 780

ctc aag gac ccg tcc gtc ctg ccc aag gag ctc act gcc gag gag gaa      2400
Leu Lys Asp Pro Ser Val Leu Pro Lys Glu Leu Thr Ala Glu Glu Glu
785                 790                 795                 800

atc ggc ggc ctt cag acg atc ctt cgt gac gat gac aag ctc ccg cgc      2448
Ile Gly Gly Leu Gln Thr Ile Leu Arg Asp Asp Asp Lys Leu Pro Arg
                805                 810                 815

aac gtc gca acg ggc agt gtc aag gcc acc gtc ggt gac acc ggt tat      2496
Asn Val Ala Thr Gly Ser Val Lys Ala Thr Val Gly Asp Thr Gly Tyr
            820                 825                 830

gcc tct ggt gct gcc agc ctc atc aag gct gcg ctt tgc atc tac aac      2544
Ala Ser Gly Ala Ala Ser Leu Ile Lys Ala Ala Leu Cys Ile Tyr Asn
        835                 840                 845
```

-continued

```
cgc tac ctg ccc agc aac ggc gac gac tgg gat gaa ccc gcc cct gag     2592
Arg Tyr Leu Pro Ser Asn Gly Asp Asp Trp Asp Glu Pro Ala Pro Glu
    850                 855                 860

gcg ccc tgg gac agc acc ctc ttt gcg tgc cag acc tcg cgc gct tgg     2640
Ala Pro Trp Asp Ser Thr Leu Phe Ala Cys Gln Thr Ser Arg Ala Trp
865                 870                 875                 880

ctc aag aac cct ggc gag cgt cgc tat gcg gcc gtc tcg ggc gtc tcc     2688
Leu Lys Asn Pro Gly Glu Arg Arg Tyr Ala Ala Val Ser Gly Val Ser
                885                 890                 895

gag acg cgc tcg tgc tat tcc gtg ctc ctc tcc gaa gcc gag ggc cac     2736
Glu Thr Arg Ser Cys Tyr Ser Val Leu Leu Ser Glu Ala Glu Gly His
            900                 905                 910

tac gag cgc gag aac cgc atc tcg ctc gac gag gag gcg ccc aag ctc     2784
Tyr Glu Arg Glu Asn Arg Ile Ser Leu Asp Glu Glu Ala Pro Lys Leu
        915                 920                 925

att gtg ctt cgc gcc gac tcc cac gag gag atc ctt ggt cgc ctc gac     2832
Ile Val Leu Arg Ala Asp Ser His Glu Glu Ile Leu Gly Arg Leu Asp
    930                 935                 940

aag atc cgc gag cgc ttc ttg cag ccc acg ggc gcc gcc ccg cgc gag     2880
Lys Ile Arg Glu Arg Phe Leu Gln Pro Thr Gly Ala Ala Pro Arg Glu
945                 950                 955                 960

tcc gag ctc aag gcg cag gcc cgc cgc atc ttc ctc gag ctc ctc ggc     2928
Ser Glu Leu Lys Ala Gln Ala Arg Arg Ile Phe Leu Glu Leu Leu Gly
                965                 970                 975

gag acc ctt gcc cag gat gcc gct tct tca ggc tcg caa aag ccc ctc     2976
Glu Thr Leu Ala Gln Asp Ala Ala Ser Ser Gly Ser Gln Lys Pro Leu
            980                 985                 990

gct ctc agc ctc gtc tcc acg ccc  tcc aag ctc cag cgc  gag gtc gag   3024
Ala Leu Ser Leu Val Ser Thr Pro  Ser Lys Leu Gln Arg  Glu Val Glu
        995                 1000                 1005

ctc gcg  gcc aag ggt atc ccg  cgc tgc ctc aag atg  cgc cgc gat      3069
Leu Ala  Ala Lys Gly Ile Pro  Arg Cys Leu Lys Met  Arg Arg Asp
    1010                 1015                 1020

tgg agc  tcc cct gct ggc agc  cgc tac gcg cct gag  ccg ctc gcc      3114
Trp Ser  Ser Pro Ala Gly Ser  Arg Tyr Ala Pro Glu  Pro Leu Ala
    1025                 1030                 1035

agc gac  cgc gtc gcc ttc atg  tac ggc gaa ggt cgc  agc cct tac      3159
Ser Asp  Arg Val Ala Phe Met  Tyr Gly Glu Gly Arg  Ser Pro Tyr
    1040                 1045                 1050

tac ggc  atc acc caa gac att  cac cgc att tgg ccc  gaa ctc cac      3204
Tyr Gly  Ile Thr Gln Asp Ile  His Arg Ile Trp Pro  Glu Leu His
    1055                 1060                 1065

gag gtc  atc aac gaa aag acg  aac cgt ctc tgg gcc  gaa ggc gac      3249
Glu Val  Ile Asn Glu Lys Thr  Asn Arg Leu Trp Ala  Glu Gly Asp
    1070                 1075                 1080

cgc tgg  gtc atg ccg cgc gcc  agc ttc aag tcg gag  ctc gag agc      3294
Arg Trp  Val Met Pro Arg Ala  Ser Phe Lys Ser Glu  Leu Glu Ser
    1085                 1090                 1095

cag cag  caa gag ttt gat cgc  aac atg att gaa atg  ttc cgt ctt      3339
Gln Gln  Gln Glu Phe Asp Arg  Asn Met Ile Glu Met  Phe Arg Leu
    1100                 1105                 1110

gga atc  ctc acc tca att gcc  ttc acc aat ctg gcg  cgc gac gtt      3384
Gly Ile  Leu Thr Ser Ile Ala  Phe Thr Asn Leu Ala  Arg Asp Val
    1115                 1120                 1125

ctc aac  atc acg ccc aag gcc  gcc ttt ggc ctc agt  ctt ggc gag      3429
Leu Asn  Ile Thr Pro Lys Ala  Ala Phe Gly Leu Ser  Leu Gly Glu
    1130                 1135                 1140

att tcc  atg att ttt gcc ttt  tcc aag aag aac ggt  ctc atc tcc      3474
Ile Ser  Met Ile Phe Ala Phe  Ser Lys Lys Asn Gly  Leu Ile Ser
```

-continued

```
    1145                1150                1155

gac cag  ctc acc aag gat ctt  cgc gag tcc gac gtg  tgg aac aag      3519
Asp Gln  Leu Thr Lys Asp Leu  Arg Glu Ser Asp Val  Trp Asn Lys
    1160                1165                1170

gct ctg  gcc gtt gaa ttt aat  gcg ctg cgc gag gcc  tgg ggc att      3564
Ala Leu  Ala Val Glu Phe Asn  Ala Leu Arg Glu Ala  Trp Gly Ile
    1175                1180                1185

cca cag  agt gtc ccc aag gac  gag ttc tgg caa ggc  tac att gtg      3609
Pro Gln  Ser Val Pro Lys Asp  Glu Phe Trp Gln Gly  Tyr Ile Val
    1190                1195                1200

cgc ggc  acc aag cag gat atc  gag gcg gcc atc gcc  ccg gac agc      3654
Arg Gly  Thr Lys Gln Asp Ile  Glu Ala Ala Ile Ala  Pro Asp Ser
    1205                1210                1215

aag tac  gtg cgc ctc acc atc  atc aat gat gcc aac  acc gcc ctc      3699
Lys Tyr  Val Arg Leu Thr Ile  Ile Asn Asp Ala Asn  Thr Ala Leu
    1220                1225                1230

att agc  ggc aag ccc gac gcc  tgc aag gct gcg atc  gcg cgt ctc      3744
Ile Ser  Gly Lys Pro Asp Ala  Cys Lys Ala Ala Ile  Ala Arg Leu
    1235                1240                1245

ggt ggc  aac att cct gcg ctt  ccc gtg acc cag ggc  atg tgc ggc      3789
Gly Gly  Asn Ile Pro Ala Leu  Pro Val Thr Gln Gly  Met Cys Gly
    1250                1255                1260

cac tgc  ccc gag gtg gga cct  tat acc aag gat atc  gcc aag atc      3834
His Cys  Pro Glu Val Gly Pro  Tyr Thr Lys Asp Ile  Ala Lys Ile
    1265                1270                1275

cat gcc  aac ctt gag ttc ccc  gtt gtc gac ggc ctt  gac ctc tgg      3879
His Ala  Asn Leu Glu Phe Pro  Val Val Asp Gly Leu  Asp Leu Trp
    1280                1285                1290

acc aca  atc aac cag aag cgc  ctc gtg cca cgc gcc  acg ggc gcc      3924
Thr Thr  Ile Asn Gln Lys Arg  Leu Val Pro Arg Ala  Thr Gly Ala
    1295                1300                1305

aag gac  gaa tgg gcc cct tct  tcc ttt ggc gag tac  gcc ggc cag      3969
Lys Asp  Glu Trp Ala Pro Ser  Ser Phe Gly Glu Tyr  Ala Gly Gln
    1310                1315                1320

ctc tac  gag aag cag gct aac  ttc ccc caa atc gtc  gag acc att      4014
Leu Tyr  Glu Lys Gln Ala Asn  Phe Pro Gln Ile Val  Glu Thr Ile
    1325                1330                1335

tac aag  caa aac tac gac gtc  ttt gtc gag gtt ggg  ccc aac aac      4059
Tyr Lys  Gln Asn Tyr Asp Val  Phe Val Glu Val Gly  Pro Asn Asn
    1340                1345                1350

cac cgt  agc acc gca gtg cgc  acc acg ctt ggt ccc  cag cgc aac      4104
His Arg  Ser Thr Ala Val Arg  Thr Thr Leu Gly Pro  Gln Arg Asn
    1355                1360                1365

cac ctt  gct ggc gcc atc gac  aag cag aac gag gat  gct tgg acg      4149
His Leu  Ala Gly Ala Ile Asp  Lys Gln Asn Glu Asp  Ala Trp Thr
    1370                1375                1380

acc atc  gtc aag ctt gtg gct  tcg ctc aag gcc cac  ctt gtt cct      4194
Thr Ile  Val Lys Leu Val Ala  Ser Leu Lys Ala His  Leu Val Pro
    1385                1390                1395

ggc gtc  acg atc tcg ccg ctg  tac cac tcc aag ctt  gtg gcg gag      4239
Gly Val  Thr Ile Ser Pro Leu  Tyr His Ser Lys Leu  Val Ala Glu
    1400                1405                1410

gct gag  gct tgc tac gct gcg  ctc tgc aag ggt gaa  aag ccc aag      4284
Ala Glu  Ala Cys Tyr Ala Ala  Leu Cys Lys Gly Glu  Lys Pro Lys
    1415                1420                1425

aag aac  aag ttt gtg cgc aag  att cag ctc aac ggt  cgc ttc aac      4329
Lys Asn  Lys Phe Val Arg Lys  Ile Gln Leu Asn Gly  Arg Phe Asn
    1430                1435                1440

agc aag  gcg gac ccc atc tcc  tcg gcc gat ctt gcc  agc ttt ccg      4374
```

-continued

```
Ser Lys  Ala Asp Pro Ile Ser  Ser Ala Asp Leu Ala  Ser Phe Pro
    1445                 1450                 1455

cct gcg  gac cct gcc att gaa  gcc gcc atc tcg agc  cgc atc atg      4419
Pro Ala  Asp Pro Ala Ile Glu  Ala Ala Ile Ser Ser  Arg Ile Met
    1460                 1465                 1470

aag cct  gtc gct ccc aag ttc  tac gcg cgt ctc aac  att gac gag      4464
Lys Pro  Val Ala Pro Lys Phe  Tyr Ala Arg Leu Asn  Ile Asp Glu
    1475                 1480                 1485

cag gac  gag acc cga gat ccg  atc ctc aac aag gac  aac gcg ccg      4509
Gln Asp  Glu Thr Arg Asp Pro  Ile Leu Asn Lys Asp  Asn Ala Pro
    1490                 1495                 1500

tct tct  tct tct tct tct tct  tct tct tct tct tct  tct tct tct      4554
Ser Ser  Ser Ser Ser Ser Ser  Ser Ser Ser Ser Ser  Ser Ser Ser
    1505                 1510                 1515

ccg tcg  cct gct cct tcg gcc  ccc gtg caa aag aag  gct gct ccc      4599
Pro Ser  Pro Ala Pro Ser Ala  Pro Val Gln Lys Lys  Ala Ala Pro
    1520                 1525                 1530

gcc gcg  gag acc aag gct gtt  gct tcg gct gac gca  ctt cgc agt      4644
Ala Ala  Glu Thr Lys Ala Val  Ala Ser Ala Asp Ala  Leu Arg Ser
    1535                 1540                 1545

gcc ctg  ctc gat ctc gac agt  atg ctt gcg ctg agc  tct gcc agt      4689
Ala Leu  Leu Asp Leu Asp Ser  Met Leu Ala Leu Ser  Ser Ala Ser
    1550                 1555                 1560

gcc tcc  ggc aac ctt gtt gag  act gcg cct agc gac  gcc tcg gtc      4734
Ala Ser  Gly Asn Leu Val Glu  Thr Ala Pro Ser Asp  Ala Ser Val
    1565                 1570                 1575

att gtg  ccg ccc tgc aac att  gcg gat ctc ggc agc  cgc gcc ttc      4779
Ile Val  Pro Pro Cys Asn Ile  Ala Asp Leu Gly Ser  Arg Ala Phe
    1580                 1585                 1590

atg aaa  acg tac ggt gtt tcg  gcg cct ctg tac acg  ggc gcc atg      4824
Met Lys  Thr Tyr Gly Val Ser  Ala Pro Leu Tyr Thr  Gly Ala Met
    1595                 1600                 1605

gcc aag  ggc att gcc tct gcg  gac ctc gtc att gcc  gcc ggc cgc      4869
Ala Lys  Gly Ile Ala Ser Ala  Asp Leu Val Ile Ala  Ala Gly Arg
    1610                 1615                 1620

cag ggc  atc ctt gcg tcc ttt  ggc gcc ggc gga ctt  ccc atg cag      4914
Gln Gly  Ile Leu Ala Ser Phe  Gly Ala Gly Gly Leu  Pro Met Gln
    1625                 1630                 1635

gtt gtg  cgt gag tcc atc gaa  aag att cag gcc gcc  ctg ccc aat      4959
Val Val  Arg Glu Ser Ile Glu  Lys Ile Gln Ala Ala  Leu Pro Asn
    1640                 1645                 1650

ggc ccg  tac gct gtc aac ctt  atc cat tct ccc ttt  gac agc aac      5004
Gly Pro  Tyr Ala Val Asn Leu  Ile His Ser Pro Phe  Asp Ser Asn
    1655                 1660                 1665

ctc gaa  aag ggc aat gtc gat  ctc ttc ctc gag aag  ggt gtc acc      5049
Leu Glu  Lys Gly Asn Val Asp  Leu Phe Leu Glu Lys  Gly Val Thr
    1670                 1675                 1680

ttt gtc  gag gcc tcg gcc ttt  atg acg ctc acc ccg  cag gtc gtg      5094
Phe Val  Glu Ala Ser Ala Phe  Met Thr Leu Thr Pro  Gln Val Val
    1685                 1690                 1695

cgg tac  cgc gcg gct ggc ctc  acg cgc aac gcc gac  ggc tcg gtc      5139
Arg Tyr  Arg Ala Ala Gly Leu  Thr Arg Asn Ala Asp  Gly Ser Val
    1700                 1705                 1710

aac atc  cgc aac cgt atc att  ggc aag gtc tcg cgc  acc gag ctc      5184
Asn Ile  Arg Asn Arg Ile Ile  Gly Lys Val Ser Arg  Thr Glu Leu
    1715                 1720                 1725

gcc gag  atg ttc atg cgt cct  gcg ccc gag cac ctt  ctt cag aag      5229
Ala Glu  Met Phe Met Arg Pro  Ala Pro Glu His Leu  Leu Gln Lys
    1730                 1735                 1740
```

-continued

```
ctc att gct tcc ggc gag atc aac cag gag cag gcc gag ctc gcc      5274
Leu Ile Ala Ser Gly Glu Ile Asn Gln Glu Gln Ala Glu Leu Ala
    1745                1750                1755

cgc cgt gtt ccc gtc gct gac gac atc gcg gtc gaa gct gac tcg      5319
Arg Arg Val Pro Val Ala Asp Asp Ile Ala Val Glu Ala Asp Ser
    1760                1765                1770

ggt ggc cac acc gac aac cgc ccc atc cac gtc att ctg ccc ctc      5364
Gly Gly His Thr Asp Asn Arg Pro Ile His Val Ile Leu Pro Leu
    1775                1780                1785

atc atc aac ctt cgc gac cgc ctt cac cgc gag tgc ggc tac ccg      5409
Ile Ile Asn Leu Arg Asp Arg Leu His Arg Glu Cys Gly Tyr Pro
    1790                1795                1800

gcc aac ctt cgc gtc cgt gtg ggc gcc ggc ggt ggc att ggg tgc      5454
Ala Asn Leu Arg Val Arg Val Gly Ala Gly Gly Gly Ile Gly Cys
    1805                1810                1815

ccc cag gcg gcg ctg gcc acc ttc aac atg ggt gcc tcc ttt att      5499
Pro Gln Ala Ala Leu Ala Thr Phe Asn Met Gly Ala Ser Phe Ile
    1820                1825                1830

gtc acc ggc acc gtg aac cag gtc gcc aag cag tcg ggc acg tgc      5544
Val Thr Gly Thr Val Asn Gln Val Ala Lys Gln Ser Gly Thr Cys
    1835                1840                1845

gac aat gtg cgc aag cag ctc gcg aag gcc act tac tcg gac gta      5589
Asp Asn Val Arg Lys Gln Leu Ala Lys Ala Thr Tyr Ser Asp Val
    1850                1855                1860

tgc atg gcc ccg gct gcc gac atg ttc gag gaa ggc gtc aag ctt      5634
Cys Met Ala Pro Ala Ala Asp Met Phe Glu Glu Gly Val Lys Leu
    1865                1870                1875

cag gtc ctc aag aag gga acc atg ttt ccc tcg cgc gcc aac aag      5679
Gln Val Leu Lys Lys Gly Thr Met Phe Pro Ser Arg Ala Asn Lys
    1880                1885                1890

ctc tac gag ctc ttt tgc aag tac gac tcg ttc gag tcc atg ccc      5724
Leu Tyr Glu Leu Phe Cys Lys Tyr Asp Ser Phe Glu Ser Met Pro
    1895                1900                1905

ccc gca gag ctt gcg cgc gtc gag aag cgc atc ttc agc cgc gcg      5769
Pro Ala Glu Leu Ala Arg Val Glu Lys Arg Ile Phe Ser Arg Ala
    1910                1915                1920

ctc gaa gag gtc tgg gac gag acc aaa aac ttt tac att aac cgt      5814
Leu Glu Glu Val Trp Asp Glu Thr Lys Asn Phe Tyr Ile Asn Arg
    1925                1930                1935

ctt cac aac ccg gag aag atc cag cgc gcc gag cgc gac ccc aag      5859
Leu His Asn Pro Glu Lys Ile Gln Arg Ala Glu Arg Asp Pro Lys
    1940                1945                1950

ctc aag atg tcg ctg tgc ttt cgc tgg tac ctg agc ctg gcg agc      5904
Leu Lys Met Ser Leu Cys Phe Arg Trp Tyr Leu Ser Leu Ala Ser
    1955                1960                1965

cgc tgg gcc aac act gga gct tcc gat cgc gtc atg gac tac cag      5949
Arg Trp Ala Asn Thr Gly Ala Ser Asp Arg Val Met Asp Tyr Gln
    1970                1975                1980

gtc tgg tgc ggt cct gcc att ggt tcc ttc aac gat ttc atc aag      5994
Val Trp Cys Gly Pro Ala Ile Gly Ser Phe Asn Asp Phe Ile Lys
    1985                1990                1995

gga act tac ctt gat ccg gcc gtc gca aac gag tac ccg tgc gtc      6039
Gly Thr Tyr Leu Asp Pro Ala Val Ala Asn Glu Tyr Pro Cys Val
    2000                2005                2010

gtt cag att aac aag cag atc ctt cgt gga gcg tgc ttc ttg cgc      6084
Val Gln Ile Asn Lys Gln Ile Leu Arg Gly Ala Cys Phe Leu Arg
    2015                2020                2025

cgt ctc gaa att ctg cgc aac gca cgc ctt tcc gat ggc gct gcc      6129
Arg Leu Glu Ile Leu Arg Asn Ala Arg Leu Ser Asp Gly Ala Ala
    2030                2035                2040
```

```
gct ctt  gtg gcc agc atc gat  gac aca tac gtc ccg  gcc gag aag      6174
Ala Leu  Val Ala Ser Ile Asp  Asp Thr Tyr Val Pro  Ala Glu Lys
    2045                 2050                 2055

ctg taa                                                             6180
Leu


<210> SEQ ID NO 4
<211> LENGTH: 2059
<212> TYPE: PRT
<213> ORGANISM: Schizochytrium sp.

<400> SEQUENCE: 4

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
            180                 185                 190

Asp Ala Ala Cys Ala Thr Ala Leu Tyr Val Leu Arg Leu Ala Gln Asp
        195                 200                 205

His Leu Val Ser Gly Ala Ala Asp Val Met Leu Cys Gly Ala Thr Cys
    210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Gly Ser Ile Met Val Leu Lys
            260                 265                 270

Arg Leu Asp Asp Ala Ile Arg Asp Gly Asp His Ile Tyr Gly Thr Leu
        275                 280                 285

Leu Gly Ala Asn Val Ser Asn Ser Gly Thr Gly Leu Pro Leu Lys Pro
    290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335
```

-continued

```
Thr Pro Gln Gly Asp Arg Val Glu Ile Asp Ala Val Lys Ala Cys Phe
            340                 345                 350

Glu Gly Lys Val Pro Arg Phe Gly Thr Thr Lys Gly Asn Phe Gly His
        355                 360                 365

Thr Leu Val Ala Ala Gly Phe Ala Gly Met Cys Lys Val Leu Leu Ser
    370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
                405                 410                 415

Thr Asn Gly Glu Pro Lys Arg Ala Gly Leu Ser Ala Phe Gly Phe Gly
            420                 425                 430

Gly Thr Asn Ala His Ala Val Phe Glu Glu His Asp Pro Ser Asn Ala
        435                 440                 445

Ala Cys Thr Gly His Asp Ser Ile Ser Ala Leu Ser Ala Arg Cys Gly
    450                 455                 460

Gly Glu Ser Asn Met Arg Ile Ala Ile Thr Gly Met Asp Ala Thr Phe
465                 470                 475                 480

Gly Ala Leu Lys Gly Leu Asp Ala Phe Glu Arg Ala Ile Tyr Thr Gly
                485                 490                 495

Ala His Gly Ala Ile Pro Leu Pro Glu Lys Arg Trp Arg Phe Leu Gly
            500                 505                 510

Lys Asp Lys Asp Phe Leu Asp Leu Cys Gly Val Lys Ala Thr Pro His
        515                 520                 525

Gly Cys Tyr Ile Glu Asp Val Glu Val Asp Phe Gln Arg Leu Arg Thr
    530                 535                 540

Pro Met Thr Pro Glu Asp Met Leu Leu Pro Gln Gln Leu Leu Ala Val
545                 550                 555                 560

Thr Thr Ile Asp Arg Ala Ile Leu Asp Ser Gly Met Lys Lys Gly Gly
                565                 570                 575

Asn Val Ala Val Phe Val Gly Leu Gly Thr Asp Leu Glu Leu Tyr Arg
            580                 585                 590

His Arg Ala Arg Val Ala Leu Lys Glu Arg Val Arg Pro Glu Ala Ser
        595                 600                 605

Lys Lys Leu Asn Asp Met Met Gln Tyr Ile Asn Asp Cys Gly Thr Ser
    610                 615                 620

Thr Ser Tyr Thr Ser Tyr Ile Gly Asn Leu Val Ala Thr Arg Val Ser
625                 630                 635                 640

Ser Gln Trp Gly Phe Thr Gly Pro Ser Phe Thr Ile Thr Glu Gly Asn
                645                 650                 655

Asn Ser Val Tyr Arg Cys Ala Glu Leu Gly Lys Tyr Leu Leu Glu Thr
            660                 665                 670

Gly Glu Val Asp Gly Val Val Val Ala Gly Val Asp Leu Cys Gly Ser
        675                 680                 685

Ala Glu Asn Leu Tyr Val Lys Ser Arg Arg Phe Lys Val Ser Thr Ser
    690                 695                 700

Asp Thr Pro Arg Ala Ser Phe Asp Ala Ala Ala Asp Gly Tyr Phe Val
705                 710                 715                 720

Gly Glu Gly Cys Gly Ala Phe Val Leu Lys Arg Glu Thr Ser Cys Thr
                725                 730                 735

Lys Asp Asp Arg Ile Tyr Ala Cys Met Asp Ala Ile Val Pro Gly Asn
            740                 745                 750

Val Pro Ser Ala Cys Leu Arg Glu Ala Leu Asp Gln Ala Arg Val Lys
```

-continued

```
        755                 760                 765

Pro Gly Asp Ile Glu Met Leu Glu Leu Ser Ala Asp Ser Ala Arg His
    770                 775                 780

Leu Lys Asp Pro Ser Val Leu Pro Lys Glu Leu Thr Ala Glu Glu Glu
785                 790                 795                 800

Ile Gly Gly Leu Gln Thr Ile Leu Arg Asp Asp Asp Lys Leu Pro Arg
                805                 810                 815

Asn Val Ala Thr Gly Ser Val Lys Ala Thr Val Gly Asp Thr Gly Tyr
            820                 825                 830

Ala Ser Gly Ala Ala Ser Leu Ile Lys Ala Ala Leu Cys Ile Tyr Asn
        835                 840                 845

Arg Tyr Leu Pro Ser Asn Gly Asp Asp Trp Asp Glu Pro Ala Pro Glu
    850                 855                 860

Ala Pro Trp Asp Ser Thr Leu Phe Ala Cys Gln Thr Ser Arg Ala Trp
865                 870                 875                 880

Leu Lys Asn Pro Gly Glu Arg Arg Tyr Ala Ala Val Ser Gly Val Ser
                885                 890                 895

Glu Thr Arg Ser Cys Tyr Ser Val Leu Leu Ser Glu Ala Glu Gly His
            900                 905                 910

Tyr Glu Arg Glu Asn Arg Ile Ser Leu Asp Glu Glu Ala Pro Lys Leu
        915                 920                 925

Ile Val Leu Arg Ala Asp Ser His Glu Glu Ile Leu Gly Arg Leu Asp
    930                 935                 940

Lys Ile Arg Glu Arg Phe Leu Gln Pro Thr Gly Ala Ala Pro Arg Glu
945                 950                 955                 960

Ser Glu Leu Lys Ala Gln Ala Arg Arg Ile Phe Leu Glu Leu Leu Gly
                965                 970                 975

Glu Thr Leu Ala Gln Asp Ala Ala Ser Ser Gly Ser Gln Lys Pro Leu
            980                 985                 990

Ala Leu Ser Leu Val Ser Thr Pro  Ser Lys Leu Gln Arg  Glu Val Glu
        995                 1000                1005

Leu Ala  Ala Lys Gly Ile Pro  Arg Cys Leu Lys Met  Arg Arg Asp
    1010                1015                1020

Trp Ser  Ser Pro Ala Gly Ser  Arg Tyr Ala Pro Glu  Pro Leu Ala
    1025                1030                1035

Ser Asp  Arg Val Ala Phe Met  Tyr Gly Glu Gly Arg  Ser Pro Tyr
    1040                1045                1050

Tyr Gly  Ile Thr Gln Asp Ile  His Arg Ile Trp Pro  Glu Leu His
    1055                1060                1065

Glu Val  Ile Asn Glu Lys Thr  Asn Arg Leu Trp Ala  Glu Gly Asp
    1070                1075                1080

Arg Trp  Val Met Pro Arg Ala  Ser Phe Lys Ser Glu  Leu Glu Ser
    1085                1090                1095

Gln Gln  Gln Glu Phe Asp Arg  Asn Met Ile Glu Met  Phe Arg Leu
    1100                1105                1110

Gly Ile  Leu Thr Ser Ile Ala  Phe Thr Asn Leu Ala  Arg Asp Val
    1115                1120                1125

Leu Asn  Ile Thr Pro Lys Ala  Ala Phe Gly Leu Ser  Leu Gly Glu
    1130                1135                1140

Ile Ser  Met Ile Phe Ala Phe  Ser Lys Lys Asn Gly  Leu Ile Ser
    1145                1150                1155

Asp Gln  Leu Thr Lys Asp Leu  Arg Glu Ser Asp Val  Trp Asn Lys
    1160                1165                1170
```

```
Ala Leu  Ala Val Glu Phe Asn  Ala Leu Arg Glu Ala  Trp Gly Ile
    1175                 1180                 1185

Pro Gln  Ser Val Pro Lys Asp  Glu Phe Trp Gln Gly  Tyr Ile Val
    1190                 1195                 1200

Arg Gly  Thr Lys Gln Asp Ile  Glu Ala Ala Ile Ala  Pro Asp Ser
    1205                 1210                 1215

Lys Tyr  Val Arg Leu Thr Ile  Ile Asn Asp Ala Asn  Thr Ala Leu
    1220                 1225                 1230

Ile Ser  Gly Lys Pro Asp Ala  Cys Lys Ala Ala Ile  Ala Arg Leu
    1235                 1240                 1245

Gly Gly  Asn Ile Pro Ala Leu  Pro Val Thr Gln Gly  Met Cys Gly
    1250                 1255                 1260

His Cys  Pro Glu Val Gly Pro  Tyr Thr Lys Asp Ile  Ala Lys Ile
    1265                 1270                 1275

His Ala  Asn Leu Glu Phe Pro  Val Val Asp Gly Leu  Asp Leu Trp
    1280                 1285                 1290

Thr Thr  Ile Asn Gln Lys Arg  Leu Val Pro Arg Ala  Thr Gly Ala
    1295                 1300                 1305

Lys Asp  Glu Trp Ala Pro Ser  Ser Phe Gly Glu Tyr  Ala Gly Gln
    1310                 1315                 1320

Leu Tyr  Glu Lys Gln Ala Asn  Phe Pro Gln Ile Val  Glu Thr Ile
    1325                 1330                 1335

Tyr Lys  Gln Asn Tyr Asp Val  Phe Val Glu Val Gly  Pro Asn Asn
    1340                 1345                 1350

His Arg  Ser Thr Ala Val Arg  Thr Thr Leu Gly Pro  Gln Arg Asn
    1355                 1360                 1365

His Leu  Ala Gly Ala Ile Asp  Lys Gln Asn Glu Asp  Ala Trp Thr
    1370                 1375                 1380

Thr Ile  Val Lys Leu Val Ala  Ser Leu Lys Ala His  Leu Val Pro
    1385                 1390                 1395

Gly Val  Thr Ile Ser Pro Leu  Tyr His Ser Lys Leu  Val Ala Glu
    1400                 1405                 1410

Ala Glu  Ala Cys Tyr Ala Ala  Leu Cys Lys Gly Glu  Lys Pro Lys
    1415                 1420                 1425

Lys Asn  Lys Phe Val Arg Lys  Ile Gln Leu Asn Gly  Arg Phe Asn
    1430                 1435                 1440

Ser Lys  Ala Asp Pro Ile Ser  Ser Ala Asp Leu Ala  Ser Phe Pro
    1445                 1450                 1455

Pro Ala  Asp Pro Ala Ile Glu  Ala Ala Ile Ser Ser  Arg Ile Met
    1460                 1465                 1470

Lys Pro  Val Ala Pro Lys Phe  Tyr Ala Arg Leu Asn  Ile Asp Glu
    1475                 1480                 1485

Gln Asp  Glu Thr Arg Asp Pro  Ile Leu Asn Lys Asp  Asn Ala Pro
    1490                 1495                 1500

Ser Ser  Ser Ser Ser Ser Ser  Ser Ser Ser Ser Ser  Ser Ser Ser
    1505                 1510                 1515

Pro Ser  Pro Ala Pro Ser Ala  Pro Val Gln Lys Lys  Ala Ala Pro
    1520                 1525                 1530

Ala Ala  Glu Thr Lys Ala Val  Ala Ser Ala Asp Ala  Leu Arg Ser
    1535                 1540                 1545

Ala Leu  Leu Asp Leu Asp Ser  Met Leu Ala Leu Ser  Ser Ala Ser
    1550                 1555                 1560
```

-continued

```
Ala Ser  Gly Asn Leu Val Glu  Thr Ala Pro Ser Asp  Ala Ser Val
    1565                 1570                 1575

Ile Val  Pro Pro Cys Asn Ile  Ala Asp Leu Gly Ser  Arg Ala Phe
    1580                 1585                 1590

Met Lys  Thr Tyr Gly Val Ser  Ala Pro Leu Tyr Thr  Gly Ala Met
    1595                 1600                 1605

Ala Lys  Gly Ile Ala Ser Ala  Asp Leu Val Ile Ala  Ala Gly Arg
    1610                 1615                 1620

Gln Gly  Ile Leu Ala Ser Phe  Gly Ala Gly Gly Leu  Pro Met Gln
    1625                 1630                 1635

Val Val  Arg Glu Ser Ile Glu  Lys Ile Gln Ala Ala  Leu Pro Asn
    1640                 1645                 1650

Gly Pro  Tyr Ala Val Asn Leu  Ile His Ser Pro Phe  Asp Ser Asn
    1655                 1660                 1665

Leu Glu  Lys Gly Asn Val Asp  Leu Phe Leu Glu Lys  Gly Val Thr
    1670                 1675                 1680

Phe Val  Glu Ala Ser Ala Phe  Met Thr Leu Thr Pro  Gln Val Val
    1685                 1690                 1695

Arg Tyr  Arg Ala Ala Gly Leu  Thr Arg Asn Ala Asp  Gly Ser Val
    1700                 1705                 1710

Asn Ile  Arg Asn Arg Ile Ile  Gly Lys Val Ser Arg  Thr Glu Leu
    1715                 1720                 1725

Ala Glu  Met Phe Met Arg Pro  Ala Pro Glu His Leu  Leu Gln Lys
    1730                 1735                 1740

Leu Ile  Ala Ser Gly Glu Ile  Asn Gln Glu Gln Ala  Glu Leu Ala
    1745                 1750                 1755

Arg Arg  Val Pro Val Ala Asp  Asp Ile Ala Val Glu  Ala Asp Ser
    1760                 1765                 1770

Gly Gly  His Thr Asp Asn Arg  Pro Ile His Val Ile  Leu Pro Leu
    1775                 1780                 1785

Ile Ile  Asn Leu Arg Asp Arg  Leu His Arg Glu Cys  Gly Tyr Pro
    1790                 1795                 1800

Ala Asn  Leu Arg Val Arg Val  Gly Ala Gly Gly Gly  Ile Gly Cys
    1805                 1810                 1815

Pro Gln  Ala Ala Leu Ala Thr  Phe Asn Met Gly Ala  Ser Phe Ile
    1820                 1825                 1830

Val Thr  Gly Thr Val Asn Gln  Val Ala Lys Gln Ser  Gly Thr Cys
    1835                 1840                 1845

Asp Asn  Val Arg Lys Gln Leu  Ala Lys Ala Thr Tyr  Ser Asp Val
    1850                 1855                 1860

Cys Met  Ala Pro Ala Ala Asp  Met Phe Glu Glu Gly  Val Lys Leu
    1865                 1870                 1875

Gln Val  Leu Lys Lys Gly Thr  Met Phe Pro Ser Arg  Ala Asn Lys
    1880                 1885                 1890

Leu Tyr  Glu Leu Phe Cys Lys  Tyr Asp Ser Phe Glu  Ser Met Pro
    1895                 1900                 1905

Pro Ala  Glu Leu Ala Arg Val  Glu Lys Arg Ile Phe  Ser Arg Ala
    1910                 1915                 1920

Leu Glu  Glu Val Trp Asp Glu  Thr Lys Asn Phe Tyr  Ile Asn Arg
    1925                 1930                 1935

Leu His  Asn Pro Glu Lys Ile  Gln Arg Ala Glu Arg  Asp Pro Lys
    1940                 1945                 1950

Leu Lys  Met Ser Leu Cys Phe  Arg Trp Tyr Leu Ser  Leu Ala Ser
```

```
    1955                1960                1965

Arg Trp  Ala Asn Thr Gly Ala  Ser Asp Arg Val Met  Asp Tyr Gln
    1970                1975                1980

Val Trp  Cys Gly Pro Ala Ile  Gly Ser Phe Asn Asp  Phe Ile Lys
    1985                1990                1995

Gly Thr  Tyr Leu Asp Pro Ala  Val Ala Asn Glu Tyr  Pro Cys Val
    2000                2005                2010

Val Gln  Ile Asn Lys Gln Ile  Leu Arg Gly Ala Cys  Phe Leu Arg
    2015                2020                2025

Arg Leu  Glu Ile Leu Arg Asn  Ala Arg Leu Ser Asp  Gly Ala Ala
    2030                2035                2040

Ala Leu  Val Ala Ser Ile Asp  Asp Thr Tyr Val Pro  Ala Glu Lys
    2045                2050                2055

Leu


<210> SEQ ID NO 5
<211> LENGTH: 4509
<212> TYPE: DNA
<213> ORGANISM: Schizochytrium sp.
<220> FEATURE:
<221> NAME/KEY: CDS
<222> LOCATION: (1)..(4509)

<400> SEQUENCE: 5

atg gcg ctc cgt gtc aag acg aac aag aag cca tgc tgg gag atg acc       48
Met Ala Leu Arg Val Lys Thr Asn Lys Lys Pro Cys Trp Glu Met Thr
1               5                   10                  15

aag gag gag ctg acc agc ggc aag acc gag gtg ttc aac tat gag gaa       96
Lys Glu Glu Leu Thr Ser Gly Lys Thr Glu Val Phe Asn Tyr Glu Glu
            20                  25                  30

ctc ctc gag ttc gca gag ggc gac atc gcc aag gtc ttc gga ccc gag      144
Leu Leu Glu Phe Ala Glu Gly Asp Ile Ala Lys Val Phe Gly Pro Glu
        35                  40                  45

ttc gcc gtc atc gac aag tac ccg cgc cgc gtg cgc ctg ccc gcc cgc      192
Phe Ala Val Ile Asp Lys Tyr Pro Arg Arg Val Arg Leu Pro Ala Arg
    50                  55                  60

gag tac ctg ctc gtg acc cgc gtc acc ctc atg gac gcc gag gtc aac      240
Glu Tyr Leu Leu Val Thr Arg Val Thr Leu Met Asp Ala Glu Val Asn
65                  70                  75                  80

aac tac cgc gtc ggc gcc cgc atg gtc acc gag tac gat ctc ccc gtc      288
Asn Tyr Arg Val Gly Ala Arg Met Val Thr Glu Tyr Asp Leu Pro Val
                85                  90                  95

aac gga gag ctc tcc gag ggc gga gac tgc ccc tgg gcc gtc ctg gtc      336
Asn Gly Glu Leu Ser Glu Gly Gly Asp Cys Pro Trp Ala Val Leu Val
            100                 105                 110

gag agt ggc cag tgc gat ctc atg ctc atc tcc tac atg ggc att gac      384
Glu Ser Gly Gln Cys Asp Leu Met Leu Ile Ser Tyr Met Gly Ile Asp
        115                 120                 125

ttc cag aac cag ggc gac cgc gtc tac cgc ctg ctc aac acc acg ctc      432
Phe Gln Asn Gln Gly Asp Arg Val Tyr Arg Leu Leu Asn Thr Thr Leu
    130                 135                 140

acc ttt tac ggc gtg gcc cac gag ggc gag acc ctc gag tac gac att      480
Thr Phe Tyr Gly Val Ala His Glu Gly Glu Thr Leu Glu Tyr Asp Ile
145                 150                 155                 160

cgc gtc acc ggc ttc gcc aag cgt ctc gac ggc ggc atc tcc atg ttc      528
Arg Val Thr Gly Phe Ala Lys Arg Leu Asp Gly Gly Ile Ser Met Phe
                165                 170                 175

ttc ttc gag tac gac tgc tac gtc aac ggc cgc ctc ctc atc gag atg      576
Phe Phe Glu Tyr Asp Cys Tyr Val Asn Gly Arg Leu Leu Ile Glu Met
```

-continued

```
        180                 185                 190

cgc gat ggc tgc gcc ggc ttc ttc acc aac gag gag ctc gac gcc ggc      624
Arg Asp Gly Cys Ala Gly Phe Phe Thr Asn Glu Glu Leu Asp Ala Gly
            195                 200                 205

aag ggc gtc gtc ttc acc cgc ggc gac ctc gcc gcc cgc gcc aag atc      672
Lys Gly Val Val Phe Thr Arg Gly Asp Leu Ala Ala Arg Ala Lys Ile
    210                 215                 220

cca aag cag gac gtc tcc ccc tac gcc gtc gcc ccc tgc ctc cac aag      720
Pro Lys Gln Asp Val Ser Pro Tyr Ala Val Ala Pro Cys Leu His Lys
225                 230                 235                 240

acc aag ctc aac gaa aag gag atg cag acc ctc gtc gac aag gac tgg      768
Thr Lys Leu Asn Glu Lys Glu Met Gln Thr Leu Val Asp Lys Asp Trp
                245                 250                 255

gca tcc gtc ttt ggc tcc aag aac ggc atg ccg gaa atc aac tac aaa      816
Ala Ser Val Phe Gly Ser Lys Asn Gly Met Pro Glu Ile Asn Tyr Lys
            260                 265                 270

ctc tgc gcg cgt aag atg ctc atg att gac cgc gtc acc agc att gac      864
Leu Cys Ala Arg Lys Met Leu Met Ile Asp Arg Val Thr Ser Ile Asp
        275                 280                 285

cac aag ggc ggt gtc tac ggc ctc ggt cag ctc gtc ggt gaa aag atc      912
His Lys Gly Gly Val Tyr Gly Leu Gly Gln Leu Val Gly Glu Lys Ile
    290                 295                 300

ctc gag cgc gac cac tgg tac ttt ccc tgc cac ttt gtc aag gat cag      960
Leu Glu Arg Asp His Trp Tyr Phe Pro Cys His Phe Val Lys Asp Gln
305                 310                 315                 320

gtc atg gcc gga tcc ctc gtc tcc gac ggc tgc agc cag atg ctc aag     1008
Val Met Ala Gly Ser Leu Val Ser Asp Gly Cys Ser Gln Met Leu Lys
                325                 330                 335

atg tac atg atc tgg ctc ggc ctc cac ctc acc acc gga ccc ttt gac     1056
Met Tyr Met Ile Trp Leu Gly Leu His Leu Thr Thr Gly Pro Phe Asp
            340                 345                 350

ttc cgc ccg gtc aac ggc cac ccc aac aag gtc cgc tgc cgc ggc caa     1104
Phe Arg Pro Val Asn Gly His Pro Asn Lys Val Arg Cys Arg Gly Gln
        355                 360                 365

atc tcc ccg cac aag ggc aag ctc gtc tac gtc atg gag atc aag gag     1152
Ile Ser Pro His Lys Gly Lys Leu Val Tyr Val Met Glu Ile Lys Glu
    370                 375                 380

atg ggc ttc gac gag gac aac gac ccg tac gcc att gcc gac gtc aac     1200
Met Gly Phe Asp Glu Asp Asn Asp Pro Tyr Ala Ile Ala Asp Val Asn
385                 390                 395                 400

atc att gat gtc gac ttc gaa aag ggc cag gac ttt agc ctc gac cgc     1248
Ile Ile Asp Val Asp Phe Glu Lys Gly Gln Asp Phe Ser Leu Asp Arg
                405                 410                 415

atc agc gac tac ggc aag ggc gac ctc aac aag aag atc gtc gtc gac     1296
Ile Ser Asp Tyr Gly Lys Gly Asp Leu Asn Lys Lys Ile Val Val Asp
            420                 425                 430

ttt aag ggc atc gct ctc aag atg cag aag cgc tcc acc aac aag aac     1344
Phe Lys Gly Ile Ala Leu Lys Met Gln Lys Arg Ser Thr Asn Lys Asn
        435                 440                 445

ccc tcc aag gtt cag ccc gtc ttt gcc aac ggc gcc gcc act gtc ggc     1392
Pro Ser Lys Val Gln Pro Val Phe Ala Asn Gly Ala Ala Thr Val Gly
    450                 455                 460

ccc gag gcc tcc aag gct tcc tcc ggc gcc agc gcc agc gcc agc gcc     1440
Pro Glu Ala Ser Lys Ala Ser Ser Gly Ala Ser Ala Ser Ala Ser Ala
465                 470                 475                 480

gcc ccg gcc aag cct gcc ttc agc gcc gat gtt ctt gcg ccc aag ccc     1488
Ala Pro Ala Lys Pro Ala Phe Ser Ala Asp Val Leu Ala Pro Lys Pro
                485                 490                 495

gtt gcc ctt ccc gag cac atc ctc aag ggc gac gcc ctc gcc ccc aag     1536
```

-continued

```
Val Ala Leu Pro Glu His Ile Leu Lys Gly Asp Ala Leu Ala Pro Lys
            500                 505                 510

gag atg tcc tgg cac ccc atg gcc cgc atc ccg ggc aac ccg acg ccc      1584
Glu Met Ser Trp His Pro Met Ala Arg Ile Pro Gly Asn Pro Thr Pro
        515                 520                 525

tct ttt gcg ccc tcg gcc tac aag ccg cgc aac atc gcc ttt acg ccc      1632
Ser Phe Ala Pro Ser Ala Tyr Lys Pro Arg Asn Ile Ala Phe Thr Pro
    530                 535                 540

ttc ccc ggc aac ccc aac gat aac gac cac acc ccg ggc aag atg ccg      1680
Phe Pro Gly Asn Pro Asn Asp Asn Asp His Thr Pro Gly Lys Met Pro
545                 550                 555                 560

ctc acc tgg ttc aac atg gcc gag ttc atg gcc ggc aag gtc agc atg      1728
Leu Thr Trp Phe Asn Met Ala Glu Phe Met Ala Gly Lys Val Ser Met
                565                 570                 575

tgc ctc ggc ccc gag ttc gcc aag ttc gac gac tcg aac acc agc cgc      1776
Cys Leu Gly Pro Glu Phe Ala Lys Phe Asp Asp Ser Asn Thr Ser Arg
            580                 585                 590

agc ccc gct tgg gac ctc gct ctc gtc acc cgc gcc gtg tct gtg tct      1824
Ser Pro Ala Trp Asp Leu Ala Leu Val Thr Arg Ala Val Ser Val Ser
        595                 600                 605

gac ctc aag cac gtc aac tac cgc aac atc gac ctc gac ccc tcc aag      1872
Asp Leu Lys His Val Asn Tyr Arg Asn Ile Asp Leu Asp Pro Ser Lys
    610                 615                 620

ggt acc atg gtc ggc gag ttc gac tgc ccc gcg gac gcc tgg ttc tac      1920
Gly Thr Met Val Gly Glu Phe Asp Cys Pro Ala Asp Ala Trp Phe Tyr
625                 630                 635                 640

aag ggc gcc tgc aac gat gcc cac atg ccg tac tcg atc ctc atg gag      1968
Lys Gly Ala Cys Asn Asp Ala His Met Pro Tyr Ser Ile Leu Met Glu
                645                 650                 655

atc gcc ctc cag acc tcg ggt gtg ctc acc tcg gtg ctc aag gcg ccc      2016
Ile Ala Leu Gln Thr Ser Gly Val Leu Thr Ser Val Leu Lys Ala Pro
            660                 665                 670

ctg acc atg gag aag gac gac atc ctc ttc cgc aac ctc gac gcc aac      2064
Leu Thr Met Glu Lys Asp Asp Ile Leu Phe Arg Asn Leu Asp Ala Asn
        675                 680                 685

gcc gag ttc gtg cgc gcc gac ctc gac tac cgc ggc aag act atc cgc      2112
Ala Glu Phe Val Arg Ala Asp Leu Asp Tyr Arg Gly Lys Thr Ile Arg
    690                 695                 700

aac gtc acc aag tgc act ggc tac agc atg ctc ggc gag atg ggc gtc      2160
Asn Val Thr Lys Cys Thr Gly Tyr Ser Met Leu Gly Glu Met Gly Val
705                 710                 715                 720

cac cgc ttc acc ttt gag ctc tac gtc gat gat gtg ctc ttt tac aag      2208
His Arg Phe Thr Phe Glu Leu Tyr Val Asp Asp Val Leu Phe Tyr Lys
                725                 730                 735

ggc tcg acc tcg ttc ggc tgg ttc gtg ccc gag gtc ttt gcc gcc cag      2256
Gly Ser Thr Ser Phe Gly Trp Phe Val Pro Glu Val Phe Ala Ala Gln
            740                 745                 750

gcc ggc ctc gac aac ggc cgc aag tcg gag ccc tgg ttc att gag aac      2304
Ala Gly Leu Asp Asn Gly Arg Lys Ser Glu Pro Trp Phe Ile Glu Asn
        755                 760                 765

aag gtt ccg gcc tcg cag gtc tcc tcc ttt gac gtg cgc ccc aac ggc      2352
Lys Val Pro Ala Ser Gln Val Ser Ser Phe Asp Val Arg Pro Asn Gly
    770                 775                 780

agc ggc cgc acc gcc atc ttc gcc aac gcc ccc agc ggc gcc cag ctc      2400
Ser Gly Arg Thr Ala Ile Phe Ala Asn Ala Pro Ser Gly Ala Gln Leu
785                 790                 795                 800

aac cgc cgc acg gac cag ggc cag tac ctc gac gcc gtc gac att gtc      2448
Asn Arg Arg Thr Asp Gln Gly Gln Tyr Leu Asp Ala Val Asp Ile Val
                805                 810                 815
```

-continued

```
tcc ggc agc ggc aag aag agc ctc ggc tac gcc cac ggt tcc aag acg     2496
Ser Gly Ser Gly Lys Lys Ser Leu Gly Tyr Ala His Gly Ser Lys Thr
            820                 825                 830

gtc aac ccg aac gac tgg ttc ttc tcg tgc cac ttt tgg ttt gac tcg     2544
Val Asn Pro Asn Asp Trp Phe Phe Ser Cys His Phe Trp Phe Asp Ser
        835                 840                 845

gtc atg ccc gga agt ctc ggt gtc gag tcc atg ttc cag ctc gtc gag     2592
Val Met Pro Gly Ser Leu Gly Val Glu Ser Met Phe Gln Leu Val Glu
    850                 855                 860

gcc atc gcc gcc cac gag gat ctc gct ggc aag cac ggc att gcc aac     2640
Ala Ile Ala Ala His Glu Asp Leu Ala Gly Lys His Gly Ile Ala Asn
865                 870                 875                 880

ccc acc ttt gtg cac gcc ccg ggc aag atc agc tgg aag tac cgc ggc     2688
Pro Thr Phe Val His Ala Pro Gly Lys Ile Ser Trp Lys Tyr Arg Gly
                885                 890                 895

cag ctc acg ccc aag agc aag aag atg gac tcg gag gtc cac atc gtg     2736
Gln Leu Thr Pro Lys Ser Lys Lys Met Asp Ser Glu Val His Ile Val
            900                 905                 910

tcc gtg gac gcc cac gac ggc gtt gtc gac ctc gtc gcc gac ggc ttc     2784
Ser Val Asp Ala His Asp Gly Val Val Asp Leu Val Ala Asp Gly Phe
        915                 920                 925

ctc tgg gcc gac agc ctc cgc gtc tac tcg gtg agc aac att cgc gtg     2832
Leu Trp Ala Asp Ser Leu Arg Val Tyr Ser Val Ser Asn Ile Arg Val
    930                 935                 940

cgc atc gcc tcc ggt gag gcc cct gcc gcc gcc tcc tcc gcc gcc tct     2880
Arg Ile Ala Ser Gly Glu Ala Pro Ala Ala Ala Ser Ser Ala Ala Ser
945                 950                 955                 960

gtg ggc tcc tcg gct tcg tcc gtc gag cgc acg cgc tcg agc ccc gct     2928
Val Gly Ser Ser Ala Ser Ser Val Glu Arg Thr Arg Ser Ser Pro Ala
                965                 970                 975

gtc gcc tcc ggc ccg gcc cag acc atc gac ctc aag cag ctc aag acc     2976
Val Ala Ser Gly Pro Ala Gln Thr Ile Asp Leu Lys Gln Leu Lys Thr
            980                 985                 990

gag ctc ctc gag ctc gat gcc ccg  ctc tac ctc tcg cag  gac ccg acc   3024
Glu Leu Leu Glu Leu Asp Ala Pro  Leu Tyr Leu Ser Gln  Asp Pro Thr
        995                 1000                 1005

agc ggc  cag ctc aag aag cac  acc gac gtg gcc tcc  ggc cag gcc      3069
Ser Gly  Gln Leu Lys Lys His  Thr Asp Val Ala Ser  Gly Gln Ala
    1010                 1015                 1020

acc atc  gtg cag ccc tgc acg  ctc ggc gac ctc ggt  gac cgc tcc      3114
Thr Ile  Val Gln Pro Cys Thr  Leu Gly Asp Leu Gly  Asp Arg Ser
    1025                 1030                 1035

ttc atg  gag acc tac ggc gtc  gtc gcc ccg ctg tac  acg ggc gcc      3159
Phe Met  Glu Thr Tyr Gly Val  Val Ala Pro Leu Tyr  Thr Gly Ala
    1040                 1045                 1050

atg gcc  aag ggc att gcc tcg  gcg gac ctc gtc atc  gcc gcc ggc      3204
Met Ala  Lys Gly Ile Ala Ser  Ala Asp Leu Val Ile  Ala Ala Gly
    1055                 1060                 1065

aag cgc  aag atc ctc ggc tcc  ttt ggc gcc ggc ggc  ctc ccc atg      3249
Lys Arg  Lys Ile Leu Gly Ser  Phe Gly Ala Gly Gly  Leu Pro Met
    1070                 1075                 1080

cac cac  gtg cgc gcc gcc ctc  gag aag atc cag gcc  gcc ctg cct      3294
His His  Val Arg Ala Ala Leu  Glu Lys Ile Gln Ala  Ala Leu Pro
    1085                 1090                 1095

cag ggc  ccc tac gcc gtc aac  ctc atc cac tcg cct  ttt gac agc      3339
Gln Gly  Pro Tyr Ala Val Asn  Leu Ile His Ser Pro  Phe Asp Ser
    1100                 1105                 1110

aac ctc  gag aag ggc aac gtc  gat ctc ttc ctc gag  aag ggc gtc      3384
Asn Leu  Glu Lys Gly Asn Val  Asp Leu Phe Leu Glu  Lys Gly Val
    1115                 1120                 1125
```

-continued

```
act gtg  gtg gag gcc tcg gca  ttc atg acc ctc acc  ccg cag gtc      3429
Thr Val  Val Glu Ala Ser Ala  Phe Met Thr Leu Thr  Pro Gln Val
    1130                 1135                 1140

gtg cgc  tac cgc gcc gcc ggc  ctc tcg cgc aac gcc  gac ggt tcg      3474
Val Arg  Tyr Arg Ala Ala Gly  Leu Ser Arg Asn Ala  Asp Gly Ser
    1145                 1150                 1155

gtc aac  atc cgc aac cgc atc  atc ggc aag gtc tcg  cgc acc gag      3519
Val Asn  Ile Arg Asn Arg Ile  Ile Gly Lys Val Ser  Arg Thr Glu
    1160                 1165                 1170

ctc gcc  gag atg ttc atc cgc  ccg gcc ccg gag cac  ctc ctc gag      3564
Leu Ala  Glu Met Phe Ile Arg  Pro Ala Pro Glu His  Leu Leu Glu
    1175                 1180                 1185

aag ctc  atc gcc tcg ggc gag  atc acc cag gag cag  gcc gag ctc      3609
Lys Leu  Ile Ala Ser Gly Glu  Ile Thr Gln Glu Gln  Ala Glu Leu
    1190                 1195                 1200

gcg cgc  cgc gtt ccc gtc gcc  gac gat atc gct gtc  gag gct gac      3654
Ala Arg  Arg Val Pro Val Ala  Asp Asp Ile Ala Val  Glu Ala Asp
    1205                 1210                 1215

tcg ggc  ggc cac acc gac aac  cgc ccc atc cac gtc  atc ctc ccg      3699
Ser Gly  Gly His Thr Asp Asn  Arg Pro Ile His Val  Ile Leu Pro
    1220                 1225                 1230

ctc atc  atc aac ctc cgc aac  cgc ctg cac cgc gag  tgc ggc tac      3744
Leu Ile  Ile Asn Leu Arg Asn  Arg Leu His Arg Glu  Cys Gly Tyr
    1235                 1240                 1245

ccc gcg  cac ctc cgc gtc cgc  gtt ggc gcc ggc ggt  ggc gtc ggc      3789
Pro Ala  His Leu Arg Val Arg  Val Gly Ala Gly Gly  Gly Val Gly
    1250                 1255                 1260

tgc ccg  cag gcc gcc gcc gcc  gcg ctc acc atg ggc  gcc gcc ttc      3834
Cys Pro  Gln Ala Ala Ala Ala  Ala Leu Thr Met Gly  Ala Ala Phe
    1265                 1270                 1275

atc gtc  acc ggc act gtc aac  cag gtc gcc aag cag  tcc ggc acc      3879
Ile Val  Thr Gly Thr Val Asn  Gln Val Ala Lys Gln  Ser Gly Thr
    1280                 1285                 1290

tgc gac  aac gtg cgc aag cag  ctc tcg cag gcc acc  tac tcg gat      3924
Cys Asp  Asn Val Arg Lys Gln  Leu Ser Gln Ala Thr  Tyr Ser Asp
    1295                 1300                 1305

atc tgc  atg gcc ccg gcc gcc  gac atg ttc gag gag  ggc gtc aag      3969
Ile Cys  Met Ala Pro Ala Ala  Asp Met Phe Glu Glu  Gly Val Lys
    1310                 1315                 1320

ctc cag  gtc ctc aag aag gga  acc atg ttc ccc tcg  cgc gcc aac      4014
Leu Gln  Val Leu Lys Lys Gly  Thr Met Phe Pro Ser  Arg Ala Asn
    1325                 1330                 1335

aag ctc  tac gag ctc ttt tgc  aag tac gac tcc ttc  gac tcc atg      4059
Lys Leu  Tyr Glu Leu Phe Cys  Lys Tyr Asp Ser Phe  Asp Ser Met
    1340                 1345                 1350

cct cct  gcc gag ctc gag cgc  atc gag aag cgt atc  ttc aag cgc      4104
Pro Pro  Ala Glu Leu Glu Arg  Ile Glu Lys Arg Ile  Phe Lys Arg
    1355                 1360                 1365

gca ctc  cag gag gtc tgg gag  gag acc aag gac ttt  tac att aac      4149
Ala Leu  Gln Glu Val Trp Glu  Glu Thr Lys Asp Phe  Tyr Ile Asn
    1370                 1375                 1380

ggt ctc  aag aac ccg gag aag  atc cag cgc gcc gag  cac gac ccc      4194
Gly Leu  Lys Asn Pro Glu Lys  Ile Gln Arg Ala Glu  His Asp Pro
    1385                 1390                 1395

aag ctc  aag atg tcg ctc tgc  ttc cgc tgg tac ctt  ggt ctt gcc      4239
Lys Leu  Lys Met Ser Leu Cys  Phe Arg Trp Tyr Leu  Gly Leu Ala
    1400                 1405                 1410

agc cgc  tgg gcc aac atg ggc  gcc ccg gac cgc gtc  atg gac tac      4284
Ser Arg  Trp Ala Asn Met Gly  Ala Pro Asp Arg Val  Met Asp Tyr
```

-continued

```
    1415                1420                1425

cag gtc  tgg tgt ggc ccg gcc  att ggc gcc ttc aac  gac ttc atc      4329
Gln Val  Trp Cys Gly Pro Ala  Ile Gly Ala Phe Asn  Asp Phe Ile
    1430                1435                1440

aag ggc  acc tac ctc gac ccc  gct gtc tcc aac gag  tac ccc tgt      4374
Lys Gly  Thr Tyr Leu Asp Pro  Ala Val Ser Asn Glu  Tyr Pro Cys
    1445                1450                1455

gtc gtc  cag atc aac ctg caa  atc ctc cgt ggt gcc  tgc tac ctg      4419
Val Val  Gln Ile Asn Leu Gln  Ile Leu Arg Gly Ala  Cys Tyr Leu
    1460                1465                1470

cgc cgt  ctc aac gcc ctg cgc  aac gac ccg cgc att  gac ctc gag      4464
Arg Arg  Leu Asn Ala Leu Arg  Asn Asp Pro Arg Ile  Asp Leu Glu
    1475                1480                1485

acc gag  gat gct gcc ttt gtc  tac gag ccc acc aac  gcg ctc taa      4509
Thr Glu  Asp Ala Ala Phe Val  Tyr Glu Pro Thr Asn  Ala Leu
    1490                1495                1500


<210> SEQ ID NO 6
<211> LENGTH: 1502
<212> TYPE: PRT
<213> ORGANISM: Schizochytrium sp.

<400> SEQUENCE: 6

Met Ala Leu Arg Val Lys Thr Asn Lys Lys Pro Cys Trp Glu Met Thr
1               5                   10                  15

Lys Glu Glu Leu Thr Ser Gly Lys Thr Glu Val Phe Asn Tyr Glu Glu
            20                  25                  30

Leu Leu Glu Phe Ala Glu Gly Asp Ile Ala Lys Val Phe Gly Pro Glu
        35                  40                  45

Phe Ala Val Ile Asp Lys Tyr Pro Arg Arg Val Arg Leu Pro Ala Arg
    50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
        115                 120                 125

Phe Gln Asn Gln Gly Asp Arg Val Tyr Arg Leu Leu Asn Thr Thr Leu
    130                 135                 140

Thr Phe Tyr Gly Val Ala His Glu Gly Glu Thr Leu Glu Tyr Asp Ile
145                 150                 155                 160

Arg Val Thr Gly Phe Ala Lys Arg Leu Asp Gly Gly Ile Ser Met Phe
                165                 170                 175

Phe Phe Glu Tyr Asp Cys Tyr Val Asn Gly Arg Leu Leu Ile Glu Met
            180                 185                 190

Arg Asp Gly Cys Ala Gly Phe Phe Thr Asn Glu Glu Leu Asp Ala Gly
        195                 200                 205

Lys Gly Val Val Phe Thr Arg Gly Asp Leu Ala Ala Arg Ala Lys Ile
    210                 215                 220

Pro Lys Gln Asp Val Ser Pro Tyr Ala Val Ala Pro Cys Leu His Lys
225                 230                 235                 240

Thr Lys Leu Asn Glu Lys Glu Met Gln Thr Leu Val Asp Lys Asp Trp
                245                 250                 255

Ala Ser Val Phe Gly Ser Lys Asn Gly Met Pro Glu Ile Asn Tyr Lys
```

-continued

```
            260                 265                 270

Leu Cys Ala Arg Lys Met Leu Met Ile Asp Arg Val Thr Ser Ile Asp
        275                 280                 285

His Lys Gly Gly Val Tyr Gly Leu Gly Gln Leu Val Gly Glu Lys Ile
    290                 295                 300

Leu Glu Arg Asp His Trp Tyr Phe Pro Cys His Phe Val Lys Asp Gln
305                 310                 315                 320

Val Met Ala Gly Ser Leu Val Ser Asp Gly Cys Ser Gln Met Leu Lys
                325                 330                 335

Met Tyr Met Ile Trp Leu Gly Leu His Leu Thr Thr Gly Pro Phe Asp
            340                 345                 350

Phe Arg Pro Val Asn Gly His Pro Asn Lys Val Arg Cys Arg Gly Gln
        355                 360                 365

Ile Ser Pro His Lys Gly Lys Leu Val Tyr Val Met Glu Ile Lys Glu
    370                 375                 380

Met Gly Phe Asp Glu Asp Asn Asp Pro Tyr Ala Ile Ala Asp Val Asn
385                 390                 395                 400

Ile Ile Asp Val Asp Phe Glu Lys Gly Gln Asp Phe Ser Leu Asp Arg
                405                 410                 415

Ile Ser Asp Tyr Gly Lys Gly Asp Leu Asn Lys Lys Ile Val Val Asp
            420                 425                 430

Phe Lys Gly Ile Ala Leu Lys Met Gln Lys Arg Ser Thr Asn Lys Asn
        435                 440                 445

Pro Ser Lys Val Gln Pro Val Phe Ala Asn Gly Ala Ala Thr Val Gly
    450                 455                 460

Pro Glu Ala Ser Lys Ala Ser Ser Gly Ala Ser Ala Ser Ala Ser Ala
465                 470                 475                 480

Ala Pro Ala Lys Pro Ala Phe Ser Ala Asp Val Leu Ala Pro Lys Pro
                485                 490                 495

Val Ala Leu Pro Glu His Ile Leu Lys Gly Asp Ala Leu Ala Pro Lys
            500                 505                 510

Glu Met Ser Trp His Pro Met Ala Arg Ile Pro Gly Asn Pro Thr Pro
        515                 520                 525

Ser Phe Ala Pro Ser Ala Tyr Lys Pro Arg Asn Ile Ala Phe Thr Pro
    530                 535                 540

Phe Pro Gly Asn Pro Asn Asp Asn Asp His Thr Pro Gly Lys Met Pro
545                 550                 555                 560

Leu Thr Trp Phe Asn Met Ala Glu Phe Met Ala Gly Lys Val Ser Met
                565                 570                 575

Cys Leu Gly Pro Glu Phe Ala Lys Phe Asp Asp Ser Asn Thr Ser Arg
            580                 585                 590

Ser Pro Ala Trp Asp Leu Ala Leu Val Thr Arg Ala Val Ser Val Ser
        595                 600                 605

Asp Leu Lys His Val Asn Tyr Arg Asn Ile Asp Leu Asp Pro Ser Lys
    610                 615                 620

Gly Thr Met Val Gly Glu Phe Asp Cys Pro Ala Asp Ala Trp Phe Tyr
625                 630                 635                 640

Lys Gly Ala Cys Asn Asp Ala His Met Pro Tyr Ser Ile Leu Met Glu
                645                 650                 655

Ile Ala Leu Gln Thr Ser Gly Val Leu Thr Ser Val Leu Lys Ala Pro
            660                 665                 670

Leu Thr Met Glu Lys Asp Asp Ile Leu Phe Arg Asn Leu Asp Ala Asn
        675                 680                 685
```

-continued

```
Ala Glu Phe Val Arg Ala Asp Leu Asp Tyr Arg Gly Lys Thr Ile Arg
    690                 695                 700

Asn Val Thr Lys Cys Thr Gly Tyr Ser Met Leu Gly Glu Met Gly Val
705                 710                 715                 720

His Arg Phe Thr Phe Glu Leu Tyr Val Asp Asp Val Leu Phe Tyr Lys
                725                 730                 735

Gly Ser Thr Ser Phe Gly Trp Phe Val Pro Glu Val Phe Ala Ala Gln
            740                 745                 750

Ala Gly Leu Asp Asn Gly Arg Lys Ser Glu Pro Trp Phe Ile Glu Asn
        755                 760                 765

Lys Val Pro Ala Ser Gln Val Ser Ser Phe Asp Val Arg Pro Asn Gly
    770                 775                 780

Ser Gly Arg Thr Ala Ile Phe Ala Asn Ala Pro Ser Gly Ala Gln Leu
785                 790                 795                 800

Asn Arg Arg Thr Asp Gln Gly Gln Tyr Leu Asp Ala Val Asp Ile Val
                805                 810                 815

Ser Gly Ser Gly Lys Lys Ser Leu Gly Tyr Ala His Gly Ser Lys Thr
            820                 825                 830

Val Asn Pro Asn Asp Trp Phe Phe Ser Cys His Phe Trp Phe Asp Ser
        835                 840                 845

Val Met Pro Gly Ser Leu Gly Val Glu Ser Met Phe Gln Leu Val Glu
    850                 855                 860

Ala Ile Ala Ala His Glu Asp Leu Ala Gly Lys His Gly Ile Ala Asn
865                 870                 875                 880

Pro Thr Phe Val His Ala Pro Gly Lys Ile Ser Trp Lys Tyr Arg Gly
                885                 890                 895

Gln Leu Thr Pro Lys Ser Lys Lys Met Asp Ser Glu Val His Ile Val
            900                 905                 910

Ser Val Asp Ala His Asp Gly Val Val Asp Leu Val Ala Asp Gly Phe
        915                 920                 925

Leu Trp Ala Asp Ser Leu Arg Val Tyr Ser Val Ser Asn Ile Arg Val
    930                 935                 940

Arg Ile Ala Ser Gly Glu Ala Pro Ala Ala Ala Ser Ser Ala Ala Ser
945                 950                 955                 960

Val Gly Ser Ser Ala Ser Ser Val Glu Arg Thr Arg Ser Ser Pro Ala
                965                 970                 975

Val Ala Ser Gly Pro Ala Gln Thr Ile Asp Leu Lys Gln Leu Lys Thr
            980                 985                 990

Glu Leu Leu Glu Leu Asp Ala Pro  Leu Tyr Leu Ser Gln  Asp Pro Thr
        995                 1000                1005

Ser Gly  Gln Leu Lys Lys His  Thr Asp Val Ala Ser  Gly Gln Ala
    1010                1015                1020

Thr Ile  Val Gln Pro Cys Thr  Leu Gly Asp Leu Gly  Asp Arg Ser
    1025                1030                1035

Phe Met  Glu Thr Tyr Gly Val  Val Ala Pro Leu Tyr  Thr Gly Ala
    1040                1045                1050

Met Ala  Lys Gly Ile Ala Ser  Ala Asp Leu Val Ile  Ala Ala Gly
    1055                1060                1065

Lys Arg  Lys Ile Leu Gly Ser  Phe Gly Ala Gly Gly  Leu Pro Met
    1070                1075                1080

His His  Val Arg Ala Ala Leu  Glu Lys Ile Gln Ala  Ala Leu Pro
    1085                1090                1095
```

-continued

```
Gln Gly  Pro Tyr Ala Val Asn  Leu Ile His Ser Pro  Phe Asp Ser
    1100                 1105                 1110

Asn Leu  Glu Lys Gly Asn Val  Asp Leu Phe Leu Glu  Lys Gly Val
    1115                 1120                 1125

Thr Val  Val Glu Ala Ser Ala  Phe Met Thr Leu Thr  Pro Gln Val
    1130                 1135                 1140

Val Arg  Tyr Arg Ala Ala Gly  Leu Ser Arg Asn Ala  Asp Gly Ser
    1145                 1150                 1155

Val Asn  Ile Arg Asn Arg Ile  Ile Gly Lys Val Ser  Arg Thr Glu
    1160                 1165                 1170

Leu Ala  Glu Met Phe Ile Arg  Pro Ala Pro Glu His  Leu Leu Glu
    1175                 1180                 1185

Lys Leu  Ile Ala Ser Gly Glu  Ile Thr Gln Glu Gln  Ala Glu Leu
    1190                 1195                 1200

Ala Arg  Arg Val Pro Val Ala  Asp Asp Ile Ala Val  Glu Ala Asp
    1205                 1210                 1215

Ser Gly  Gly His Thr Asp Asn  Arg Pro Ile His Val  Ile Leu Pro
    1220                 1225                 1230

Leu Ile  Ile Asn Leu Arg Asn  Arg Leu His Arg Glu  Cys Gly Tyr
    1235                 1240                 1245

Pro Ala  His Leu Arg Val Arg  Val Gly Ala Gly Gly  Gly Val Gly
    1250                 1255                 1260

Cys Pro  Gln Ala Ala Ala Ala  Ala Leu Thr Met Gly  Ala Ala Phe
    1265                 1270                 1275

Ile Val  Thr Gly Thr Val Asn  Gln Val Ala Lys Gln  Ser Gly Thr
    1280                 1285                 1290

Cys Asp  Asn Val Arg Lys Gln  Leu Ser Gln Ala Thr  Tyr Ser Asp
    1295                 1300                 1305

Ile Cys  Met Ala Pro Ala Ala  Asp Met Phe Glu Glu  Gly Val Lys
    1310                 1315                 1320

Leu Gln  Val Leu Lys Lys Gly  Thr Met Phe Pro Ser  Arg Ala Asn
    1325                 1330                 1335

Lys Leu  Tyr Glu Leu Phe Cys  Lys Tyr Asp Ser Phe  Asp Ser Met
    1340                 1345                 1350

Pro Pro  Ala Glu Leu Glu Arg  Ile Glu Lys Arg Ile  Phe Lys Arg
    1355                 1360                 1365

Ala Leu  Gln Glu Val Trp Glu  Glu Thr Lys Asp Phe  Tyr Ile Asn
    1370                 1375                 1380

Gly Leu  Lys Asn Pro Glu Lys  Ile Gln Arg Ala Glu  His Asp Pro
    1385                 1390                 1395

Lys Leu  Lys Met Ser Leu Cys  Phe Arg Trp Tyr Leu  Gly Leu Ala
    1400                 1405                 1410

Ser Arg  Trp Ala Asn Met Gly  Ala Pro Asp Arg Val  Met Asp Tyr
    1415                 1420                 1425

Gln Val  Trp Cys Gly Pro Ala  Ile Gly Ala Phe Asn  Asp Phe Ile
    1430                 1435                 1440

Lys Gly  Thr Tyr Leu Asp Pro  Ala Val Ser Asn Glu  Tyr Pro Cys
    1445                 1450                 1455

Val Val  Gln Ile Asn Leu Gln  Ile Leu Arg Gly Ala  Cys Tyr Leu
    1460                 1465                 1470

Arg Arg  Leu Asn Ala Leu Arg  Asn Asp Pro Arg Ile  Asp Leu Glu
    1475                 1480                 1485

Thr Glu  Asp Ala Ala Phe Val  Tyr Glu Pro Thr Asn  Ala Leu
```

-continued

```
1490 1495 1500


<210> SEQ ID NO 7
<211> LENGTH: 1500
<212> TYPE: DNA
<213> ORGANISM: Schizochytrium sp.
<220> FEATURE:
<221> NAME/KEY: CDS
<222> LOCATION: (1)..(1500)

<400> SEQUENCE: 7

atg gcg gcc cgt ctg cag gag caa aag gga ggc gag atg gat acc cgc       48
Met Ala Ala Arg Leu Gln Glu Gln Lys Gly Gly Glu Met Asp Thr Arg
1               5                   10                  15

att gcc atc atc ggc atg tcg gcc atc ctc ccc tgc ggc acg acc gtg       96
Ile Ala Ile Ile Gly Met Ser Ala Ile Leu Pro Cys Gly Thr Thr Val
            20                  25                  30

cgc gag tcg tgg gag acc atc cgc gcc ggc atc gac tgc ctg tcg gat      144
Arg Glu Ser Trp Glu Thr Ile Arg Ala Gly Ile Asp Cys Leu Ser Asp
        35                  40                  45

ctc ccc gag gac cgc gtc gac gtg acg gcg tac ttt gac ccc gtc aag      192
Leu Pro Glu Asp Arg Val Asp Val Thr Ala Tyr Phe Asp Pro Val Lys
    50                  55                  60

acc acc aag gac aag atc tac tgc aag cgc ggt ggc ttc att ccc gag      240
Thr Thr Lys Asp Lys Ile Tyr Cys Lys Arg Gly Gly Phe Ile Pro Glu
65                  70                  75                  80

tac gac ttt gac gcc cgc gag ttc gga ctc aac atg ttc cag atg gag      288
Tyr Asp Phe Asp Ala Arg Glu Phe Gly Leu Asn Met Phe Gln Met Glu
                85                  90                  95

gac tcg gac gca aac cag acc atc tcg ctt ctc aag gtc aag gag gcc      336
Asp Ser Asp Ala Asn Gln Thr Ile Ser Leu Leu Lys Val Lys Glu Ala
            100                 105                 110

ctc cag gac gcc ggc atc gac gcc ctc ggc aag gaa aag aag aac atc      384
Leu Gln Asp Ala Gly Ile Asp Ala Leu Gly Lys Glu Lys Lys Asn Ile
        115                 120                 125

ggc tgc gtg ctc ggc att ggc ggc ggc caa aag tcc agc cac gag ttc      432
Gly Cys Val Leu Gly Ile Gly Gly Gly Gln Lys Ser Ser His Glu Phe
    130                 135                 140

tac tcg cgc ctt aat tat gtt gtc gtg gag aag gtc ctc cgc aag atg      480
Tyr Ser Arg Leu Asn Tyr Val Val Val Glu Lys Val Leu Arg Lys Met
145                 150                 155                 160

ggc atg ccc gag gag gac gtc aag gtc gcc gtc gaa aag tac aag gcc      528
Gly Met Pro Glu Glu Asp Val Lys Val Ala Val Glu Lys Tyr Lys Ala
                165                 170                 175

aac ttc ccc gag tgg cgc ctc gac tcc ttc cct ggc ttc ctc ggc aac      576
Asn Phe Pro Glu Trp Arg Leu Asp Ser Phe Pro Gly Phe Leu Gly Asn
            180                 185                 190

gtc acc gcc ggt cgc tgc acc aac acc ttc aac ctc gac ggc atg aac      624
Val Thr Ala Gly Arg Cys Thr Asn Thr Phe Asn Leu Asp Gly Met Asn
        195                 200                 205

tgc gtt gtc gac gcc gca tgc gcc tcg tcc ctc atc gcc gtc aag gtc      672
Cys Val Val Asp Ala Ala Cys Ala Ser Ser Leu Ile Ala Val Lys Val
    210                 215                 220

gcc atc gac gag ctg ctc tac ggt gac tgc gac atg atg gtc acc ggt      720
Ala Ile Asp Glu Leu Leu Tyr Gly Asp Cys Asp Met Met Val Thr Gly
225                 230                 235                 240

gcc acc tgc acg gat aac tcc atc ggc atg tac atg gcc ttc tcc aag      768
Ala Thr Cys Thr Asp Asn Ser Ile Gly Met Tyr Met Ala Phe Ser Lys
                245                 250                 255

acc ccc gtg ttc tcc acg gac ccc agc gtg cgc gcc tac gac gaa aag      816
Thr Pro Val Phe Ser Thr Asp Pro Ser Val Arg Ala Tyr Asp Glu Lys
```

-continued

```
        260                 265                 270

aca aag ggc atg ctc atc ggc gag ggc tcc gcc atg ctc gtc ctc aag      864
Thr Lys Gly Met Leu Ile Gly Glu Gly Ser Ala Met Leu Val Leu Lys
        275                 280                 285

cgc tac gcc gac gcc gtc cgc gac ggc gat gag atc cac gct gtt att      912
Arg Tyr Ala Asp Ala Val Arg Asp Gly Asp Glu Ile His Ala Val Ile
    290                 295                 300

cgc ggc tgc gcc tcc tcc agt gat ggc aag gcc gcc ggc atc tac acg      960
Arg Gly Cys Ala Ser Ser Ser Asp Gly Lys Ala Ala Gly Ile Tyr Thr
305                 310                 315                 320

ccc acc att tcg ggc cag gag gag gcc ctc cgc cgc gcc tac aac cgc     1008
Pro Thr Ile Ser Gly Gln Glu Glu Ala Leu Arg Arg Ala Tyr Asn Arg
                325                 330                 335

gcc tgt gtc gac ccg gcc acc gtc act ctc gtc gag ggt cac ggc acc     1056
Ala Cys Val Asp Pro Ala Thr Val Thr Leu Val Glu Gly His Gly Thr
            340                 345                 350

ggt act ccc gtt ggc gac cgc atc gag ctc acc gcc ttg cgc aac ctc     1104
Gly Thr Pro Val Gly Asp Arg Ile Glu Leu Thr Ala Leu Arg Asn Leu
        355                 360                 365

ttt gac aag gcc tac ggc gag ggc aac acc gaa aag gtc gct gtg ggc     1152
Phe Asp Lys Ala Tyr Gly Glu Gly Asn Thr Glu Lys Val Ala Val Gly
    370                 375                 380

agc atc aag tcc agc atc ggc cat ctc aag gcc gtc gcc ggt ctc gcc     1200
Ser Ile Lys Ser Ser Ile Gly His Leu Lys Ala Val Ala Gly Leu Ala
385                 390                 395                 400

ggt atg atc aag gtc atc atg gcg ctc aag cac aag act ctc ccg ggc     1248
Gly Met Ile Lys Val Ile Met Ala Leu Lys His Lys Thr Leu Pro Gly
                405                 410                 415

acc atc aac gtc gac aac cca ccc aac ctc tac gac aac acg ccc atc     1296
Thr Ile Asn Val Asp Asn Pro Pro Asn Leu Tyr Asp Asn Thr Pro Ile
            420                 425                 430

aac gag tcc tcg ctc tac att aac acc atg aac cgc ccc tgg ttc ccg     1344
Asn Glu Ser Ser Leu Tyr Ile Asn Thr Met Asn Arg Pro Trp Phe Pro
        435                 440                 445

ccc cct ggt gtg ccc cgc cgc gcc ggc att tcg agc ttt ggc ttt ggt     1392
Pro Pro Gly Val Pro Arg Arg Ala Gly Ile Ser Ser Phe Gly Phe Gly
    450                 455                 460

ggc gcc aac tac cac gcc gtc ctc gag gag gcc gag ccc gag cac acg     1440
Gly Ala Asn Tyr His Ala Val Leu Glu Glu Ala Glu Pro Glu His Thr
465                 470                 475                 480

acc gcg tac cgc ctc aac aag cgc ccg cag ccc gtg ctc atg atg gcc     1488
Thr Ala Tyr Arg Leu Asn Lys Arg Pro Gln Pro Val Leu Met Met Ala
                485                 490                 495

gcc acg ccc gcg                                                     1500
Ala Thr Pro Ala
            500


<210> SEQ ID NO 8
<211> LENGTH: 500
<212> TYPE: PRT
<213> ORGANISM: Schizochytrium sp.

<400> SEQUENCE: 8

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45
```

-continued

```
Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Lys Asn Ile
        115                 120                 125

Gly Cys Val Leu Gly Ile Gly Gly Gly Gln Lys Ser Ser His Glu Phe
    130                 135                 140

Tyr Ser Arg Leu Asn Tyr Val Val Val Glu Lys Val Leu Arg Lys Met
145                 150                 155                 160

Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
            180                 185                 190

Val Thr Ala Gly Arg Cys Thr Asn Thr Phe Asn Leu Asp Gly Met Asn
        195                 200                 205

Cys Val Val Asp Ala Ala Cys Ala Ser Ser Leu Ile Ala Val Lys Val
    210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
            260                 265                 270

Thr Lys Gly Met Leu Ile Gly Glu Gly Ser Ala Met Leu Val Leu Lys
        275                 280                 285

Arg Tyr Ala Asp Ala Val Arg Asp Gly Asp Glu Ile His Ala Val Ile
    290                 295                 300

Arg Gly Cys Ala Ser Ser Ser Asp Gly Lys Ala Ala Gly Ile Tyr Thr
305                 310                 315                 320

Pro Thr Ile Ser Gly Gln Glu Glu Ala Leu Arg Arg Ala Tyr Asn Arg
                325                 330                 335

Ala Cys Val Asp Pro Ala Thr Val Thr Leu Val Glu Gly His Gly Thr
            340                 345                 350

Gly Thr Pro Val Gly Asp Arg Ile Glu Leu Thr Ala Leu Arg Asn Leu
        355                 360                 365

Phe Asp Lys Ala Tyr Gly Glu Gly Asn Thr Glu Lys Val Ala Val Gly
    370                 375                 380

Ser Ile Lys Ser Ser Ile Gly His Leu Lys Ala Val Ala Gly Leu Ala
385                 390                 395                 400

Gly Met Ile Lys Val Ile Met Ala Leu Lys His Lys Thr Leu Pro Gly
                405                 410                 415

Thr Ile Asn Val Asp Asn Pro Pro Asn Leu Tyr Asp Asn Thr Pro Ile
            420                 425                 430

Asn Glu Ser Ser Leu Tyr Ile Asn Thr Met Asn Arg Pro Trp Phe Pro
        435                 440                 445

Pro Pro Gly Val Pro Arg Arg Ala Gly Ile Ser Ser Phe Gly Phe Gly
    450                 455                 460

Gly Ala Asn Tyr His Ala Val Leu Glu Glu Ala Glu Pro Glu His Thr
```

-continued

```
465                 470                 475                 480

Thr Ala Tyr Arg Leu Asn Lys Arg Pro Gln Pro Val Leu Met Met Ala
                485                 490                 495

Ala Thr Pro Ala
            500


<210> SEQ ID NO 9
<211> LENGTH: 1278
<212> TYPE: DNA
<213> ORGANISM: Schizochytrium sp.
<220> FEATURE:
<221> NAME/KEY: CDS
<222> LOCATION: (1)..(1278)

<400> SEQUENCE: 9

gat gtc acc aag gag gcc tgg cgc ctc ccc cgc gag ggc gtc agc ttc       48
Asp Val Thr Lys Glu Ala Trp Arg Leu Pro Arg Glu Gly Val Ser Phe
1               5                   10                  15

cgc gcc aag ggc atc gcc acc aac ggc gct gtc gcc gcg ctc ttc tcc       96
Arg Ala Lys Gly Ile Ala Thr Asn Gly Ala Val Ala Ala Leu Phe Ser
            20                  25                  30

ggc cag ggc gcg cag tac acg cac atg ttt agc gag gtg gcc atg aac      144
Gly Gln Gly Ala Gln Tyr Thr His Met Phe Ser Glu Val Ala Met Asn
        35                  40                  45

tgg ccc cag ttc cgc cag agc att gcc gcc atg gac gcc gcc cag tcc      192
Trp Pro Gln Phe Arg Gln Ser Ile Ala Ala Met Asp Ala Ala Gln Ser
    50                  55                  60

aag gtc gct gga agc gac aag gac ttt gag cgc gtc tcc cag gtc ctc      240
Lys Val Ala Gly Ser Asp Lys Asp Phe Glu Arg Val Ser Gln Val Leu
65                  70                  75                  80

tac ccg cgc aag ccg tac gag cgt gag ccc gag cag gac cac aag aag      288
Tyr Pro Arg Lys Pro Tyr Glu Arg Glu Pro Glu Gln Asp His Lys Lys
                85                  90                  95

atc tcc ctc acc gcc tac tcg cag ccc tcg acc ctg gcc tgc gct ctc      336
Ile Ser Leu Thr Ala Tyr Ser Gln Pro Ser Thr Leu Ala Cys Ala Leu
            100                 105                 110

ggt gcc ttt gag atc ttc aag gag gcc ggc ttc acc ccg gac ttt gcc      384
Gly Ala Phe Glu Ile Phe Lys Glu Ala Gly Phe Thr Pro Asp Phe Ala
        115                 120                 125

gcc ggc cat tcg ctc ggt gag ttc gcc gcc ctc tac gcc gcg ggc tgc      432
Ala Gly His Ser Leu Gly Glu Phe Ala Ala Leu Tyr Ala Ala Gly Cys
    130                 135                 140

gtc gac cgc gac gag ctc ttt gag ctt gtc tgc cgc cgc gcc cgc atc      480
Val Asp Arg Asp Glu Leu Phe Glu Leu Val Cys Arg Arg Ala Arg Ile
145                 150                 155                 160

atg ggc ggc aag gac gca ccg gcc acc ccc aag ggc tgc atg gcc gcc      528
Met Gly Gly Lys Asp Ala Pro Ala Thr Pro Lys Gly Cys Met Ala Ala
                165                 170                 175

gtc att ggc ccc aac gcc gag aac atc aag gtc cag gcc gcc aac gtc      576
Val Ile Gly Pro Asn Ala Glu Asn Ile Lys Val Gln Ala Ala Asn Val
            180                 185                 190

tgg ctc ggc aac tcc aac tcg cct tcg cag acc gtc atc acc ggc tcc      624
Trp Leu Gly Asn Ser Asn Ser Pro Ser Gln Thr Val Ile Thr Gly Ser
        195                 200                 205

gtc gaa ggt atc cag gcc gag agc gcc cgc ctc cag aag gag ggc ttc      672
Val Glu Gly Ile Gln Ala Glu Ser Ala Arg Leu Gln Lys Glu Gly Phe
    210                 215                 220

cgc gtc gtg cct ctt gcc tgc gag agc gcc ttc cac tcg ccc cag atg      720
Arg Val Val Pro Leu Ala Cys Glu Ser Ala Phe His Ser Pro Gln Met
225                 230                 235                 240
```

-continued

```
gag aac gcc tcg tcg gcc ttc aag gac gtc atc tcc aag gtc tcc ttc      768
Glu Asn Ala Ser Ser Ala Phe Lys Asp Val Ile Ser Lys Val Ser Phe
                245                 250                 255

cgc acc ccc aag gcc gag acc aag ctc ttc agc aac gtc tct ggc gag      816
Arg Thr Pro Lys Ala Glu Thr Lys Leu Phe Ser Asn Val Ser Gly Glu
            260                 265                 270

acc tac ccc acg gac gcc cgc gag atg ctt acg cag cac atg acc agc      864
Thr Tyr Pro Thr Asp Ala Arg Glu Met Leu Thr Gln His Met Thr Ser
        275                 280                 285

agc gtc aag ttc ctc acc cag gtc cgc aac atg cac cag gcc ggt gcg      912
Ser Val Lys Phe Leu Thr Gln Val Arg Asn Met His Gln Ala Gly Ala
    290                 295                 300

cgc atc ttt gtc gag ttc gga ccc aag cag gtg ctc tcc aag ctt gtc      960
Arg Ile Phe Val Glu Phe Gly Pro Lys Gln Val Leu Ser Lys Leu Val
305                 310                 315                 320

tcc gag acc ctc aag gat gac ccc tcg gtt gtc acc gtc tct gtc aac     1008
Ser Glu Thr Leu Lys Asp Asp Pro Ser Val Val Thr Val Ser Val Asn
                325                 330                 335

ccg gcc tcg ggc acg gat tcg gac atc cag ctc cgc gac gcg gcc gtc     1056
Pro Ala Ser Gly Thr Asp Ser Asp Ile Gln Leu Arg Asp Ala Ala Val
            340                 345                 350

cag ctc gtt gtc gct ggc gtc aac ctt cag ggc ttt gac aag tgg gac     1104
Gln Leu Val Val Ala Gly Val Asn Leu Gln Gly Phe Asp Lys Trp Asp
        355                 360                 365

gcc ccc gat gcc acc cgc atg cag gcc atc aag aag aag cgc act acc     1152
Ala Pro Asp Ala Thr Arg Met Gln Ala Ile Lys Lys Lys Arg Thr Thr
    370                 375                 380

ctc cgc ctt tcg gcc gcc acc tac gtc tcg gac aag acc aag aag gtc     1200
Leu Arg Leu Ser Ala Ala Thr Tyr Val Ser Asp Lys Thr Lys Lys Val
385                 390                 395                 400

cgc gac gcc gcc atg aac gat ggc cgc tgc gtc acc tac ctc aag ggc     1248
Arg Asp Ala Ala Met Asn Asp Gly Arg Cys Val Thr Tyr Leu Lys Gly
                405                 410                 415

gcc gca ccg ctc atc aag gcc ccg gag ccc                             1278
Ala Ala Pro Leu Ile Lys Ala Pro Glu Pro
            420                 425


<210> SEQ ID NO 10
<211> LENGTH: 426
<212> TYPE: PRT
<213> ORGANISM: Schizochytrium sp.

<400> SEQUENCE: 10

Asp Val Thr Lys Glu Ala Trp Arg Leu Pro Arg Glu Gly Val Ser Phe
1               5                   10                  15

Arg Ala Lys Gly Ile Ala Thr Asn Gly Ala Val Ala Ala Leu Phe Ser
            20                  25                  30

Gly Gln Gly Ala Gln Tyr Thr His Met Phe Ser Glu Val Ala Met Asn
        35                  40                  45

Trp Pro Gln Phe Arg Gln Ser Ile Ala Ala Met Asp Ala Ala Gln Ser
    50                  55                  60

Lys Val Ala Gly Ser Asp Lys Asp Phe Glu Arg Val Ser Gln Val Leu
65                  70                  75                  80

Tyr Pro Arg Lys Pro Tyr Glu Arg Glu Pro Glu Gln Asp His Lys Lys
                85                  90                  95

Ile Ser Leu Thr Ala Tyr Ser Gln Pro Ser Thr Leu Ala Cys Ala Leu
            100                 105                 110

Gly Ala Phe Glu Ile Phe Lys Glu Ala Gly Phe Thr Pro Asp Phe Ala
        115                 120                 125
```

```
Ala Gly His Ser Leu Gly Glu Phe Ala Ala Leu Tyr Ala Ala Gly Cys
    130                 135                 140

Val Asp Arg Asp Glu Leu Phe Glu Leu Val Cys Arg Arg Ala Arg Ile
145                 150                 155                 160

Met Gly Gly Lys Asp Ala Pro Ala Thr Pro Lys Gly Cys Met Ala Ala
                165                 170                 175

Val Ile Gly Pro Asn Ala Glu Asn Ile Lys Val Gln Ala Ala Asn Val
            180                 185                 190

Trp Leu Gly Asn Ser Asn Ser Pro Ser Gln Thr Val Ile Thr Gly Ser
        195                 200                 205

Val Glu Gly Ile Gln Ala Glu Ser Ala Arg Leu Gln Lys Glu Gly Phe
    210                 215                 220

Arg Val Val Pro Leu Ala Cys Glu Ser Ala Phe His Ser Pro Gln Met
225                 230                 235                 240

Glu Asn Ala Ser Ser Ala Phe Lys Asp Val Ile Ser Lys Val Ser Phe
                245                 250                 255

Arg Thr Pro Lys Ala Glu Thr Lys Leu Phe Ser Asn Val Ser Gly Glu
            260                 265                 270

Thr Tyr Pro Thr Asp Ala Arg Glu Met Leu Thr Gln His Met Thr Ser
        275                 280                 285

Ser Val Lys Phe Leu Thr Gln Val Arg Asn Met His Gln Ala Gly Ala
    290                 295                 300

Arg Ile Phe Val Glu Phe Gly Pro Lys Gln Val Leu Ser Lys Leu Val
305                 310                 315                 320

Ser Glu Thr Leu Lys Asp Asp Pro Ser Val Val Thr Val Ser Val Asn
                325                 330                 335

Pro Ala Ser Gly Thr Asp Ser Asp Ile Gln Leu Arg Asp Ala Ala Val
            340                 345                 350

Gln Leu Val Val Ala Gly Val Asn Leu Gln Gly Phe Asp Lys Trp Asp
        355                 360                 365

Ala Pro Asp Ala Thr Arg Met Gln Ala Ile Lys Lys Lys Arg Thr Thr
    370                 375                 380

Leu Arg Leu Ser Ala Ala Thr Tyr Val Ser Asp Lys Thr Lys Lys Val
385                 390                 395                 400

Arg Asp Ala Ala Met Asn Asp Gly Arg Cys Val Thr Tyr Leu Lys Gly
                405                 410                 415

Ala Ala Pro Leu Ile Lys Ala Pro Glu Pro
            420                 425
```

<210> SEQ ID NO 11
<211> LENGTH: 5
<212> TYPE: PRT
<213> ORGANISM: Schizochytrium sp.
<220> FEATURE:
<221> NAME/KEY: MISC_FEATURE
<222> LOCATION: (4)..(4)
<223> OTHER INFORMATION: X = any amino acid

<400> SEQUENCE: 11

```
Gly His Ser Xaa Gly
1               5
```

<210> SEQ ID NO 12
<211> LENGTH: 258
<212> TYPE: DNA
<213> ORGANISM: Schizochytrium sp.
<220> FEATURE:

```
<221> NAME/KEY: CDS
<222> LOCATION: (1)..(258)

<400> SEQUENCE: 12

gct gtc tcg aac gag ctt ctt gag aag gcc gag act gtc gtc atg gag       48
Ala Val Ser Asn Glu Leu Leu Glu Lys Ala Glu Thr Val Val Met Glu
1               5                   10                  15

gtc ctc gcc gcc aag acc ggc tac gag acc gac atg atc gag gct gac       96
Val Leu Ala Ala Lys Thr Gly Tyr Glu Thr Asp Met Ile Glu Ala Asp
            20                  25                  30

atg gag ctc gag acc gag ctc ggc att gac tcc atc aag cgt gtc gag      144
Met Glu Leu Glu Thr Glu Leu Gly Ile Asp Ser Ile Lys Arg Val Glu
        35                  40                  45

atc ctc tcc gag gtc cag gcc atg ctc aat gtc gag gcc aag gat gtc      192
Ile Leu Ser Glu Val Gln Ala Met Leu Asn Val Glu Ala Lys Asp Val
    50                  55                  60

gat gcc ctc agc cgc act cgc act gtt ggt gag gtt gtc aac gcc atg      240
Asp Ala Leu Ser Arg Thr Arg Thr Val Gly Glu Val Val Asn Ala Met
65                  70                  75                  80

aag gcc gag atc gct ggc                                              258
Lys Ala Glu Ile Ala Gly
                85


<210> SEQ ID NO 13
<211> LENGTH: 86
<212> TYPE: PRT
<213> ORGANISM: Schizochytrium sp.

<400> SEQUENCE: 13

Ala Val Ser Asn Glu Leu Leu Glu Lys Ala Glu Thr Val Val Met Glu
1               5                   10                  15

Val Leu Ala Ala Lys Thr Gly Tyr Glu Thr Asp Met Ile Glu Ala Asp
            20                  25                  30

Met Glu Leu Glu Thr Glu Leu Gly Ile Asp Ser Ile Lys Arg Val Glu
        35                  40                  45

Ile Leu Ser Glu Val Gln Ala Met Leu Asn Val Glu Ala Lys Asp Val
    50                  55                  60

Asp Ala Leu Ser Arg Thr Arg Thr Val Gly Glu Val Val Asn Ala Met
65                  70                  75                  80

Lys Ala Glu Ile Ala Gly
                85


<210> SEQ ID NO 14
<211> LENGTH: 5
<212> TYPE: PRT
<213> ORGANISM: Schizochytrium sp.

<400> SEQUENCE: 14

Leu Gly Ile Asp Ser
1               5


<210> SEQ ID NO 15
<211> LENGTH: 21
<212> TYPE: PRT
<213> ORGANISM: Schizochytrium sp.

<400> SEQUENCE: 15

Ala Pro Ala Pro Val Lys Ala Ala Ala Pro Ala Ala Pro Val Ala Ser
1               5                   10                  15

Ala Pro Ala Pro Ala
            20
```

-continued

<210> SEQ ID NO 16
<211> LENGTH: 3006
<212> TYPE: DNA
<213> ORGANISM: Schizochytrium sp.

<400> SEQUENCE: 16
gcccccgccc cggtcaaggc tgctgcgcct gccgcccccg ttgcctcggc ccctgccccg 60
gctgtctcga acgagcttct tgagaaggcc gagactgtcg tcatggaggt cctcgccgcc 120
aagaccggct acgagaccga catgatcgag gctgacatgg agctcgagac cgagctcggc 180
attgactcca tcaagcgtgt cgagatcctc tccgaggtcc aggccatgct caatgtcgag 240
gccaaggatg tcgatgccct cagccgcact cgcactgttg gtgaggttgt caacgccatg 300
aaggccgaga tcgctggcag ctctgccccg gcgcctgctg ccgctgctcc ggctccggcc 360
aaggctgccc ctgccgccgc tgcgcctgct gtctcgaacg agcttctcga gaaggccgag 420
accgtcgtca tggaggtcct cgccgccaag actggctacg agactgacat gatcgagtcc 480
gacatggagc tcgagactga gctcggcatt gactccatca agcgtgtcga gatcctctcc 540
gaggttcagg ccatgctcaa cgtcgaggcc aaggacgtcg acgctctcag ccgcactcgc 600
actgtgggtg aggtcgtcaa cgccatgaag gctgagatcg ctggtggctc tgccccggcg 660
cctgccgccg ctgccccagg tccggctgct gccgcccctg cgcctgccgc cgccgcccct 720
gctgtctcga acgagcttct tgagaaggcc gagaccgtcg tcatggaggt cctcgccgcc 780
aagactggct acgagactga catgatcgag tccgacatgg agctcgagac cgagctcggc 840
attgactcca tcaagcgtgt cgagattctc tccgaggtcc aggccatgct caacgtcgag 900
gccaaggacg tcgacgctct cagccgcacc cgcactgttg gcgaggtcgt cgatgccatg 960
aaggccgaga tcgctggtgg ctctgccccg gcgcctgccg ccgctgctcc tgctccggct 1020
gctgccgccc ctgcgcctgc cgcccctgcg cctgctgtct cgagcgagct tctcgagaag 1080
gccgagactg tcgtcatgga ggtcctcgcc gccaagactg gctacgagac tgacatgatc 1140
gagtccgaca tggagctcga gaccgagctc ggcattgact ccatcaagcg tgtcgagatt 1200
ctctccgagg tccaggccat gctcaacgtc gaggccaagg acgtcgacgc tctcagccgc 1260
acccgcactg ttggcgaggt cgtcgatgcc atgaaggccg agatcgctgg tggctctgcc 1320
ccggcgcctg ccgccgctgc tcctgctccg gctgctgccg cccctgcgcc tgccgcccct 1380
gcgcctgccg cccctgcgcc tgctgtctcg agcgagcttc tcgagaaggc cgagactgtc 1440
gtcatggagg tcctcgccgc caagactggc tacgagactg acatgattga gtccgacatg 1500
gagctcgaga ccgagctcgg cattgactcc atcaagcgtg tcgagattct ctccgaggtt 1560
caggccatgc tcaacgtcga ggccaaggac gtcgacgctc tcagccgcac tcgcactgtt 1620
ggtgaggtcg tcgatgccat gaaggctgag atcgctggca gctccgcctc ggcgcctgcc 1680
gccgctgctc ctgctccggc tgctgccgct cctgcgcccg ctgccgccgc ccctgctgtc 1740
tcgaacgagc ttctcgagaa agccgagact gtcgtcatgg aggtcctcgc cgccaagact 1800
ggctacgaga ctgacatgat cgagtccgac atggagctcg agactgagct cggcattgac 1860
tccatcaagc gtgtcgagat cctctccgag gttcaggcca tgctcaacgt cgaggccaag 1920
gacgtcgatg ccctcagccg cacccgcact gttggcgagg ttgtcgatgc catgaaggcc 1980
gagatcgctg gtggctctgc cccggcgcct gccgccgctg cccctgctcc ggctgccgcc 2040
gcccctgctg tctcgaacga gcttctcgag aaggccgaga ctgtcgtcat ggaggtcctc 2100

-continued

```
gccgccaaga ctggctacga gaccgacatg atcgagtccg acatggagct cgagaccgag   2160

ctcggcattg actccatcaa gcgtgtcgag attctctccg aggttcaggc catgctcaac   2220

gtcgaggcca aggacgtcga tgctctcagc cgcactcgca ctgttggcga ggtcgtcgat   2280

gccatgaagg ctgagatcgc cggcagctcc gccccggcgc ctgccgccgc tgctcctgct   2340

ccggctgctg ccgctcctgc gcccgctgcc gctgcccctg ctgtctcgag cgagcttctc   2400

gagaaggccg agaccgtcgt catggaggtc ctcgccgcca agactggcta cgagactgac   2460

atgattgagt ccgacatgga gctcgagact gagctcggca ttgactccat caagcgtgtc   2520

gagatcctct ccgaggttca ggccatgctc aacgtcgagg ccaaggacgt cgatgccctc   2580

agccgcaccc gcactgttgg cgaggttgtc gatgccatga aggccgagat cgctggtggc   2640

tctgccccgg cgcctgccgc cgctgcccct gctccggctg ccgccgcccc tgctgtctcg   2700

aacgagcttc ttgagaaggc cgagaccgtc gtcatggagg tcctcgccgc caagactggc   2760

tacgagaccg acatgatcga gtccgacatg gagctcgaga ccgagctcgg cattgactcc   2820

atcaagcgtg tcgagattct ctccgaggtt caggccatgc tcaacgtcga ggccaaggac   2880

gtcgacgctc tcagccgcac tcgcactgtt ggcgaggtcg tcgatgccat gaaggctgag   2940

atcgctggtg gctctgcccc ggcgcctgcc gccgctgctc ctgcctcggc tggcgccgcg   3000

cctgcg                                                              3006
```

<210> SEQ ID NO 17
<211> LENGTH: 2133
<212> TYPE: DNA
<213> ORGANISM: Schizochytrium sp.
<220> FEATURE:
<221> NAME/KEY: CDS
<222> LOCATION: (1)..(2133)

<400> SEQUENCE: 17

```
ttt ggc gct ctc ggc ggc ttc atc tcg cag cag gcg gag cgc ttc gag       48
Phe Gly Ala Leu Gly Gly Phe Ile Ser Gln Gln Ala Glu Arg Phe Glu
1               5                   10                  15

ccc gcc gaa atc ctc ggc ttc acg ctc atg tgc gcc aag ttc gcc aag       96
Pro Ala Glu Ile Leu Gly Phe Thr Leu Met Cys Ala Lys Phe Ala Lys
            20                  25                  30

gct tcc ctc tgc acg gct gtg gct ggc ggc cgc ccg gcc ttt atc ggt      144
Ala Ser Leu Cys Thr Ala Val Ala Gly Gly Arg Pro Ala Phe Ile Gly
        35                  40                  45

gtg gcg cgc ctt gac ggc cgc ctc gga ttc act tcg cag ggc act tct      192
Val Ala Arg Leu Asp Gly Arg Leu Gly Phe Thr Ser Gln Gly Thr Ser
    50                  55                  60

gac gcg ctc aag cgt gcc cag cgt ggt gcc atc ttt ggc ctc tgc aag      240
Asp Ala Leu Lys Arg Ala Gln Arg Gly Ala Ile Phe Gly Leu Cys Lys
65                  70                  75                  80

acc atc ggc ctc gag tgg tcc gag tct gac gtc ttt tcc cgc ggc gtg      288
Thr Ile Gly Leu Glu Trp Ser Glu Ser Asp Val Phe Ser Arg Gly Val
                85                  90                  95

gac att gct cag ggc atg cac ccc gag gat gcc gcc gtg gcg att gtg      336
Asp Ile Ala Gln Gly Met His Pro Glu Asp Ala Ala Val Ala Ile Val
            100                 105                 110

cgc gag atg gcg tgc gct gac att cgc att cgc gag gtc ggc att ggc      384
Arg Glu Met Ala Cys Ala Asp Ile Arg Ile Arg Glu Val Gly Ile Gly
        115                 120                 125

gca aac cag cag cgc tgc acg atc cgt gcc gcc aag ctc gag acc ggc      432
Ala Asn Gln Gln Arg Cys Thr Ile Arg Ala Ala Lys Leu Glu Thr Gly
    130                 135                 140
```

-continued

```
aac ccg cag cgc cag atc gcc aag gac gac gtg ctg ctc gtt tct ggc      480
Asn Pro Gln Arg Gln Ile Ala Lys Asp Asp Val Leu Leu Val Ser Gly
145                 150                 155                 160

ggc gct cgc ggc atc acg cct ctt tgc atc cgg gag atc acg cgc cag      528
Gly Ala Arg Gly Ile Thr Pro Leu Cys Ile Arg Glu Ile Thr Arg Gln
                165                 170                 175

atc gcg ggc ggc aag tac att ctg ctt ggc cgc agc aag gtc tct gcg      576
Ile Ala Gly Gly Lys Tyr Ile Leu Leu Gly Arg Ser Lys Val Ser Ala
            180                 185                 190

agc gaa ccg gca tgg tgc gct ggc atc act gac gag aag gct gtg caa      624
Ser Glu Pro Ala Trp Cys Ala Gly Ile Thr Asp Glu Lys Ala Val Gln
        195                 200                 205

aag gct gct acc cag gag ctc aag cgc gcc ttt agc gct ggc gag ggc      672
Lys Ala Ala Thr Gln Glu Leu Lys Arg Ala Phe Ser Ala Gly Glu Gly
    210                 215                 220

ccc aag ccc acg ccc cgc gct gtc act aag ctt gtg ggc tct gtt ctt      720
Pro Lys Pro Thr Pro Arg Ala Val Thr Lys Leu Val Gly Ser Val Leu
225                 230                 235                 240

ggc gct cgc gag gtg cgc agc tct att gct gcg att gaa gcg ctc ggc      768
Gly Ala Arg Glu Val Arg Ser Ser Ile Ala Ala Ile Glu Ala Leu Gly
                245                 250                 255

ggc aag gcc atc tac tcg tcg tgc gac gtg aac tct gcc gcc gac gtg      816
Gly Lys Ala Ile Tyr Ser Ser Cys Asp Val Asn Ser Ala Ala Asp Val
            260                 265                 270

gcc aag gcc gtg cgc gat gcc gag tcc cag ctc ggt gcc cgc gtc tcg      864
Ala Lys Ala Val Arg Asp Ala Glu Ser Gln Leu Gly Ala Arg Val Ser
        275                 280                 285

ggc atc gtt cat gcc tcg ggc gtg ctc cgc gac cgt ctc atc gag aag      912
Gly Ile Val His Ala Ser Gly Val Leu Arg Asp Arg Leu Ile Glu Lys
    290                 295                 300

aag ctc ccc gac gag ttc gac gcc gtc ttt ggc acc aag gtc acc ggt      960
Lys Leu Pro Asp Glu Phe Asp Ala Val Phe Gly Thr Lys Val Thr Gly
305                 310                 315                 320

ctc gag aac ctc ctc gcc gcc gtc gac cgc gcc aac ctc aag cac atg     1008
Leu Glu Asn Leu Leu Ala Ala Val Asp Arg Ala Asn Leu Lys His Met
                325                 330                 335

gtc ctc ttc agc tcg ctc gcc ggc ttc cac ggc aac gtc ggc cag tct     1056
Val Leu Phe Ser Ser Leu Ala Gly Phe His Gly Asn Val Gly Gln Ser
            340                 345                 350

gac tac gcc atg gcc aac gag gcc ctt aac aag atg ggc ctc gag ctc     1104
Asp Tyr Ala Met Ala Asn Glu Ala Leu Asn Lys Met Gly Leu Glu Leu
        355                 360                 365

gcc aag gac gtc tcg gtc aag tcg atc tgc ttc ggt ccc tgg gac ggt     1152
Ala Lys Asp Val Ser Val Lys Ser Ile Cys Phe Gly Pro Trp Asp Gly
    370                 375                 380

ggc atg gtg acg ccg cag ctc aag aag cag ttc cag gag atg ggc gtg     1200
Gly Met Val Thr Pro Gln Leu Lys Lys Gln Phe Gln Glu Met Gly Val
385                 390                 395                 400

cag atc atc ccc cgc gag ggc ggc gct gat acc gtg gcg cgc atc gtg     1248
Gln Ile Ile Pro Arg Glu Gly Gly Ala Asp Thr Val Ala Arg Ile Val
                405                 410                 415

ctc ggc tcc tcg ccg gct gag atc ctt gtc ggc aac tgg cgc acc ccg     1296
Leu Gly Ser Ser Pro Ala Glu Ile Leu Val Gly Asn Trp Arg Thr Pro
            420                 425                 430

tcc aag aag gtc ggc tcg gac acc atc acc ctg cac cgc aag att tcc     1344
Ser Lys Lys Val Gly Ser Asp Thr Ile Thr Leu His Arg Lys Ile Ser
        435                 440                 445

gcc aag tcc aac ccc ttc ctc gag gac cac gtc atc cag ggc cgc cgc     1392
Ala Lys Ser Asn Pro Phe Leu Glu Asp His Val Ile Gln Gly Arg Arg
    450                 455                 460
```

```
gtg ctg ccc atg acg ctg gcc att ggc tcg ctc gcg gag acc tgc ctc      1440
Val Leu Pro Met Thr Leu Ala Ile Gly Ser Leu Ala Glu Thr Cys Leu
465                 470                 475                 480

ggc ctc ttc ccc ggc tac tcg ctc tgg gcc att gac gac gcc cag ctc      1488
Gly Leu Phe Pro Gly Tyr Ser Leu Trp Ala Ile Asp Asp Ala Gln Leu
                485                 490                 495

ttc aag ggt gtc act gtc gac ggc gac gtc aac tgc gag gtg acc ctc      1536
Phe Lys Gly Val Thr Val Asp Gly Asp Val Asn Cys Glu Val Thr Leu
            500                 505                 510

acc ccg tcg acg gcg ccc tcg ggc cgc gtc aac gtc cag gcc acg ctc      1584
Thr Pro Ser Thr Ala Pro Ser Gly Arg Val Asn Val Gln Ala Thr Leu
        515                 520                 525

aag acc ttt tcc agc ggc aag ctg gtc ccg gcc tac cgc gcc gtc atc      1632
Lys Thr Phe Ser Ser Gly Lys Leu Val Pro Ala Tyr Arg Ala Val Ile
    530                 535                 540

gtg ctc tcc aac cag ggc gcg ccc ccg gcc aac gcc acc atg cag ccg      1680
Val Leu Ser Asn Gln Gly Ala Pro Pro Ala Asn Ala Thr Met Gln Pro
545                 550                 555                 560

ccc tcg ctc gat gcc gat ccg gcg ctc cag ggc tcc gtc tac gac ggc      1728
Pro Ser Leu Asp Ala Asp Pro Ala Leu Gln Gly Ser Val Tyr Asp Gly
                565                 570                 575

aag acc ctc ttc cac ggc ccg gcc ttc cgc ggc atc gat gac gtg ctc      1776
Lys Thr Leu Phe His Gly Pro Ala Phe Arg Gly Ile Asp Asp Val Leu
            580                 585                 590

tcg tgc acc aag agc cag ctt gtg gcc aag tgc agc gct gtc ccc ggc      1824
Ser Cys Thr Lys Ser Gln Leu Val Ala Lys Cys Ser Ala Val Pro Gly
        595                 600                 605

tcc gac gcc gct cgc ggc gag ttt gcc acg gac act gac gcc cat gac      1872
Ser Asp Ala Ala Arg Gly Glu Phe Ala Thr Asp Thr Asp Ala His Asp
    610                 615                 620

ccc ttc gtg aac gac ctg gcc ttt cag gcc atg ctc gtc tgg gtg cgc      1920
Pro Phe Val Asn Asp Leu Ala Phe Gln Ala Met Leu Val Trp Val Arg
625                 630                 635                 640

cgc acg ctc ggc cag gct gcg ctc ccc aac tcg atc cag cgc atc gtc      1968
Arg Thr Leu Gly Gln Ala Ala Leu Pro Asn Ser Ile Gln Arg Ile Val
                645                 650                 655

cag cac cgc ccg gtc ccg cag gac aag ccc ttc tac att acc ctc cgc      2016
Gln His Arg Pro Val Pro Gln Asp Lys Pro Phe Tyr Ile Thr Leu Arg
            660                 665                 670

tcc aac cag tcg ggc ggt cac tcc cag cac aag cac gcc ctt cag ttc      2064
Ser Asn Gln Ser Gly Gly His Ser Gln His Lys His Ala Leu Gln Phe
        675                 680                 685

cac aac gag cag ggc gat ctc ttc att gat gtc cag gct tcg gtc atc      2112
His Asn Glu Gln Gly Asp Leu Phe Ile Asp Val Gln Ala Ser Val Ile
    690                 695                 700

gcc acg gac agc ctt gcc ttc                                          2133
Ala Thr Asp Ser Leu Ala Phe
705                 710


<210> SEQ ID NO 18
<211> LENGTH: 711
<212> TYPE: PRT
<213> ORGANISM: Schizochytrium sp.

<400> SEQUENCE: 18

Phe Gly Ala Leu Gly Gly Phe Ile Ser Gln Gln Ala Glu Arg Phe Glu
1               5                   10                  15

Pro Ala Glu Ile Leu Gly Phe Thr Leu Met Cys Ala Lys Phe Ala Lys
            20                  25                  30
```

-continued

```
Ala Ser Leu Cys Thr Ala Val Ala Gly Gly Arg Pro Ala Phe Ile Gly
        35                  40                  45

Val Ala Arg Leu Asp Gly Arg Leu Gly Phe Thr Ser Gln Gly Thr Ser
    50                  55                  60

Asp Ala Leu Lys Arg Ala Gln Arg Gly Ala Ile Phe Gly Leu Cys Lys
65                  70                  75                  80

Thr Ile Gly Leu Glu Trp Ser Glu Ser Asp Val Phe Ser Arg Gly Val
                85                  90                  95

Asp Ile Ala Gln Gly Met His Pro Glu Asp Ala Ala Val Ala Ile Val
            100                 105                 110

Arg Glu Met Ala Cys Ala Asp Ile Arg Ile Arg Glu Val Gly Ile Gly
        115                 120                 125

Ala Asn Gln Gln Arg Cys Thr Ile Arg Ala Ala Lys Leu Glu Thr Gly
    130                 135                 140

Asn Pro Gln Arg Gln Ile Ala Lys Asp Asp Val Leu Leu Val Ser Gly
145                 150                 155                 160

Gly Ala Arg Gly Ile Thr Pro Leu Cys Ile Arg Glu Ile Thr Arg Gln
                165                 170                 175

Ile Ala Gly Gly Lys Tyr Ile Leu Leu Gly Arg Ser Lys Val Ser Ala
            180                 185                 190

Ser Glu Pro Ala Trp Cys Ala Gly Ile Thr Asp Glu Lys Ala Val Gln
        195                 200                 205

Lys Ala Ala Thr Gln Glu Leu Lys Arg Ala Phe Ser Ala Gly Glu Gly
    210                 215                 220

Pro Lys Pro Thr Pro Arg Ala Val Thr Lys Leu Val Gly Ser Val Leu
225                 230                 235                 240

Gly Ala Arg Glu Val Arg Ser Ser Ile Ala Ala Ile Glu Ala Leu Gly
                245                 250                 255

Gly Lys Ala Ile Tyr Ser Ser Cys Asp Val Asn Ser Ala Ala Asp Val
            260                 265                 270

Ala Lys Ala Val Arg Asp Ala Glu Ser Gln Leu Gly Ala Arg Val Ser
        275                 280                 285

Gly Ile Val His Ala Ser Gly Val Leu Arg Asp Arg Leu Ile Glu Lys
    290                 295                 300

Lys Leu Pro Asp Glu Phe Asp Ala Val Phe Gly Thr Lys Val Thr Gly
305                 310                 315                 320

Leu Glu Asn Leu Leu Ala Ala Val Asp Arg Ala Asn Leu Lys His Met
                325                 330                 335

Val Leu Phe Ser Ser Leu Ala Gly Phe His Gly Asn Val Gly Gln Ser
            340                 345                 350

Asp Tyr Ala Met Ala Asn Glu Ala Leu Asn Lys Met Gly Leu Glu Leu
        355                 360                 365

Ala Lys Asp Val Ser Val Lys Ser Ile Cys Phe Gly Pro Trp Asp Gly
    370                 375                 380

Gly Met Val Thr Pro Gln Leu Lys Lys Gln Phe Gln Glu Met Gly Val
385                 390                 395                 400

Gln Ile Ile Pro Arg Glu Gly Gly Ala Asp Thr Val Ala Arg Ile Val
                405                 410                 415

Leu Gly Ser Ser Pro Ala Glu Ile Leu Val Gly Asn Trp Arg Thr Pro
            420                 425                 430

Ser Lys Lys Val Gly Ser Asp Thr Ile Thr Leu His Arg Lys Ile Ser
        435                 440                 445

Ala Lys Ser Asn Pro Phe Leu Glu Asp His Val Ile Gln Gly Arg Arg
```

-continued

```
    450                 455                 460

Val Leu Pro Met Thr Leu Ala Ile Gly Ser Leu Ala Glu Thr Cys Leu
465                 470                 475                 480

Gly Leu Phe Pro Gly Tyr Ser Leu Trp Ala Ile Asp Asp Ala Gln Leu
                485                 490                 495

Phe Lys Gly Val Thr Val Asp Gly Asp Val Asn Cys Glu Val Thr Leu
            500                 505                 510

Thr Pro Ser Thr Ala Pro Ser Gly Arg Val Asn Val Gln Ala Thr Leu
        515                 520                 525

Lys Thr Phe Ser Ser Gly Lys Leu Val Pro Ala Tyr Arg Ala Val Ile
    530                 535                 540

Val Leu Ser Asn Gln Gly Ala Pro Pro Ala Asn Ala Thr Met Gln Pro
545                 550                 555                 560

Pro Ser Leu Asp Ala Asp Pro Ala Leu Gln Gly Ser Val Tyr Asp Gly
                565                 570                 575

Lys Thr Leu Phe His Gly Pro Ala Phe Arg Gly Ile Asp Asp Val Leu
            580                 585                 590

Ser Cys Thr Lys Ser Gln Leu Val Ala Lys Cys Ser Ala Val Pro Gly
        595                 600                 605

Ser Asp Ala Ala Arg Gly Glu Phe Ala Thr Asp Thr Asp Ala His Asp
    610                 615                 620

Pro Phe Val Asn Asp Leu Ala Phe Gln Ala Met Leu Val Trp Val Arg
625                 630                 635                 640

Arg Thr Leu Gly Gln Ala Ala Leu Pro Asn Ser Ile Gln Arg Ile Val
                645                 650                 655

Gln His Arg Pro Val Pro Gln Asp Lys Pro Phe Tyr Ile Thr Leu Arg
            660                 665                 670

Ser Asn Gln Ser Gly Gly His Ser Gln His Lys His Ala Leu Gln Phe
        675                 680                 685

His Asn Glu Gln Gly Asp Leu Phe Ile Asp Val Gln Ala Ser Val Ile
    690                 695                 700

Ala Thr Asp Ser Leu Ala Phe
705                 710


<210> SEQ ID NO 19
<211> LENGTH: 1350
<212> TYPE: DNA
<213> ORGANISM: Schizochytrium sp.
<220> FEATURE:
<221> NAME/KEY: CDS
<222> LOCATION: (1)..(1350)

<400> SEQUENCE: 19

atg gcc gct cgg aat gtg agc gcc gcg cat gag atg cac gat gaa aag       48
Met Ala Ala Arg Asn Val Ser Ala Ala His Glu Met His Asp Glu Lys
1               5                   10                  15

cgc atc gcc gtc gtc ggc atg gcc gtc cag tac gcc gga tgc aaa acc       96
Arg Ile Ala Val Val Gly Met Ala Val Gln Tyr Ala Gly Cys Lys Thr
            20                  25                  30

aag gac gag ttc tgg gag gtg ctc atg aac ggc aag gtc gag tcc aag      144
Lys Asp Glu Phe Trp Glu Val Leu Met Asn Gly Lys Val Glu Ser Lys
        35                  40                  45

gtg atc agc gac aaa cga ctc ggc tcc aac tac cgc gcc gag cac tac      192
Val Ile Ser Asp Lys Arg Leu Gly Ser Asn Tyr Arg Ala Glu His Tyr
    50                  55                  60

aaa gca gag cgc agc aag tat gcc gac acc ttt tgc aac gaa acg tac      240
Lys Ala Glu Arg Ser Lys Tyr Ala Asp Thr Phe Cys Asn Glu Thr Tyr
```

-continued

```
65                  70                  75                  80

ggc acc ctt gac gag aac gag atc gac aac gag cac gaa ctc ctc ctc      288
Gly Thr Leu Asp Glu Asn Glu Ile Asp Asn Glu His Glu Leu Leu Leu
                85                  90                  95

aac ctc gcc aag cag gca ctc gca gag aca tcc gtc aaa gac tcg aca      336
Asn Leu Ala Lys Gln Ala Leu Ala Glu Thr Ser Val Lys Asp Ser Thr
            100                 105                 110

cgc tgc ggc atc gtc agc ggc tgc ctc tcg ttc ccc atg gac aac ctc      384
Arg Cys Gly Ile Val Ser Gly Cys Leu Ser Phe Pro Met Asp Asn Leu
        115                 120                 125

cag ggt gaa ctc ctc aac gtg tac caa aac cat gtc gag aaa aag ctc      432
Gln Gly Glu Leu Leu Asn Val Tyr Gln Asn His Val Glu Lys Lys Leu
    130                 135                 140

ggg gcc cgc gtc ttc aag gac gcc tcc cat tgg tcc gaa cgc gag cag      480
Gly Ala Arg Val Phe Lys Asp Ala Ser His Trp Ser Glu Arg Glu Gln
145                 150                 155                 160

tcc aac aaa ccc gag gcc ggt gac cgc cgc atc ttc atg gac ccg gcc      528
Ser Asn Lys Pro Glu Ala Gly Asp Arg Arg Ile Phe Met Asp Pro Ala
                165                 170                 175

tcc ttc gtc gcc gaa gaa ctc aac ctc ggc gcc ctt cac tac tcc gtc      576
Ser Phe Val Ala Glu Glu Leu Asn Leu Gly Ala Leu His Tyr Ser Val
            180                 185                 190

gac gca gca tgc gcc acg gcg ctc tac gtg ctc cgc ctc gcg cag gat      624
Asp Ala Ala Cys Ala Thr Ala Leu Tyr Val Leu Arg Leu Ala Gln Asp
        195                 200                 205

cat ctc gtc tcc ggc gcc gcc gac gtc atg ctc tgc ggt gcc acc tgc      672
His Leu Val Ser Gly Ala Ala Asp Val Met Leu Cys Gly Ala Thr Cys
    210                 215                 220

ctg ccg gag ccc ttt ttc atc ctt tcg ggc ttt tcc acc ttc cag gcc      720
Leu Pro Glu Pro Phe Phe Ile Leu Ser Gly Phe Ser Thr Phe Gln Ala
225                 230                 235                 240

atg ccc gtc ggc acg ggc cag aac gtg tcc atg ccg ctg cac aag gac      768
Met Pro Val Gly Thr Gly Gln Asn Val Ser Met Pro Leu His Lys Asp
                245                 250                 255

agc cag ggc ctc acc ccg ggt gag ggc ggc tcc atc atg gtc ctc aag      816
Ser Gln Gly Leu Thr Pro Gly Glu Gly Gly Ser Ile Met Val Leu Lys
            260                 265                 270

cgt ctc gat gat gcc atc cgc gac ggc gac cac atc tac ggc acc ctt      864
Arg Leu Asp Asp Ala Ile Arg Asp Gly Asp His Ile Tyr Gly Thr Leu
        275                 280                 285

ctc ggc gcc aat gtc agc aac tcc ggc aca ggt ctg ccc ctc aag ccc      912
Leu Gly Ala Asn Val Ser Asn Ser Gly Thr Gly Leu Pro Leu Lys Pro
    290                 295                 300

ctt ctc ccc agc gag aaa aag tgc ctc atg gac acc tac acg cgc att      960
Leu Leu Pro Ser Glu Lys Lys Cys Leu Met Asp Thr Tyr Thr Arg Ile
305                 310                 315                 320

aac gtg cac ccg cac aag att cag tac gtc gag tgc cac gcc acc ggc     1008
Asn Val His Pro His Lys Ile Gln Tyr Val Glu Cys His Ala Thr Gly
                325                 330                 335

acg ccc cag ggt gat cgt gtg gaa atc gac gcc gtc aag gcc tgc ttt     1056
Thr Pro Gln Gly Asp Arg Val Glu Ile Asp Ala Val Lys Ala Cys Phe
            340                 345                 350

gaa ggc aag gtc ccc cgt ttc ggt acc aca aag ggc aac ttt gga cac     1104
Glu Gly Lys Val Pro Arg Phe Gly Thr Thr Lys Gly Asn Phe Gly His
        355                 360                 365

acc ctc gtc gca gcc ggc ttt gcc ggt atg tgc aag gtc ctc ctc tcc     1152
Thr Leu Val Ala Ala Gly Phe Ala Gly Met Cys Lys Val Leu Leu Ser
    370                 375                 380

atg aag cat ggc atc atc ccg ccc acc ccg ggt atc gat gac gag acc     1200
```

-continued

```
Met Lys His Gly Ile Ile Pro Pro Thr Pro Gly Ile Asp Asp Glu Thr
385                 390                 395                 400

aag atg gac cct ctc gtc gtc tcc ggt gag gcc atc cca tgg cca gag     1248
Lys Met Asp Pro Leu Val Val Ser Gly Glu Ala Ile Pro Trp Pro Glu
                405                 410                 415

acc aac ggc gag ccc aag cgc gcc ggt ctc tcg gcc ttt ggc ttt ggt     1296
Thr Asn Gly Glu Pro Lys Arg Ala Gly Leu Ser Ala Phe Gly Phe Gly
            420                 425                 430

ggc acc aac gcc cat gcc gtc ttt gag gag cat gac ccc tcc aac gcc     1344
Gly Thr Asn Ala His Ala Val Phe Glu Glu His Asp Pro Ser Asn Ala
        435                 440                 445

gcc tgc                                                             1350
Ala Cys
    450


<210> SEQ ID NO 20
<211> LENGTH: 450
<212> TYPE: PRT
<213> ORGANISM: Schizochytrium sp.

<400> SEQUENCE: 20

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
            180                 185                 190

Asp Ala Ala Cys Ala Thr Ala Leu Tyr Val Leu Arg Leu Ala Gln Asp
        195                 200                 205

His Leu Val Ser Gly Ala Ala Asp Val Met Leu Cys Gly Ala Thr Cys
    210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Gly Ser Ile Met Val Leu Lys
            260                 265                 270

Arg Leu Asp Asp Ala Ile Arg Asp Gly Asp His Ile Tyr Gly Thr Leu
```

-continued

```
        275                 280                 285

Leu Gly Ala Asn Val Ser Asn Ser Gly Thr Gly Leu Pro Leu Lys Pro
    290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
            340                 345                 350

Glu Gly Lys Val Pro Arg Phe Gly Thr Thr Lys Gly Asn Phe Gly His
        355                 360                 365

Thr Leu Val Ala Ala Gly Phe Ala Gly Met Cys Lys Val Leu Leu Ser
    370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
                405                 410                 415

Thr Asn Gly Glu Pro Lys Arg Ala Gly Leu Ser Ala Phe Gly Phe Gly
            420                 425                 430

Gly Thr Asn Ala His Ala Val Phe Glu Glu His Asp Pro Ser Asn Ala
        435                 440                 445

Ala Cys
    450


<210> SEQ ID NO 21
<211> LENGTH: 1323
<212> TYPE: DNA
<213> ORGANISM: Schizochytrium sp.
<220> FEATURE:
<221> NAME/KEY: CDS
<222> LOCATION: (1)..(1323)

<400> SEQUENCE: 21

tcg gcc cgc tgc ggc ggt gaa agc aac atg cgc atc gcc atc act ggt      48
Ser Ala Arg Cys Gly Gly Glu Ser Asn Met Arg Ile Ala Ile Thr Gly
1               5                   10                  15

atg gac gcc acc ttt ggc gct ctc aag gga ctc gac gcc ttc gag cgc      96
Met Asp Ala Thr Phe Gly Ala Leu Lys Gly Leu Asp Ala Phe Glu Arg
            20                  25                  30

gcc att tac acc ggc gct cac ggt gcc atc cca ctc cca gaa aag cgc     144
Ala Ile Tyr Thr Gly Ala His Gly Ala Ile Pro Leu Pro Glu Lys Arg
        35                  40                  45

tgg cgc ttt ctc ggc aag gac aag gac ttt ctt gac ctc tgc ggc gtc     192
Trp Arg Phe Leu Gly Lys Asp Lys Asp Phe Leu Asp Leu Cys Gly Val
    50                  55                  60

aag gcc acc ccg cac ggc tgc tac att gaa gat gtt gag gtc gac ttc     240
Lys Ala Thr Pro His Gly Cys Tyr Ile Glu Asp Val Glu Val Asp Phe
65                  70                  75                  80

cag cgc ctc cgc acg ccc atg acc cct gaa gac atg ctc ctc cct cag     288
Gln Arg Leu Arg Thr Pro Met Thr Pro Glu Asp Met Leu Leu Pro Gln
                85                  90                  95

cag ctt ctg gcc gtc acc acc att gac cgc gcc atc ctc gac tcg gga     336
Gln Leu Leu Ala Val Thr Thr Ile Asp Arg Ala Ile Leu Asp Ser Gly
            100                 105                 110

atg aaa aag ggt ggc aat gtc gcc gtc ttt gtc ggc ctc ggc acc gac     384
Met Lys Lys Gly Gly Asn Val Ala Val Phe Val Gly Leu Gly Thr Asp
        115                 120                 125

ctc gag ctc tac cgt cac cgt gct cgc gtc gct ctc aag gag cgc gtc     432
```

-continued

```
Leu Glu Leu Tyr Arg His Arg Ala Arg Val Ala Leu Lys Glu Arg Val
    130                 135                 140

cgc cct gaa gcc tcc aag aag ctc aat gac atg atg cag tac att aac      480
Arg Pro Glu Ala Ser Lys Lys Leu Asn Asp Met Met Gln Tyr Ile Asn
145                 150                 155                 160

gac tgc ggc aca tcc aca tcg tac acc tcg tac att ggc aac ctc gtc      528
Asp Cys Gly Thr Ser Thr Ser Tyr Thr Ser Tyr Ile Gly Asn Leu Val
                165                 170                 175

gcc acg cgc gtc tcg tcg cag tgg ggc ttc acg ggc ccc tcc ttt acg      576
Ala Thr Arg Val Ser Ser Gln Trp Gly Phe Thr Gly Pro Ser Phe Thr
            180                 185                 190

atc acc gag ggc aac aac tcc gtc tac cgc tgc gcc gag ctc ggc aag      624
Ile Thr Glu Gly Asn Asn Ser Val Tyr Arg Cys Ala Glu Leu Gly Lys
        195                 200                 205

tac ctc ctc gag acc ggc gag gtc gat ggc gtc gtc gtt gcg ggt gtc      672
Tyr Leu Leu Glu Thr Gly Glu Val Asp Gly Val Val Val Ala Gly Val
    210                 215                 220

gat ctc tgc ggc agt gcc gaa aac ctt tac gtc aag tct cgc cgc ttc      720
Asp Leu Cys Gly Ser Ala Glu Asn Leu Tyr Val Lys Ser Arg Arg Phe
225                 230                 235                 240

aag gtg tcc acc tcc gat acc ccg cgc gcc agc ttt gac gcc gcc gcc      768
Lys Val Ser Thr Ser Asp Thr Pro Arg Ala Ser Phe Asp Ala Ala Ala
                245                 250                 255

gat ggc tac ttt gtc ggc gag ggc tgc ggt gcc ttt gtg ctc aag cgt      816
Asp Gly Tyr Phe Val Gly Glu Gly Cys Gly Ala Phe Val Leu Lys Arg
            260                 265                 270

gag act agc tgc acc aag gac gac cgt atc tac gct tgc atg gat gcc      864
Glu Thr Ser Cys Thr Lys Asp Asp Arg Ile Tyr Ala Cys Met Asp Ala
        275                 280                 285

atc gtc cct ggc aac gtc cct agc gcc tgc ttg cgc gag gcc ctc gac      912
Ile Val Pro Gly Asn Val Pro Ser Ala Cys Leu Arg Glu Ala Leu Asp
    290                 295                 300

cag gcg cgc gtc aag ccg ggc gat atc gag atg ctc gag ctc agc gcc      960
Gln Ala Arg Val Lys Pro Gly Asp Ile Glu Met Leu Glu Leu Ser Ala
305                 310                 315                 320

gac tcc gcc cgc cac ctc aag gac ccg tcc gtc ctg ccc aag gag ctc     1008
Asp Ser Ala Arg His Leu Lys Asp Pro Ser Val Leu Pro Lys Glu Leu
                325                 330                 335

act gcc gag gag gaa atc ggc ggc ctt cag acg atc ctt cgt gac gat     1056
Thr Ala Glu Glu Glu Ile Gly Gly Leu Gln Thr Ile Leu Arg Asp Asp
            340                 345                 350

gac aag ctc ccg cgc aac gtc gca acg ggc agt gtc aag gcc acc gtc     1104
Asp Lys Leu Pro Arg Asn Val Ala Thr Gly Ser Val Lys Ala Thr Val
        355                 360                 365

ggt gac acc ggt tat gcc tct ggt gct gcc agc ctc atc aag gct gcg     1152
Gly Asp Thr Gly Tyr Ala Ser Gly Ala Ala Ser Leu Ile Lys Ala Ala
    370                 375                 380

ctt tgc atc tac aac cgc tac ctg ccc agc aac ggc gac gac tgg gat     1200
Leu Cys Ile Tyr Asn Arg Tyr Leu Pro Ser Asn Gly Asp Asp Trp Asp
385                 390                 395                 400

gaa ccc gcc cct gag gcg ccc tgg gac agc acc ctc ttt gcg tgc cag     1248
Glu Pro Ala Pro Glu Ala Pro Trp Asp Ser Thr Leu Phe Ala Cys Gln
                405                 410                 415

acc tcg cgc gct tgg ctc aag aac cct ggc gag cgt cgc tat gcg gcc     1296
Thr Ser Arg Ala Trp Leu Lys Asn Pro Gly Glu Arg Arg Tyr Ala Ala
            420                 425                 430

gtc tcg ggc gtc tcc gag acg cgc tcg                                 1323
Val Ser Gly Val Ser Glu Thr Arg Ser
        435                 440
```

<210> SEQ ID NO 22
<211> LENGTH: 441
<212> TYPE: PRT
<213> ORGANISM: Schizochytrium sp.

<400> SEQUENCE: 22

```
Ser Ala Arg Cys Gly Gly Glu Ser Asn Met Arg Ile Ala Ile Thr Gly
1               5                   10                  15

Met Asp Ala Thr Phe Gly Ala Leu Lys Gly Leu Asp Ala Phe Glu Arg
            20                  25                  30

Ala Ile Tyr Thr Gly Ala His Gly Ala Ile Pro Leu Pro Glu Lys Arg
        35                  40                  45

Trp Arg Phe Leu Gly Lys Asp Lys Asp Phe Leu Asp Leu Cys Gly Val
    50                  55                  60

Lys Ala Thr Pro His Gly Cys Tyr Ile Glu Asp Val Glu Val Asp Phe
65                  70                  75                  80

Gln Arg Leu Arg Thr Pro Met Thr Pro Glu Asp Met Leu Leu Pro Gln
                85                  90                  95

Gln Leu Leu Ala Val Thr Thr Ile Asp Arg Ala Ile Leu Asp Ser Gly
            100                 105                 110

Met Lys Lys Gly Gly Asn Val Ala Val Phe Val Gly Leu Gly Thr Asp
        115                 120                 125

Leu Glu Leu Tyr Arg His Arg Ala Arg Val Ala Leu Lys Glu Arg Val
    130                 135                 140

Arg Pro Glu Ala Ser Lys Lys Leu Asn Asp Met Met Gln Tyr Ile Asn
145                 150                 155                 160

Asp Cys Gly Thr Ser Thr Ser Tyr Thr Ser Tyr Ile Gly Asn Leu Val
                165                 170                 175

Ala Thr Arg Val Ser Ser Gln Trp Gly Phe Thr Gly Pro Ser Phe Thr
            180                 185                 190

Ile Thr Glu Gly Asn Asn Ser Val Tyr Arg Cys Ala Glu Leu Gly Lys
        195                 200                 205

Tyr Leu Leu Glu Thr Gly Glu Val Asp Gly Val Val Val Ala Gly Val
    210                 215                 220

Asp Leu Cys Gly Ser Ala Glu Asn Leu Tyr Val Lys Ser Arg Arg Phe
225                 230                 235                 240

Lys Val Ser Thr Ser Asp Thr Pro Arg Ala Ser Phe Asp Ala Ala Ala
                245                 250                 255

Asp Gly Tyr Phe Val Gly Glu Gly Cys Gly Ala Phe Val Leu Lys Arg
            260                 265                 270

Glu Thr Ser Cys Thr Lys Asp Asp Arg Ile Tyr Ala Cys Met Asp Ala
        275                 280                 285

Ile Val Pro Gly Asn Val Pro Ser Ala Cys Leu Arg Glu Ala Leu Asp
    290                 295                 300

Gln Ala Arg Val Lys Pro Gly Asp Ile Glu Met Leu Glu Leu Ser Ala
305                 310                 315                 320

Asp Ser Ala Arg His Leu Lys Asp Pro Ser Val Leu Pro Lys Glu Leu
                325                 330                 335

Thr Ala Glu Glu Glu Ile Gly Gly Leu Gln Thr Ile Leu Arg Asp Asp
            340                 345                 350

Asp Lys Leu Pro Arg Asn Val Ala Thr Gly Ser Val Lys Ala Thr Val
        355                 360                 365

Gly Asp Thr Gly Tyr Ala Ser Gly Ala Ala Ser Leu Ile Lys Ala Ala
    370                 375                 380
```

```
Leu Cys Ile Tyr Asn Arg Tyr Leu Pro Ser Asn Gly Asp Asp Trp Asp
385                 390                 395                 400

Glu Pro Ala Pro Glu Ala Pro Trp Asp Ser Thr Leu Phe Ala Cys Gln
                405                 410                 415

Thr Ser Arg Ala Trp Leu Lys Asn Pro Gly Glu Arg Arg Tyr Ala Ala
            420                 425                 430

Val Ser Gly Val Ser Glu Thr Arg Ser
        435                 440


<210> SEQ ID NO 23
<211> LENGTH: 1500
<212> TYPE: DNA
<213> ORGANISM: Schizochytrium sp.
<220> FEATURE:
<221> NAME/KEY: CDS
<222> LOCATION: (1)..(1500)

<400> SEQUENCE: 23

tgc tat tcc gtg ctc ctc tcc gaa gcc gag ggc cac tac gag cgc gag      48
Cys Tyr Ser Val Leu Leu Ser Glu Ala Glu Gly His Tyr Glu Arg Glu
1               5                   10                  15

aac cgc atc tcg ctc gac gag gag gcg ccc aag ctc att gtg ctt cgc      96
Asn Arg Ile Ser Leu Asp Glu Glu Ala Pro Lys Leu Ile Val Leu Arg
            20                  25                  30

gcc gac tcc cac gag gag atc ctt ggt cgc ctc gac aag atc cgc gag     144
Ala Asp Ser His Glu Glu Ile Leu Gly Arg Leu Asp Lys Ile Arg Glu
        35                  40                  45

cgc ttc ttg cag ccc acg ggc gcc gcc ccg cgc gag tcc gag ctc aag     192
Arg Phe Leu Gln Pro Thr Gly Ala Ala Pro Arg Glu Ser Glu Leu Lys
    50                  55                  60

gcg cag gcc cgc cgc atc ttc ctc gag ctc ctc ggc gag acc ctt gcc     240
Ala Gln Ala Arg Arg Ile Phe Leu Glu Leu Leu Gly Glu Thr Leu Ala
65                  70                  75                  80

cag gat gcc gct tct tca ggc tcg caa aag ccc ctc gct ctc agc ctc     288
Gln Asp Ala Ala Ser Ser Gly Ser Gln Lys Pro Leu Ala Leu Ser Leu
                85                  90                  95

gtc tcc acg ccc tcc aag ctc cag cgc gag gtc gag ctc gcg gcc aag     336
Val Ser Thr Pro Ser Lys Leu Gln Arg Glu Val Glu Leu Ala Ala Lys
            100                 105                 110

ggt atc ccg cgc tgc ctc aag atg cgc cgc gat tgg agc tcc cct gct     384
Gly Ile Pro Arg Cys Leu Lys Met Arg Arg Asp Trp Ser Ser Pro Ala
        115                 120                 125

ggc agc cgc tac gcg cct gag ccg ctc gcc agc gac cgc gtc gcc ttc     432
Gly Ser Arg Tyr Ala Pro Glu Pro Leu Ala Ser Asp Arg Val Ala Phe
    130                 135                 140

atg tac ggc gaa ggt cgc agc cct tac tac ggc atc acc caa gac att     480
Met Tyr Gly Glu Gly Arg Ser Pro Tyr Tyr Gly Ile Thr Gln Asp Ile
145                 150                 155                 160

cac cgc att tgg ccc gaa ctc cac gag gtc atc aac gaa aag acg aac     528
His Arg Ile Trp Pro Glu Leu His Glu Val Ile Asn Glu Lys Thr Asn
                165                 170                 175

cgt ctc tgg gcc gaa ggc gac cgc tgg gtc atg ccg cgc gcc agc ttc     576
Arg Leu Trp Ala Glu Gly Asp Arg Trp Val Met Pro Arg Ala Ser Phe
            180                 185                 190

aag tcg gag ctc gag agc cag cag caa gag ttt gat cgc aac atg att     624
Lys Ser Glu Leu Glu Ser Gln Gln Gln Glu Phe Asp Arg Asn Met Ile
        195                 200                 205

gaa atg ttc cgt ctt gga atc ctc acc tca att gcc ttc acc aat ctg     672
Glu Met Phe Arg Leu Gly Ile Leu Thr Ser Ile Ala Phe Thr Asn Leu
    210                 215                 220
```

-continued

```
gcg cgc gac gtt ctc aac atc acg ccc aag gcc gcc ttt ggc ctc agt      720
Ala Arg Asp Val Leu Asn Ile Thr Pro Lys Ala Ala Phe Gly Leu Ser
225                 230                 235                 240

ctt ggc gag att tcc atg att ttt gcc ttt tcc aag aag aac ggt ctc      768
Leu Gly Glu Ile Ser Met Ile Phe Ala Phe Ser Lys Lys Asn Gly Leu
                245                 250                 255

atc tcc gac cag ctc acc aag gat ctt cgc gag tcc gac gtg tgg aac      816
Ile Ser Asp Gln Leu Thr Lys Asp Leu Arg Glu Ser Asp Val Trp Asn
            260                 265                 270

aag gct ctg gcc gtt gaa ttt aat gcg ctg cgc gag gcc tgg ggc att      864
Lys Ala Leu Ala Val Glu Phe Asn Ala Leu Arg Glu Ala Trp Gly Ile
        275                 280                 285

cca cag agt gtc ccc aag gac gag ttc tgg caa ggc tac att gtg cgc      912
Pro Gln Ser Val Pro Lys Asp Glu Phe Trp Gln Gly Tyr Ile Val Arg
    290                 295                 300

ggc acc aag cag gat atc gag gcg gcc atc gcc ccg gac agc aag tac      960
Gly Thr Lys Gln Asp Ile Glu Ala Ala Ile Ala Pro Asp Ser Lys Tyr
305                 310                 315                 320

gtg cgc ctc acc atc atc aat gat gcc aac acc gcc ctc att agc ggc     1008
Val Arg Leu Thr Ile Ile Asn Asp Ala Asn Thr Ala Leu Ile Ser Gly
                325                 330                 335

aag ccc gac gcc tgc aag gct gcg atc gcg cgt ctc ggt ggc aac att     1056
Lys Pro Asp Ala Cys Lys Ala Ala Ile Ala Arg Leu Gly Gly Asn Ile
            340                 345                 350

cct gcg ctt ccc gtg acc cag ggc atg tgc ggc cac tgc ccc gag gtg     1104
Pro Ala Leu Pro Val Thr Gln Gly Met Cys Gly His Cys Pro Glu Val
        355                 360                 365

gga cct tat acc aag gat atc gcc aag atc cat gcc aac ctt gag ttc     1152
Gly Pro Tyr Thr Lys Asp Ile Ala Lys Ile His Ala Asn Leu Glu Phe
    370                 375                 380

ccc gtt gtc gac ggc ctt gac ctc tgg acc aca atc aac cag aag cgc     1200
Pro Val Val Asp Gly Leu Asp Leu Trp Thr Thr Ile Asn Gln Lys Arg
385                 390                 395                 400

ctc gtg cca cgc gcc acg ggc gcc aag gac gaa tgg gcc cct tct tcc     1248
Leu Val Pro Arg Ala Thr Gly Ala Lys Asp Glu Trp Ala Pro Ser Ser
                405                 410                 415

ttt ggc gag tac gcc ggc cag ctc tac gag aag cag gct aac ttc ccc     1296
Phe Gly Glu Tyr Ala Gly Gln Leu Tyr Glu Lys Gln Ala Asn Phe Pro
            420                 425                 430

caa atc gtc gag acc att tac aag caa aac tac gac gtc ttt gtc gag     1344
Gln Ile Val Glu Thr Ile Tyr Lys Gln Asn Tyr Asp Val Phe Val Glu
        435                 440                 445

gtt ggg ccc aac aac cac cgt agc acc gca gtg cgc acc acg ctt ggt     1392
Val Gly Pro Asn Asn His Arg Ser Thr Ala Val Arg Thr Thr Leu Gly
    450                 455                 460

ccc cag cgc aac cac ctt gct ggc gcc atc gac aag cag aac gag gat     1440
Pro Gln Arg Asn His Leu Ala Gly Ala Ile Asp Lys Gln Asn Glu Asp
465                 470                 475                 480

gct tgg acg acc atc gtc aag ctt gtg gct tcg ctc aag gcc cac ctt     1488
Ala Trp Thr Thr Ile Val Lys Leu Val Ala Ser Leu Lys Ala His Leu
                485                 490                 495

gtt cct ggc gtc                                                     1500
Val Pro Gly Val
            500
```

<210> SEQ ID NO 24
<211> LENGTH: 500
<212> TYPE: PRT
<213> ORGANISM: Schizochytrium sp.

-continued

<400> SEQUENCE: 24

```
Cys Tyr Ser Val Leu Leu Ser Glu Ala Glu Gly His Tyr Glu Arg Glu
1               5                   10                  15

Asn Arg Ile Ser Leu Asp Glu Glu Ala Pro Lys Leu Ile Val Leu Arg
            20                  25                  30

Ala Asp Ser His Glu Glu Ile Leu Gly Arg Leu Asp Lys Ile Arg Glu
        35                  40                  45

Arg Phe Leu Gln Pro Thr Gly Ala Ala Pro Arg Glu Ser Glu Leu Lys
    50                  55                  60

Ala Gln Ala Arg Arg Ile Phe Leu Glu Leu Leu Gly Glu Thr Leu Ala
65                  70                  75                  80

Gln Asp Ala Ala Ser Ser Gly Ser Gln Lys Pro Leu Ala Leu Ser Leu
                85                  90                  95

Val Ser Thr Pro Ser Lys Leu Gln Arg Glu Val Glu Leu Ala Ala Lys
            100                 105                 110

Gly Ile Pro Arg Cys Leu Lys Met Arg Arg Asp Trp Ser Ser Pro Ala
        115                 120                 125

Gly Ser Arg Tyr Ala Pro Glu Pro Leu Ala Ser Asp Arg Val Ala Phe
    130                 135                 140

Met Tyr Gly Glu Gly Arg Ser Pro Tyr Tyr Gly Ile Thr Gln Asp Ile
145                 150                 155                 160

His Arg Ile Trp Pro Glu Leu His Glu Val Ile Asn Glu Lys Thr Asn
                165                 170                 175

Arg Leu Trp Ala Glu Gly Asp Arg Trp Val Met Pro Arg Ala Ser Phe
            180                 185                 190

Lys Ser Glu Leu Glu Ser Gln Gln Gln Glu Phe Asp Arg Asn Met Ile
        195                 200                 205

Glu Met Phe Arg Leu Gly Ile Leu Thr Ser Ile Ala Phe Thr Asn Leu
    210                 215                 220

Ala Arg Asp Val Leu Asn Ile Thr Pro Lys Ala Ala Phe Gly Leu Ser
225                 230                 235                 240

Leu Gly Glu Ile Ser Met Ile Phe Ala Phe Ser Lys Lys Asn Gly Leu
                245                 250                 255

Ile Ser Asp Gln Leu Thr Lys Asp Leu Arg Glu Ser Asp Val Trp Asn
            260                 265                 270

Lys Ala Leu Ala Val Glu Phe Asn Ala Leu Arg Glu Ala Trp Gly Ile
        275                 280                 285

Pro Gln Ser Val Pro Lys Asp Glu Phe Trp Gln Gly Tyr Ile Val Arg
    290                 295                 300

Gly Thr Lys Gln Asp Ile Glu Ala Ala Ile Ala Pro Asp Ser Lys Tyr
305                 310                 315                 320

Val Arg Leu Thr Ile Ile Asn Asp Ala Asn Thr Ala Leu Ile Ser Gly
                325                 330                 335

Lys Pro Asp Ala Cys Lys Ala Ala Ile Ala Arg Leu Gly Gly Asn Ile
            340                 345                 350

Pro Ala Leu Pro Val Thr Gln Gly Met Cys Gly His Cys Pro Glu Val
        355                 360                 365

Gly Pro Tyr Thr Lys Asp Ile Ala Lys Ile His Ala Asn Leu Glu Phe
    370                 375                 380

Pro Val Val Asp Gly Leu Asp Leu Trp Thr Thr Ile Asn Gln Lys Arg
385                 390                 395                 400

Leu Val Pro Arg Ala Thr Gly Ala Lys Asp Glu Trp Ala Pro Ser Ser
                405                 410                 415
```

```
Phe Gly Glu Tyr Ala Gly Gln Leu Tyr Glu Lys Gln Ala Asn Phe Pro
            420                 425                 430

Gln Ile Val Glu Thr Ile Tyr Lys Gln Asn Tyr Asp Val Phe Val Glu
        435                 440                 445

Val Gly Pro Asn Asn His Arg Ser Thr Ala Val Arg Thr Thr Leu Gly
    450                 455                 460

Pro Gln Arg Asn His Leu Ala Gly Ala Ile Asp Lys Gln Asn Glu Asp
465                 470                 475                 480

Ala Trp Thr Thr Ile Val Lys Leu Val Ala Ser Leu Lys Ala His Leu
                485                 490                 495

Val Pro Gly Val
            500


<210> SEQ ID NO 25
<211> LENGTH: 1530
<212> TYPE: DNA
<213> ORGANISM: Schizochytrium sp.
<220> FEATURE:
<221> NAME/KEY: CDS
<222> LOCATION: (1)..(1530)

<400> SEQUENCE: 25

ctg ctc gat ctc gac agt atg ctt gcg ctg agc tct gcc agt gcc tcc      48
Leu Leu Asp Leu Asp Ser Met Leu Ala Leu Ser Ser Ala Ser Ala Ser
1               5                   10                  15

ggc aac ctt gtt gag act gcg cct agc gac gcc tcg gtc att gtg ccg      96
Gly Asn Leu Val Glu Thr Ala Pro Ser Asp Ala Ser Val Ile Val Pro
            20                  25                  30

ccc tgc aac att gcg gat ctc ggc agc cgc gcc ttc atg aaa acg tac     144
Pro Cys Asn Ile Ala Asp Leu Gly Ser Arg Ala Phe Met Lys Thr Tyr
        35                  40                  45

ggt gtt tcg gcg cct ctg tac acg ggc gcc atg gcc aag ggc att gcc     192
Gly Val Ser Ala Pro Leu Tyr Thr Gly Ala Met Ala Lys Gly Ile Ala
    50                  55                  60

tct gcg gac ctc gtc att gcc gcc ggc cgc cag ggc atc ctt gcg tcc     240
Ser Ala Asp Leu Val Ile Ala Ala Gly Arg Gln Gly Ile Leu Ala Ser
65                  70                  75                  80

ttt ggc gcc ggc gga ctt ccc atg cag gtt gtg cgt gag tcc atc gaa     288
Phe Gly Ala Gly Gly Leu Pro Met Gln Val Val Arg Glu Ser Ile Glu
                85                  90                  95

aag att cag gcc gcc ctg ccc aat ggc ccg tac gct gtc aac ctt atc     336
Lys Ile Gln Ala Ala Leu Pro Asn Gly Pro Tyr Ala Val Asn Leu Ile
            100                 105                 110

cat tct ccc ttt gac agc aac ctc gaa aag ggc aat gtc gat ctc ttc     384
His Ser Pro Phe Asp Ser Asn Leu Glu Lys Gly Asn Val Asp Leu Phe
        115                 120                 125

ctc gag aag ggt gtc acc ttt gtc gag gcc tcg gcc ttt atg acg ctc     432
Leu Glu Lys Gly Val Thr Phe Val Glu Ala Ser Ala Phe Met Thr Leu
    130                 135                 140

acc ccg cag gtc gtg cgg tac cgc gcg gct ggc ctc acg cgc aac gcc     480
Thr Pro Gln Val Val Arg Tyr Arg Ala Ala Gly Leu Thr Arg Asn Ala
145                 150                 155                 160

gac ggc tcg gtc aac atc cgc aac cgt atc att ggc aag gtc tcg cgc     528
Asp Gly Ser Val Asn Ile Arg Asn Arg Ile Ile Gly Lys Val Ser Arg
                165                 170                 175

acc gag ctc gcc gag atg ttc atg cgt cct gcg ccc gag cac ctt ctt     576
Thr Glu Leu Ala Glu Met Phe Met Arg Pro Ala Pro Glu His Leu Leu
            180                 185                 190

cag aag ctc att gct tcc ggc gag atc aac cag gag cag gcc gag ctc     624
```

-continued

```
Gln Lys Leu Ile Ala Ser Gly Glu Ile Asn Gln Glu Gln Ala Glu Leu
        195                 200                 205

gcc cgc cgt gtt ccc gtc gct gac gac atc gcg gtc gaa gct gac tcg      672
Ala Arg Arg Val Pro Val Ala Asp Asp Ile Ala Val Glu Ala Asp Ser
    210                 215                 220

ggt ggc cac acc gac aac cgc ccc atc cac gtc att ctg ccc ctc atc      720
Gly Gly His Thr Asp Asn Arg Pro Ile His Val Ile Leu Pro Leu Ile
225                 230                 235                 240

atc aac ctt cgc gac cgc ctt cac cgc gag tgc ggc tac ccg gcc aac      768
Ile Asn Leu Arg Asp Arg Leu His Arg Glu Cys Gly Tyr Pro Ala Asn
                245                 250                 255

ctt cgc gtc cgt gtg ggc gcc ggc ggt ggc att ggg tgc ccc cag gcg      816
Leu Arg Val Arg Val Gly Ala Gly Gly Gly Ile Gly Cys Pro Gln Ala
            260                 265                 270

gcg ctg gcc acc ttc aac atg ggt gcc tcc ttt att gtc acc ggc acc      864
Ala Leu Ala Thr Phe Asn Met Gly Ala Ser Phe Ile Val Thr Gly Thr
        275                 280                 285

gtg aac cag gtc gcc aag cag tcg ggc acg tgc gac aat gtg cgc aag      912
Val Asn Gln Val Ala Lys Gln Ser Gly Thr Cys Asp Asn Val Arg Lys
    290                 295                 300

cag ctc gcg aag gcc act tac tcg gac gta tgc atg gcc ccg gct gcc      960
Gln Leu Ala Lys Ala Thr Tyr Ser Asp Val Cys Met Ala Pro Ala Ala
305                 310                 315                 320

gac atg ttc gag gaa ggc gtc aag ctt cag gtc ctc aag aag gga acc     1008
Asp Met Phe Glu Glu Gly Val Lys Leu Gln Val Leu Lys Lys Gly Thr
                325                 330                 335

atg ttt ccc tcg cgc gcc aac aag ctc tac gag ctc ttt tgc aag tac     1056
Met Phe Pro Ser Arg Ala Asn Lys Leu Tyr Glu Leu Phe Cys Lys Tyr
            340                 345                 350

gac tcg ttc gag tcc atg ccc ccc gca gag ctt gcg cgc gtc gag aag     1104
Asp Ser Phe Glu Ser Met Pro Pro Ala Glu Leu Ala Arg Val Glu Lys
        355                 360                 365

cgc atc ttc agc cgc gcg ctc gaa gag gtc tgg gac gag acc aaa aac     1152
Arg Ile Phe Ser Arg Ala Leu Glu Glu Val Trp Asp Glu Thr Lys Asn
    370                 375                 380

ttt tac att aac cgt ctt cac aac ccg gag aag atc cag cgc gcc gag     1200
Phe Tyr Ile Asn Arg Leu His Asn Pro Glu Lys Ile Gln Arg Ala Glu
385                 390                 395                 400

cgc gac ccc aag ctc aag atg tcg ctg tgc ttt cgc tgg tac ctg agc     1248
Arg Asp Pro Lys Leu Lys Met Ser Leu Cys Phe Arg Trp Tyr Leu Ser
                405                 410                 415

ctg gcg agc cgc tgg gcc aac act gga gct tcc gat cgc gtc atg gac     1296
Leu Ala Ser Arg Trp Ala Asn Thr Gly Ala Ser Asp Arg Val Met Asp
            420                 425                 430

tac cag gtc tgg tgc ggt cct gcc att ggt tcc ttc aac gat ttc atc     1344
Tyr Gln Val Trp Cys Gly Pro Ala Ile Gly Ser Phe Asn Asp Phe Ile
        435                 440                 445

aag gga act tac ctt gat ccg gcc gtc gca aac gag tac ccg tgc gtc     1392
Lys Gly Thr Tyr Leu Asp Pro Ala Val Ala Asn Glu Tyr Pro Cys Val
    450                 455                 460

gtt cag att aac aag cag atc ctt cgt gga gcg tgc ttc ttg cgc cgt     1440
Val Gln Ile Asn Lys Gln Ile Leu Arg Gly Ala Cys Phe Leu Arg Arg
465                 470                 475                 480

ctc gaa att ctg cgc aac gca cgc ctt tcc gat ggc gct gcc gct ctt     1488
Leu Glu Ile Leu Arg Asn Ala Arg Leu Ser Asp Gly Ala Ala Ala Leu
                485                 490                 495

gtg gcc agc atc gat gac aca tac gtc ccg gcc gag aag ctg             1530
Val Ala Ser Ile Asp Asp Thr Tyr Val Pro Ala Glu Lys Leu
            500                 505                 510
```

<210> SEQ ID NO 26
<211> LENGTH: 510
<212> TYPE: PRT
<213> ORGANISM: Schizochytrium sp.

<400> SEQUENCE: 26

```
Leu Leu Asp Leu Asp Ser Met Leu Ala Leu Ser Ser Ala Ser Ala Ser
1               5                   10                  15

Gly Asn Leu Val Glu Thr Ala Pro Ser Asp Ala Ser Val Ile Val Pro
            20                  25                  30

Pro Cys Asn Ile Ala Asp Leu Gly Ser Arg Ala Phe Met Lys Thr Tyr
        35                  40                  45

Gly Val Ser Ala Pro Leu Tyr Thr Gly Ala Met Ala Lys Gly Ile Ala
    50                  55                  60

Ser Ala Asp Leu Val Ile Ala Ala Gly Arg Gln Gly Ile Leu Ala Ser
65                  70                  75                  80

Phe Gly Ala Gly Gly Leu Pro Met Gln Val Val Arg Glu Ser Ile Glu
                85                  90                  95

Lys Ile Gln Ala Ala Leu Pro Asn Gly Pro Tyr Ala Val Asn Leu Ile
            100                 105                 110

His Ser Pro Phe Asp Ser Asn Leu Glu Lys Gly Asn Val Asp Leu Phe
        115                 120                 125

Leu Glu Lys Gly Val Thr Phe Val Glu Ala Ser Ala Phe Met Thr Leu
    130                 135                 140

Thr Pro Gln Val Val Arg Tyr Arg Ala Ala Gly Leu Thr Arg Asn Ala
145                 150                 155                 160

Asp Gly Ser Val Asn Ile Arg Asn Arg Ile Ile Gly Lys Val Ser Arg
                165                 170                 175

Thr Glu Leu Ala Glu Met Phe Met Arg Pro Ala Pro Glu His Leu Leu
            180                 185                 190

Gln Lys Leu Ile Ala Ser Gly Glu Ile Asn Gln Glu Gln Ala Glu Leu
        195                 200                 205

Ala Arg Arg Val Pro Val Ala Asp Asp Ile Ala Val Glu Ala Asp Ser
    210                 215                 220

Gly Gly His Thr Asp Asn Arg Pro Ile His Val Ile Leu Pro Leu Ile
225                 230                 235                 240

Ile Asn Leu Arg Asp Arg Leu His Arg Glu Cys Gly Tyr Pro Ala Asn
                245                 250                 255

Leu Arg Val Arg Val Gly Ala Gly Gly Gly Ile Gly Cys Pro Gln Ala
            260                 265                 270

Ala Leu Ala Thr Phe Asn Met Gly Ala Ser Phe Ile Val Thr Gly Thr
        275                 280                 285

Val Asn Gln Val Ala Lys Gln Ser Gly Thr Cys Asp Asn Val Arg Lys
    290                 295                 300

Gln Leu Ala Lys Ala Thr Tyr Ser Asp Val Cys Met Ala Pro Ala Ala
305                 310                 315                 320

Asp Met Phe Glu Glu Gly Val Lys Leu Gln Val Leu Lys Lys Gly Thr
                325                 330                 335

Met Phe Pro Ser Arg Ala Asn Lys Leu Tyr Glu Leu Phe Cys Lys Tyr
            340                 345                 350

Asp Ser Phe Glu Ser Met Pro Pro Ala Glu Leu Ala Arg Val Glu Lys
        355                 360                 365

Arg Ile Phe Ser Arg Ala Leu Glu Glu Val Trp Asp Glu Thr Lys Asn
    370                 375                 380
```

```
Phe Tyr Ile Asn Arg Leu His Asn Pro Glu Lys Ile Gln Arg Ala Glu
385                 390                 395                 400

Arg Asp Pro Lys Leu Lys Met Ser Leu Cys Phe Arg Trp Tyr Leu Ser
                405                 410                 415

Leu Ala Ser Arg Trp Ala Asn Thr Gly Ala Ser Asp Arg Val Met Asp
            420                 425                 430

Tyr Gln Val Trp Cys Gly Pro Ala Ile Gly Ser Phe Asn Asp Phe Ile
        435                 440                 445

Lys Gly Thr Tyr Leu Asp Pro Ala Val Ala Asn Glu Tyr Pro Cys Val
    450                 455                 460

Val Gln Ile Asn Lys Gln Ile Leu Arg Gly Ala Cys Phe Leu Arg Arg
465                 470                 475                 480

Leu Glu Ile Leu Arg Asn Ala Arg Leu Ser Asp Gly Ala Ala Ala Leu
                485                 490                 495

Val Ala Ser Ile Asp Asp Thr Tyr Val Pro Ala Glu Lys Leu
            500                 505                 510


<210> SEQ ID NO 27
<211> LENGTH: 1350
<212> TYPE: DNA
<213> ORGANISM: Schizochytrium sp.
<220> FEATURE:
<221> NAME/KEY: CDS
<222> LOCATION: (1)..(1350)

<400> SEQUENCE: 27

atg gcg ctc cgt gtc aag acg aac aag aag cca tgc tgg gag atg acc       48
Met Ala Leu Arg Val Lys Thr Asn Lys Lys Pro Cys Trp Glu Met Thr
1               5                   10                  15

aag gag gag ctg acc agc ggc aag acc gag gtg ttc aac tat gag gaa       96
Lys Glu Glu Leu Thr Ser Gly Lys Thr Glu Val Phe Asn Tyr Glu Glu
            20                  25                  30

ctc ctc gag ttc gca gag ggc gac atc gcc aag gtc ttc gga ccc gag      144
Leu Leu Glu Phe Ala Glu Gly Asp Ile Ala Lys Val Phe Gly Pro Glu
        35                  40                  45

ttc gcc gtc atc gac aag tac ccg cgc cgc gtg cgc ctg ccc gcc cgc      192
Phe Ala Val Ile Asp Lys Tyr Pro Arg Arg Val Arg Leu Pro Ala Arg
    50                  55                  60

gag tac ctg ctc gtg acc cgc gtc acc ctc atg gac gcc gag gtc aac      240
Glu Tyr Leu Leu Val Thr Arg Val Thr Leu Met Asp Ala Glu Val Asn
65                  70                  75                  80

aac tac cgc gtc ggc gcc cgc atg gtc acc gag tac gat ctc ccc gtc      288
Asn Tyr Arg Val Gly Ala Arg Met Val Thr Glu Tyr Asp Leu Pro Val
                85                  90                  95

aac gga gag ctc tcc gag ggc gga gac tgc ccc tgg gcc gtc ctg gtc      336
Asn Gly Glu Leu Ser Glu Gly Gly Asp Cys Pro Trp Ala Val Leu Val
            100                 105                 110

gag agt ggc cag tgc gat ctc atg ctc atc tcc tac atg ggc att gac      384
Glu Ser Gly Gln Cys Asp Leu Met Leu Ile Ser Tyr Met Gly Ile Asp
        115                 120                 125

ttc cag aac cag ggc gac cgc gtc tac cgc ctg ctc aac acc acg ctc      432
Phe Gln Asn Gln Gly Asp Arg Val Tyr Arg Leu Leu Asn Thr Thr Leu
    130                 135                 140

acc ttt tac ggc gtg gcc cac gag ggc gag acc ctc gag tac gac att      480
Thr Phe Tyr Gly Val Ala His Glu Gly Glu Thr Leu Glu Tyr Asp Ile
145                 150                 155                 160

cgc gtc acc ggc ttc gcc aag cgt ctc gac ggc ggc atc tcc atg ttc      528
Arg Val Thr Gly Phe Ala Lys Arg Leu Asp Gly Gly Ile Ser Met Phe
                165                 170                 175
```

-continued

```
ttc ttc gag tac gac tgc tac gtc aac ggc cgc ctc ctc atc gag atg      576
Phe Phe Glu Tyr Asp Cys Tyr Val Asn Gly Arg Leu Leu Ile Glu Met
            180                 185                 190

cgc gat ggc tgc gcc ggc ttc ttc acc aac gag gag ctc gac gcc ggc      624
Arg Asp Gly Cys Ala Gly Phe Phe Thr Asn Glu Glu Leu Asp Ala Gly
        195                 200                 205

aag ggc gtc gtc ttc acc cgc ggc gac ctc gcc gcc cgc gcc aag atc      672
Lys Gly Val Val Phe Thr Arg Gly Asp Leu Ala Ala Arg Ala Lys Ile
    210                 215                 220

cca aag cag gac gtc tcc ccc tac gcc gtc gcc ccc tgc ctc cac aag      720
Pro Lys Gln Asp Val Ser Pro Tyr Ala Val Ala Pro Cys Leu His Lys
225                 230                 235                 240

acc aag ctc aac gaa aag gag atg cag acc ctc gtc gac aag gac tgg      768
Thr Lys Leu Asn Glu Lys Glu Met Gln Thr Leu Val Asp Lys Asp Trp
                245                 250                 255

gca tcc gtc ttt ggc tcc aag aac ggc atg ccg gaa atc aac tac aaa      816
Ala Ser Val Phe Gly Ser Lys Asn Gly Met Pro Glu Ile Asn Tyr Lys
            260                 265                 270

ctc tgc gcg cgt aag atg ctc atg att gac cgc gtc acc agc att gac      864
Leu Cys Ala Arg Lys Met Leu Met Ile Asp Arg Val Thr Ser Ile Asp
        275                 280                 285

cac aag ggc ggt gtc tac ggc ctc ggt cag ctc gtc ggt gaa aag atc      912
His Lys Gly Gly Val Tyr Gly Leu Gly Gln Leu Val Gly Glu Lys Ile
    290                 295                 300

ctc gag cgc gac cac tgg tac ttt ccc tgc cac ttt gtc aag gat cag      960
Leu Glu Arg Asp His Trp Tyr Phe Pro Cys His Phe Val Lys Asp Gln
305                 310                 315                 320

gtc atg gcc gga tcc ctc gtc tcc gac ggc tgc agc cag atg ctc aag     1008
Val Met Ala Gly Ser Leu Val Ser Asp Gly Cys Ser Gln Met Leu Lys
                325                 330                 335

atg tac atg atc tgg ctc ggc ctc cac ctc acc acc gga ccc ttt gac     1056
Met Tyr Met Ile Trp Leu Gly Leu His Leu Thr Thr Gly Pro Phe Asp
            340                 345                 350

ttc cgc ccg gtc aac ggc cac ccc aac aag gtc cgc tgc cgc ggc caa     1104
Phe Arg Pro Val Asn Gly His Pro Asn Lys Val Arg Cys Arg Gly Gln
        355                 360                 365

atc tcc ccg cac aag ggc aag ctc gtc tac gtc atg gag atc aag gag     1152
Ile Ser Pro His Lys Gly Lys Leu Val Tyr Val Met Glu Ile Lys Glu
    370                 375                 380

atg ggc ttc gac gag gac aac gac ccg tac gcc att gcc gac gtc aac     1200
Met Gly Phe Asp Glu Asp Asn Asp Pro Tyr Ala Ile Ala Asp Val Asn
385                 390                 395                 400

atc att gat gtc gac ttc gaa aag ggc cag gac ttt agc ctc gac cgc     1248
Ile Ile Asp Val Asp Phe Glu Lys Gly Gln Asp Phe Ser Leu Asp Arg
                405                 410                 415

atc agc gac tac ggc aag ggc gac ctc aac aag aag atc gtc gtc gac     1296
Ile Ser Asp Tyr Gly Lys Gly Asp Leu Asn Lys Lys Ile Val Val Asp
            420                 425                 430

ttt aag ggc atc gct ctc aag atg cag aag cgc tcc acc aac aag aac     1344
Phe Lys Gly Ile Ala Leu Lys Met Gln Lys Arg Ser Thr Asn Lys Asn
        435                 440                 445

ccc tcc                                                             1350
Pro Ser
    450
```

<210> SEQ ID NO 28
<211> LENGTH: 450
<212> TYPE: PRT
<213> ORGANISM: Schizochytrium sp.

-continued

```
<400> SEQUENCE: 28

Met Ala Leu Arg Val Lys Thr Asn Lys Lys Pro Cys Trp Glu Met Thr
1               5                   10                  15

Lys Glu Glu Leu Thr Ser Gly Lys Thr Glu Val Phe Asn Tyr Glu Glu
            20                  25                  30

Leu Leu Glu Phe Ala Glu Gly Asp Ile Ala Lys Val Phe Gly Pro Glu
        35                  40                  45

Phe Ala Val Ile Asp Lys Tyr Pro Arg Arg Val Arg Leu Pro Ala Arg
    50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
        115                 120                 125

Phe Gln Asn Gln Gly Asp Arg Val Tyr Arg Leu Leu Asn Thr Thr Leu
    130                 135                 140

Thr Phe Tyr Gly Val Ala His Glu Gly Glu Thr Leu Glu Tyr Asp Ile
145                 150                 155                 160

Arg Val Thr Gly Phe Ala Lys Arg Leu Asp Gly Gly Ile Ser Met Phe
                165                 170                 175

Phe Phe Glu Tyr Asp Cys Tyr Val Asn Gly Arg Leu Leu Ile Glu Met
            180                 185                 190

Arg Asp Gly Cys Ala Gly Phe Phe Thr Asn Glu Glu Leu Asp Ala Gly
        195                 200                 205

Lys Gly Val Val Phe Thr Arg Gly Asp Leu Ala Ala Arg Ala Lys Ile
    210                 215                 220

Pro Lys Gln Asp Val Ser Pro Tyr Ala Val Ala Pro Cys Leu His Lys
225                 230                 235                 240

Thr Lys Leu Asn Glu Lys Glu Met Gln Thr Leu Val Asp Lys Asp Trp
                245                 250                 255

Ala Ser Val Phe Gly Ser Lys Asn Gly Met Pro Glu Ile Asn Tyr Lys
            260                 265                 270

Leu Cys Ala Arg Lys Met Leu Met Ile Asp Arg Val Thr Ser Ile Asp
        275                 280                 285

His Lys Gly Gly Val Tyr Gly Leu Gly Gln Leu Val Gly Glu Lys Ile
    290                 295                 300

Leu Glu Arg Asp His Trp Tyr Phe Pro Cys His Phe Val Lys Asp Gln
305                 310                 315                 320

Val Met Ala Gly Ser Leu Val Ser Asp Gly Cys Ser Gln Met Leu Lys
                325                 330                 335

Met Tyr Met Ile Trp Leu Gly Leu His Leu Thr Thr Gly Pro Phe Asp
            340                 345                 350

Phe Arg Pro Val Asn Gly His Pro Asn Lys Val Arg Cys Arg Gly Gln
        355                 360                 365

Ile Ser Pro His Lys Gly Lys Leu Val Tyr Val Met Glu Ile Lys Glu
    370                 375                 380

Met Gly Phe Asp Glu Asp Asn Asp Pro Tyr Ala Ile Ala Asp Val Asn
385                 390                 395                 400

Ile Ile Asp Val Asp Phe Glu Lys Gly Gln Asp Phe Ser Leu Asp Arg
                405                 410                 415
```

```
Ile Ser Asp Tyr Gly Lys Gly Asp Leu Asn Lys Lys Ile Val Val Asp
            420                 425                 430

Phe Lys Gly Ile Ala Leu Lys Met Gln Lys Arg Ser Thr Asn Lys Asn
        435                 440                 445

Pro Ser
    450


<210> SEQ ID NO 29
<211> LENGTH: 1497
<212> TYPE: DNA
<213> ORGANISM: Schizochytrium sp.
<220> FEATURE:
<221> NAME/KEY: CDS
<222> LOCATION: (1)..(1497)

<400> SEQUENCE: 29

aag gtt cag ccc gtc ttt gcc aac ggc gcc gcc act gtc ggc ccc gag       48
Lys Val Gln Pro Val Phe Ala Asn Gly Ala Ala Thr Val Gly Pro Glu
1               5                   10                  15

gcc tcc aag gct tcc tcc ggc gcc agc gcc agc gcc agc gcc gcc ccg       96
Ala Ser Lys Ala Ser Ser Gly Ala Ser Ala Ser Ala Ser Ala Ala Pro
            20                  25                  30

gcc aag cct gcc ttc agc gcc gat gtt ctt gcg ccc aag ccc gtt gcc      144
Ala Lys Pro Ala Phe Ser Ala Asp Val Leu Ala Pro Lys Pro Val Ala
        35                  40                  45

ctt ccc gag cac atc ctc aag ggc gac gcc ctc gcc ccc aag gag atg      192
Leu Pro Glu His Ile Leu Lys Gly Asp Ala Leu Ala Pro Lys Glu Met
    50                  55                  60

tcc tgg cac ccc atg gcc cgc atc ccg ggc aac ccg acg ccc tct ttt      240
Ser Trp His Pro Met Ala Arg Ile Pro Gly Asn Pro Thr Pro Ser Phe
65                  70                  75                  80

gcg ccc tcg gcc tac aag ccg cgc aac atc gcc ttt acg ccc ttc ccc      288
Ala Pro Ser Ala Tyr Lys Pro Arg Asn Ile Ala Phe Thr Pro Phe Pro
                85                  90                  95

ggc aac ccc aac gat aac gac cac acc ccg ggc aag atg ccg ctc acc      336
Gly Asn Pro Asn Asp Asn Asp His Thr Pro Gly Lys Met Pro Leu Thr
            100                 105                 110

tgg ttc aac atg gcc gag ttc atg gcc ggc aag gtc agc atg tgc ctc      384
Trp Phe Asn Met Ala Glu Phe Met Ala Gly Lys Val Ser Met Cys Leu
        115                 120                 125

ggc ccc gag ttc gcc aag ttc gac gac tcg aac acc agc cgc agc ccc      432
Gly Pro Glu Phe Ala Lys Phe Asp Asp Ser Asn Thr Ser Arg Ser Pro
    130                 135                 140

gct tgg gac ctc gct ctc gtc acc cgc gcc gtg tct gtg tct gac ctc      480
Ala Trp Asp Leu Ala Leu Val Thr Arg Ala Val Ser Val Ser Asp Leu
145                 150                 155                 160

aag cac gtc aac tac cgc aac atc gac ctc gac ccc tcc aag ggt acc      528
Lys His Val Asn Tyr Arg Asn Ile Asp Leu Asp Pro Ser Lys Gly Thr
                165                 170                 175

atg gtc ggc gag ttc gac tgc ccc gcg gac gcc tgg ttc tac aag ggc      576
Met Val Gly Glu Phe Asp Cys Pro Ala Asp Ala Trp Phe Tyr Lys Gly
            180                 185                 190

gcc tgc aac gat gcc cac atg ccg tac tcg atc ctc atg gag atc gcc      624
Ala Cys Asn Asp Ala His Met Pro Tyr Ser Ile Leu Met Glu Ile Ala
        195                 200                 205

ctc cag acc tcg ggt gtg ctc acc tcg gtg ctc aag gcg ccc ctg acc      672
Leu Gln Thr Ser Gly Val Leu Thr Ser Val Leu Lys Ala Pro Leu Thr
    210                 215                 220

atg gag aag gac gac atc ctc ttc cgc aac ctc gac gcc aac gcc gag      720
Met Glu Lys Asp Asp Ile Leu Phe Arg Asn Leu Asp Ala Asn Ala Glu
```

-continued

```
225                 230                 235                 240

ttc gtg cgc gcc gac ctc gac tac cgc ggc aag act atc cgc aac gtc      768
Phe Val Arg Ala Asp Leu Asp Tyr Arg Gly Lys Thr Ile Arg Asn Val
                245                 250                 255

acc aag tgc act ggc tac agc atg ctc ggc gag atg ggc gtc cac cgc      816
Thr Lys Cys Thr Gly Tyr Ser Met Leu Gly Glu Met Gly Val His Arg
            260                 265                 270

ttc acc ttt gag ctc tac gtc gat gat gtg ctc ttt tac aag ggc tcg      864
Phe Thr Phe Glu Leu Tyr Val Asp Asp Val Leu Phe Tyr Lys Gly Ser
        275                 280                 285

acc tcg ttc ggc tgg ttc gtg ccc gag gtc ttt gcc gcc cag gcc ggc      912
Thr Ser Phe Gly Trp Phe Val Pro Glu Val Phe Ala Ala Gln Ala Gly
    290                 295                 300

ctc gac aac ggc cgc aag tcg gag ccc tgg ttc att gag aac aag gtt      960
Leu Asp Asn Gly Arg Lys Ser Glu Pro Trp Phe Ile Glu Asn Lys Val
305                 310                 315                 320

ccg gcc tcg cag gtc tcc tcc ttt gac gtg cgc ccc aac ggc agc ggc     1008
Pro Ala Ser Gln Val Ser Ser Phe Asp Val Arg Pro Asn Gly Ser Gly
                325                 330                 335

cgc acc gcc atc ttc gcc aac gcc ccc agc ggc gcc cag ctc aac cgc     1056
Arg Thr Ala Ile Phe Ala Asn Ala Pro Ser Gly Ala Gln Leu Asn Arg
            340                 345                 350

cgc acg gac cag ggc cag tac ctc gac gcc gtc gac att gtc tcc ggc     1104
Arg Thr Asp Gln Gly Gln Tyr Leu Asp Ala Val Asp Ile Val Ser Gly
        355                 360                 365

agc ggc aag aag agc ctc ggc tac gcc cac ggt tcc aag acg gtc aac     1152
Ser Gly Lys Lys Ser Leu Gly Tyr Ala His Gly Ser Lys Thr Val Asn
    370                 375                 380

ccg aac gac tgg ttc ttc tcg tgc cac ttt tgg ttt gac tcg gtc atg     1200
Pro Asn Asp Trp Phe Phe Ser Cys His Phe Trp Phe Asp Ser Val Met
385                 390                 395                 400

ccc gga agt ctc ggt gtc gag tcc atg ttc cag ctc gtc gag gcc atc     1248
Pro Gly Ser Leu Gly Val Glu Ser Met Phe Gln Leu Val Glu Ala Ile
                405                 410                 415

gcc gcc cac gag gat ctc gct ggc aag cac ggc att gcc aac ccc acc     1296
Ala Ala His Glu Asp Leu Ala Gly Lys His Gly Ile Ala Asn Pro Thr
            420                 425                 430

ttt gtg cac gcc ccg ggc aag atc agc tgg aag tac cgc ggc cag ctc     1344
Phe Val His Ala Pro Gly Lys Ile Ser Trp Lys Tyr Arg Gly Gln Leu
        435                 440                 445

acg ccc aag agc aag aag atg gac tcg gag gtc cac atc gtg tcc gtg     1392
Thr Pro Lys Ser Lys Lys Met Asp Ser Glu Val His Ile Val Ser Val
    450                 455                 460

gac gcc cac gac ggc gtt gtc gac ctc gtc gcc gac ggc ttc ctc tgg     1440
Asp Ala His Asp Gly Val Val Asp Leu Val Ala Asp Gly Phe Leu Trp
465                 470                 475                 480

gcc gac agc ctc cgc gtc tac tcg gtg agc aac att cgc gtg cgc atc     1488
Ala Asp Ser Leu Arg Val Tyr Ser Val Ser Asn Ile Arg Val Arg Ile
                485                 490                 495

gcc tcc ggt                                                         1497
Ala Ser Gly


<210> SEQ ID NO 30
<211> LENGTH: 499
<212> TYPE: PRT
<213> ORGANISM: Schizochytrium sp.

<400> SEQUENCE: 30

Lys Val Gln Pro Val Phe Ala Asn Gly Ala Ala Thr Val Gly Pro Glu
1               5                   10                  15
```

-continued

```
Ala Ser Lys Ala Ser Ser Gly Ala Ser Ala Ser Ala Ser Ala Ala Pro
            20                  25                  30

Ala Lys Pro Ala Phe Ser Ala Asp Val Leu Ala Pro Lys Pro Val Ala
        35                  40                  45

Leu Pro Glu His Ile Leu Lys Gly Asp Ala Leu Ala Pro Lys Glu Met
    50                  55                  60

Ser Trp His Pro Met Ala Arg Ile Pro Gly Asn Pro Thr Pro Ser Phe
65                  70                  75                  80

Ala Pro Ser Ala Tyr Lys Pro Arg Asn Ile Ala Phe Thr Pro Phe Pro
                85                  90                  95

Gly Asn Pro Asn Asp Asn Asp His Thr Pro Gly Lys Met Pro Leu Thr
            100                 105                 110

Trp Phe Asn Met Ala Glu Phe Met Ala Gly Lys Val Ser Met Cys Leu
        115                 120                 125

Gly Pro Glu Phe Ala Lys Phe Asp Asp Ser Asn Thr Ser Arg Ser Pro
    130                 135                 140

Ala Trp Asp Leu Ala Leu Val Thr Arg Ala Val Ser Val Ser Asp Leu
145                 150                 155                 160

Lys His Val Asn Tyr Arg Asn Ile Asp Leu Asp Pro Ser Lys Gly Thr
                165                 170                 175

Met Val Gly Glu Phe Asp Cys Pro Ala Asp Ala Trp Phe Tyr Lys Gly
            180                 185                 190

Ala Cys Asn Asp Ala His Met Pro Tyr Ser Ile Leu Met Glu Ile Ala
        195                 200                 205

Leu Gln Thr Ser Gly Val Leu Thr Ser Val Leu Lys Ala Pro Leu Thr
    210                 215                 220

Met Glu Lys Asp Asp Ile Leu Phe Arg Asn Leu Asp Ala Asn Ala Glu
225                 230                 235                 240

Phe Val Arg Ala Asp Leu Asp Tyr Arg Gly Lys Thr Ile Arg Asn Val
                245                 250                 255

Thr Lys Cys Thr Gly Tyr Ser Met Leu Gly Glu Met Gly Val His Arg
            260                 265                 270

Phe Thr Phe Glu Leu Tyr Val Asp Asp Val Leu Phe Tyr Lys Gly Ser
        275                 280                 285

Thr Ser Phe Gly Trp Phe Val Pro Glu Val Phe Ala Ala Gln Ala Gly
    290                 295                 300

Leu Asp Asn Gly Arg Lys Ser Glu Pro Trp Phe Ile Glu Asn Lys Val
305                 310                 315                 320

Pro Ala Ser Gln Val Ser Ser Phe Asp Val Arg Pro Asn Gly Ser Gly
                325                 330                 335

Arg Thr Ala Ile Phe Ala Asn Ala Pro Ser Gly Ala Gln Leu Asn Arg
            340                 345                 350

Arg Thr Asp Gln Gly Gln Tyr Leu Asp Ala Val Asp Ile Val Ser Gly
        355                 360                 365

Ser Gly Lys Lys Ser Leu Gly Tyr Ala His Gly Ser Lys Thr Val Asn
    370                 375                 380

Pro Asn Asp Trp Phe Phe Ser Cys His Phe Trp Phe Asp Ser Val Met
385                 390                 395                 400

Pro Gly Ser Leu Gly Val Glu Ser Met Phe Gln Leu Val Glu Ala Ile
                405                 410                 415

Ala Ala His Glu Asp Leu Ala Gly Lys His Gly Ile Ala Asn Pro Thr
            420                 425                 430
```

-continued

```
Phe Val His Ala Pro Gly Lys Ile Ser Trp Lys Tyr Arg Gly Gln Leu
        435                 440                 445

Thr Pro Lys Ser Lys Lys Met Asp Ser Glu Val His Ile Val Ser Val
    450                 455                 460

Asp Ala His Asp Gly Val Val Asp Leu Val Ala Asp Gly Phe Leu Trp
465                 470                 475                 480

Ala Asp Ser Leu Arg Val Tyr Ser Val Ser Asn Ile Arg Val Arg Ile
                485                 490                 495

Ala Ser Gly


<210> SEQ ID NO 31
<211> LENGTH: 1512
<212> TYPE: DNA
<213> ORGANISM: Schizochytrium sp.
<220> FEATURE:
<221> NAME/KEY: CDS
<222> LOCATION: (1)..(1512)

<400> SEQUENCE: 31

gcc ccg ctc tac ctc tcg cag gac ccg acc agc ggc cag ctc aag aag      48
Ala Pro Leu Tyr Leu Ser Gln Asp Pro Thr Ser Gly Gln Leu Lys Lys
1               5                   10                  15

cac acc gac gtg gcc tcc ggc cag gcc acc atc gtg cag ccc tgc acg      96
His Thr Asp Val Ala Ser Gly Gln Ala Thr Ile Val Gln Pro Cys Thr
            20                  25                  30

ctc ggc gac ctc ggt gac cgc tcc ttc atg gag acc tac ggc gtc gtc     144
Leu Gly Asp Leu Gly Asp Arg Ser Phe Met Glu Thr Tyr Gly Val Val
        35                  40                  45

gcc ccg ctg tac acg ggc gcc atg gcc aag ggc att gcc tcg gcg gac     192
Ala Pro Leu Tyr Thr Gly Ala Met Ala Lys Gly Ile Ala Ser Ala Asp
    50                  55                  60

ctc gtc atc gcc gcc ggc aag cgc aag atc ctc ggc tcc ttt ggc gcc     240
Leu Val Ile Ala Ala Gly Lys Arg Lys Ile Leu Gly Ser Phe Gly Ala
65                  70                  75                  80

ggc ggc ctc ccc atg cac cac gtg cgc gcc gcc ctc gag aag atc cag     288
Gly Gly Leu Pro Met His His Val Arg Ala Ala Leu Glu Lys Ile Gln
                85                  90                  95

gcc gcc ctg cct cag ggc ccc tac gcc gtc aac ctc atc cac tcg cct     336
Ala Ala Leu Pro Gln Gly Pro Tyr Ala Val Asn Leu Ile His Ser Pro
            100                 105                 110

ttt gac agc aac ctc gag aag ggc aac gtc gat ctc ttc ctc gag aag     384
Phe Asp Ser Asn Leu Glu Lys Gly Asn Val Asp Leu Phe Leu Glu Lys
        115                 120                 125

ggc gtc act gtg gtg gag gcc tcg gca ttc atg acc ctc acc ccg cag     432
Gly Val Thr Val Val Glu Ala Ser Ala Phe Met Thr Leu Thr Pro Gln
    130                 135                 140

gtc gtg cgc tac cgc gcc gcc ggc ctc tcg cgc aac gcc gac ggt tcg     480
Val Val Arg Tyr Arg Ala Ala Gly Leu Ser Arg Asn Ala Asp Gly Ser
145                 150                 155                 160

gtc aac atc cgc aac cgc atc atc ggc aag gtc tcg cgc acc gag ctc     528
Val Asn Ile Arg Asn Arg Ile Ile Gly Lys Val Ser Arg Thr Glu Leu
                165                 170                 175

gcc gag atg ttc atc cgc ccg gcc ccg gag cac ctc ctc gag aag ctc     576
Ala Glu Met Phe Ile Arg Pro Ala Pro Glu His Leu Leu Glu Lys Leu
            180                 185                 190

atc gcc tcg ggc gag atc acc cag gag cag gcc gag ctc gcg cgc cgc     624
Ile Ala Ser Gly Glu Ile Thr Gln Glu Gln Ala Glu Leu Ala Arg Arg
        195                 200                 205

gtt ccc gtc gcc gac gat atc gct gtc gag gct gac tcg ggc ggc cac     672
Val Pro Val Ala Asp Asp Ile Ala Val Glu Ala Asp Ser Gly Gly His
```

-continued

```
    210                 215                 220

acc gac aac cgc ccc atc cac gtc atc ctc ccg ctc atc atc aac ctc      720
Thr Asp Asn Arg Pro Ile His Val Ile Leu Pro Leu Ile Ile Asn Leu
225                 230                 235                 240

cgc aac cgc ctg cac cgc gag tgc ggc tac ccc gcg cac ctc cgc gtc      768
Arg Asn Arg Leu His Arg Glu Cys Gly Tyr Pro Ala His Leu Arg Val
            245                 250                 255

cgc gtt ggc gcc ggc ggt ggc gtc ggc tgc ccg cag gcc gcc gcc gcc      816
Arg Val Gly Ala Gly Gly Gly Val Gly Cys Pro Gln Ala Ala Ala Ala
            260                 265                 270

gcg ctc acc atg ggc gcc gcc ttc atc gtc acc ggc act gtc aac cag      864
Ala Leu Thr Met Gly Ala Ala Phe Ile Val Thr Gly Thr Val Asn Gln
        275                 280                 285

gtc gcc aag cag tcc ggc acc tgc gac aac gtg cgc aag cag ctc tcg      912
Val Ala Lys Gln Ser Gly Thr Cys Asp Asn Val Arg Lys Gln Leu Ser
    290                 295                 300

cag gcc acc tac tcg gat atc tgc atg gcc ccg gcc gcc gac atg ttc      960
Gln Ala Thr Tyr Ser Asp Ile Cys Met Ala Pro Ala Ala Asp Met Phe
305                 310                 315                 320

gag gag ggc gtc aag ctc cag gtc ctc aag aag gga acc atg ttc ccc     1008
Glu Glu Gly Val Lys Leu Gln Val Leu Lys Lys Gly Thr Met Phe Pro
            325                 330                 335

tcg cgc gcc aac aag ctc tac gag ctc ttt tgc aag tac gac tcc ttc     1056
Ser Arg Ala Asn Lys Leu Tyr Glu Leu Phe Cys Lys Tyr Asp Ser Phe
            340                 345                 350

gac tcc atg cct cct gcc gag ctc gag cgc atc gag aag cgt atc ttc     1104
Asp Ser Met Pro Pro Ala Glu Leu Glu Arg Ile Glu Lys Arg Ile Phe
        355                 360                 365

aag cgc gca ctc cag gag gtc tgg gag gag acc aag gac ttt tac att     1152
Lys Arg Ala Leu Gln Glu Val Trp Glu Glu Thr Lys Asp Phe Tyr Ile
    370                 375                 380

aac ggt ctc aag aac ccg gag aag atc cag cgc gcc gag cac gac ccc     1200
Asn Gly Leu Lys Asn Pro Glu Lys Ile Gln Arg Ala Glu His Asp Pro
385                 390                 395                 400

aag ctc aag atg tcg ctc tgc ttc cgc tgg tac ctt ggt ctt gcc agc     1248
Lys Leu Lys Met Ser Leu Cys Phe Arg Trp Tyr Leu Gly Leu Ala Ser
            405                 410                 415

cgc tgg gcc aac atg ggc gcc ccg gac cgc gtc atg gac tac cag gtc     1296
Arg Trp Ala Asn Met Gly Ala Pro Asp Arg Val Met Asp Tyr Gln Val
            420                 425                 430

tgg tgt ggc ccg gcc att ggc gcc ttc aac gac ttc atc aag ggc acc     1344
Trp Cys Gly Pro Ala Ile Gly Ala Phe Asn Asp Phe Ile Lys Gly Thr
        435                 440                 445

tac ctc gac ccc gct gtc tcc aac gag tac ccc tgt gtc gtc cag atc     1392
Tyr Leu Asp Pro Ala Val Ser Asn Glu Tyr Pro Cys Val Val Gln Ile
    450                 455                 460

aac ctg caa atc ctc cgt ggt gcc tgc tac ctg cgc cgt ctc aac gcc     1440
Asn Leu Gln Ile Leu Arg Gly Ala Cys Tyr Leu Arg Arg Leu Asn Ala
465                 470                 475                 480

ctg cgc aac gac ccg cgc att gac ctc gag acc gag gat gct gcc ttt     1488
Leu Arg Asn Asp Pro Arg Ile Asp Leu Glu Thr Glu Asp Ala Ala Phe
            485                 490                 495

gtc tac gag ccc acc aac gcg ctc                                     1512
Val Tyr Glu Pro Thr Asn Ala Leu
            500
```

<210> SEQ ID NO 32
<211> LENGTH: 504
<212> TYPE: PRT
<213> ORGANISM: Schizochytrium sp.

<400> SEQUENCE: 32

```
Ala Pro Leu Tyr Leu Ser Gln Asp Pro Thr Ser Gly Gln Leu Lys Lys
1               5                   10                  15

His Thr Asp Val Ala Ser Gly Gln Ala Thr Ile Val Gln Pro Cys Thr
            20                  25                  30

Leu Gly Asp Leu Gly Asp Arg Ser Phe Met Glu Thr Tyr Gly Val Val
        35                  40                  45

Ala Pro Leu Tyr Thr Gly Ala Met Ala Lys Gly Ile Ala Ser Ala Asp
    50                  55                  60

Leu Val Ile Ala Ala Gly Lys Arg Lys Ile Leu Gly Ser Phe Gly Ala
65                  70                  75                  80

Gly Gly Leu Pro Met His His Val Arg Ala Ala Leu Glu Lys Ile Gln
                85                  90                  95

Ala Ala Leu Pro Gln Gly Pro Tyr Ala Val Asn Leu Ile His Ser Pro
            100                 105                 110

Phe Asp Ser Asn Leu Glu Lys Gly Asn Val Asp Leu Phe Leu Glu Lys
        115                 120                 125

Gly Val Thr Val Val Glu Ala Ser Ala Phe Met Thr Leu Thr Pro Gln
    130                 135                 140

Val Val Arg Tyr Arg Ala Ala Gly Leu Ser Arg Asn Ala Asp Gly Ser
145                 150                 155                 160

Val Asn Ile Arg Asn Arg Ile Ile Gly Lys Val Ser Arg Thr Glu Leu
                165                 170                 175

Ala Glu Met Phe Ile Arg Pro Ala Pro Glu His Leu Leu Glu Lys Leu
            180                 185                 190

Ile Ala Ser Gly Glu Ile Thr Gln Glu Gln Ala Glu Leu Ala Arg Arg
        195                 200                 205

Val Pro Val Ala Asp Asp Ile Ala Val Glu Ala Asp Ser Gly Gly His
    210                 215                 220

Thr Asp Asn Arg Pro Ile His Val Ile Leu Pro Leu Ile Ile Asn Leu
225                 230                 235                 240

Arg Asn Arg Leu His Arg Glu Cys Gly Tyr Pro Ala His Leu Arg Val
                245                 250                 255

Arg Val Gly Ala Gly Gly Gly Val Gly Cys Pro Gln Ala Ala Ala Ala
            260                 265                 270

Ala Leu Thr Met Gly Ala Ala Phe Ile Val Thr Gly Thr Val Asn Gln
        275                 280                 285

Val Ala Lys Gln Ser Gly Thr Cys Asp Asn Val Arg Lys Gln Leu Ser
    290                 295                 300

Gln Ala Thr Tyr Ser Asp Ile Cys Met Ala Pro Ala Ala Asp Met Phe
305                 310                 315                 320

Glu Glu Gly Val Lys Leu Gln Val Leu Lys Lys Gly Thr Met Phe Pro
                325                 330                 335

Ser Arg Ala Asn Lys Leu Tyr Glu Leu Phe Cys Lys Tyr Asp Ser Phe
            340                 345                 350

Asp Ser Met Pro Pro Ala Glu Leu Glu Arg Ile Glu Lys Arg Ile Phe
        355                 360                 365

Lys Arg Ala Leu Gln Glu Val Trp Glu Glu Thr Lys Asp Phe Tyr Ile
    370                 375                 380

Asn Gly Leu Lys Asn Pro Glu Lys Ile Gln Arg Ala Glu His Asp Pro
385                 390                 395                 400

Lys Leu Lys Met Ser Leu Cys Phe Arg Trp Tyr Leu Gly Leu Ala Ser
```

-continued

```
                405                 410                 415

Arg Trp Ala Asn Met Gly Ala Pro Asp Arg Val Met Asp Tyr Gln Val
            420                 425                 430

Trp Cys Gly Pro Ala Ile Gly Ala Phe Asn Asp Phe Ile Lys Gly Thr
        435                 440                 445

Tyr Leu Asp Pro Ala Val Ser Asn Glu Tyr Pro Cys Val Val Gln Ile
    450                 455                 460

Asn Leu Gln Ile Leu Arg Gly Ala Cys Tyr Leu Arg Arg Leu Asn Ala
465                 470                 475                 480

Leu Arg Asn Asp Pro Arg Ile Asp Leu Glu Thr Glu Asp Ala Ala Phe
                485                 490                 495

Val Tyr Glu Pro Thr Asn Ala Leu
            500


<210> SEQ ID NO 33
<211> LENGTH: 9
<212> TYPE: PRT
<213> ORGANISM: Artificial sequence
<220> FEATURE:
<223> OTHER INFORMATION: motif
<220> FEATURE:
<221> NAME/KEY: MISC_FEATURE
<222> LOCATION: (2)..(3)
<223> OTHER INFORMATION: x = any amino acid
<220> FEATURE:
<221> NAME/KEY: MISC_FEATURE
<222> LOCATION: (6)..(6)
<223> OTHER INFORMATION: x = A or S
<220> FEATURE:
<221> NAME/KEY: MISC_FEATURE
<222> LOCATION: (7)..(8)
<223> OTHER INFORMATION: x = any amino acid

<400> SEQUENCE: 33

Trp Xaa Xaa Lys Glu Xaa Xaa Xaa Lys
1               5


<210> SEQ ID NO 34
<211> LENGTH: 6
<212> TYPE: PRT
<213> ORGANISM: Artificial sequence
<220> FEATURE:
<223> OTHER INFORMATION: motif
<220> FEATURE:
<221> NAME/KEY: MISC_FEATURE
<222> LOCATION: (3)..(3)
<223> OTHER INFORMATION: x = I or L or V

<400> SEQUENCE: 34

Phe Asn Xaa Ser His Ser
1               5


<210> SEQ ID NO 35
<211> LENGTH: 5
<212> TYPE: PRT
<213> ORGANISM: Artificial sequence
<220> FEATURE:
<223> OTHER INFORMATION: motif
<220> FEATURE:
<221> NAME/KEY: MISC_FEATURE
<222> LOCATION: (1)..(5)
<223> OTHER INFORMATION: x = I or L or V

<400> SEQUENCE: 35

Xaa Gly Xaa Asp Xaa
1               5
```

<210> SEQ ID NO 36
<211> LENGTH: 4244
<212> TYPE: DNA
<213> ORGANISM: Schizochytrium sp.

<400> SEQUENCE: 36

```
tttctctctc tcgagctgtt gctgctgctg ctgctgctgc tgcttccttg ctggttctca     60
cgtccgttcg atcaagcgct cgctcgctcg accgatcggt gcgtgcgtgc gtgcgtgagt    120
cttgttgcca ggcagccgca ggctgtctgt ctgtttgtgt agttttaccc tcggggttcg    180
gggtctgcct gcctcccgct cccgcccgcc gccgcccgta tccaccccgc tcgcctccgc    240
ccatcgggcc tcgcctcctc gcgccgcacg catcgcgcgc atcgcatgca tcatgctgcc    300
acgcacgggg ggacgcgcgc cccgcgtccc ccgccgccgc cgtcgtcgtc tggcgatgcc    360
gtcgccgccc tccttccttc cctcgcctcc tcttcctccc gagcccccct gtcttccttc    420
gcccccgcag cggcgcgcag gaagcgagga gagcggggag gagagaagaa aagaaaagaa    480
aagaaaagaa aataacagcg ccgtctcgcg cagacgcgcg cggccgcgtg cgaggcggcg    540
tgatggggct tctcgtggcg cggctgcggc ctggcccggc ctcgcctttg aggtgcaggc    600
tttgggagag aagagtggga cgcggagaag ataagatggt gccatggcgc aggacggaga    660
ggttgctgaa acttcttcga gcggcacagg cgatggcgag agaccgacag ctgccggcgc    720
ggaggggatg gatacctccc gaggctggca tggacgagct ggccgcgcgg atctggctgg    780
ccgcgcggcg gtgggtccgg aggcgcgagg ttggttttct tcatacctga taccatacgg    840
tattcattct tcctctccag gaaggaagca agtcacatag agtatcacta gcctaatgat    900
ggactctatg ttttagggca cgtcggagca gaaggcgcga gcgattcgaa tgcgagcgat    960
agatacagca cagagacctt gccggcgacg cggatgcagg cgagcacgca cgcaccgcac   1020
gcacggcagc ggtgcacgcg ctcctcggca gatgcacggt tctgcgccgc gcctttacat   1080
tttttgattt taggtggtgt gcctgccact ttgaacatca tccacaagtc aacgcagcat   1140
caagaggcaa gcaagtacat acatccattc gaattcaagt tcaagagacg cagcaacagc   1200
cgccgctccg ctcaagctgc agctagctgg ctgacagggc tcgctggctg tagtggaaaa   1260
ttccattcac ttttctgcat ccgcggccag caggcccgta cgcacgttct ctcgtttgtt   1320
tgttcgttcg tgcgtgcgtg cgtgcgtccc agctgcctgt ctaatctgcc gcgcgatcca   1380
acgaccctcg gtcgtcgccg caagcgaaac ccgacgccga cctggccaat gccgcaagaa   1440
tgctaagcgc gcagcaatgc tgagagtaat cttcagccca ccaagtcatt atcgctgccc   1500
aagtctccat cgcagccaca ttcaggcttt ctctctctct ccctccctct ctttctgccg   1560
ggagagaagg aaagacccgc cgccgccgcc tctgcgcctg tgacgggctg tccgttgtaa   1620
gccctcttag acagttccta ggtgccgggc gccgccgcgc ctccgtcgca ggcacacgta   1680
ggcggccacg ggttcccccc gcaccttcca caccttcttc ccccgcagcc ggaccgcgcg   1740
ccgtctgctt acgcacttcg cgcggccgcc gcccgcgaac ccgagcgcgt gctgtgggcg   1800
ccgtcttccg gccgcgtcgg aggtcgtccc cgcgccgcgc tactccgggt cctgtgcggt   1860
acgtacttaa tattaacagt gggacctcgc acaggacctg acggcagcac agacgtcgcc   1920
gcctcgcatc gctggggacg caggcgaggc atcccggcgc ggccccgcac cggggaggct   1980
gcggggcggc ctcttccggc cggcggccgc atcaggcgga tgacgcaaga gccctcgcag   2040
tcgctcgctc gcgggagcgc agcgcggcgc cagcgtggcc aagctcccgc cccttctggc   2100
tggctgcatg cctgcctgcc tgcctgcctg cgtgcgtgcg tgcgtgcgtg ccttcgtgcg   2160
```

```
tgcctgcctt cgtgcgtgcg tgcgtgagtg cggcggaaga gggatcatgc gaggatcaat   2220
cacccgccgc acctcgactt ttgaagaagc cgcgatgcga tgcgatgcga tgcgatgcga   2280
cgcgataccg tgcgaggcta cgaagcgagt ctggccggcc gtcatacaac gcacgttttc   2340
gagaaggagg gctggcggag gcgtgcatgc cggcgaccat tgcgaacgcg gcgtctcgtg   2400
gctggcgaag gtgcctggag gatctaacga tcgctgctat gatgctatag ctgtgctgat   2460
ccccggtcca ttccaccacg tctgtgcctg ccgcctgacc tgcgcttggc tttccttcaa   2520
gttctcctcc gccgggcctt caggaccgag acgagacctg cagctgcagc tagactcgcg   2580
ctcgctcgcg gaggattcgc cggccgccgg gccggacggg actcgcgagg tcacacggcc   2640
gccggcgatc gcgatggctg tgctgacgta ctcgtgcgtg gcagccgtac gtcagcgacg   2700
ccgcctccgt attgtggatt cgttagttgg ttgttggttg atttgttgat taattttttt   2760
gttcgtaggc ttggttatag ctaatagttt agtttatact ggtgctcttc ggtgctgatt   2820
tagctcgact tgggtccaca ccactgcccc tctactgtga atggatcaat ggacgcacga   2880
cgggccgacg aaagtgcgcg agtgaggtaa cctaagcaac ggcggtcttc agaggggacg   2940
cacgccctcc gtcgcagtca gtccagacag gcagaaaagc gtcttaggga ccacgcacgc   3000
acgcacgcac gcacgcacgc ccgcacgcac gctccctccc tcgcgtgcct attttttttag   3060
gcttccttcc gcacgggcct acctctcgct ccctcgcctc gccgcaccag gcggcagcag   3120
cgatacctgc cggtgccgcc tccgtcacgc gctcagccgc agctcagccc agccgcgagc   3180
tagggtttgt tcgtcctgaa ttgtttgatt tgatttgatt tgatttgatc cgatccgatc   3240
cgatctgatc tgatttgctt tgctttgctt tgtctccctc ccggcgcgga ccaagcgtcc   3300
gtctgcgcgc cgcagcttcc cttcttctcc cagccctcct tctgctcccg cctctcgcgc   3360
aagcacgcag cttcgccgcc gcatccggtc ggtcggtcgg tcgatcgacc cgcctgccgc   3420
tgctgctgtg gccgggcttt tctccatcgg cgactctttc ttctccatac gtcctactac   3480
gtacatacat actgccggct tcctcctctt ccagcgcggc gacggcggca ggctgcgacg   3540
tcgtcgccgc cgcgggcgcc gcgcgcgccg ccgccgccgc ccgcgtcgca gggcctcgtc   3600
gccgccgccg ctccgctccg ctccgaggcc gcgagagggc cgcggcggcg cgatggatgg   3660
atggatggat ggatggatgg atggattttg ttgatcgatg gcggcgcatg ggcggagatg   3720
agcgaggacg agcgcgcgag cgcggcagcc ggattcgcag ggcctcgctc gcctcgcgcc   3780
cgctgccgcg cccgccttgc gagcctgcgc cgcgagcgag cgagcgagcg agcggggctt   3840
tctttgtctc gcgcgccgct tggcctcgtg tgtcttgtgc ttgcgtagcg ggcgccgcgg   3900
tggaagatgg ctcattcaat cgacccattc acgcacgcac tccggcgcgc agagaaggcc   3960
gaggaggagc agcaagcaaa ccaaaagctc tcgcgctcgc ggtctcgggc tcgagcggtc   4020
tcggagagag agtcttgcgg cgaccaccgg cagcagcagc agcagcagca gcgctgtcga   4080
gcacgagcac gagcacgagc acgagcacga gcattcgagc aagaggacag acacggttgt   4140
cagcgcctag ctcgctcgat acagaaagag gcgggttggg cgtaaaaaaa aaggagcacg   4200
caagccgcca gccagccagc tagctagcca gcctgcctgc caaa                     4244
```

<210> SEQ ID NO 37
<211> LENGTH: 3886
<212> TYPE: DNA
<213> ORGANISM: Schizochytrium sp.
<220> FEATURE:
<221> NAME/KEY: misc_feature
<222> LOCATION: (2115)..(2115)

-continued

<223> OTHER INFORMATION: n = a, c, g, or t

<400> SEQUENCE: 37

```
gatcttgatt gccaagctct ggattgtcga ttccgatgaa tcgagctctt tgttgtcgag     60
ctctggcttg ccgagctttc agaaatagac aaaattgccg agttcctgat tgcggggctc    120
tcgattgcca aggtctggtg gattctcgaa ctctcgattg tcaaaatctt ggtcgtctcg    180
tcggattctt tcctgatttg ttttgtcaag accttgagat tgtgcaaaac cttgatcgtt    240
gacaaaccct tgatcgacag cagcctttca tcacgctcag ctcttgtcat tgattatatt    300
ccccctgaca gccaacacct tgatgcaggg tctcaacctt gatttttgga ggccatcatc    360
agcatcacgc cccggcactc accctcaaca ttcgacagcc aacgcttttt tttcttcgac    420
taggatctga gaataaaagc aggtcaccac gaccgtaggc caacgcgaca accatggaaa    480
taaagtgaca acgaacgact tgcaagttta aatgtaaaga gcagcaattg cccgcccaca    540
gacaaatgaa agcaggcgcc gagtcttatt tgaggaggtg ggcctgtggc aatgggcgaa    600
agaaaatcaa ggacaaggag agcaggttac gtaccggtat actggtatac gtacatggat    660
ggttcttggc aagttgacgg gatgtgtgcg agtgaccgtg gtagttaacg aaagagccgc    720
aagggcaagg aaagcaagag aatgcagact tttccacagg atggatgggt ccgcagcttg    780
ccgcatgatg aaacgctgta tttcacctgg cacgtggtgg cgcacgcgcc cacatatgat    840
cgcggcggcg ggtgtattat acattttccc cctcaggtct actgccatcc ctccatgcgt    900
cgctcgtgcg aacgacgcaa gcctttcgca tcgtgcagcc tctttctggt aaggcaagag    960
ctaaacccaa acctaaacga aagaacattt ttacctctct ctctctccca ttggtcgcgt   1020
gcgctccgcc gctcgctcct cctcctgcca gtgtcgcgcc ctaacttccc ccctccctcc   1080
ctccctccct ccctccctct ctcctgccac cgcccctctc tccgcgctgc gtgcggtgct   1140
gccctggacc aatggcatgc tgctgcacgc tcggcggatg acgcaagccg cttcgcaatt   1200
tccggatcag atctcggcgg ggcgtgcgcc gcggggtcac tgcggacctg ccgcggcccc   1260
tgcttctttc acatccatca tgtcctccaa acctccgcct cctccacgca cgtacgcacg   1320
cccgctcgca cgcgcgcact gccgctgcga aagcaagcgc ccgcccgccg cccggcgacg   1380
ggaaggcggc cgcggtctcc ctccgcggtt gcctcgctcc cgcgcggggc tgggcgggca   1440
gcagaaggcg ggtggcggcg gcggcttccg tcttcgtcag cggcctacgt cggcggcggc   1500
gcgcgagact acgcatgccc ttgcgtcatg cgctcgcagg tagccgccgc gggcctagcg   1560
tttccgctgg cgccgcgcct aagcccccgg cgcgcacggt attgccgcga taccgtacgg   1620
ccaagaccgc cgcagacgtc ggccctctcg cggccagcca gccagcagcg cagcggagga   1680
agagcgcgca ggcgcggcgg gagggcggcc gcggagcagc gcagagcggg gcggagcagc   1740
gcggagcaga acgggcagac tcggagcggg cagggcgggc agagctttgg ggtttaagga   1800
ccgggttacc ggcgaagtga gcggctgcgg ggagcggctg tgggaggggt gagtacgcaa   1860
gcacgatgcg agcgagagag agacgctgcc gcgaatcaag aaggtaggcg cgctgcgagg   1920
cgcggcggcg gagcggagcg agggagaggg agagggagag agagggaggg agacgtcgcc   1980
gcggcggggc ctggcctggc ctggtttggc ttggtcagcg cggccttgtc cgagcgtgca   2040
gctggagttg ggtggattca tttggatttt cttttgtttt tgtttttctc tctttcccgg   2100
aaagtgttgg ccggncggtg ttctttgttt tgatttcttc aaaagttttg gtggttggtt   2160
ctctctcttg gctctctgtc aggcggtccg gtccacgccc cggcctctcc tctcctctcc   2220
tctcctctcc tctccgtgcg tatacgtacg tacgtttgta tacgtacata catcccgccc   2280
```

-continued

```
gccgtgccgg cgagggtttg ctcagcctgg agcaatgcga tgcgatgcga tgcgatgcga   2340
cgcgacgcga cgcgagtcac tggttcgcgc tgtggctgtg gcttgcttgc ttacttgctt   2400
tcgagctctc ccgctttctt ctttccttct cacgccacca ccaacgaaag aagatcggcc   2460
ccggcacgcc gctgagaagg gctggcggcg atgacggcac gcgcgcccgc tgccacgttg   2520
gcgctcgctg ctgctgctgc tgctgctgct gctgctgctg ctgctgctgc tgctgcttct   2580
gcgcgcaggc tttgccacga ggccggcgtg ctggccgctg ccgcttccag tccgcgtgga   2640
gagatcgaat gagagataaa ctggatggat tcatcgaggg atgaatgaac gatggttgga   2700
tgcctttttc ctttttcagg tccacagcgg gaagcaggag cgcgtgaatc tgccgccatc   2760
cgcatacgtc tgcatcgcat cgcatcgcat gcacgcatcg ctcgccggga gccacagacg   2820
ggcgacaggg cggccagcca gccaggcagc cagccaggca ggcaccagag ggccagagag   2880
cgcgcctcac gcacgcgccg cagtgcgcgc atcgctcgca gtgcagacct tgattccccg   2940
cgcggatctc cgcgagcccg aaacgaagag cgccgtacgg gcccatccta gcgtcgcctc   3000
gcaccgcatc gcatcgcatc gcgttcccta gagagtagta ctcgacgaag gcaccatttc   3060
cgcgctcctc ttcggcgcga tcgaggcccc cggcgccgcg acgatcgcgg cggccgcggc   3120
gctggcggcg gccctggcgc tcgcgctggc ggccgccgcg ggcgtctggc cctggcgcgc   3180
gcgggcgccg caggaggagc ggcagcggct gctcgccgcc agagaagagc gcgccgggcc   3240
cggggaggga cggggaggag aaggagaagg cgcgcaaggc ggccccgaaa gagaagaccc   3300
tggacttgaa cgcgaagaag aagaagaagg agaagaagtt gaagaagaag aagaagaagg   3360
agaggaagtt gaagaagacg aggagcaggc gcgttccaag gcgcgttctc ttccggaggc   3420
gcgttccagc tgcggcggcg ggcgggctg cggggcgggc gcgggcgcgg gtgcgggcag   3480
aggggacgcg cgcgcggagg cggaggggc cgagcgggag cccctgctgc tgcggggcgc   3540
ccgggccgca ggtgtggcgc gcgcgacgac ggaggcgacg acgccagcgg ccgcgacgac   3600
aaggccggcg gcgtcggcgg gcggaaggcc ccgcgcggag caggggcggg agcaggacaa   3660
ggcgcaggag caggagcagg gccgggagcg ggagcgggag cgggcggcgg agcccgaggc   3720
agaacccaat cgagatccag agcgagcaga ggccggccgc gagcccgagc ccgcgccgca   3780
gatcactagt accgctgcgg aatcacagca gcagcagcag cagcagcagc agcagcagca   3840
gcagcagcag ccacgagagg gagataaaga aaaagcggca gagacg                 3886
```

```
<210> SEQ ID NO 38
<211> LENGTH: 192
<212> TYPE: DNA
<213> ORGANISM: Schizochytrium sp.

<400> SEQUENCE: 38

tcatgaagcc ggttgctccg aagttctacg cgcgtctcaa cattgacgag caggacgaga    60
cccgtgatcc gatcctcaac aaggacaacg cgccgtcttc cagctctagc tcctcttcca   120
gctcttccag ctcttccagc ccgtcgccag ctccgtccgc cccagtgcaa aagaaggctg   180
ctccggccgc gg                                                       192
```

```
<210> SEQ ID NO 39
<211> LENGTH: 30
<212> TYPE: DNA
<213> ORGANISM: Artificial
<220> FEATURE:
<223> OTHER INFORMATION: oligonucleotide primer
```

<400> SEQUENCE: 39
cggggtaccc gggagccgcc ttggctttgt 30

<210> SEQ ID NO 40
<211> LENGTH: 35
<212> TYPE: DNA
<213> ORGANISM: Artificial
<220> FEATURE:
<223> OTHER INFORMATION: oligonucleotide primer

<400> SEQUENCE: 40
aaactgcagc ccgggtccag ctggcaggca ccctg 35

<210> SEQ ID NO 41
<211> LENGTH: 237
<212> TYPE: PRT
<213> ORGANISM: Nostoc sp.

<400> SEQUENCE: 41

```
Leu Leu Gln His Thr Trp Leu Pro Lys Pro Pro Asn Leu Thr Leu Leu
1               5                   10                  15

Ser Asp Glu Val His Leu Trp Arg Ile Pro Leu Asp Gln Pro Glu Ser
            20                  25                  30

Gln Leu Gln Asp Leu Ala Ala Thr Leu Ser Ser Asp Glu Leu Ala Arg
        35                  40                  45

Ala Asn Arg Phe Tyr Phe Pro Glu His Arg Arg Arg Phe Thr Ala Gly
    50                  55                  60

Arg Gly Ile Leu Arg Ser Ile Leu Gly Gly Tyr Leu Gly Val Glu Pro
65                  70                  75                  80

Gly Gln Val Lys Phe Asp Tyr Glu Ser Arg Gly Lys Pro Ile Leu Gly
                85                  90                  95

Asp Arg Phe Ala Glu Ser Gly Leu Leu Phe Asn Leu Ser His Ser Gln
            100                 105                 110

Asn Leu Ala Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Ala Pro Ala Trp
        195                 200                 205

Ser Leu Leu Glu Leu Val Pro Asp Asp Asn Cys Val Ala Ala Val Ala
    210                 215                 220

Val Ala Gly Phe Gly Trp Gln Pro Lys Phe Trp His Tyr
225                 230                 235
```

<210> SEQ ID NO 42
<211> LENGTH: 35
<212> TYPE: PRT
<213> ORGANISM: Brassica napus

<400> SEQUENCE: 42

```
Met Leu Lys Leu Ser Cys Asn Val Thr Asn His Leu His Thr Phe Ser
1               5                   10                  15
```

```
Phe Phe Ser Asp Ser Ser Leu Phe Ile Pro Val Asn Arg Arg Thr Leu
            20                  25                  30

Ala Val Ser
        35


<210> SEQ ID NO 43
<211> LENGTH: 8730
<212> TYPE: DNA
<213> ORGANISM: Artificial
<220> FEATURE:
<223> OTHER INFORMATION: synthetic DNA

<400> SEQUENCE: 43

atggctgcta ggttgcaaga acaaaaaggt ggtgagatgg atactagaat tgctatcatt      60

ggaatgtctg ctattttgcc atgtggtact actgttagag aatcttggga aactattaga     120

gctggtattg attgtttgtc tgatttgcct gaagatagag ttgatgttac tgcttacttt     180

gatccagtta aaactactaa agataaaatc tattgtaaga gaggtggttt cattccagaa     240

tatgattttg atgctagaga atttggtttg aatatgtttc agatggaaga ttctgatgct     300

aatcaaacta tttctttgtt gaaagttaaa gaagcattgc aagatgctgg catcgatgct     360

ttgggtaaag agaagaagaa tattggttgt gttttgggta ttggtggtgg tcaaaaatct     420

tctcatgaat tttactcaag attgaattat gttgttgttg agaaggtatt gagaaaaatg     480

ggtatgccag aagaagatgt taaagttgct gttgaaaaat acaaagctaa ttttccagag     540

tggagattgg attcttttcc aggtttcttg ggaaatgtta ctgcaggaag atgtactaat     600

acttttaatc ttgatggcat gaattgtgtt gttgatgctg cttgtgcttc ttctttgatt     660

gctgttaaag ttgctattga tgaattgttg tacggtgatt gtgatatgat ggttactggt     720

gctacttgta ctgataattc tattggaatg tacatggctt tttctaaaac tccagttttc     780

tctactgatc catctgttag agcttatgat gaaaaaacta aaggaatgtt gattggtgaa     840

ggttctgcta tgttggtttt gaaaagatat gctgatgctg ttagagatgg tgatgaaatt     900

catgctgtta ttagaggttg tgcttcttct tctgatggta aagctgctgg tatctatact     960

ccaactattt ctggtcaaga agaagcattg agaagagctt ataatagagc ttgtgttgat    1020

ccagctactg ttactttggt tgaaggtcat ggtactggta ctccagttgg tgatagaatt    1080

gaattgactg ctttgagaaa tttgtttgat aaagcatatg gtgaaggtaa tactgaaaaa    1140

gttgctgttg gttctattaa atcttctatt ggtcatttga aagctgttgc tggtttggct    1200

ggaatgatta aagttatcat ggctttgaaa cataaaactt tgccaggaac tattaatgtt    1260

gataatccac caaacttgta cgataatact ccaattaacg aatcttcttt gtacattaat    1320

actatgaata gaccttggtt tccaccacca ggtgttccaa gaagagctgg tatttcttct    1380

tttggttttg gtggtgctaa ttatcatgct gttttggaag aagctgaacc agaacatact    1440

actgcttata ggttgaacaa aagaccacaa ccagttttga tgatggctgc tactccagct    1500

gctttgcaat ctttgtgtga agctcaattg aaagaatttg aagctgctat taaagaaaac    1560

gaaactgtta aaaatactgc ttatattaaa tgtgttaaat ttggtgaaca attcaaattc    1620

cctggtagta ttccagctac taatgctagg ttgggtttct tggttaaaga tgctgaagat    1680

gcttgttcta ctttgagagc tatttgtgct caatttgcta aagatgttac taaagaagca    1740

tggagattgc caagagaagg tgtttctttt agagctaaag gtattgctac taatggtgct    1800

gttgctgctt tgttttctgg tcaaggtgct caatatactc atatgttttc tgaagttgct    1860
```

-continued

```
atgaattggc cacaattcag acaatctatt gctgctatgg atgctgctca atctaaagtt   1920
gctggttctg ataaagattt tgaaagagtt tctcaagttt tgtatccaag aaaaccatac   1980
gagagagaac cagagcaaga tcataagaag atttctttga ctgcttattc tcaaccatct   2040
actttggctt gtgctttggg tgcttttgaa atttttaaag aagctggttt tactccagat   2100
tttgctgctg gtcattcttt gggtgaattt gctgctttgt acgctgctgg ttgtgttgat   2160
agagatgaat tgtttgaatt ggtttgtaga agagctagaa ttatgggtgg taaagatgct   2220
ccagctactc caaaaggttg catggctgct gttattggtc caaatgctga aaatattaaa   2280
gttcaagctg ctaatgtttg gttaggaaat tctaattctc catctcaaac tgttattact   2340
ggttctgttg aaggtattca agctgaatct gctaggttgc aaaaagaagg ttttagagtt   2400
gttccattgg cttgtgaatc tgcttttcat tctccacaga tggaaaatgc ttcttctgct   2460
tttaaagatg ttatctctaa agtttctttt agaactccaa aagctgaaac taaattgttt   2520
tctaatgttt ctggtgaaac ttatccaact gatgctagag aaatgttgac tcaacatatg   2580
acttcttctg ttaaattttt gactcaagtt agaaatatgc atcaagctgg tgctagaatt   2640
tttgttgaat tcggtccaaa acaagttttg tctaaattgg tttctgaaac tttgaaagat   2700
gatccatctg ttgttactgt ttctgttaat ccagcttctg gtactgattc tgatattcaa   2760
ttgagagatg ctgctgttca attggttgtt gctggtgtta atttgcaagg ttttgataaa   2820
tgggatgctc cagatgctac tagaatgcaa gctattaaaa aaaaaagaac tactttgaga   2880
ttgtctgctg ctacttatgt ttctgataaa actaagaaag ttagagatgc tgctatgaat   2940
gatggtagat gtgttactta cttgaaaggt gctgctccat tgattaaagc tccagaacca   3000
gttgttgatg aagctgctaa aagagaagct gaaagattgc aaaaagaatt gcaagatgct   3060
caaagacaat tggatgatgc taaaagagct gctgctgaag ctaattctaa attggctgct   3120
gctaaagaag aagctaaaac tgctgctgct tctgctaaac cagctgttga tactgctgtt   3180
gttgaaaaac atagagctat tttgaaatct atgttggctg aattggatgg ttatggttct   3240
gttgatgctt cttctttgca acaacaacaa caacaacaaa ctgctccagc tccagttaaa   3300
gctgctgctc cagctgctcc agttgcttct gctccagcac ccgcagttag caacgaactc   3360
ttagaaaaag ccgagacagt agtgatggaa gttcttgcag ctaaaacggg gtacgaaaca   3420
gatatgattg aagcagatat ggaacttgaa actgaactgg gcattgattc gattaaacgc   3480
gtggaaattc tgtcagaagt gcaagctatg ttaaatgttg aagcgaaaga tgttgatgca   3540
ctgtcacgca cacgcaccgt gggcgaagta gtgaacgcca tgaaagcaga aattgcaggc   3600
tcctcagcac ccgcgccggc cgcagcagca ccagcccccg caaaagccgc ccccgcagcg   3660
gcggctccag ccgtttcaaa cgaattactc gaaaaagcag aaaccgtagt gatggaagtc   3720
cttgccgcca aaacgggtta tgagaccgat atgatcgaaa gcgatatgga attagaaacc   3780
gaattaggga ttgatagtat taaacgcgta gaaattctgt ccgaagtaca agctatgctg   3840
aatgtagaag caaaagatgt agatgcgtta agccgcacac gcactgttgg tgaagttgtg   3900
aatgctatga aagctgaaat tgcaggaggt tcagcaccgg ccccagcagc cgcagcccca   3960
ggtccagcag cagccgcacc ggccccccgcc gccgccgcac cggcagtatc aaacgagttg   4020
ttagagaaag cggaaaccgt tgtgatggaa gtacttgccg cgaagacagg ttacgagacc   4080
gatatgatcg aaagtgacat ggaattagaa accgaattgg gcattgatag cattaaacgc   4140
gtagaaattt tatccgaagt tcaagccatg ttaaatgttg aagccaaaga tgtggatgcg   4200
ttatcccgca cgcgtaccgt cggagaagta gtggacgcta tgaaagcaga gattgcagga   4260
```

-continued

```
ggaagtgcac cggctccagc agcagcagca cccgccccag cggcagcggc gccggcaccg   4320
gccgctccgg ccccagccgt tagttcagaa ctcctcgaaa aagcagaaac tgttgtcatg   4380
gaagtattag ctgcaaaaac aggttacgag acggatatga ttgaaagcga tatggaatta   4440
gaaaccgaat taggcattga ttcaattaaa cgtgttgaaa tcttaagtga agtccaagcc   4500
atgcttaatg ttgaagccaa agatgtagat gcattatctc gcacgcgtac agtgggtgaa   4560
gttgtcgatg cgatgaaagc agaaatcgcg ggaggatcag cgccagcccc ggcagcagca   4620
gcccccgcgc ccgccgcggc cgcacctgcg ccggccgccc cagcccctgc agcaccggcc   4680
ccagcagtgt cgtcggaatt actcgaaaaa gctgaaacgg tcgttatgga agtacttgct   4740
gcaaagacgg gctatgaaac ggatatgatt gaatcggata tggaattaga aacagaactt   4800
ggtattgact ctattaaacg cgtggaaatt ctgagcgaag tacaggcaat gttaaacgta   4860
gaagccaaag atgtagacgc tttgtcacgc acacggacgg taggagaagt tgtggatgcg   4920
atgaaagctg aaattgccgg ttcaagtgct agcgcccctg ctgccgccgc ccctgcccct   4980
gccgccgcag caccggcccc ggcagccgca gctccagcag ttagtaacga attactcgaa   5040
aaagcagaaa cggtggtcat ggaagtgtta gcagcaaaaa ctggatatga aacggacatg   5100
attgaaagcg atatggaatt agaaacagaa ctgggaattg atagtattaa acgtgttgag   5160
attttatctg aggttcaagc tatgctgaat gttgaagcga aagatgtaga cgcactgtct   5220
cggacccgca cagtaggtga agtggtggac gcgatgaaag cagaaatcgc aggtggaagt   5280
gctccggccc cggcggcagc cgcacccgcg cccgcggccg cagccccagc agttagcaac   5340
gaattactcg agaaagcaga aactgtagtg atggaagtgt tagccgcaaa aacgggttat   5400
gaaacggata tgattgaaag cgatatggaa ctggaaaccg aactgggcat tgattctatt   5460
aaacgtgtcg aaatcttatc ggaagtccaa gcaatgctga acgtagaggc aaaggatgtt   5520
gatgccctgt cacgtacccg taccgtaggt gaagttgtag atgccatgaa agctgaaatc   5580
gcaggcagta gcgccccggc accagccgcc gccgcccccg cgccggcagc cgccgcaccc   5640
gcgccagccg cagctgctcc agctgtatct agtgagctgc tcgaaaaagc agaaaccgtg   5700
gttatggaag tgctcgccgc taaaacagga tatgaaaccg atatgattga aagcgatatg   5760
gaattagaaa ccgaactggg tattgatagt attaagcgtg ttgaaatttt gtcagaagtt   5820
caagctatgt tgaatgtaga agccaaagat gtagacgctt taagtcggac gcgtactgtt   5880
ggagaagtcg tagacgccat gaaagcagag attgcaggcg gaagtgcacc ggccccggca   5940
gcagcagccc cagcaccagc ggccgccgct cctgcagtgt caaacgaact tctggaaaaa   6000
gctgaaaccg tcgtcatgga agtgctggct gcaaaaactg gatatgaaac agacatgatt   6060
gaatcagata tggaactcga aaccgaactg ggattgata gcattaaacg tgtggaaatt   6120
ttatcggagg tacaagcaat gttaaatgtg gaagcaaaag atgtggatgc actgagccgt   6180
actcgtactg ttggtgaggt cgtggatgcg atgaaagcag aaattgctgg agggagtgcg   6240
cctgccccgg ccgccgccgc acccgcgtct gccggtgctg cccccgctgt caaaattgat   6300
tctgttcatg gtgctgattg tgatgatttg tctttgatgc atgctaaagt tgttgatatt   6360
agaagaccag atgaattgat tttggaaaga ccagaaaata gaccagtttt ggttgttgat   6420
gatggttctg aattgacttt ggctttggtt agagttttgg gtgcttgtgc tgttgttttg   6480
acttttgaag gtttgcaatt ggctcaaaga gctggtgctg ctgctattag acatgttttg   6540
gctaaagatt tgtctgctga atctgctgaa aaagctatta aagaagctga acaaagattt   6600
```

-continued

```
ggtgctttgg gtggttttat ctctcaacaa gctgaaagat ttgaaccagc tgaaattttg   6660

ggttttactt tgatgtgtgc taaatttgct aaagcatctt tgtgcactgc tgttgctggt   6720

ggtagaccag ctttcattgg tgttgctagg ttggatggta ggttgggttt tacttctcaa   6780

ggaacttctg atgctttgaa aagagctcaa agaggtgcta tttttggttt gtgcaagact   6840

attggtttgg aatggtctga atctgatgtt ttctcaagag gtgttgatat tgctcaaggt   6900

atgcatccag aagatgctgc tgttgctatt gttagagaaa tggcttgtgc tgatattaga   6960

attagagaag ttggtattgg tgctaatcaa caaagatgta ctattagagc tgctaaattg   7020

gaaactggaa atccacaaag acaaattgct aaagatgatg ttttgttggt ttctggtggt   7080

gctagaggaa ttactccatt gtgcattaga gaaattacta gacaaattgc tggtggaaag   7140

tatattttgt tgggtaggtc taaagtttct gcttctgaac cagcttggtg tgctggtatt   7200

actgatgaaa aagctgttca aaaagctgct actcaagaat tgaaaagagc tttttctgct   7260

ggtgaaggtc caaaaccaac tccaagagct gttactaaat tggttggttc tgttttgggt   7320

gctagagaag ttaggtcttc tattgctgct attgaagcat tgggtggaaa agctatctat   7380

tcttcttgtg atgttaattc tgctgctgat gttgctaaag ctgttagaga tgctgaatct   7440

caattgggtg ctagagtttc tggtattgtt catgcttctg gtgttttgag agataggttg   7500

attgaaaaaa aattgccaga tgaatttgat gctgtttttg gtactaaagt tactggtttg   7560

gaaaatttgt tggctgctgt tgatagagct aatttgaaac atatggtttt gttttcttct   7620

ttggctggtt ttcatggtaa tgttggtcaa tctgattatg ctatggctaa cgaagcattg   7680

aacaaaatgg gtttggaatt ggctaaagat gtttctgtta aatctatttg ttttggtcct   7740

tgggatggtg gtatggttac tccacaattg aaaaaacaat ttcaagaaat gggtgttcaa   7800

attattccaa gagaaggtgg tgctgatact gttgctagaa ttgttttggg ttcttctcca   7860

gctgaaattt tggttggtaa ttggagaact ccatctaaaa aagttggttc tgatactatt   7920

actttgcaca gaaaaatttc tgctaaatct aatccatttt tggaagatca tgtcattcaa   7980

ggtagaagag ttttgccaat gactttggct attggttctt tggctgaaac ttgtttgggt   8040

ttgtttcctg gatattcttt gtgggctatt gatgatgctc aattgtttaa aggtgttact   8100

gttgatggtg atgttaattg tgaagttact ttgactccat ctactgctcc ttctggtaga   8160

gttaatgttc aagctacttt gaaaactttt tcttctggta aattggttcc agcttataga   8220

gctgttattg ttttgtctaa tcaaggtgct ccaccagcta atgctactat gcaaccacca   8280

tctttggatg ctgatccagc tttgcaaggt tctgtttatg atggaaagac tttgtttcat   8340

ggtccagctt ttagaggtat tgatgatgtt ttgtcttgta ctaaatctca attggttgct   8400

aaatgttctg ctgttccagg ttctgatgct gctagaggtg aatttgctac tgatactgat   8460

gctcatgatc catttgttaa tgatttggct tttcaagcta tgttggtttg ggttagaaga   8520

actttgggtc aagctgcttt gccaaattct attcaaagaa ttgttcaaca cagaccagtt   8580

ccacaagata aaccatttta tattactttg agatctaatc aatctggtgg tcattctcaa   8640

cataaacatg ctttgcaatt tcataacgaa caaggtgatt tgttcattga tgttcaagca   8700

tctgttattg ctactgattc tttggctttt                                    8730
```

<210> SEQ ID NO 44
<211> LENGTH: 6177
<212> TYPE: DNA
<213> ORGANISM: Artificial
<220> FEATURE:
<223> OTHER INFORMATION: Synthetic DNA -continued

<400> SEQUENCE: 44

```
atggctgcta gaaatgtttc tgctgctcat gaaatgcatg atgaaaaaag aattgctgtt     60
gttggtatgg ctgttcaata tgctggttgt aagactaaag atgaattttg ggaagttttg    120
atgaatggta aagttgaatc taaagttatc tctgataaaa gattgggttc taattaccga    180
gctgaacatt acaaggctga aagatccaaa tacgctgata ctttttgtaa cgaaacttat    240
ggtactttgg atgaaaacga aattgataac gaacatgaat tgttgttgaa tttggctaaa    300
caagcattgg ctgaaacttc tgttaaagat tctactagat gtggtattgt ttctggttgt    360
ttgtcttttc ctatggataa tttgcaaggt gaattgttga atgtctatca aaatcatgtt    420
gagaagaaat tgggtgctag agtttttaaa gatgcttctc attggtctga aagagaacaa    480
tctaacaaac cagaagctgg tgatagaaga attttcatgg acccagcttc ttttgttgct    540
gaagaattga atttgggtgc tttgcattat tctgttgatg ctgcttgtgc tactgcttta    600
tacgttttga gattggctca agatcatttg gtttctggtg ctgctgatgt tatgttgtgt    660
ggtgctactt gtttgccaga accattcttt atcttgtctg gtttttctac ttttcaagct    720
atgccagttg gtactggtca aaatgtttct atgccattgc ataaagattc tcaaggtttg    780
actccaggtg aaggtggttc tatcatggtt ttgaaaagat tggatgatgc tattagagat    840
ggtgatcata tctatggtac tttgttgggt gctaatgttt ctaattctgg cactggtttg    900
ccattgaaac cattgttgcc atctgaaaaa aaatgtttga tggatactta tactagaatt    960
aatgttcatc cacataaaat tcaatatgtt gaatgtcatg ctactggtac tccacaaggt   1020
gatagggttg aaattgatgc tgttaaagca tgttttgaag gaaaagttcc aagatttggt   1080
actactaaag gaaactttgg tcatactttg gttgctgctg gttttgctgg aatgtgcaaa   1140
gttttgttgt ctatgaaaca tggtatcatt ccaccaactc caggtattga tgatgaaact   1200
aagatggacc cattggttgt ttctggtgaa gctattcctt ggccagaaac taatggtgaa   1260
ccaaaaagag ctggtttgtc tgcttttggt tttggtggta ctaatgctca tgctgttttt   1320
gaagaacatg atccatctaa tgctgcttgt actggtcatg attctatttc tgctttgtct   1380
gctagatgtg gtggtgaatc taatatgaga attgctatta ctggtatgga tgctactttt   1440
ggtgctttga aggtttggaa tgcttttgaa agagccatct acactggtgc tcatggtgct   1500
attccattgc cagaaaagag atggagattt ttgggcaaag ataaagattt cttggatttg   1560
tgtggtgtta aagctactcc acatggttgt tatattgaag atgttgaagt tgattttcaa   1620
agattgagaa ctccaatgac tccagaagat atgttgttgc cacaacaatt gttggctgtt   1680
actactattg atagagctat tttggattct ggtatgaaaa aaggtggtaa tgttgctgtt   1740
tttgttggtt tgggtaccga tttggaattg tacagacata gagctagagt tgctttgaaa   1800
gaaagagtta gaccagaagc atctaaaaaa ttgaatgata tgatgcagta cattaatgat   1860
tgtggcacct ctacttctta tacttcttat attggtaatt tggttgctac tagagtttct   1920
tctcaatggg gttttactgg tccatctttt actattactg aagggaataa ctctgtttat   1980
agatgtgctg aattgggaaa gtatttgttg gaaactggtg aagttgatgg tgttgttgtt   2040
gctggtgttg atttgtgtgg ttctgctgaa aacttatacg ttaaatcaag aagattcaaa   2100
gtttctactt ctgatactcc aagagcttct tttgatgctg ctgctgatgg ttactttgtt   2160
ggtgaaggtt gtggtgcttt tgttttgaaa agagaaactt cttgtactaa agatgataga   2220
atctatgctt gcatggatgc tattgttcca ggtaatgttc catctgcttg tttgagagaa   2280
```

-continued

```
gcattggatc aagctagagt taaaccaggt gatattgaaa tgttggaatt gtctgctgat   2340
tctgctagac atttgaaaga tccatctgtt ttgccaaaag aattgactgc tgaagaagaa   2400
attggtggtt tgcaaactat tttgagagat gatgataaat tgccaagaaa tgttgctact   2460
ggttctgtta aagctactgt tggtgatact ggttatgctt ctggtgctgc ttctttgatt   2520
aaagctgctt tgtgcatcta taataggtat ttgccatcta atggtgatga ttgggatgaa   2580
ccagctccag aagctccttg ggattctact ttgtttgctt gtcaaacttc aagagcttgg   2640
ttgaaaaatc ctggagagag aagatatgct gctgtttctg gtgtttctga aactaggtct   2700
tgttattctg ttttgttgtc tgaagctgaa ggtcattatg aaagagaaaa tagaatttct   2760
ttggatgaag aagctccaaa attgattgtt ttgagagctg attctcatga agaaattttg   2820
ggtaggttgg ataaaattag agaaagattt ttgcaaccaa ctggtgctgc tccaagagaa   2880
tctgaattga aagctcaagc tagaagaatt ttcttggaat tgttgggtga aactttggct   2940
caagatgctg cttcttctgg ttctcaaaaa ccattggctt tgtctttggt ttctactcca   3000
tctaaattgc aaagagaagt tgaattggct gctaaaggta ttccaagatg tttgaaaatg   3060
agaagagatt ggtcttctcc agctggttca agatatgctc cagaaccatt ggcttctgat   3120
agagttgctt tcatgtacgg tgaaggaagg tctccatact atggaatcac tcaagatatt   3180
catagaattt ggccagaatt gcatgaagtt attaacgaaa aaactaatag gttgtgggct   3240
gaaggtgata gatgggttat gccaagagct tcttttaaat ctgaattgga atctcaacaa   3300
caagaatttg atagaaatat gattgaaatg tttaggttgg gtattttgac ttctattgct   3360
tttactaatt tggctagaga tgttttgaat attactccaa aagctgcttt tggtttgtct   3420
ttgggtgaaa tttctatgat ttttgctttt tctaaaaaaa atggtttgat ttctgatcaa   3480
ttgactaaag atttgagaga atctgatgtt tggaacaaag cattggctgt tgaattcaat   3540
gctttgagag aagcatgggg tattccacaa tctgttccaa aagatgaatt ttggcaaggt   3600
tatattgtta gaggtactaa acaagatatt gaagctgcta ttgctccaga ttccaaatac   3660
gttaggttga ctatcattaa tgatgctaat actgctttga tttctggtaa accagatgct   3720
tgtaaagctg ctattgctag gttgggtggt aatattccag ctttgccagt tactcaagga   3780
atgtgtggtc attgtccaga agttggtcca tatactaaag atattgctaa aattcatgct   3840
aatttggaat ttccagttgt tgatggtttg gatttgtgga ctactattaa tcaaaaaaga   3900
ttggttccaa gagctactgg tgctaaagat gaatgggctc catcttcttt tggtgaatat   3960
gctggtcaac tttacgaaaa acaagctaat tttccacaaa ttgttgaaac tatctacaaa   4020
caaaattatg atgtttttgt tgaggttggt ccaaacaacc ataggtctac tgctgttaga   4080
actactttgg gtccacaaag aaatcatttg gctggtgcta ttgataaaca aaacgaagat   4140
gcttggacta ctattgttaa attggttgct tctttgaaag ctcatttggt tccaggtgtt   4200
actatttctc cattgtatca ttctaaattg gttgctgaag ctgaagcatg ttatgctgct   4260
ctgtgcaaag gagaaaaacc taagaagaac aaatttgtta gaaaaattca attgaatggt   4320
aggttcaatt ctaaagctga tccaatttct tctgctgatt tggcttcttt tccaccagct   4380
gatccagcta ttgaagctgc tatttcttca agaattatga aaccagttgc tccaaaattt   4440
tatgctaggt tgaatattga tgaacaagac gaaacaagag atccaatttt gaacaaagat   4500
aatgctccat ctagttcatc tagttcctct tcatctagtt cttcatctag ttctccatct   4560
ccagctcctt ctgctccagt tcaaaaaaaa gctgctccag ctgctgaaac taaagctgtt   4620
gcttctgctg atgctttgag atctgctttg ttggatttgg attctatgtt ggctttgtct   4680
```

-continued

```
tctgcttctg cttctggtaa tttggttgaa actgctccat ctgatgcttc tgttattgtt   4740
ccaccatgta atattgctga tttgggttca agagctttta tgaaaactta tggtgtttct   4800
gctccattgt acactggtgc tatggctaaa ggtattgctt ctgctgattt ggttattgct   4860
gctggtagac aaggcatttt ggcttctttt ggtgctggtg gtttgccaat gcaagttgtt   4920
agagaatcta ttgaaaaaat tcaagctgct ttgccaaatg gtccatatgc tgttaatttg   4980
attcattctc catttgattc taatttggaa aaaggtaatg ttgatttgtt tttggaaaaa   5040
ggtgttactt ttgttgaagc atctgctttt atgactttga ctccacaagt tgttaggtac   5100
agagctgctg gtttgactag aaatgctgat ggttctgtta atattagaaa tagaattatc   5160
ggaaaggttt caagaactga attggctgaa atgtttatga gacctgcccc agaacacttg   5220
ttgcaaaaat tgattgcttc tggtgaaatt aatcaagaac aagctgaatt ggctagaaga   5280
gttccagttg ctgatgatat tgctgttgaa gctgattctg gtggtcatac tgataataga   5340
ccaattcatg ttatcttgcc attgattatt aatttgagag acagattgca tagagaatgt   5400
ggttatccag ctaatttgag agttagagtt ggtgctggtg gtggtattgg ttgtccacaa   5460
gctgctttgg ctacttttaa tatgggtgct tctttcattg ttactggcac tgttaatcaa   5520
gttgctaaac aatctggtac ttgtgataat gttagaaaac aattggctaa agctacttat   5580
tctgatgttt gcatggctcc agctgctgat atgtttgaag aaggtgttaa attgcaagtt   5640
ttgaagaaag ggacaatgtt tccatcaaga gctaataagt tatacgaatt gttttgcaag   5700
tatgattctt ttgaatctat gccaccagct gaattggcta gagttgaaaa aagaattttc   5760
tcaagagctt tggaagaagt ttgggatgaa actaaaaatt tttacattaa taggttgcac   5820
aatccagaaa aaattcaaag agctgaaaga gatccaaaat tgaaaatgtc tttgtgtttt   5880
agatggtatt tgtctttggc ttcaagatgg gctaatactg gtgcttctga tagagttatg   5940
gattatcaag tttggtgtgg tccagctatt ggttctttta atgatttcat taaaggcacc   6000
tacttggacc cagctgttgc taacgaatat ccatgcgttg ttcaaattaa caaacaaatt   6060
ttgagaggtg cttgtttcct cagaagattg gaaattttga gaaatgctag gttgtctgat   6120
ggtgctgctg ctttggttgc ttctattgat gatacttatg ttccagctga aaaattg      6177
```